US012679836B2

(12) United States Patent
Siegel et al.

(10) Patent No.: US 12,679,836 B2
(45) Date of Patent: Jul. 14, 2026

(54) 4H-PYRROLO[3,2-C]PYRIDIN-4-ONE COMPOUNDS

(71) Applicants: Bayer Aktiengesellschaft, Leverkusen (DE); The Broad Institute, Inc., Cambridge, MA (US); Dana-Farber Cancer Institute, Inc., Boston, MA (US)

(72) Inventors: Stephan Siegel, Berlin (DE); Franziska Siegel, Cambridge, MA (US); Volker Schulze, Hohen Neuendorf OT Bergfelde (DE); Markus Berger, Berlin (DE); Keith Graham, Berlin (DE); Detlev Sülzle, Berlin (DE); Ulf Bömer, Glienicke (DE); Daniel Korr, Berlin (DE); Jens Schröder, Berlin (DE); Ursula Mönning, Woltersdorf (DE); Michael Niehues, Berlin (DE); Matthew Meyerson, Boston, MA (US); Heidi Greulich, Cambridge, MA (US); Bethany Kaplan, Cambridge, MA (US)

(73) Assignees: Bayer Aktiengesellschaft, Leverkusen (DE); The Broad Institute, Inc., Cambridge, MA (US); Dana-Farber Cancer Institute, Inc., Boston, MA (US)

( * ) Notice: Subject to any disclaimer, the term of this patent is extended or adjusted under 35 U.S.C. 154(b) by 1301 days.

(21) Appl. No.: 17/605,975

(22) PCT Filed: Apr. 22, 2020

(86) PCT No.: PCT/EP2020/061176
§ 371 (c)(1),
(2) Date: Oct. 22, 2021

(87) PCT Pub. No.: WO2020/216781
PCT Pub. Date: Oct. 29, 2020

(65) Prior Publication Data

US 2022/0298157 A1 Sep. 22, 2022

Related U.S. Application Data

(60) Provisional application No. 62/940,036, filed on Nov. 25, 2019, provisional application No. 62/838,051, filed on Apr. 24, 2019.

(51) Int. Cl.
*C07D 471/04* (2006.01)
*A61K 31/437* (2006.01)
(Continued)

(52) U.S. Cl.
CPC .......... *C07D 471/04* (2013.01); *A61K 31/437* (2013.01); *A61K 31/5377* (2013.01); *A61K 45/06* (2013.01); *A61P 35/00* (2018.01)

(58) Field of Classification Search
CPC ................ C07D 471/04; A61K 31/437; A61K 31/5377; A61K 45/06; A61K 31/444;
(Continued)

(56) References Cited

U.S. PATENT DOCUMENTS 6,673,908 B1 * 1/2004 Stanton, Jr. ........ C07K 14/7151 435/6.16
10,428,063 B2 * 10/2019 Graham .................... A61P 9/08
(Continued)

FOREIGN PATENT DOCUMENTS

CA 2974853 C 8/2016
CN 106715415 A 5/2017
(Continued)

OTHER PUBLICATIONS

Arafah, et al., (2023). The Future of Precision Medicine in the Cure of Alzheimer's Disease. Biomedicines, 11(2), 335. https://doi.org/10.3390/biomedicines 11020335 (Year: 2023) (Year: 2023).*
(Continued)

*Primary Examiner* — James H Alstrum-Acevedo
*Assistant Examiner* — Chantal Adlam
(74) *Attorney, Agent, or Firm* — Greenberg Traurig, LLP; Melissa Hunter-Ensor; Scott Goncher

(57) ABSTRACT

Compounds of formula (I), formula (I), processes for their production and their use as pharmaceuticals.

(I)

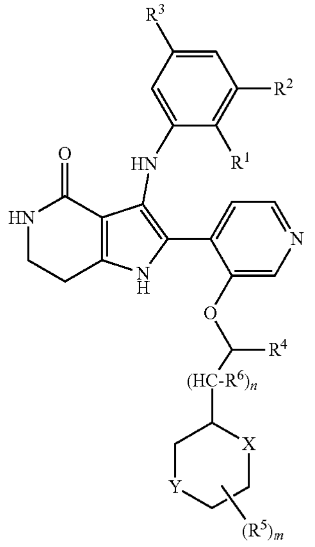

44 Claims, No Drawings

Specification includes a Sequence Listing.

(51) Int. Cl.
*A61K 31/5377* (2006.01)
*A61K 45/06* (2006.01)
*A61P 35/00* (2006.01)

(58) Field of Classification Search
CPC .. A61P 35/00; A61P 7/00; A61P 11/00; A61P 35/04
See application file for complete search history.

(56) References Cited

U.S. PATENT DOCUMENTS

| | | | | |
|---|---|---|---|---|
| 11,339,157 | B1 * | 5/2022 | Siegel | A61P 35/00 |
| 2004/0122237 | A1 | 6/2004 | Amiri et al. | |
| 2006/0122168 | A1 | 6/2006 | Flohr et al. | |
| 2009/0253767 | A1 | 10/2009 | Klein et al. | |
| 2015/0307493 | A1 | 10/2015 | Combs et al. | |
| 2016/0046610 | A1 | 2/2016 | Hitchcock et al. | |
| 2018/0016272 | A1 | 1/2018 | Graham et al. | |

FOREIGN PATENT DOCUMENTS

| | | | | |
|---|---|---|---|---|
| CN | 107406417 | A | 11/2017 | |
| EP | 2151431 | A1 | 2/2010 | |
| EP | 2179998 | B1 | 8/2012 | |
| JP | 2017518282 | A | 7/2017 | |
| TW | 201639828 | A | 11/2016 | |
| WO | 2005026124 | A1 | 3/2005 | |
| WO | 2009020990 | A1 | 2/2009 | |
| WO | 2010042699 | A1 | 4/2010 | |
| WO | 2010145998 | A1 | 12/2010 | |
| WO | 2014147203 | A1 | 9/2014 | |
| WO | 2015022073 | A1 | 2/2015 | |
| WO | 2015193339 | A1 | 12/2015 | |
| WO | 2016091845 | A1 | 6/2016 | |
| WO | 2016100166 | A1 | 6/2016 | |
| WO | WO-2016120196 | A1 * | 8/2016 | A61K 31/437 |
| WO | 2016185333 | A1 | 11/2016 | |
| WO | 2019081486 | A1 | 5/2019 | |
| WO | 2020216773 | A1 | 10/2020 | |
| WO | 2020216774 | A1 | 10/2020 | |
| WO | 2021198020 | A1 | 10/2021 | |

OTHER PUBLICATIONS

Golub et al., Science, vol. 286, Oct. 15, 1999, pp. 531-537 (Year: 1999).*

International Search Report and Written Opinion mailed Sep. 28, 2020 in corresponding PCT Patent Application No. PCT/EP2020/061176 (9 pages).

International Search Report and Written Opinion mailed Aug. 3, 2020 in corresponding PCT Patent Application No. PCT/EP2020/061176 (12 pages).

Office Action mailed Jan. 3, 2023 in corresponding Chilean Patent Application No. 2770-2021 (16 pages, English Summary included pp. 1-2).

Office Action and Search Report mailed Mar. 23, 2023 in corresponding Chinese Patent Application No. 202080031189.4 (7 pages).

English Translation of Office Action and Search Report mailed Mar. 23, 2023 in corresponding Chinese Patent Application No. 202080031189.4 (6 pages).

Written Opinion mailed May 1, 2023 in corresponding Singaporean Patent Application No. 11202111304U (7 pages).

Documentary Decision and Search Report mailed Sep. 7, 2023 in corresponding Georgian Patent Application No. AP 2020 15804 (17 pages).

English Translation of Documentary Decision and Search Report mailed Sep. 7, 2023 in corresponding Georgian Patent Application No. AP 2020 15804 (11 pages).

Examination Report mailed Oct. 28, 2023 in corresponding Indian Patent Application No. 202117051266 (6 pages).

Office Action and Search Report mailed Jul. 11, 2024 in corresponding Malaysian Patent Application No. PI2021006316 (6 pages).

Examination Search Report dated Jan. 24, 2025 in corresponding Canadian Patent Application No. 3137218 (6 pages).

Office Action and Search Report in corresponding United Arab Emirates Patent Application No. P6001914/2021 (9 pages).

Notice of Opposition mailed Jul. 18, 2022 in corresponding Colombian Patent Application No. NC2021/0014022 (18 pages, English summary included pp. 1-6).

English Translation of Examination Report received on Jan. 2, 2023 in corresponding Saudi Arabian Patent Application No. 521430651 (2 pages).

English Translation of Office Action and Search Report mailed Aug. 15, 2023 in corresponding Taiwanese Patent Application No. TW109113538A (5 pages).

Office Action mailed Sep. 19, 2023 in corresponding Dominican Patent Application No. P2021-0216 (5 pages).

English Summary and Translation of Office Action mailed Sep. 19, 2023 in corresponding Dominican Patent Application No. P2021-0216 (17 pages).

Anderson et al., "Pyrrolopyridine Inhibitors of Mitogen-Activated Protein Kinase-Activated Protein Kinase 2 (MK-2)," Journal of Medicinal Chemistry, 2007, vol. 50, No. 11, pp. 2647-2654.

Arcila et al., "Prevalence, Clinicopathologic Associations, and Molecular Spectrum of ERBB2 (HER2) Tyrosine Kinase Mutations in Lung Adenocarcinomas," Clinical Cancer Research, Sep. 15, 2012, vol. 18, No. 18, pp. 4910-4918.

Bellale et al., "Diarylthiazole: an anti-mycobacterial scaffold potentially targeting PrrB-PrrA two component system," Journal of Medicinal Chemistry, 2014, vol. 57, pp. 6572-6582.

Bertini et al., "Alkylamino Derivatives of 4-Aminomethylpyridine as Inhibitors of Copper-Containing Amine Oxidases," Journal of Medicinal Chemistry, 2005, vol. 48, No. 3, pp. 664-670.

Chan et al., "Turnover Is Rate-Limited by Deglycosylation for Micromonospora viridifaciens Sialidase-Catalyzed Hydrolyses: Conformational Implications for the Michaelis Complex," Journal of the American Chemical Society, 2011, vol. 133, 2989-2997.

Chen et al., "Clinical efficacy of first-generation EGFR-TKIs in patients with advanced non-small-cell lung cancer harboring EGFR exon 20 mutations," OncoTargets and Therapy, 2016, vol. 9, pp. 4181-4186.

Chiu et al., "Epidermal Growth Factor Receptor Tyrosine Kinase Inhibitor Treatment Response in Advanced Lung Adenocarcinomas with G719X/L861Q/S7681 Mutations," Journal of Thoracic Oncology, May 2015, vol. 10, No. 5, pp. 793-799.

Chong et al., "Rational Design of Potent Non-Nucleoside Inhibitors of HIV Reverse Transcriptase," Journal of Medicinal Chemistry, 2012, vol. 55, pp. 10601-10609.

Doebele et al., "Poster 338: First Report of Safety, Pharmacokinetics, and Preliminary Antitumor Activity of the Oral EGFR/HER2 Exon 20 Inhibitor TAK-788 (AP32788) in Non-Small Cell Lung Cancer," Presented at the 54th Annual Meeting of the American Society of Clinical Oncology, Jun. 1-5, 2018, Chicago, Illinois.

Fairhurst et al., "Synthesis of the Marine Sponge Derived β2-Adrenoceptor Agonist S1319," Organic Letters, 2005, vol. 7, No. 21, 4697-4700.

Floc'H et al., "Antitumor Activity of Osimertinib, an Irreversible Mutant-Selective EGFR Tyrosine Kinase Inhibitor, in NSCLC Harboring EGFR Exon 20 Insertions," Molecular Cancer Therapeutics, May 2018, vol. 17, No. 5, pp. 885-896.

Gridelli et al., "Non-small-cell lung cancer," Nature Reviews Disease Primers, 2015, vol. 1, Article No. 15009, pp. 1-16.

Guo et al., "Efficient synthesis of 2-arylamino substituted pyridinyl nitriles by Buchwald-Hartwig amination," Tetrahedron Letters, 2013, vol. 54, pp. 3233-3237.

Harris et al., "Discovery and Evaluation of 2-Anilino-5-aryloxazoles as a Novel Class of VEGFR2 Kinase Inhibitors," Journal of Medicinal Chemistry, 2005, vol. 48, No. 5, pp. 1610-1619.

Iasako et al., "TAS6417, A Novel EGFR Inhibitor Targeting Exon 20 Insertion Mutations," Molecular Cancer Therapeutics, Aug. 2018, vol. 17, No. 8, pp. 1648-1658.

(56) References Cited

OTHER PUBLICATIONS

Jang et al., "Discovery of a Highly Potent and Broadly Effective Epidermal Growth Factor Receptor and HER2 Exon 20 Insertion Mutant Inhibitor," Angewandte Chemie International Edition, Sep. 3, 2018, vol. 57, No. 36, p. 11629-11633.
Kuramochi et al., "Discovery of an N-(2-aminopyridin-4-ylmethyl)nicotinamide derivative: a potent and orally pioavailable NCX inhibitor," Bioorganic & Medicinal Chemistry, 2005, vol. 13, pp. 4022-4036.
Macias et al., "New Herbicide Models from Benzoxazinones: Aromatic Ring Functionalization Effects," Journal of Agricultural and Food Chemistry, 2006, vol. 54, No. 26, pp. 9843-9851.
Mok et al., "Gefitinib or Carboplatin-Paclitaxel in Pulmonary Adenocarcinoma," The New England Journal of Medicine, Sep. 3, 2009, vol. 361, No. 10, pp. 947-957.
Mok et al., "Osimertinib or Platinum-Pemetrexed in EGFR T790M-Positive Lung Cancer," The New England Journal of Medicine, Feb. 16, 2017, vol. 376, No. 7, pp. 629-640.
Muro et al., "Discovery of trans-4-[1-[[2,5-Dichloro-4-(1-methyl-3-indolylcarboxamido)phenyl]acetyl]-(4S)-methoxy-(2S)-pyrrolidinylmethoxy]cyclohexanecarboxylic Acid: An Orally Active, Selective Very Late Antigen-4 Antagonist," Journal of Medicinal Chemistry, 2009, vol. 52, No. 24, pp. 7974-7992.
Oxnard et al., "Assessment of Resistance Mechanisms and Clinical Implications in Patients With EGFR T790M-Positive Lung Cancer and Acquired Resistance to Osimertinib," JAMA Oncology, 2018, vol. 4, No. 11, pp. 1527-1534.
Oxnard et al., "Natural History and Molecular Characteristics of Lung Cancers Harboring EGFR Exon 20 Insertions," Journal of Thoracic Oncology, Feb. 2013, vol. 8, No. 2, pp. 179-184.
Paez et al., "EGFR Mutations in Lung Cancer: Correlation with Clinical Response to Gefitinib Therapy," Science, Jun. 4, 2004, vol. 304, pp. 1497-1500.
Pao et al., "Acquired Resistance of Lung Adenocarcinomas to Gefitinib or Erlotinib Is Associated with a Second Mutation in the EGFR Kinase Domain," PLoS Medicine, Mar. 2005, vol. 2, No. 3, e73, pp. 0225-0235.
Pao et al., "Rational, biologically based treatment of EGFR-mutant non-small-cell lung cancer," Nature Reviews Cancer, Nov. 2010, vol. 10, No. 11, pp. 760-774.
Ramalingam et al., "Mechanisms of acquired resistance to first-line osimertinib: Preliminary data from the phase III Flaura study," ESMO, Annals of Oncology, Oct. 2018, vol. 29, Suppl. 8, p. viii740.
Ramalingam et al., "Osimertinib As First-Line Treatment of EGFR Mutation-Positive Advanced Non-Small-Cell Lung Cancer," Journal of Clinical Oncology, Mar. 20, 2018, vol. 36, No. 9, pp. 841-849.
Robichaux et al., "Mechanisms and Clinical Activity of an EGFR and HER2 Exon 20-selective Kinase Inhibitor in Non-small Cell Lung Cancer," Nature Medicine, May 2018, vol. 24, No. 5, pp. 638-646.
Sehon et al., "Potent, Selective and Orally Bioavailable Dihydropyrimidine Inhibitors of Rho Kinase (ROCK1) as Potential Therapeutic Agents for Cardiovascular Diseases," Journal of Medicinal Chemistry, 2008, vol. 51, No. 21, pp. 6631-6634.
Sequist et al., "Phase III Study of Afatinib or Cisplatin Plus Pemetrexed in Patients With Metastatic Lung Adenocarcinoma With EGFR Mutations," Journal of Clinical Oncology, Sep. 20, 2013, vol. 31, No. 27, pp. 3327-3334.
Soria et al., "Osimertinib in Untreated EGFR-Mutated Advanced Non-Small-Cell Lung Cancer," The New England Journal of Medicine, Jan. 11, 2018, vol. 378, No. 2, pp. 113-125.
Sweeney et al., "Discovery of triazolinone non-nucleoside inhibitors of HIV reverse transcriptase," Bioorganic & Medicinal Chemistry Letters, 2008, vol. 18, 4348-4351.
Thress et al., "Acquired EGFR C797S mediates resistance to AZD9291 in advanced non-small cell lung cancer harboring EGFR T790M," Nature Medicine, Jun. 2015, vol. 21, No. 6, pp. 560-562.
Watterson et al., "Acridone-Based Inhibitors of Inosine 5'-Monophosphate Dehydrogenase: Discovery and SAR Leading to the Identification of N-(2-(6-(4-Ethylpiperazin-1-yl)pyridin-3-yl)propan-2-yl)-2-fluoro-9-oxo-9,10- dihydroacridine-3-carboxamide (BMS-566419)," Journal of Medicinal Chemistry, 2007, vol. 50, No. 15, pp. 3730-3742.
Worrall, David E., "The Action of Methyl Isothiocyanate on Ethyl Acetonedicarboxylate," Journal of the American Chemical Society, Mar. 1940, vol. 62, p. 675.
Yang et al., "Clinical activity of afatinib in patients with advanced non-small-cell lung cancer harbouring uncommon EGFR mutations: a combined post-hoc analysis of LUX-Lung 2, LUX-Lung 3, and LUX-Lung 6," The Lancet Oncology, 2015, vol. 16, No. 7, pp. 830-838.
Yasuda et al., "Structural, Biochemical and Clinical Characterization of Epidermal Growth Factor Receptor (EGFR) Exon 20 Insertion Mutations in Lung Cancer," Science Translational Medicine, Dec. 18, 2013, vol. 5, No. 216, p. 216ra177.
Written Opinion mailed Jul. 12, 2023 in corresponding Brazilian Patent Application BR112021019998-5 (10 pages, English Summary included pp. 1-5).
Office Action received Apr. 7, 2025 in corresponding Colombian Application No. NC2021/0014022 (9 pages).
Foreign associate summary in English of the Office Action received Apr. 7, 2025 in corresponding Colombian Application No. NC2021/0014022 (3 pages).

* cited by examiner

4H-PYRROLO[3,2-C]PYRIDIN-4-ONE COMPOUNDS

CROSS REFERENCE TO RELATED APPLICATIONS

This application is a National Phase Application of Int'l App. No. PCT/EP2020/061176, filed Apr. 22, 2020, which claims priority to and the benefit of U.S. App. No. 62/838,051, filed Apr. 24, 2019, and U.S. App. No. 62/940,036, filed Nov. 25, 2019, each of which are hereby incorporated by reference in their entirety.

SEQUENCE LISTING

This application contains a Sequence Listing which has been submitted electronically in ASCII format and is hereby incorporated by reference in its entirety. Said ASCII copy, created on May 23, 2022, is named $BHC_{183053}$-SL2.txt and is 36,140 bytes in size.

Field of Application of the Invention

The invention relates to substituted 4H-pyrrolo[3,2-c]pyridin-4-one compounds, a process for their production and uses thereof.

BACKGROUND OF THE INVENTION

The Epidermal Growth Factor Receptor (EGFR or EGF-receptor) receptor tyrosine kinase family consists of 4 members: EGFR (Erbb1, Her1), ERBB2 (Her2), ERBB3 (Her3), and ERBB4 (Her4). EGFR mediates activation of MAPK and PI3K signaling pathways and thereby regulates cell proliferation, differentiation, migration and survival (Pao et al., 2010). EGFR gene amplification, overexpression, and mutations are frequently observed in various cancer indications and are associated with a poor prognosis (Gridelli et al., 2015).

In lung adenocarcinoma, mutations of EGFR are prevalent in approximately 15% of Western patients and up to 50% of East Asian patients (Paez et al., 2004). These mutations typically occur in one of four exons, exons 18-21, in the kinase domain of EGFR (Paez et al., 2004). The most common activating mutations in EGFR are a point mutation in exon 21, substituting an arginine for a leucine (L858R), and a small in-frame deletion in exon 19 that removes four amino acids (del 19/del746-750) (Pao et al., 2010). The FDA-approved inhibitors gefitinib, erlotinib, and afatinib, targeting mutations in exons 18, 19, and 21 of EGFR, are effective in patients but the response is often not durable (Mok et al., 2009; Sequist et al., 2013). Resistance frequently occurs in these patients in response to acquisition of a second mutation, T790M (Pao et al., 2005). Second generation inhibitors, e.g. afatinib, irreversibly target this mutation but are still potent inhibitors of wild-type EGFR, leading to dose-limiting toxicity and lack of efficacy in patients. A third-generation irreversible inhibitor, osimertinib, that maximizes activity towards T790M while minimizing activity towards wild-type EGFR, is effective in T790M mutant patients and is currently the standard treatment for T790M positive patients (Mok et al., 2017). Osimertinib is also approved as a front-line therapy for patients with mutations of EGFR exons 19 or 21 (Soria et al., 2018).

However, patients also develop resistance to irreversible third-generation EGFR inhibitors, such as osimertinib. One of the major osimertinib resistance mechanisms identified is mutation of the cysteine in position 797 to a serine, resulting in loss of the covalently interacting cysteine and loss of sensitivity to irreversible EGFR inhibitors, at which point progressing patients have currently only limited treatment options (Thress et al., 2015; Oxnard et al., 2018). Such C797S mutations can also occur when osimertinib is used as a first-line therapy, in the absence of the T790M mutation (Ramalingham et al., 2018a; Ramalingham et al., 2018b). A novel targeted therapy that is able to specifically address the EGFR-C797S acquired resistance mutation would be highly beneficial for those patients.

By contrast, and with the exception of A763_Y764insFQEA, small in-frame insertions of EGFR exon20 are resistant to all clinically-approved EGFR inhibitors at doses achievable in lung cancer patients and comprise an unmet medical need (Yasuda et. al., 2013).

Patients with EGFR exon20 insertions, such as V769_D770insASV, D770_N771insSVD, D770_N771insNPG, N771_P772insH, H773_V774insH, H773_V774insNPH, V774_C775insHV show particular low response rates to all currently approved EGFR-targeted therapies, resulting in significantly reduced progression-free survival as well as overall survival (Chen et al., 2016). This has been shown for the first-generation inhibitors erlotinib and gefitinib as well as for the second-generation inhibitor afatinib (Chen et al., 2016; Yang et al., 2015).

Therefore, the standard treatment for EGFR exon20 insertion patients is currently chemotherapy.

The same resistance profile has been observed for exon20 insertion mutations in ERBB2 (e.g. ERBB2 A775_G776insYVMA with the highest prevalence), another member of the EGF-receptor family (Arcila et al., 2012) and some of the uncommon EGFR mutations like L681Q (Chiu et al., 2015).

Several irreversible inhibitors are currently in clinical trials for the treatment of EGFR exon20 insertion patients: Osimertinib, initially approved for the treatment of T790M mutant NSCLC patients (Floc'h et al., 2018); poziotinib (HM-781-36B), a non-approved pan-Her inhibitor targeting EGFR, Her2/neu, and Her4 (Robichaux et al., 2018); as well as TAK-788 (AP32788) (Doebele et al., ASCO 2018). Of these, the first clinical data have been published for poziotinib and TAK-788. Both compounds clearly show clinical efficacy in EGFR exon20 insertion patients. However, major adverse events, mediated by inhibition of wild-type EGFR, have been reported for both clinical trials and these adverse events may limit clinical utility.

More recently, new preclinical data has been published for two additional compounds showing activity on EGFR exon20 insertions: TAS6417 (TCP-064) and compound 1a (Hasako et al., 2018; Jang et al., 2018). No clinical results are yet available for these two compounds.

In summary, mutant EGFR is a promising drug target for cancer therapy. In particular, patients with primary resistance to approved anti-EGFR therapies, due to EGFR exon20 insertions, have only few treatment options to date and there is a great need for novel alternative and/or improved therapeutics to provide these patients with an efficacious, well-tolerable therapy (Oxnard et al., 2013). Therefore, potent inhibitors of mutant EGFR, particularly of mutant EGFR with exon20 insertion mutations that show improved selectivity versus wild-type EGFR, represent valuable compounds that should complement therapeutic options either as single agents or in combination with other drugs.

SUMMARY OF THE INVENTION

The invention provides compounds that inhibit a mutant EGFR; specifically, an EGFR comprising one or more exon 20 insertion mutations, an L858R mutation, or a small in-frame deletion of exon 19, in the presence or absence of a C797S mutation. These compounds furthermore have reduced activity towards the wild-type-EGFR.

It has now been found that the compounds of the present invention have surprising and advantageous properties.

In particular, said compounds of the present invention have surprisingly been found to effectively inhibit mutant EGFR with exon 20 insertion mutations, particularly those harboring a D770_N771ins SVD exon 20 insertion with an $IC_{50}$ below 5 nM. Furthermore it has been found that these compounds additionally show cellular potency below 1 μM in EGFR V769_D770insASV, D770_N771insSVD, D770_N771insNPG, N771_P772insH, or H773_V774insNPH exon 20 insertion harboring BA/F3 cell lines. Furthermore, the here described compounds are active in BA/F3 cell lines harboring D770_N771insSVD C797S. In addition, the here described compounds potently inhibit proliferation of BA/F3 cell lines carrying EGFR activating mutations with or without C797S acquired resistance mutations (EGFR E746_A750del, L858R, E746_A750del C797S, L858R C797S), uncommon EGFR mutations (EGFR L681Q) or ERBB2 exon20 insertion A775_G776insYVMA.

Surprisingly these compounds additionally show at least 5-fold selectivity in an antiproliferative assay of EGFR D770_N771ins SVD exon 20 insertion harboring BA/F3 cell lines versus wild-type EGFR harboring BA/F3 cells and may therefore be used for the treatment or prophylaxis of diseases of uncontrolled cell growth, proliferation and/or survival, inappropriate cellular immune responses, or inappropriate cellular inflammatory responses or diseases which are accompanied with uncontrolled cell growth, proliferation and/or survival, inappropriate cellular immune responses, or inappropriate cellular inflammatory responses mediated by mutant EGFR with exon 20 insertion mutations and/or reduce (or block) proliferation in cells harboring EGFR exon 20 insertion mutations, for example, haematological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

DESCRIPTION OF THE INVENTION

In accordance with a first aspect, the invention relates to compounds of formula (I), (I)

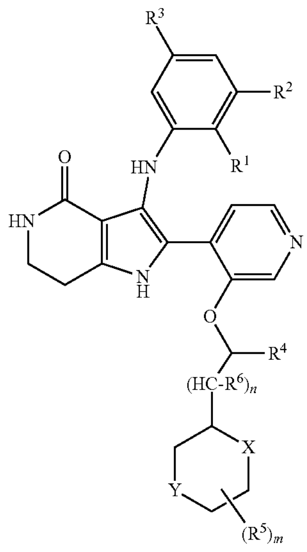

in which:

$R^1$ represents methyl, ethyl, trifluoromethyl, 2,2-difluoroethyl, cyano, chloro, bromo, methoxy or difluoromethoxy;
$R^2$ represents hydrogen, methyl, ethyl, fluoro, chloro or bromo;
$R^3$ represents hydrogen or fluoro;
$R^4$ represents hydrogen or methyl;
$R^5$ independently at each occurrence represents hydrogen, trifluoromethyl or $C_1$-$C_3$ alkyl,
$R^5$ being bound to any carbon atom of the ring;
$R^6$ independently at each occurrence represents hydrogen, $C_1$-$C_3$-alkyl or $C_1$-$C_3$-haloalkyl;
$R^7$ represents $C_1$-$C_3$-alkyl or $C_2$-$C_3$-haloalkyl;
$R^8$ represents $C_1$-$C_3$-alkyl or $C_2$-$C_3$-haloalkyl;
X represents $NR^7$ or O;
Y represents $NR^8$ or O;
m represents 0, 1, 2 or 3;
n represents 0 or 1;
or an N-oxide, a salt or a tautomer of said compound, or a salt of said N-oxide or tautomer. In some embodiments at least two $R^5$ groups are geminal groups (i.e., attached to the same carbon atom).

In a second aspect, the invention relates to compounds of formula (I) as described supra, wherein:

$R^1$ represents methyl, ethyl, chloro, methoxy or difluoromethoxy;
$R^2$ represents methyl, ethyl, fluoro or chloro;
$R^3$ represents hydrogen or fluoro;
$R^4$ represents hydrogen or methyl;
$R^5$ represents hydrogen, methyl or trifluoromethyl,
$R^5$ being bound to any carbon atom of the ring;
$R^6$ represents hydrogen, methyl or trifluoromethyl;
$R^7$ represents $C_1$-$C_2$-alkyl or $C_2$-$C_3$-fluoroalkyl;
$R^8$ represents $C_1$-$C_2$-alkyl or $C_2$-$C_3$-fluoroalkyl;
X represents $NR^7$ or O;
Y represents $NR^8$ or O;
m represents 0, 1 or 2;

n represents 0 or 1;

or an N-oxide, a salt or a tautomer of said compound, or a salt of said N-oxide or tautomer.

In a third aspect, the invention relates to compounds of formula (I) as described supra, wherein:

$R^1$ represents methyl, ethyl, chloro or methoxy;

$R^2$ represents, fluoro or chloro;

$R^3$ represents hydrogen or fluoro;

$R^4$ represents hydrogen;

$R^5$ represents hydrogen or methyl, $R^5$ being bound to any carbon atom of the ring;

$R^6$ represents hydrogen;

$R^7$ represents methyl;

$R^8$ represents methyl, 2,2,2-trifluoroethyl or 2,2-difluoroethyl;

X represents $NR^7$ or O;

Y represents $NR^8$ or O;

m represents 0, 1, or 2;

n represents 0 or 1;

or an N-oxide, a salt or a tautomer of said compound, or a salt of said N-oxide or tautomer.

In a fourth aspect, the invention relates to compounds of formula (I) as described supra, which is selected from the group consisting of:

3-(3-chloro-2-methoxyanilino)-2-{3-[(1,4-dioxan-2-yl)methoxy]pyridin-4-yl}-1,5,6,7-tetrahydro-4H-pyrrolo[3,2-c]pyridin-4-one 3-(3-chloro-2-methoxyanilino)-2-(3-{[(2S)-1,4-dioxan-2-yl]methoxy}pyridin-4-yl)-1,5,6,7-tetrahydro-4H-pyrrolo[3,2-c]pyridin-4-one 3-(3-chloro-2-methoxyanilino)-2-(3-{[(2R)-1,4-dioxan-2-yl]methoxy}pyridin-4-yl)-1,5,6,7-tetrahydro-4H-pyrrolo[3,2-c]pyridin-4-one 2-{3-[(1,4-dioxan-2-yl)methoxy]pyridin-4-yl}-3-(3-fluoro-2-methoxyanilino)-1,5,6,7-tetrahydro-4H-pyrrolo[3,2-c]pyridin-4-one 2-(3-{[(2S)-1,4-dioxan-2-yl]methoxy}pyridin-4-yl)-3-(3-fluoro-2-methoxyanilino)-1,5,6,7-tetrahydro-4H-pyrrolo[3,2-c]pyridin-4-one 2-(3-{[(2R)-1,4-dioxan-2-yl]methoxy}pyridin-4-yl)-3-(3-fluoro-2-methoxyanilino)-1,5,6,7-tetrahydro-4H-pyrrolo[3,2-c]pyridin-4-one 3-(2,3-dichloroanilino)-2-{3-[(1,4-dioxan-2-yl)methoxy]pyridin-4-yl}-1,5,6,7-tetrahydro-4H-pyrrolo[3,2-c]pyridin-4-one 3-(2,3-dichloroanilino)-2-(3-{[(2S)-1,4-dioxan-2-yl]methoxy}pyridin-4-yl)-1,5,6,7-tetrahydro-4H-pyrrolo[3,2-c]pyridin-4-one 3-(2,3-dichloroanilino)-2-(3-{[(2R)-1,4-dioxan-2-yl]methoxy}pyridin-4-yl)-1,5,6,7-tetrahydro-4H-pyrrolo[3,2-c]pyridin-4-one 3-(3-chloro-2-methylanilino)-2-{3-[(1,4-dioxan-2-yl)methoxy]pyridin-4-yl}-1,5,6,7-tetrahydro-4H-pyrrolo[3,2-c]pyridin-4-one 3-(3-chloro-2-methoxyanilino)-2-(3-{[(3R)-4-methylmorpholin-3-yl]methoxy}pyridin-4-yl)-1,5,6,7-tetrahydro-4H-pyrrolo[3,2-c]pyridin-4-one 3-(3-fluoro-2-methoxyanilino)-2-{3-[(4-methylmorpholin-2-yl)methoxy]pyridin-4-yl}-1,5,6,7-tetrahydro-4H-pyrrolo[3,2-c]pyridin-4-one 3-(3-fluoro-2-methoxyanilino)-2-(3-{[(2R)-4-methylmorpholin-2-yl]methoxy}pyridin-4-yl)-1,5,6,7-tetrahydro-4H-pyrrolo[3,2-c]pyridin-4-one 3-(3-fluoro-2-methoxyanilino)-2-(3-{[(2S)-4-methylmorpholin-2-yl]methoxy}pyridin-4-yl)-1,5,6,7-tetrahydro-4H-pyrrolo[3,2-c]pyridin-4-one 3-(3-chloro-2-methoxyanilino)-2-{3-[(4-methylmorpholin-2-yl)methoxy]pyridin-4-yl}-1,5,6,7-tetrahydro-4H-pyrrolo[3,2-c]pyridin-4-one 3-(3-chloro-2-methoxyanilino)-2-(3-{[(2R)-4-methylmorpholin-2-yl]methoxy}pyridin-4-yl)-1,5,6,7-tetrahydro-4H-pyrrolo[3,2-c]pyridin-4-one 3-(3-chloro-2-methoxyanilino)-2-(3-{[(2S)-4-methylmorpholin-2-yl]methoxy}pyridin-4-yl)-1,5,6,7-tetrahydro-4H-pyrrolo[3,2-c]pyridin-4-one 3-(3-chloro-5-fluoro-2-methoxyanilino)-2-(3-{[4-methylmorpholin-2-yl]methoxy}pyridin-4-yl)-1,5,6,7-tetrahydro-4H-pyrrolo[3,2-c]pyridin-4-one 3-(3-chloro-5-fluoro-2-methoxyanilino)-2-(3-{[1,4-dioxan-2-yl]methoxy}pyridin-4-yl)-1,5,6,7-tetrahydro-4H-pyrrolo[3,2-c]pyridin-4-one 3-(3-fluoro-2-methoxyanilino)-2-(3-{[(3S)-4-methylmorpholin-3-yl]methoxy}pyridin-4-yl)-1,5,6,7-tetrahydro-4H-pyrrolo[3,2-c]pyridin-4-one 3-(3-chloro-2-methoxyanilino)-2-(3-{[(3S)-4-methylmorpholin-3-yl]methoxy}pyridin-4-yl)-1,5,6,7-tetrahydro-4H-pyrrolo[3,2-c]pyridin-4-one 2-(3-{[(2S)-4-(2,2-difluoroethyl)morpholin-2-yl]methoxy}pyridin-4-yl)-3-(3-fluoro-2-methoxyanilino)-1,5,6,7-tetrahydro-4H-pyrrolo[3,2-c]pyridin-4-one 3-(3-fluoro-2-methoxyanilino)-2-(3-{[(2S)-4-(2,2,2-trifluoroethyl)morpholin-2-yl]methoxy}pyridin-4-yl)-1,5,6,7-tetrahydro-4H-pyrrolo[3,2-c]pyridin-4-one 3-(3-chloro-2-methoxyanilino)-2-{3-[2-(4-dioxan-2-yl)ethoxy]pyridin-4-yl}-1,5,6,7-tetrahydro-4H-pyrrolo[3,2-c]pyridin-4-one 3-(3-chloro-2-methoxyanilino)-2-(3-{2-[(2R)-1,4-dioxan-2-yl]ethoxy}pyridin-4-yl)-1,5,6,7-tetrahydro-4H-pyrrolo[3,2-c]pyridin-4-one 3-(3-chloro-2-methoxyanilino)-2-(3-{2-[(2S)-1,4-dioxan-2-yl]ethoxy}pyridin-4-yl)-1,5,6,7-tetrahydro-4H-pyrrolo[3,2-c]pyridin-4-one 3-(3-chloro-5-fluoro-2-methoxyanilino)-2-(3-{[(2S)-4-methylmorpholin-2-yl]methoxy}pyridin-4-yl)-1,5,6,7-tetrahydro-4H-pyrrolo[3,2-c]pyridin-4-one 3-(3-chloro-5-fluoro-2-methoxyanilino)-2-(3-{[(2S)-4-(2,2,2-trifluoroethyl)morpholin-2-yl]methoxy}pyridin-4-yl)-1,5,6,7-tetrahydro-4H-pyrrolo[3,2-c]pyridin-4-one 3-(3-chloro-2-ethylanilino)-2-{3-[(4-methylmorpholin-2-yl)methoxy]pyridin-4-yl}-1,5,6,7-tetrahydro-4H-pyrrolo[3,2-c]pyridin-4-one 3-(3-chloro-2-methoxyanilino)-2-{3-[(5,5-dimethyl-1,4-dioxan-2-yl)methoxy]pyridin-4-yl}-1,5,6,7-tetrahydro-4H-pyrrolo[3,2-c]pyridin-4-one 3-(3-chloro-2-methoxyanilino)-2-(3-{[(2R)-5,5-dimethyl-1,4-dioxan-2-yl]methoxy}pyridin-4-yl)-1,5,6,7-tetrahydro-4H-pyrrolo[3,2-c]pyridin-4-one 3-(3-chloro-2-methoxyanilino)-2-(3-{[(2S)-5,5-dimethyl-1,4-dioxan-2-yl]methoxy}pyridin-4-yl)-1,5,6,7-tetrahydro-4H-pyrrolo[3,2-c]pyridin-4-one 2-(3-{[(2R)-5,5-dimethyl-1,4-dioxan-2-yl]methoxy}pyridin-4-yl)-3-(3-fluoro-2-methoxyanilino)-1,5,6,7-tetrahydro-4H-pyrrolo[3,2-c]pyridin-4-one 2-(3-{[(2S)-5,5-dimethyl-1,4-dioxan-2-yl]methoxy}pyridin-4-yl)-3-(3-fluoro-2-methoxyanilino)-1,5,6,7-tetrahydro-4H-pyrrolo[3,2-c]pyridin-4-one 2-(3-{2-[(2R)-1,4-dioxan-2-yl]ethoxy}pyridin-4-yl)-3-(3-fluoro-2-methoxyanilino)-1,5,6,7-tetrahydro-4H-pyrrolo[3,2-c]pyridin-4-one 2-(3-{2-[(2S)-1,4-dioxan-2-yl]ethoxy}pyridin-4-yl)-3-(3-fluoro-2-methoxyanilino)-1,5,6,7-tetrahydro-4H-pyrrolo[3,2-c]pyridin-4-one 3-(3-fluoro-2-methoxyanilino)-2-(3-{[(3R)-4-methylmorpholin-3-yl]methoxy}pyridin-4-yl)-1,5,6,7-tetrahydro-4H-pyrrolo[3,2-c]pyridin-4-one 2-{3-[(5,5-dimethyl-1,4-dioxan-2-yl)methoxy]pyridin-4-yl}-3-(3-fluoro-2-methylanilino)-1,5,6,7-tetrahydro-4H-pyrrolo[3,2-c]pyridin-4-one 2-(3-{[(2S)-5,5-dimethyl-1,4-dioxan-2-yl]methoxy}pyridin-4-yl)-3-(3-fluoro-2-methylanilino)-1,5,6,7-tetrahydro-4H-pyrrolo[3,2-c]pyridin-4-one 3-[2-(2,2-difluoroethyl)-3-fluoroanilino]-2-{3-[(1,4-dioxan-2-yl)methoxy]pyridin-4-yl}-1,5,6,7-tetrahydro-4H-pyrrolo[3,2-c]pyridin-4-one 3-[2-(2,2-difluoroethyl)-3-fluoroanilino]-2-(3-{[(2S)-4-methylmorpholin-2-yl]methoxy}pyridin-4-yl)-1,5,6,7-tetrahydro-4H-pyrrolo[3,2-c]pyridin-4-one 3-(3-chloro-2-methylanilino)-2-(3-{[(2S)-4-methylmorpholin-2-yl]methoxy}pyridin-4-yl)-1,5,6,7-tetrahydro-4H-pyrrolo[3,2-c]pyridin-4-one 3-(3-chloro-2-methylanilino)-2-(3-{[(3R)-4-methylmorpholin-3-yl]methoxy}pyridin-4-yl)-1,5,6,7-tetrahydro-4H-pyrrolo[3,2-c]pyridin-4-one 3-(3-chloro-2-methylanilino)-2-{3-[(5,5-dimethyl-1,4-dioxan-2-yl)methoxy]pyridin-4-yl}-1,5,6,7-tetrahydro-4H-pyrrolo[3,2-c]pyridin-4-one 3-(3-chloro-2-methylanilino)-2-(3-{[(2S)-5,5-dimethyl-1,4-dioxan-2-yl]methoxy}pyridin-4-yl)-1,5,6,7-tetrahydro-4H-pyrrolo[3,2-c]pyridin-4-one 3-(3-chloro-2-methylanilino)-2-(3-{[(2R)-5,5-dimethyl-1,4-dioxan-2-yl]methoxy}pyridin-4-yl)-1,5,6,7-tetrahydro-4H-pyrrolo[3,2-c]pyridin-4-one 2-{3-[(1,4-dioxan-2-yl)methoxy]pyridin-4-yl}-3-(3-fluoro-2-methylanilino)-1,5,6,7-tetrahydro-4H-pyrrolo[3,2-c]pyridin-4-one 2-(3-{[(2S)-1,4-dioxan-2-yl]methoxy}pyridin-4-yl)-3-(3-fluoro-2-methylanilino)-1,5,6,7-tetrahydro-4H-pyrrolo[3,2-c]pyridin-4-one 2-(3-{[(2R)-1,4-dioxan-2-yl]methoxy}pyridin-4-yl)-3-(3-fluoro-2-methylanilino)-1,5,6,7-tetrahydro-4H-pyrrolo[3,2-c]pyridin-4-one 3-(3-chloro-2-methylanilino)-2-(3-{[(2S)-1,4-dioxan-2-yl]methoxy}pyridin-4-yl)-1,5,6,7-tetrahydro-4H-pyrrolo[3,2-c]pyridin-4-one 3-(3-chloro-2-methylanilino)-2-(3-{[(2R)-1,4-dioxan-2-yl]methoxy}pyridin-4-yl)-1,5,6,7-tetrahydro-4H-pyrrolo[3,2-c]pyridin-4-one 3-(3-chloro-2-ethylanilino)-2-{3-[(1,4-dioxan-2-yl)methoxy]pyridin-4-yl}-1,5,6,7-tetrahydro-4H-pyrrolo[3,2-c]pyridin-4-one 3-(3-chloro-2-ethylanilino)-2-(3-{[(2S)-1,4-dioxan-2-yl]methoxy}pyridin-4-yl)-1,5,6,7-tetrahydro-4H-pyrrolo[3,2-c]pyridin-4-one 3-(3-chloro-2-ethylanilino)-2-(3-{[(2R)-1,4-dioxan-2-yl]methoxy}pyridin-4-yl)-1,5,6,7-tetrahydro-4H-pyrrolo[3,2-c]pyridin-4-one 3-(3-chloro-2-ethylanilino)-2-(3-{[(2R)-4-methylmorpholin-2-yl]methoxy}pyridin-4-yl)-1,5,6,7-tetrahydro-4H-pyrrolo[3,2-c]pyridin-4-one 3-(3-chloro-2-ethylanilino)-2-(3-{[(2S)-4-methylmorpholin-2-yl]methoxy}pyridin-4-yl)-1,5,6,7-tetrahydro-4H-pyrrolo[3,2-c]pyridin-4-one 3-(3-chloro-2-methoxyanilino)-2-(3-{1-[1,4-dioxan-2-yl]ethoxy}pyridin-4-yl)-1,5,6,7-tetrahydro-4H-pyrrolo[3,2-c]pyridin-4-one 3-(3-chloro-2-methoxyanilino)-2-(3-{(1 S)-1-[(2S)-1,4-dioxan-2-yl]ethoxy}pyridin-4-yl)-1,5,6,7-tetrahydro-4H-pyrrolo[3,2-c]pyridin-4-one 3-(3-chloro-2-methoxyanilino)-2-(3-{(1S)-1-[(2R)-1,4-dioxan-2-yl]ethoxy}pyridin-4-yl)-1,5,6,7-tetrahydro-4H-pyrrolo[3,2-c]pyridin-4-one 3-(3-chloro-2-methoxyanilino)-2-(3-{(1R)-1-[(2S)-1,4-dioxan-2-yl]ethoxy}pyridin-4-yl)-1,5,6,7-tetrahydro-4H-pyrrolo[3,2-c]pyridin-4-one 3-(3-chloro-2-methoxyanilino)-2-(3-{(1R)-1-[(2R)-1,4-dioxan-2-yl]ethoxy}pyridin-4-yl)-1,5,6,7-tetrahydro-4H-pyrrolo[3,2-c]pyridin-4-one 3-(3-fluoro-2-methylanilino)-2-{3-[(4-methylmorpholin-2-yl)methoxy]pyridin-4-yl}-1,5,6,7-tetrahydro-4H-pyrrolo[3,2-c]pyridin-4-one 3-(3-fluoro-2-methylanilino)-2-(3-{[(2R)-4-methylmorpholin-2-yl]methoxy}pyridin-4-yl)-1,5,6,7-tetrahydro-4H-pyrrolo[3,2-c]pyridin-4-one 3-(3-fluoro-2-methylanilino)-2-(3-{[(2S)-4-methylmorpholin-2-yl]methoxy}pyridin-4-yl)-1,5,6,7-tetrahydro-4H-pyrrolo[3,2-c]pyridin-4-one 2-(3-{[1,4-dioxan-2-yl]methoxy}pyridin-4-yl)-3-(2-ethyl-3-fluoroanilino)-1,5,6,7-tetrahydro-4H-pyrrolo[3,2-c]pyridin-4-one 2-(3-{[(2R)-1,4-dioxan-2-yl]methoxy}pyridin-4-yl)-3-(2-ethyl-3-fluoroanilino)-1,5,6,7-tetrahydro-4H-pyrrolo[3,2-c]pyridin-4-one 2-(3-{[(2S)-1,4-dioxan-2-yl]methoxy}pyridin-4-yl)-3-(2-ethyl-3-fluoroanilino)-1,5,6,7-tetrahydro-4H-pyrrolo[3,2-c]pyridin-4-one 2-(3-{[5,5-dimethyl-1,4-dioxan-2-yl]methoxy}pyridin-4-yl)-3-(2-ethyl-3-fluoroanilino)-1,5,6,7-tetrahydro-4H-pyrrolo[3,2-c]pyridin-4-one 2-(3-{[(2R)-5,5-dimethyl-1,4-dioxan-2-yl]methoxy}pyridin-4-yl)-3-(2-ethyl-3-fluoroanilino)-1,5,6,7-tetrahydro-4H-pyrrolo[3,2-c]pyridin-4-one 2-(3-{[(2S)-5,5-dimethyl-1,4-dioxan-2-yl]methoxy}pyridin-4-yl)-3-(2-ethyl-3-fluoroanilino)-1,5,6,7-tetrahydro-4H-pyrrolo[3,2-c]pyridin-4-one 3-(3-chloro-2-methoxyanilino)-2-[3-({1-[4-methylmorpholin-2-yl]ethyl}oxy)pyridin-4-yl]-1,5,6,7-tetrahydro-4H-pyrrolo[3,2-c]pyridin-4-one 3-(3-chloro-2-methoxyanilino)-2-[3-({(1R)-1-[(2R)-4-methylmorpholin-2-yl]ethyl}oxy)pyridin-4-yl]-1,5,6,7-tetrahydro-4H-pyrrolo[3,2-c]pyridin-4-one 3-(3-chloro-2-methoxyanilino)-2-[3-({(1S)-1-[(2S)-4-methylmorpholin-2-yl]ethyl}oxy)pyridin-4-yl]-1,5,6,7-tetrahydro-4H-pyrrolo[3,2-c]pyridin-4-one 3-(3-chloro-2-methoxyanilino)-2-[3-({(1R)-1-[(2S)-4-methylmorpholin-2-yl]ethyl}oxy)pyridin-4-yl]-1,5,6,7-tetrahydro-4H-pyrrolo[3,2-c]pyridin-4-one 3-(3-chloro-2-methoxyanilino)-2-[3-({(1S)-1-[(2R)-4-methylmorpholin-2-yl]ethyl}oxy)pyridin-4-yl]-1,5,6,7-tetrahydro-4H-pyrrolo[3,2-c]pyridin-4-one A further aspect of the invention relates to compounds of formula (I), which are present as their salts.

It is to be understood that the present invention relates to any sub-combination within any embodiment or aspect of the present invention of compounds of general formula (I), supra.

More particularly still, the present invention covers compounds of general formula (I) which are disclosed in the Example section of this text, infra.

In accordance with another aspect, the present invention covers methods of preparing compounds of the present invention, said methods comprising the steps as described in the Experimental Section herein.

Another embodiment of the invention are compounds according as disclosed in the Claims section or disclosed analogs of the exemplified compounds and subcombinations thereof.

Definitions

It is to be understood that embodiments disclosed herein are not meant to be understood as individual embodiments which would not relate to one another. Features discussed with one embodiment or aspect of the invention are meant to be disclosed also in connection with other embodiments or aspects of the invention shown herein. If, in one case, a specific feature is not disclosed with one embodiment or aspect of the invention, but with another, the skilled person would understand that does not necessarily mean that said feature is not meant to be disclosed with said other embodiment or aspect of the invention. The skilled person would understand that it is the gist of this application to disclose said feature also for the other embodiment or aspect of the invention, but that just for purposes of clarity and to keep the length of this specification manageable. For example, it is to be understood that all aspects, embodiments, pharmaceutical compositions, combinations, uses and/or methods of the present invention defined herein for the compounds of formula (I) also relate to more specific embodiments of the compounds of formula (I), such as, but not limited to, the compounds of formula (Ia) and vice-versa, for example.

It is further to be understood that the content of the documents referred to herein is incorporated by reference in their entirety, e.g., for enablement purposes, namely when e.g. a method is discussed details of which are described in said document. This approach serves to keep the length of this specification manageable.

Constituents, which are optionally substituted as stated herein, may be substituted, unless otherwise noted, one or more times, independently of one another at any possible position.

When any variable occurs more than one time in any constituent, each definition is independent. For example, when $R^1$, $R^{1a}$, $R^{1b}$, $R^{1c}$, $R^2$, $R^3$ and/or $R^4$ occur more than one time in any compound of formula (I) each definition of $R^1$, $R^{1a}$, $R^{1b}$, $R^{1c}$, $R^2$, $R^3$ and $R^4$ is independent.

Should a constituent be composed of more than one part, e.g. $C_1$-$C_4$-alkoxy-$C_2$-$C_4$-alkyl, the position of a possible substituent can be at any of these parts at any suitable position. A hyphen at the beginning or at the end of the constituent marks the point of attachment to the rest of the molecule. Should a ring be substituted the substituent could be at any suitable position of the ring, also on a ring nitrogen atom, if suitable.

The term "comprising" when used in the specification includes "consisting of".

If it is referred to "as mentioned above" or "mentioned above", "supra" within the description it is referred to any of the disclosures made within the specification in any of the preceding pages.

If it is referred to "as mentioned herein", "described herein", "provided herein," or "as mentioned in the present text," or "stated herein" within the description it is referred to any of the disclosures made within the specification in any of the preceding or subsequent pages.

"Suitable" within the sense of the invention means chemically possible to be made by methods within the knowledge of a skilled person.

The terms as mentioned in the present text may have the following meanings:

The term "halogen atom", "halo-" or "Hal-" is to be understood as meaning a fluorine, chlorine, bromine or iodine atom.

The term "$C_1$-$C_6$-alkyl" is to be understood as meaning a linear or branched, saturated, monovalent hydrocarbon group having 1, 2, 3, 4, 5, or 6 carbon atoms, e.g. a methyl, ethyl, propyl, butyl, pentyl, hexyl, iso-propyl, iso-butyl, sec-butyl, tert-butyl, iso-pentyl, 2-methylbutyl, 1-methylbutyl, 1-ethylpropyl, 1,2-dimethylpropyl, neo-pentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl or 1,2-dimethylbutyl group, or an isomer thereof. Particularly, said group has 1, 2, 3 or 4 carbon atoms ("$C_1$-$C_4$-alkyl"), e.g. a methyl, ethyl, propyl, butyl, iso-propyl, iso-butyl, sec-butyl, tert-butyl group, more particularly 1, 2 or 3 carbon atoms ("$C_1$-$C_3$-alkyl"), e.g. a methyl, ethyl, n-propyl or iso-propyl group.

The term "$C_1$-$C_4$-haloalkyl" is to be understood as meaning a linear or branched, saturated, monovalent hydrocarbon group in which the term "$C_1$-$C_4$-alkyl" is defined supra, and in which one or more hydrogen atoms is replaced by a halogen atom, in identically or differently, i.e. one halogen atom being independent from another. Particularly, said halogen atom is F. Said $C_1$-$C_4$-haloalkyl group is, for example, $-CF_3$, $-CHF_2$, $-CH_2F$, $-CF_2CF_3$, $-CH_2CH_2F$, $-CH_2CHF_2$, $-CH_2CF_3$, $-CH_2CH_2CF_3$, or $-CH(CH_2F)_2$.

The term "$C_2$-$C_3$-fluoroalkyl" is to be understood as meaning a linear or branched, saturated, monovalent hydrocarbon group in which the term "$C_2$-$C_3$-alkyl" is defined supra, and in which one or more hydrogen atoms is replaced by a fluoro atom. Said $C_2$-$C_3$-fluoroalkyl group is, for example, $-CF_2CF_3$, $-CH_2CH_2F$, $-CH_2CHF_2$, $-CH_2CF_3$, $-CH_2CH_2CF_3$, or $-CH(CH_2F)_2$.

The term "$C_1$-$C_4$-alkoxy" is to be understood as meaning a linear or branched, saturated, monovalent, hydrocarbon group of formula —O-alkyl, in which the term "alkyl" is defined supra, e.g. a methoxy, ethoxy, n-propoxy, iso-propoxy, n-butoxy, iso-butoxy, tert-butoxy or sec-butoxy group, or an isomer thereof.

Unless defined otherwise, the term "5- to 6-membered heterocycloalkyl" or "5- to 6-membered heterocyclic ring", is to be understood as meaning a saturated, monovalent, monocyclic hydrocarbon ring which contains 4 or 5 carbon atoms, and one heteroatom-containing group selected from O and NR, wherein R means a hydrogen atom, a $C_1$-$C_3$-alkyl or a $C_1$-$C_3$-haloalkyl group, it being possible for said heterocycloalkyl group to be attached to the rest of the molecule via any one of the carbon atoms.

Particularly, without being limited thereto, said heterocycloalkyl can be a 5-membered ring, such as tetrahydrofuranyl, pyrazolidinyl, or a 6-membered ring, such as tetrahydropyranyl, piperidinyl, for example.

The term "$C_1$-$C_6$", as used throughout this text, e.g. in the context of the definition of "$C_1$-$C_6$-alkyl" or "$C_1$-$C_6$-haloalkyl" is to be understood as meaning an alkyl group having a finite number of carbon atoms of 1 to 6, i.e. 1, 2, 3, 4, 5 or 6 carbon atoms. It is to be understood further that said term "$C_1$-$C_6$" is to be interpreted as any sub-range comprised therein, e.g. $C_1$-$C_8$, $C_2$-$C_6$, $C_3$-$C_6$, $C_1$-$C_2$, $C_1$-$C_3$, particularly $C_1$-$C_2$, $C_1$-$C_3$, $C_1$-$C_4$.

The term "$C_1$-$C_4$", as used throughout this text, e.g. in the context of the definition of "$C_1$-$C_4$-alkyl", "$C_1$-$C_4$-haloalkyl", "$C_1$-$C_4$-alkoxy", or "$C_1$-$C_4$-haloalkoxy" is to be understood as meaning an alkyl group having a finite number of carbon atoms of 1 to 4, i.e. 1, 2, 3 or 4 carbon atoms. It is to be understood further that said term "$C_1$-$C_4$" is to be interpreted as any sub-range comprised therein, e.g. $C_1$-$C_4$, $C_2$-$C_4$, $C_3$-$C_4$, $C_1$-$C_2$, $C_1$-$C_3$, particularly $C_1$-$C_2$, $C_1$-$C_3$, $C_1$-$C_4$, in the case of "$C_1$-$C_6$-haloalkyl" or "$C_1$-$C_4$-haloalkoxy" even more particularly $C_1$-$C_2$.

Further, as used herein, the term "$C_3$-$C_6$", as used throughout this text, e.g. in the context of the definition of "$C_3$-$C_6$-cycloalkyl", is to be understood as meaning a cycloalkyl group having a finite number of carbon atoms of 3 to 6, i.e. 3, 4, 5 or 6 carbon atoms. It is to be understood further that said term "$C_3$-$C_6$" is to be interpreted as any sub-range comprised therein, e.g. $C_3$-$C_6$, $C_4$-$C_5$, $C_3$-$C_5$, $C_3$-$C_4$, $C_4$-$C_6$, $C_5$-$C_6$; particularly $C_3$-$C_6$.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds.

The term "optionally substituted" means optional substitution with the specified groups, radicals or moieties.

Ring system substituent means a substituent attached to an aromatic or nonaromatic ring system which, for example, replaces an available hydrogen on the ring system.

As used herein, the term "one or more", e.g. in the definition of the substituents of the compounds of the general formulae of the present invention, is understood as meaning "one, two, three, four, five, etc. particularly one, two, three or four, more particularly one, two or three, even more particularly one or two".

The compounds of general formula (I) may exist as isotopic variants. The invention therefore includes one or more isotopic variant(s) of the compounds of general formula (I), particularly deuterium-containing compounds of general formula (I).

The term "isotopic variant" of a compound or a reagent is defined as a compound exhibiting an unnatural proportion of one or more of the isotopes that constitute such a compound.

The term "isotopic variant of the compound of general formula (I)" is defined as a compound of general formula (I) exhibiting an unnatural proportion of one or more of the isotopes that constitute such a compound.

The expression "unnatural proportion" is to be understood as meaning a proportion of such isotope which is higher than its natural abundance. The natural abundances of isotopes to be applied in this context are described in "Isotopic Compositions of the Elements 1997", Pure Appl. Chem., 70(1), 217-235, 1998. Examples of such isotopes include stable and radioactive isotopes of hydrogen, carbon, nitrogen, oxygen, phosphorus, sulfur, fluorine, chlorine, bromine and iodine, such as $^{2}H$ (deuterium), $^{3}H$ (tritium), $^{11}C$, $^{13}C$, $^{14}C$, $^{15}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{125}I$, $^{129}I$ and $^{131}I$, respectively.

With respect to the treatment and/or prophylaxis of the disorders specified herein the isotopic variant(s) of the compounds of general formula (I) in one embodiment contain deuterium ("deuterium-containing compounds of general formula (I)"). Isotopic variants of the compounds of general formula (I) in which one or more radioactive isotopes, such as $^{3}H$ or $^{14}C$, are incorporated are useful e.g. in drug and/or substrate tissue distribution studies. These isotopes are particularly preferred for the ease of their incorporation and detectability. Positron emitting isotopes such as $^{18}F$ or $^{11}C$ may be incorporated into a compound of general formula (I). These isotopic variants of the compounds of general formula (I) are useful for in vivo imaging applications. Deuterium-containing and $^{13}C$-containing compounds of general formula (I) can be used in mass spectrometry analyses (H. J. Leis et al., Curr. Org. Chem., 1998, 2, 131) in the context of preclinical or clinical studies.

Isotopic variants of the compounds of general formula (I) can generally be prepared by methods known to a person skilled in the art, such as those described in the schemes and/or examples herein, by substituting a reagent for an isotopic variant of said reagent, in one embodiment for a deuterium-containing reagent. Depending on the desired sites of deuteration, in some cases deuterium from $D_2O$ can be incorporated either directly into the compounds or into reagents that are useful for synthesizing such compounds (Esaki et al., Tetrahedron, 2006, 62, 10954; Esaki et al., Chem. Eur. J., 2007, 13, 4052). Deuterium gas is also a useful reagent for incorporating deuterium into molecules. Catalytic deuteration of olefinic bonds (H. J. Leis et al., Curr. Org. Chem., 1998, 2, 131; J. R. Morandi et al., J. Org. Chem., 1969, 34 (6), 1889) and acetylenic bonds (N. H. Khan, J. Am. Chem. Soc., 1952, 74 (12), 3018; S. Chandrasekhar et al., Tetrahedron, 2011, 52, 3865) is a rapid route for incorporation of deuterium. Metal catalysts (i.e. Pd, Pt, and Rh) in the presence of deuterium gas can be used to directly exchange deuterium for hydrogen in functional groups containing hydrocarbons (J. G. Atkinson et al., U.S. Pat. No. 3,966,781). A variety of deuterated reagents and synthetic building blocks are commercially available from companies such as for example C/D/N Isotopes, Quebec, Canada; Cambridge Isotope Laboratories Inc., Andover, MA, USA; and CombiPhos Catalysts, Inc., Princeton, NJ, USA. Further information on the state of the art with respect to deuterium-hydrogen exchange is given for example in Hanzlik et al., J. Org. Chem. 55, 3992-3997, 1990; R. P. Hanzlik et al., Biochem. Biophys. Res. Commun. 160, 844, 1989; P. J. Reider et al., J. Org. Chem. 52, 3326-3334, 1987; M. Jarman et al., Carcinogenesis 16(4), 683-688, 1993; J. Atzrodt et al., Angew. Chem., Int. Ed. 2007, 46, 7744; K. Matoishi et al., J. Chem. Soc, Chem. Commun. 2000, 1519-1520; K. Kassahun et al., WO2012/112363.

The term "deuterium-containing compound of general formula (I)" is defined as a compound of general formula (I), in which one or more hydrogen atom(s) is/are replaced by one or more deuterium atom(s) and in which the abundance of deuterium at each deuterated position of the compound of general formula (I) is higher than the natural abundance of deuterium, which is about 0.015%. Particularly, in a deuterium-containing compound of general formula (I) the abundance of deuterium at each deuterated position of the compound of general formula (I) is higher than 10%, 20%, 30%, 40%, 50%, 60%, 70% or 80%, in one embodiment higher than 90%, 95%, 96% or 97%, in other embodiments higher than 98% or 99% at said position(s). It is understood that the abundance of deuterium at each deuterated position is independent of the abundance of deuterium at other deuterated position(s).

The selective incorporation of one or more deuterium atom(s) into a compound of general formula (I) may alter the physicochemical properties (such as for example acidity [A. Streitwieser et al., *J. Am. Chem. Soc.,* 1963, 85, 2759; C. L. Perrin, et al., *J. Am. Chem. Soc.,* 2007, 129, 4490], basicity [C. L. Perrin, et al., *J. Am. Chem. Soc.,* 2003, 125, 15008; C. L. Perrin in Advances in Physical Organic Chemistry, 44, 144; C. L. Perrin et al., *J. Am. Chem. Soc.,* 2005, 127, 9641], lipophilicity [B. Testa et al., *Int. J. Pharm.,* 1984, 19(3), 271]) and/or the metabolic profile of the molecule and may result in changes in the ratio of parent compound to metabolites or in the amounts of metabolites formed. Such changes may result in certain therapeutic advantages and hence may be preferred in some circumstances. Reduced rates of metabolism and metabolic switching, where the ratio of metabolites is changed, have been reported (D. J. Kushner et al., Can. J. Physiol. Pharmacol., 1999, 77, 79; A. E. Mutlib et al., Toxicol. Appl. Pharmacol., 2000, 169, 102). These changes in the exposure to parent drug and metabolites can have important consequences with respect to the pharmacodynamics, tolerability and efficacy of a deuterium-containing compound of general formula (I). In some cases deuterium substitution reduces or eliminates the formation of an undesired or toxic metabolite and enhances the formation of a desired metabolite (e.g. Nevirapine: A. M. Sharma et al., Chem. Res. Toxicol., 2013, 26, 410; Uetrecht et al., Chemical Research in Toxicology, 2008, 21, 9, 1862; Efavirenz: A. E. Mutlib et al., Toxicol. Appl. Pharmacol., 2000, 169, 102). In other cases the major effect of deuteration is to reduce the rate of systemic clearance. As a result, the biological half-life of the compound is increased. The potential clinical benefits would include the ability to maintain similar systemic exposure with decreased peak levels and increased trough levels. This could result in lower side effects and enhanced efficacy, depending on the particular compound's pharmacokinetic/pharmacodynamic relationship. Indiplon (A. J. Morales et al., Abstract 285, The 15$^{th}$ North American Meeting of the International Society of Xenobiotics, San Diego, CA, Oct. 12-16, 2008), ML-337 (C. J. Wenthur et al., J. Med. Chem., 2013, 56, 5208), and Odanacatib (K. Kassahun et al., WO2012/112363) are examples for this deuterium effect. Still other cases have been reported in which reduced rates of metabolism result in an increase in exposure of the drug without changing the rate of systemic clearance (e.g. Rofecoxib: F. Schneider et al., Arzneim. Forsch. Drug. Res., 2006, 56, 295; Telaprevir: F. Maltais et al., J. Med. Chem., 2009, 52, 7993). Deuterated drugs showing this effect may have reduced dosing requirements (e.g. lower number of doses or lower dosage to achieve the desired effect) and/or may produce lower metabolite loads.

A compound of general formula (I) may have multiple potential sites of attack for metabolism. To optimize the above-described effects on physicochemical properties and metabolic profile, deuterium-containing compounds of general formula (I) having a certain pattern of one or more deuterium-hydrogen exchange(s) can be selected. Particularly, the deuterium atom(s) of deuterium-containing compound(s) of general formula (I) is/are attached to a carbon atom and/or is/are located at those positions of the compound of general formula (I), which are sites of attack for metabolizing enzymes such as e.g. cytochrome $P_{450}$.

Where the plural form of the word compounds, salts, polymorphs, hydrates, solvates and the like, is used herein, this is taken to mean also a single compound, salt, polymorph, isomer, hydrate, solvate or the like.

By "stable compound" or "stable structure" is meant a compound that is sufficiently robust to survive isolation to a useful degree of purity from a reaction mixture, and formulation into an efficacious therapeutic agent.

The compounds of this invention may contain one or more asymmetric centre, depending upon the location and nature of the various substituents desired. Asymmetric carbon atoms may be present in the (R) or (S) configuration, resulting in racemic mixtures in the case of a single asymmetric centre, and diastereomeric mixtures in the case of multiple asymmetric centres. In certain instances, asymmetry may also be present due to restricted rotation about a given bond, for example, the central bond adjoining two substituted aromatic rings of the specified compounds.

Substituents on a ring may also be present in either cis or trans form. It is intended that all such configurations (including enantiomers and diastereomers), are included within the scope of the present invention.

Preferred compounds are those which produce the more desirable biological activity. Separated, pure or partially purified isomers and stereoisomers or racemic or diastereomeric mixtures of the compounds of this invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., chiral HPLC columns), with or without conventional derivatisation, optimally chosen to maximise the separation of the enantiomers. Suitable chiral HPLC columns are manufactured by Daicel, e.g., Chiracel OD and Chiracel OJ among many others, all routinely selectable. Enzymatic separations, with or without derivatisation, are also useful. The optically active compounds of this invention can likewise be obtained by chiral syntheses utilizing optically active starting materials.

In order to limit different types of isomers from each other reference is made to IUPAC Rules Section E (Pure Appl Chem 45, 11-30, 1976).

The present invention includes all possible stereoisomers of the compounds of the present invention as single stereoisomers, or as any mixture of said stereoisomers, e.g. R- or S-isomers, or E- or Z-isomers, in any ratio. Isolation of a single stereoisomer, e.g. a single enantiomer or a single diastereomer, of a compound of the present invention may be achieved by any suitable state of the art method, such as chromatography, especially chiral chromatography, for example.

Further, the compounds of the present invention may exist as tautomers. For example, any compound of the present invention which contains a pyrazole moiety as a heteroaryl group for example can exist as a 1H tautomer, or a 2H tautomer, or even a mixture in any amount of the two tautomers, or a triazole moiety for example can exist as a 1H tautomer, a 2H tautomer, or a 4H tautomer, or even a mixture in any amount of said 1H, 2H and 4H tautomers, namely:

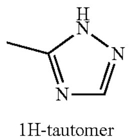
1H-tautomer

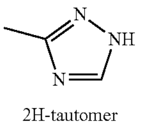
2H-tautomer

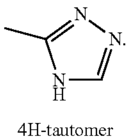
4H-tautomer

The present invention includes all possible tautomers of the compounds of the present invention as single tautomers, or as any mixture of said tautomers, in any ratio.

Further, the compounds of the present invention can exist as N-oxides, which are defined in that at least one nitrogen of the compounds of the present invention is oxidised. The present invention includes all such possible N-oxides.

The present invention also relates to useful forms of the compounds as disclosed herein, such as metabolites, hydrates, solvates, prodrugs, salts, in particular pharmaceutically acceptable salts, and co-precipitates.

The compounds of the present invention can exist as a hydrate, or as a solvate, wherein the compounds of the present invention contain polar solvents, in particular water, methanol or ethanol for example as structural element of the crystal lattice of the compounds. The amount of polar solvents, in particular water, may exist in a stoichiometric or non-stoichiometric ratio. In the case of stoichiometric solvates, e.g. a hydrate, hemi-, (semi-), mono-, sesqui-, di-, tri-, tetra-, penta- etc. solvates or hydrates, respectively, are possible. The present invention includes all such hydrates or solvates.

Further, the compounds of the present invention can exist in free form, e.g. as a free base, or as a free acid, or as a zwitterion, or can exist in the form of a salt. Said salt may be any salt, either an organic or inorganic addition salt, particularly any pharmaceutically acceptable organic or inorganic addition salt, customarily used in pharmacy.

The term "pharmaceutically acceptable salt" refers to a relatively non-toxic, inorganic or organic acid addition salt of a compound of the present invention. For example, see S. M. Berge, et al. "Pharmaceutical Salts," J. Pharm. Sci. 1977, 66, 1-19.

A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, such as hydrochloric, hydrobromic, hydroiodic, sulfuric, bisulfuric, phosphoric or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, persulfuric, 3-phenylpropionic, picric, pivalic, 2-hydroxyethanesulfonate, itaconic, sulfamic, trifluoromethanesulfonic, dodecylsulfuric, ethansulfonic, benzenesulfonic, para-toluenesulfonic, methansulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, hemisulfuric or thiocyanic acid, for example.

Further, another suitably pharmaceutically acceptable salt of a compound of the present invention which is sufficiently acidic, is an alkali metal salt, for example a sodium or potassium salt, an alkaline earth metal salt, for example a calcium or magnesium salt, an ammonium salt or a salt with an organic base which affords a physiologically acceptable cation, for example a salt with N-methyl-glucamine, dimethyl-glucamine, ethyl-glucamine, lysine, dicyclohexylamine, 1,6-hexadiamine, ethanolamine, glucosamine, sarcosine, serinol, tris-hydroxy-methyl-aminomethane, aminopropandiol, sovak-base, 1-amino-2,3,4-butantriol. Additionally, basic nitrogen containing groups may be quaternised with such agents as lower alkyl halides such as methyl, ethyl, propyl, and butyl chlorides, bromides and iodides; dialkyl sulfates like dimethyl, diethyl, and dibutyl sulfate; and diamyl sulfates, long chain halides such as decyl, lauryl, myristyl and strearyl chlorides, bromides and iodides, aralkyl halides like benzyl and phenethyl bromides and others.

Those skilled in the art will further recognise that acid addition salts of the claimed compounds may be prepared by reaction of the compounds with the appropriate inorganic or organic acid via any of a number of known methods. Alternatively, alkali and alkaline earth metal salts of acidic compounds of the invention are prepared by reacting the compounds of the invention with the appropriate base via a variety of known methods.

The present invention includes all possible salts of the compounds of the present invention as single salts, or as any mixture of said salts, in any ratio.

In the present text, in particular in the Experimental Section, for the synthesis of intermediates and of examples of the present invention, when a compound is mentioned as a salt form with the corresponding base or acid, the exact stoichiometric composition of said salt form, as obtained by the respective preparation and/or purification process, is, in most cases, unknown.

Unless specified otherwise, suffixes to chemical names or structural formulae such as "hydrochloride", "trifluoroacetate", "sodium salt", or "x HCl", "x $CF_3COOH$", "x $Na^+$", for example, are to be understood as not a stoichiometric specification, but solely as a salt form.

This applies analogously to cases in which synthesis intermediates or example compounds or salts thereof have been obtained, by the preparation and/or purification processes described, as solvates, such as hydrates with (if defined) unknown stoichiometric composition.

The salts include water-insoluble and, particularly, water-soluble salts.

Furthermore, derivatives of the compounds of formula (I) and the salts thereof which are converted into a compound of formula (I) or a salt thereof in a biological system (bioprecursors or pro-drugs) are covered by the invention. Said biological system is e.g. a mammalian organism, particularly a human subject. The bioprecursor is, for example, converted into the compound of formula (I) or a salt thereof by metabolic processes.

As used herein, the term "in vivo hydrolysable ester" is understood as meaning an in vivo hydrolysable ester of a compound of the present invention containing a carboxy or hydroxy group, for example, a pharmaceutically acceptable ester which is hydrolysed in the human or animal body to produce the parent acid or alcohol. Suitable pharmaceutically acceptable esters for carboxy include for example alkyl, cycloalkyl and optionally substituted phenylalkyl, in particular benzyl esters, $C_1$-$C_6$ alkoxymethyl esters, e.g. methoxymethyl, $C_1$-$C_6$ alkanoyloxymethyl esters, e.g. pivaloyloxymethyl, phthalidyl esters, $C_3$-C8 cycloalkoxy-carbonyloxy-$C_1$-$C_6$ alkyl esters, e.g. 1-cyclohexylcarbonyloxyethyl, 1,3-dioxolen-2-onylmethyl esters, e.g. 5-methyl-1,3-dioxolen-2-onylmethyl, and $C_1$-$C_6$-alkoxycarbonyloxyethyl esters, e.g. 1-methoxycarbonyloxyethyl, and may be formed at any carboxy group in the compounds of this invention.

An in vivo hydrolysable ester of a compound of the present invention containing a hydroxy group includes inorganic esters such as phosphate esters and [alpha]-acyloxyalkyl ethers and related compounds which as a result of the in vivo hydrolysis of the ester breakdown to give the parent hydroxy group. Examples of [alpha]-acyloxyalkyl ethers include acetoxymethoxy and 2,2-dimethylpropionyloxymethoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. The present invention covers all such esters.

Furthermore, the present invention includes all possible crystalline forms, or polymorphs, of the compounds of the present invention, either as single polymorphs, or as a mixture of more than one polymorphs, in any ratio.

In the context of the properties of the compounds of the present invention the term "pharmacokinetic profile" means one single parameter or a combination thereof including permeability, bioavailability, exposure, and pharmacodynamic parameters such as duration, or magnitude of pharmacological effect, as measured in a suitable experiment. Compounds with improved pharmacokinetic profiles can, for example, be used in lower doses to achieve the same effect, may achieve a longer duration of action, or a may achieve a combination of both effects.

The term "combination" in the present invention is used as known to persons skilled in the art and may be present as a fixed combination, a non-fixed combination or kit-of-parts.

A "fixed combination" in the present invention is used as known to persons skilled in the art and is defined as a combination wherein the said first active ingredient and the said second active ingredient are present together in one unit dosage or in a single entity. One example of a "fixed combination" is a pharmaceutical composition wherein the said first active ingredient and the said second active ingredient are present in admixture for simultaneous administration, such as in a formulation. Another example of a "fixed combination" is a pharmaceutical combination wherein the said first active ingredient and the said second active ingredient are present in one unit without being in admixture.

A non-fixed combination or "kit-of-parts" in the present invention is used as known to persons skilled in the art and is defined as a combination wherein the said first active ingredient and the said second active ingredient are present in more than one unit. One example of a non-fixed combination or kit-of-parts is a combination wherein the said first active ingredient and the said second active ingredient are present separately. The components of the non-fixed combination or kit-of-parts may be administered separately, sequentially, simultaneously, concurrently or chronologically staggered. Any such combination of a compound of formula (I) of the present invention with an anti-cancer agent as defined below is an embodiment of the invention.

The term "(chemotherapeutic) anti-cancer agents" relates to any agent that reduces the survival or proliferation of a cancer cell, and includes but is not limited to 131I-chTNT, abarelix, abiraterone, aclarubicin, ado-trastuzumab emtansine, afatinib, aflibercept, aldesleukin, alemtuzumab, Alendronic acid, alitretinoin, altretamine, amifostine, aminoglutethimide, Hexyl aminolevulinate, amrubicin, amsacrine, anastrozole, ancestim, anethole dithiolethione, angiotensin II, antithrombin III, aprepitant, arcitumomab, arglabin, arsenic trioxide, asparaginase, axitinib, azacitidine, basiliximab, belotecan, bendamustine, belinostat, bevacizumab, bexarotene, bicalutamide, bisantrene, bleomycin, bortezomib, buserelin, bosutinib, brentuximab vedotin, busulfan, cabazitaxel, cabozantinib, calcium folinate, calcium levofolinate, capecitabine, capromab, carboplatin, carfilzomib, carmofur, carmustine, catumaxomab, celecoxib, celmoleukin, ceritinib, cetuximab, chlorambucil, chlormadinone, chlormethine, cidofovir, cinacalcet, cisplatin, cladribine, clodronic acid, clofarabine, copanlisib, crisantaspase, cyclophosphamide, cyproterone, cytarabine, dacarbazine, dactinomycin, darbepoetin alfa, dabrafenib, dasatinib, daunorubicin, decitabine, degarelix, denileukin diftitox, denosumab, depreotide, deslorelin, dexrazoxane, dibrospidium chloride, dianhydrogalactitol, diclofenac, docetaxel, dolasetron, doxifluridine, doxorubicin, doxorubicin+estrone, dronabinol, eculizumab, edrecolomab, elliptinium acetate, eltrombopag, endostatin, enocitabine, enzalutamide, epirubicin, epitiostanol, epoetin alfa, epoetin beta, epoetin zeta, eptaplatin, eribulin, erlotinib, esomeprazole, estradiol, estramustine, etoposide, everolimus, exemestane, fadrozole, fentanyl, filgrastim, fluoxymesterone, floxuridine, fludarabine, fluorouracil, flutamide, folinic acid, formestane, fosaprepitant, fotemustine, fulvestrant, gadobutrol, gadoteridol, gadoteric acid meglumine, gadoversetamide, gadoxetic acid, gallium nitrate, ganirelix, gefitinib, gemcitabine, gemtuzumab, Glucarpidase, glutoxim, GM-CSF, goserelin, granisetron, granulocyte colony stimulating factor, histamine dihydrochloride, histrelin, hydroxycarbamide, 1-125 seeds, lansoprazole, ibandronic acid, ibritumomab tiuxetan, ibrutinib, idarubicin, ifosfamide, imatinib, imiquimod, improsulfan, indisetron, incadronic acid, ingenol mebutate, interferon alfa, interferon beta, interferon gamma, iobitridol, iobenguane (123I), iomeprol, ipilimumab, irinotecan, Itraconazole, ixabepilone, Ianreotide, lapatinib, lasocholine, lenalidomide, lenograstim, lentinan, letrozole, leuprorelin, levamisole, levonorgestrel, levothyroxine sodium, lisuride, lobaplatin, lomustine, Ionidamine, masoprocol, medroxyprogesterone, megestrol, melarsoprol, melphalan, mepitiostane, mercaptopurine, mesna, methadone, methotrexate, methoxsalen, methylaminolevulinate, methylprednisolone, methyltestosterone, metirosine, mifamurtide, miltefosine, miriplatin, mitobronitol, mitoguazone, mitolactol, mitomycin, mitotane, mitoxantrone, mogamulizumab, molgramostim, mopidamol, morphine hydrochloride, morphine sulfate, nabilone, nabiximols, nafarelin, naloxone+pentazocine, naltrexone, nartograstim, nedaplatin, nelarabine, neridronic acid, nivolumabpentetreotide, nilotinib, nilutamide, nimorazole, nimotuzumab, nimustine, nitracrine, nivolumab, obinutuzumab, octreotide, ofatumumab, omacetaxine mepesuccinate, omeprazole, ondansetron, oprelvekin, orgotein, orilotimod, osimertinib, oxaliplatin, oxycodone, oxymetholone, ozogamicine, p53 gene therapy, paclitaxel, palifermin, palladium-103 seed, palonosetron, pamidronic acid, panitumumab, pantoprazole, pazopanib, pegaspargase, PEG-epoetin beta (methoxy PEG-epoetin beta), pembrolizumab, pegfilgrastim, peginterferon alfa-2b, pemetrexed, pentazocine, pentostatin, peplomycin, Perflubutane, perfosfamide, Pertuzumab, picibanil, pilocarpine, pirarubicin, pixantrone, plerixafor, plicamycin, poliglusam, polyestradiol phosphate, polyvinylpyrrolidone+sodium hyaluronate, polysaccharide-K, pomalidomide, ponatinib, porfimer sodium, poziotinib, pralatrexate, prednimustine, prednisone, procarbazine, procodazole, propranolol, quinagolide, rabeprazole, racotumomab, radium-223 chloride, radotinib, raloxifene, raltitrexed, ramosetron, ramucirumab, ranimustine, rasburicase, razoxane, refametinib, regorafenib, risedronic acid, rhenium-186 etidronate, rituximab, romidepsin, romiplostim, romurtide, roniciclib, samarium (153Sm) lexidronam, sargramostim, satumomab, secretin, sipuleucel-T, sizofiran, sobuzoxane, sodium glycididazole, sorafenib, stanozolol, streptozocin, sunitinib, talaporfin, tamibarotene, tamoxifen, tapentadol, tasonermin, teceleukin, technetium (99mTc) nofetumomab merpentan, 99mTc-HYNIC-[Tyr3]-octreotide, tegafur, tegafur+gimeracil+oteracil, temoporfin, temozolomide, temsirolimus, teniposide, testosterone, tetrofosmin, thalidomide, thiotepa, thymalfasin, thyrotropin alfa, tioguanine, tocilizumab, topotecan, toremifene, tositumomab, trabectedin, tramadol, trastuzumab, trastuzumab emtansine, treosulfan, tretinoin, trifluridine+tipiracil, trilostane, triptorelin, trametinib, trofosfamide, thrombopoietin, tryptophan, ubenimex, valatinib, valrubicin, vandetanib, vapreotide, vemurafenib, vinblastine, vincristine, vindesine, vinflunine, vinorelbine, vismodegib, vorinostat, vorozole, yttrium-90 glass microspheres, zinostatin, zinostatin stimalamer, zoledronic acid, zorubicin.

By "Epidermal Growth Factor Receptor (EGFR) Polypeptide" is meant a polypeptide having at least about 95% amino acid sequence identity to the sequence provided at UniProt Accession No. P00533-1 or a fragment thereof. In some embodiments, the EGFR fragment binds an EFGR ligand and/or has kinase activity. Mutant EGFR polypeptides include those having an insertion between, for example, amino acids V769 and D770 or between D770 and N771. In other embodiments, the amino acid sequence identity is 96, 97, 98, 99, or 100% to UniProt Accession No. P00533-1.

An exemplary full length sequence of human EGFR, which indicates V769, D770, and N771 in bold, is provided at UniProt Accession No. P00533-1, which is reproduced below:

SEQ ID 1

```
        10         20         30         40
MRPSGTAGAA LLALLAALCP ASRALEEKKV CQGTSNKLTQ

        50         60         70         80
LGTFEDHFLS LQRMFNNCEV VLGNLEITYV QRNYDLSFLK

        90        100        110        120
TIQEVAGYVL IALNTVERIP LENLQIIRGN MYYENSYALA

       130        140        150        160
VLSNYDANKT GLKELPMRNL QEILHGAVRF SNNPALCNVE

       170        180        190        200
SIQWRDIVSS DFLSNMSMDF QNHLGSCQKC DPSCPNGSCW

       210        220        230        240
GAGEENCQKL TKIICAQQCS GRCRGKSPSD CCHNQCAAGC

       250        260        270        280
TGPRESDCLV CRKFRDEATC KDTCPPLMLY NPTTYQMDVN

       290        300        310        320
PEGKYSFGAT CVKKCPRNYV VTDHGSCVRA CGADSYEMEE

       330        340        350        360
DGVRKCKKCE GPCRKVCNGI GIGEFKDSLS INATNIKHFK

       370        380        390        400
NCTSISGDLH ILPVAFRGDS FTHTPPLDPQ ELDILKTVKE

       410        420        430        440
ITGFLLIQAW PENRTDLHAF ENLEIIRGRT KQHGQFSLAV

       450        460        470        480
VSLNITSLGL RSLKEISDGD VIISGNKNLC YANTINWKKL

       490        500        510        520
FGTSGQKTKI ISNRGENSCK ATGQVCHALC SPEGCWGPEP

       530        540        550        560
RDCVSCRNVS RGRECVDKCN LLEGEPREFV ENSECIQCHP

       570        580        590        600
ECLPQAMNIT CTGRGPDNCI QCAHYIDGPH CVKTCPAGVM

       610        620        630        640
GENNTLVWKY ADAGHVCHLC HPNCTYGCTG PGLEGCPTNG

       650        660        670        680
PKIPSIATGM VGALLLLLVV ALGIGLFMRR RHIVRKRTLR
```

-continued

```
       690        700        710        720
RLLQERELVE PLTPSGEAPN QALLRILKET EFKKIKVLGS

       730        740        750        760
GAFGTVYKGL WIPEGEKVKI PVAIKELREA TSPKANKEIL

       770        780        790        800
DEAYVMASVD NPHVCRLLGI CLTSTVQLIT QLMPFGCLLD

       810        820        830        840
YVREHKDNIG SQYLLNWCVQ IAKGMNYLED RRLVHRDLAA

       850        860        870        880
RNVLVKTPQH VKITDFGLAK LLGAEEKEYH AEGGKVPIKW

       890        900        910        920
MALESILHRI YTHQSDVWSY GVTVWELMTF GSKPYDGIPA

       930        940        950        960
SEISSILEKG ERLPQPPICT IDVYMIMVKC WMIDADSRPK

       970        980        990       1000
FRELIIEFSK MARDPQRYLV IQGDERMHLP SPTDSNFYRA

      1010       1020       1030       1040
LMDEEDMDDV VDADEYLIPQ QGFFSSPSTS RTPLLSSLSA

      1050       1060       1070       1080
TSNNSTVACI DRNGLQSCPI KEDSFLQRYS SDPTGALTED

      1090       1100       1110       1120
SIDDTFLPVP EYINQSVPKR PAGSVQNPVY HNQPLNPAPS

      1130       1140       1150       1160
RDPHYQDPHS TAVGNPEYLN TVQPTCVNST FDSPAHWAQK

      1170       1180       1190       1200
GSHQISLDNP DYQQDFFPKE AKPNGIFKGS TAENAEYLRV

      1210
APQSSEFIGA
```

An exemplary polynucleotide encoding EGFR is provided at NCBI Reference Sequence: NM_001346897.1, which is reproduced below:

SEQ ID 2

```
  1 gtccgggcag cccccggcgc agcgcggccg cagcagcctc
    cgccccccgc acggtgtgag

 61 cgcccgacgc ggccgaggcg gccggagtcc cgagctagcc
    ccggcggccg ccgccgccca

121 gaccggacga caggccacct cgtcggcgtc cgcccgagtc
    cccgcctcgc cgccaacgcc

181 acaaccaccg cgcacggccc cctgactccg tccagtattg
    atcgggagag ccggagcgag

241 ctcttcgggg agcagcgatg cgaccctccg ggacggccgg
    ggcagcgctc ctggcgctgc

301 tggctgcgct ctgcccggcg agtcgggctc tggaggaaaa
    gaaagtttgc caaggcacga

361 gtaacaagct cacgcagttg ggcacttttg aagatcattt
    tctcagcctc cagaggatgt

421 tcaataactg tgaggtggtc cttgggaatt tggaaattac
    ctatgtgcag aggaattatg

481 atctttcctt cttaaagacc atccaggagg tggctggtta
    tgtcctcatt gccctcaaca

541 cagtggagcg aattcctttg gaaaacctgc agatcatcag
    aggaaatatg tactacgaaa
```

-continued

```
601 attcctatgc cttagcagtc ttatctaact atgatgcaaa
    taaaaccgga ctgaaggagc

661 tgcccatgag aaatttacag ggccaaaagt gtgatccaag
    ctgtcccaat gggagctgct

721 ggggtgcagg agaggagaac tgccagaaac tgaccaaaat
    catctgtgcc cagcagtgct

781 ccgggcgctg ccgtggcaag tcccccagtg actgctgcca
    caaccagtgt gctgcaggct

841 gcacaggccc ccgggagagc gactgcctgg tctgccgcaa
    attccgagac gaagccacgt

901 gcaaggacac ctgcccccca ctcatgctct acaaccccac
    cacgtaccag atggatgtga

961 accccgaggg caaatacagc tttggtgcca cctgcgtgaa
    gaagtgtccc cgtaattatg

1021 tggtgacaga tcacggctcg tgcgtccgag cctgtggggc
     cgacagctat gagatggagg

1081 aagacggcgt ccgcaagtgt aagaagtgcg aagggccttg
     ccgcaaagtg tgtaacggaa

1141 taggtattgg tgaatttaaa gactcactct ccataaatgc
     tacgaatatt aaacacttca

1201 aaaactgcac ctccatcagt ggcgatctcc acatcctgcc
     ggtggcattt aggggtgact

1261 ccttcacaca tactcctcct ctggatccac aggaactgga
     tattctgaaa accgtaaagg

1321 aaatcacagg gtttttgctg attcaggctt ggcctgaaaa
     caggacggac ctccatgcct

1381 ttgagaacct agaaatcata cgcggcagga ccaagcaaca
     tggtcagttt tctcttgcag

1441 tcgtcagcct gaacataaca tccttgggat tacgctccct
     caaggagata agtgatggag

1501 atgtgataat ttcaggaaac aaaaatttgt gctatgcaaa
     tacaataaac tggaaaaaac

1561 tgtttgggac ctccggtcag aaaaccaaaa ttataagcaa
     cagaggtgaa aacagctgca

1621 aggccacagg ccaggtctgc catgccttgt gctcccccga
     gggctgctgg ggcccggagc

1681 ccagggactg cgtctcttgc cggaatgtca gccgaggcag
     ggaatgcgtg gacaagtgca

1741 accttctgga gggtgagcca agggagtttg tggagaactc
     tgagtgcata cagtgccacc

1801 cagagtgcct gcctcaggcc atgaacatca cctgcacagg
     acggggacca gacaactgta

1861 tccagtgtgc ccactacatt gacggccccc actgcgtcaa
     gacctgcccg gcaggagtca

1921 tgggagaaaa caacaccctg gtctggaagt acgcagacgc
     cggccatgtg tgccacctgt

1981 gccatccaaa ctgcacctac ggatgcactg ggccaggtct
     tgaaggctgt ccaacgaatg

2041 ggcctaagat cccgtccatc gccactggga tggtgggggc
     cctcctcttg ctgctggtgg

2101 tggccctggg gatcggcctc ttcatgcgaa ggcgccacat
     cgttcggaag cgcacgctgc

2161 ggaggctgct gcaggagagg gagcttgtgg agcctcttac
     acccagtgga gaagctccca

2221 accaagctct cttgaggatc ttgaaggaaa ctgaattcaa
     aaagatcaaa gtgctgggct

2281 ccggtgcgtt cggcacggtg tataagggac tctggatccc
     agaaggtgag aaagttaaaa

2341 ttcccgtcgc tatcaaggaa ttaagagaag caacatctcc
     gaaagccaac aaggaaatcc

2401 tcgatgaagc ctacgtgatg gccagcgtgg acaaccccca
     cgtgtgccgc ctgctgggca

2461 tctgcctcac ctccaccgtg cagctcatca cgcagctcat
     gcccttcggc tgcctcctgg

2521 actatgtccg ggaacacaaa gacaatattg gctcccagta
     cctgctcaac tggtgtgtgc

2581 agatcgcaaa gggcatgaac tacttggagg accgtcgctt
     ggtgcaccgc gacctggcag

2641 ccaggaacgt actggtgaaa acaccgcagc atgtcaagat
     cacagatttt gggctggcca

2701 aactgctggg tgcggaagag aaagaatacc atgcagaagg
     aggcaaagtg cctatcaagt

2761 ggatggcatt ggaatcaatt ttacacagaa tctataccca
     ccagagtgat gtctggagct

2821 acggggtgac tgtttgggag ttgatgacct ttggatccaa
     gccatatgac ggaatccctg

2881 ccagcgagat ctcctccatc ctggagaaag gagaacgcct
     ccctcagcca cccatatgta

2941 ccatcgatgt ctacatgatc atggtcaagt gctggatgat
     agacgcagat agtcgcccaa

3001 agttccgtga gttgatcatc gaattctcca aaatggcccg
     agacccccag cgctaccttg

3061 tcattcaggg ggatgaaaga atgcatttgc caagtcctac
     agactccaac ttctaccgtg

3121 ccctgatgga tgaagaagac atggacgacg tggtggatgc
     cgacgagtac ctcatcccac

3181 agcagggctt cttcagcagc ccctccacgt cacggactcc
     cctcctgagc tctctgagtg

3241 caaccagcaa caattccacc gtggcttgca ttgatagaaa
     tgggctgcaa agctgtccca

3301 tcaaggaaga cagcttcttg cagcgataca gctcagaccc
     cacaggcgcc ttgactgagg

3361 acagcataga cgacaccttc ctcccagtgc ctggtgagtg
     gcttgtctgg aaacagtcct

3421 gctcctcaac ctcctcgacc cactcagcag cagccagtct
     ccagtgtcca agccaggtgc

3481 tccctccagc atctccagag ggggaaacag tggcagattt
     gcagacacag tgaagggcgt

3541 aaggagcaga taaacacatg accgagcctg cacaagctct
     ttgttgtgtc tggttgtttg

3601 ctgtacctct gttgtaagaa tgaatctgca aaatttctag
     cttatgaagc aaatcacgga

3661 catacacatc tgtgtgtgtg agtgttcatg atgtgtgtac
     atctgtgtat gtgtgtgtgt

3721 gtatgtgtgt gtttgtgaca gatttgatcc ctgttctctc
     tgctggctct atcttgacct
```

-continued

```
3781 gtgaaacgta tatttaacta attaaatatt agttaatatt
     aataaatttt aagctttatc

3841 cagaaaaaaa aaaaaaaaa
```

The intermediates used for the synthesis of the compounds of claims 1-4 as described below, as well as their use for the synthesis of the compounds of claims 1-4, are one further aspect of the present invention. Preferred intermediates are the Intermediate Examples as disclosed below.

General Procedures

The compounds according to the invention can be prepared according to the following schemes 1-4.

The schemes and procedures described below illustrate synthetic routes to the compounds of general formula (I) of the invention and are not intended to be limiting. It is obvious to the person skilled in the art that the order of transformations as exemplified in the schemes can be modified in various ways. The order of transformations exemplified in the schemes is therefore not intended to be limiting. In addition, interconversion of any of the substituents $R^1$, $R^2$, $R^3$, $R^4$, $R^5$, Rand PG can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art. Specific examples are described in the subsequent paragraphs.

Scheme 1:

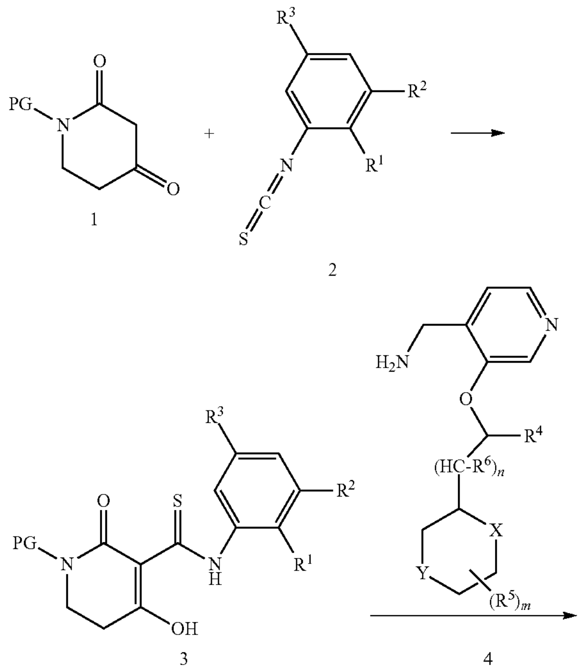

1 2 3 4

-continued

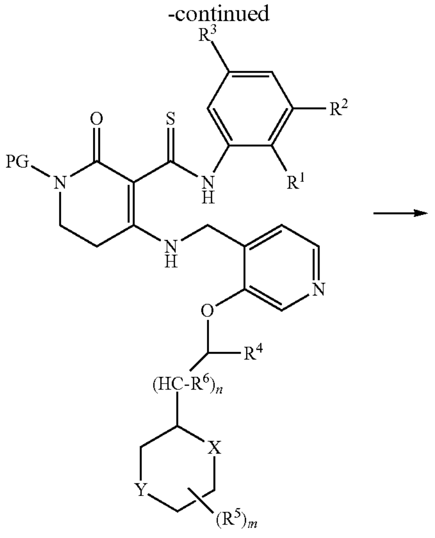

5

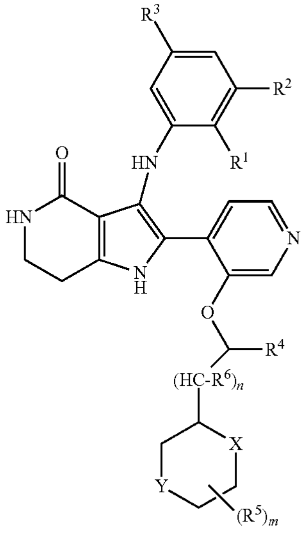

(I)

Scheme 1: Route for the preparation of compounds of general formula (I), wherein $R^1$, $R^2$, $R^3$, $R^4$, $R^5$, $R^6$, X, Y, m and n have the meaning as given for general formula (I) and PG can be hydrogen or optionally a suitable protecting group, e.g. tert-butoxycarbonyl (Boc).

Compound of formula 1, 2, and 4 are either commercially available or can be prepared according to procedures available from the public domain, as understandable to the person skilled in the art. Specific examples are described in the subsequent paragraphs.

A suitably substituted piperadine-2,4-diones of general formula (Compound of formula 1), such as, for example, 2,4-piperadinedione, can be reacted with a suitably substituted isothiocyanate (Compound of formula 2), such as, for example, 3-fluorophenylisothiocyanate, in a suitable solvent system, such as, for example, acetonitrile, in the presence of a suitable base, such as, for example, triethylamine or DBU, at temperatures ranging from −78° C. to +100° C., in some embodiments the reaction is carried out at 0° C. or +100° C., to furnish general formula (3). Similar reactions have been performed in the literature (D. E. Worrall, *J. Am. Chem. Soc.*, 1940, 62, 675).

Intermediates of general formula (3) can be converted to Intermediates of general formula (5) by reaction with a suitable amine (compounds of general formula 4), such as, for example 4-(aminomethyl)pyridine, in a suitable solvent system, such as, for example, ethanol and ethyl acetate, at a temperature between room temperature and the boiling point of the respective solvents, in some embodiments the reaction is carried out at the boiling point of the respective solvents, whereby the water formed in the reaction is removed from the reaction by methods known to those skilled in the art, such as, for example, azeotropic removal of water (Dean-Stark conditions) or with molecular sieves, to furnish general formula (5).

Intermediates of general formula (3) and intermediates of general formula (5) in which PG represents a protecting group can be converted to Intermediates in which PG represents a hydrogen atom using standard deprotection conditions known to those skilled in the art. When PG is a protecting group such as, for example, tert-butoxycarbonyl (Boc), the deprotection can be carried out using acids, such as, for example, hydrochloric acid and trifluoroacetic acid, in a suitable solvent system, such as, for example, dichloromethane and dioxane, at a temperature between 0° C. and the boiling point of the respective solvents, in one embodiment the reaction is carried out at the room temperature, to furnish compounds of general formula (3) and intermediates of general formula (5) whereby PG is hydrogen atom.

Intermediates of general formula (5) are reacted with a base and/or oxidizing reagent, in one embodiment an oxidizing agent, such as, for example hydrogen peroxide or SIBX (stabilized iodoxybenoic acid, in a suitable solvent system, such as, for example, methanol, in a temperature range from −30° C. to the boiling point of the respective solvent, in one embodiment the reaction is carried out at the boiling point of the respective solvent, to furnish compounds of general formula (I). Optionally, these types of reactions can be carried on with an additive, such as, for example, an acid or base, such as, for example, acetic acid or trifluoroacetic acid (not-limiting), and triethylamine or diispropylethylamine (not-limiting).

Intermediates of general formula (5) could be converted to compounds of general formula (I) by thermal heating them in a suitable solvent at elevated temperatures, which could be above the boiling point of the said solvent, such as, for example, RT to +250° C. These reactions could optionally be carried out in vessel whereby the pressure can be increased, such as, for example, in an autoclave. Intermediates of general formula (5) can also be converted to compounds of general formula (I) by thermal heating in the presence of a metal catalyst, such as, for example, palladium on activated charcoal, in a suitable solvent, such as, for example, DMF, DMA, EtOH, MeOH, NMP (not-limiting) at elevated temperatures, such as, for example, RT to +150° C. Optionally, these types of reactions can be carried on with an additive, such as, for example, an acid or base, such as, for example, acetic acid or trifluoroacetic acid (not-limiting), and triethylamine or diispropylethylamine (not-limiting), to furnish compounds of general formula (I).

Scheme 2:

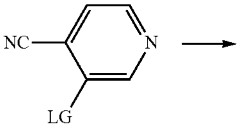

6

-continued

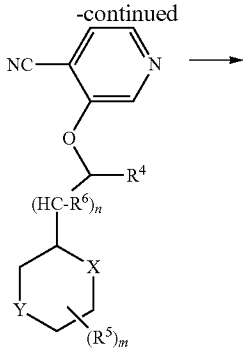

7

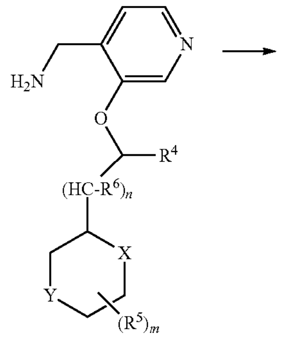

4

Scheme 2: Process for the preparation of compounds of general formula (4), wherein $R^4$, $R^5$, $R^6$, X, Y, m and n have the meaning as given for general formula (I).

Compounds of general formula (6) can be converted to compounds of general formula (7) by treatment with a suitable nucleophile, such as for example, amines, alcohols, metal alkoxides, azides, thiols or metal thiolates, under either basic, neutral, acidic, catalytic conditions, in one embodiment basic conditions, in a suitable solvent or using the nucleophile as solvent, such as, for example, DMF, tetrahydrofuran (THF), in a temperature range from −78° C. to the boiling point of the respective solvent, in one embodiment the reaction is carried out −10° C. to the boiling point of the respective solvent, to furnish general formula (7). Such substitution reactions have been previously reported (Clark et al., *J. Med. Chem.,* 2008, 51, 6631-6634; Guo et al., *Tetrahedron Letts.,* 2013, 54, 3233-3237; Watterson et al., *J. Med. Chem.,* 2007, 50, 3730-3742; Bellale et al., *J. Med. Chem.,* 2014, 57, 6572-6582; Klimesova et al., *Eur. J. Med. Chem.,* 1996, 31, 389-395; Leroy et al., *Synth. Commun.,* 1997, 27, 2905-2916; LaMattina et al., *J. Org. Chem.,* 1981, 46, 4179-4182; Beugelmans et al., *Tetrahedron,* 1983, 39, 4153-4162).

Compounds of general formula (7) can be converted to compounds of general formula (4) by many reducing methods known to those skilled in the art, using numerous different reagents and reaction conditions; such methods and reagents can be carried out with metal hydrides, such as, for example, lithium aluminum hydride in THF (Bullock et al., *J. Am.* Chem. Soc., 1956, 78, 490, Wang et al., *J. Org. Chem.,* 2006, 71, 4021-3160), or using zinc in acetic acid (Rabe, Chem. Ber., 1913, 46, 1024), or using diborane (De Munno et al., *Heterocycles,* 1996, 43, 1893-1900), or using catalytic hydrogenation methods, for example, hydrogen and palladium on carbon under acidic conditions (Stokker et al., *J. Med.* Chem., 1981, 24, 115-117; Bertini et al., *J. Med. Chem.,* 2005, 48, 664-670), hydrogen and nickel under basic conditions (Walpole et al., *J. Med. Chem.*, 1993, 36, 2362-2372, Kuramochi et al., *Bioorg. Med. Chem.*, 2005, 13, 4022-4036.)

Scheme 3:

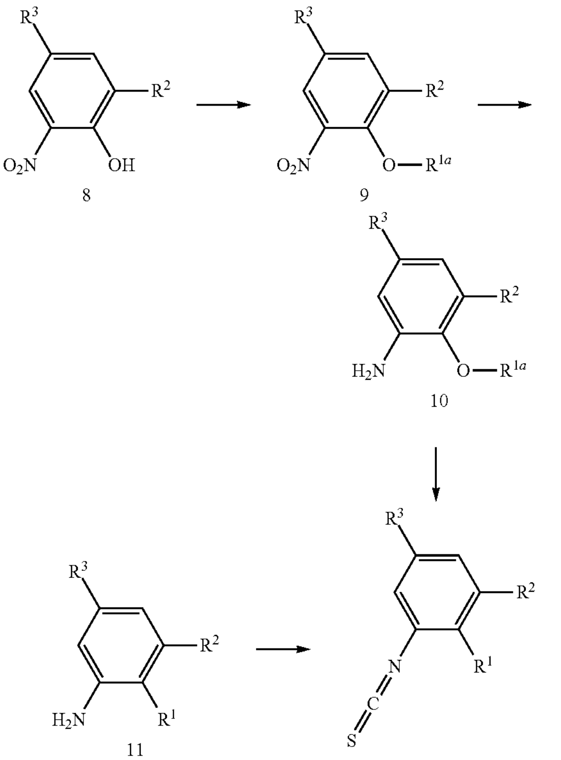

8 9 10 11 2

Scheme 3: Process for the preparation of compounds of general formula 2, wherein $R^{1a}$ represents methyl or difluoromethyl corresponding to the $R^1$ in the general formula (I) with the meaning of methoxy and difluoromethoxy. The synthesis of compounds 9 and 10 relates to alkoxy substitution of the phenyl ring. However, the isothiocyanate containing product 2 and the synthesis thereof (i.e., 10 → 2 or 11 → 2) is general to $R^1$ groups according to general formula (I).

Compounds of general formula (8), can be converted to compounds of general formula (9), using various methods which are known to those skilled in the art. Such transformations could be, for example, to alkylate the phenolic alcohol with alkylating reagents, such as, for example, alkyl halides, alkyl sulfonates, in which these alkyl groups can optionally contain fluorides, alkoxyl groups. These alkylation reactions are known to those skilled in the art using a variety of methods: i) $K_2CO_3$ in a solvent such as, DMF, acetone, DMFA (see the teachings of Muro et al., J. Med. Chem., 2009, 52, 7974 and WO2009/20990 A1); ii) KOH in EtOH (see the teachings of Macias et al., J. Agric. Food Chem., 2006, 54, 9843); iii) Mitsunobu reaction (see the teachings of US2006/122168 A1 and EP2151431 A1) to furnish intermediates of general formula (9).

Compounds of general formula (9) can be converted to compounds of general formula (10) by reduction methods and these methods are known to those skilled in the art. These reductions can be carried using: i) hydrogen gas and a catalyst (for Pd/C as catalyst see the teachings of Chan et al., J. Am. Chem. Soc., 2011, 133, 2989; for platinum see the teachings of Niemann et al., J. Am. Chem Soc., 1941, 63, 2204; for Raney-Nickel see the teachings of US2009/253767 A1); ii) iron and ammonium chloride (see the teachings of Sweeney et al., Bioorg. Med. Chem. Lett., 2008, 18, 4348); iii) sodium dithionite (see the teachings of Chong et al., J. Med. Chem., 2012, 55, 10601); iv) zinc and ammonium chloride (see the teachings of WO2010/42699 A1) to furnish intermediates of general formula (10).

Compounds of general formula (10) can be converted to compounds of general formula (2) by using reagents such as, for example, thiophosgene, carbon disulphide, 1,1"-thiocarbonyldi-2(1H)-pyridone or 1,1'-thiocarbonyldiimidazole, in one embodiment thiophosgene, under basic conditions, in a suitable solvent, such as, for example, dichloromethane, chloroform, acetone, or biphasic mixtures, such as, for example, dichloromethane, chloroform with aqueous basic solutions, in another embodiment, dichloromethane with an aqueous saturated solution of sodium hydrogen carbonate or sodium carbonate, in a temperature range from −78° C. to the boiling point of the respective solvent, in another embodiment the reaction is carried out 0° C. to room temperature, to furnish compounds of general formula (2). Such transformations reactions have been previously reported (Harris et al., J. Med. Chem., 2005, 48, 1610; Degorce et al., Tetrahedron Lett., 2011, 52, 6719; WO2016/91845 A1; Fairhurst et al., Org. Lett., 2005, 7, 4697; Chaskar et al., Synth. Commun., 2008, 38, 16940; US2004/122237 A1).

Scheme 4:

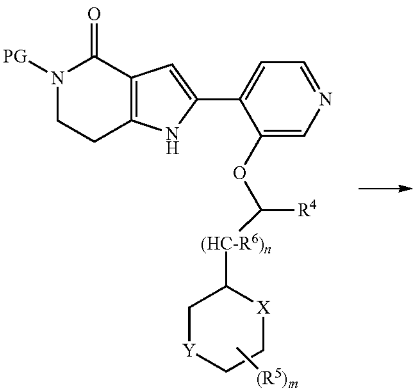

12

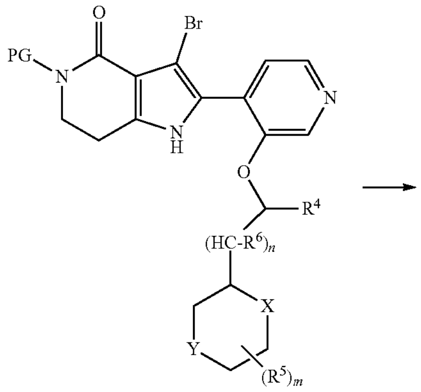

13

-continued

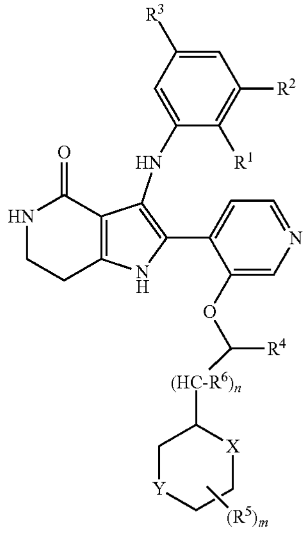

(I)

Scheme 4: Route for the preparation of compounds of general formula (I), wherein $R^1$, $R^2$, $R^3$, $R^4$, $R^5$, $R^6$, X, Y, m and n have the meaning as given for general formula (I) and PG represents hydrogen or a suitable protecting group, e.g. tert-butoxycarbonyl (Boc).

Compounds similar to those of general formula 12 are known to those skilled in the art and their syntheses have been reported in the literature (see the teachings of Voss et al., WO2015/22073 A1; Hart et al., WO2016/100166 A1; Anderson et al., J. Med. Chem., 2007, 50, 2647; Vanotti et al., J. Med. Chem., 2008, 51, 487).

Compounds of general formula (12) could be converted to compounds of general formula (13) using standard bromination methods which are known to those skilled in the art (WO2016/100166 A1). Such brominations could be carried out using a brominating agent, such as, for example, N-bromosuccinimide, in a suitable solvent, such as, for example, DMF, in a temperature range from −78° C. to the boiling point of said solvent, in one embodiment the temperature range is 0° C. to RT.

Intermediates of general formula (13) can be reacted with suitable anilines, such as, for example, 2-difluoromethoxyaniline, in the presence of a base, such as, for example, lithium bis(trimethylsilyl)amide (LHMDS), in the presence of a catalyst, such as, for example a suitable ligand, in one embodiment 2-(di-tert-butylphosphino)-2',4',6'-triisopropyl-3,6-dimethoxy-1,1'-biphenyl (tBuBrettPhos) and in the presence of a pre-catalyst, such as, for example a palladium pre-catalyst, in another embodiment chloro[2-(dicyclohexylphosphino)-3,6-dimethoxy-2',4',6'-triisopropyl-1,1'-biphenyl][2-(2-aminoethyl)phenyl]palladium(II) (BrettPhos-PreCat MTBE ether adduct) in a suitable solvent system, such as, for example, tetrahydrofuran (THF), at a temperature range of 0° C. to 200° C. In one embodiment, the reaction is carried out at 80° C., to furnish compounds of general formula (I). Similar transformations have been carried out and have been reported (WO2015/193339 A1).

Scheme 5

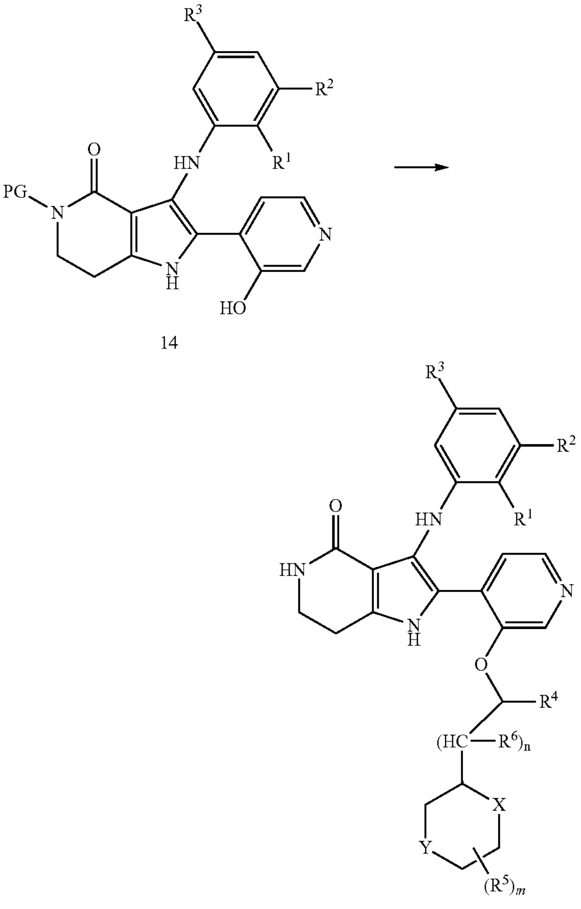

14

(I)

Scheme 5: Route for the preparation of compounds of general formula (I), wherein $R^1$, $R^2$, $R^3$, $R^4$, $R^5$, $R^6$, X, Y, m and n have the meaning as given for general formula (I) and PG represents hydrogen or a suitable protecting group, e.g. tert-butoxycarbonyl (Boc).

Compounds similar to those of general formula (14) can be prepared according to the procedure described by Scheme 1 under the use of 4-(aminomethyl)-3-hydroxypyridine instead of intermediate (4). Intermediates of general formula (14) can be converted to compounds of general formula (I) by reaction with a suitable alcohol under Mitsunobu conditions (the teachings of Oyo Mitsunobu, Synthesis, 1981, 1-28 or Tsunoda et al., Tetrahedron Lett., 1994, 35, 5081) such as, for example oxetan-3-ylmethanol, in the presence of (tributylphosphoranylidene)acetonitrile or triphenylphosphin together with diisopropyl azodicarboxylate in a suitable solvent system, such as, for example, dioxane or THF, at a temperature between room temperature and the boiling point of the respective solvents.

It is known to the person skilled in the art that, if there are a number of reactive centers on a starting or intermediate compound, it may be necessary to block one or more reactive centers temporarily by protective groups in order to allow a reaction to proceed specifically at the desired reaction center.

The compounds according to the invention are isolated and purified in a manner known per se, e.g. by distilling off the solvent in vacuo and recrystallizing the residue obtained from a suitable solvent or subjecting it to one of the customary purification methods, such as chromatography on a suitable support material. Furthermore, reverse phase preparative HPLC may be applied. The compounds of the present invention which possess a sufficiently basic or acidic functionality, may result as a salt, such as, in the case of a compound of the present invention which is sufficiently basic, a trifluoroacetate or formate salt for example, or, in the case of a compound of the present invention which is sufficiently acidic, an ammonium salt for example. Salts of this type can either be transformed into its free base or free acid form, respectively, by various methods known to the person skilled in the art, or be used as salts in subsequent biological assays. Additionally, the drying process during the isolation of the compounds of the present invention may not fully remove traces of cosolvents, especially such as formic acid or trifluoroacetic acid, to give solvates or inclusion complexes. The person skilled in the art will recognise which solvates or inclusion complexes are acceptable to be used in subsequent biological assays. It is to be understood that the specific form (e.g. salt, free base, free acid, solvate, inclusion complex) of a compound of the present invention as isolated and described herein is not necessarily the only form in which said compound can be applied to a biological assay in order to quantify the specific biological activity.

Salts of the compounds of formula (I) according to the invention can be obtained by dissolving the free compound in a suitable solvent (for example a ketone such as acetone, methylethylketone or methylisobutylketone, an ether such as diethyl ether, tetrahydrofuran or dioxane, a chlorinated hydrocarbon such as methylene chloride or chloroform, or a low molecular weight aliphatic alcohol such as methanol, ethanol or isopropanol) which contains the desired acid or base, or to which the desired acid or base is then added. The acid or base can be employed in salt preparation, depending on whether a mono- or polybasic acid or base is concerned and depending on which salt is desired, in an equimolar ratio or one differing therefrom. The salts are obtained by filtering, reprecipitating, precipitating with a non-solvent for the salt or by evaporating the solvent. Salts obtained can be converted into the free compounds which, in turn, can be converted into salts. In this manner, pharmaceutically unacceptable salts, which can be obtained, for example, as process products in the manufacturing on an industrial scale, can be converted into pharmaceutically acceptable salts by processes known to the person skilled in the art. Especially preferred are hydrochlorides and the process used in the example section.

Pure diastereomers and pure enantiomers of the compounds and salts according to the invention can be obtained e.g. by asymmetric synthesis, by using chiral starting compounds in synthesis or by splitting up enantiomeric and diasteriomeric mixtures obtained in synthesis.

Enantiomeric and diastereomeric mixtures can be split up into the pure enantiomers and pure diastereomers by methods known to the person skilled in the art. In one embodiment, diastereomeric mixtures are separated by crystallization, in particular fractional crystallization, or chromatography. Enantiomeric mixtures can be separated e.g. by forming diastereomers with a chiral auxillary agent, resolving the diastereomers obtained and removing the chiral auxillary agent. As chiral auxillary agents, for example, chiral acids can be used to separate enantiomeric bases such as e.g. mandelic acid and chiral bases can be used to separate enantiomeric acids by formation of diastereomeric salts. Furthermore, diastereomeric derivatives such as diastereomeric esters can be formed from enantiomeric mixtures of alcohols or enantiomeric mixtures of acids, respectively, using chiral acids or chiral alcohols, respectively, as chiral auxillary agents. Additionally, diastereomeric complexes or diastereomeric clathrates may be used for separating enantiomeric mixtures. Alternatively, enantiomeric mixtures can be split up using chiral separating columns in chromatography. Another suitable method for the isolation of enantiomers is the enzymatic separation.

One preferred aspect of the invention is the process for the preparation of the compounds of claims 1-4 according to the examples as well as the intermediates used for their preparation.

Optionally, compounds of the formula (I) can be converted into their salts, or, optionally, salts of the compounds of the formula (I) can be converted into the free compounds. Corresponding processes are customary for the skilled person.

Commercial Utility

As mentioned supra, the compounds of the present invention have surprisingly been found to effectively inhibit mutant EGFR in a cell (e.g., a cancer cell) contacted with the compound, thereby inducing cell death (e.g., apoptosis) and may therefore be used for the treatment or prophylaxis of diseases of uncontrolled cell growth, proliferation and/or survival, inappropriate cellular immune responses, or inappropriate cellular inflammatory responses, or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by mutant EGFR, such as, for example, benign and malignant neoplasia, more specifically haematological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof, especially haematological tumours, solid tumours, and/or metastases of breast, bladder, bone, brain, central and peripheral nervous system, cervix, colon, endocrine glands (e.g., thyroid and adrenal cortex), endocrine tumours, endometrium, esophagus, gastrointestinal tumours, germ cells, kidney, liver, lung, larynx and hypopharynx, mesothelioma, ovary, pancreas, prostate, rectum, renal, small intestine, soft tissue, stomach, skin, testis, ureter, vagina and vulva as well as malignant neoplasias including primary tumours in said organs and corresponding secondary tumours in distant organs ("tumour metastases"). Haematological tumours can, e.g., be exemplified by aggressive and indolent forms of leukemia and lymphoma, namely non-Hodgkins disease, chronic and acute myeloid leukemia (CML/AML), acute lymphoblastic leukemia (ALL), Hodgkins disease, multiple myeloma and T-cell lymphoma. Also included are myelodysplastic syndrome, plasma cell neoplasia, paraneoplastic syndromes, and cancers of unknown primary site, as well as AIDS related malignancies.

A further aspect of the invention is the use of the compounds according to formula (I) for the treatment of lung cancer, particularly lung cancer harboring mutant EGFR with exon 20 insertion mutations, more particularly lung cancer harboring V769_770ins ASV and/or D770_N771ins SVD exon 20 insertions, and/or metastases thereof, comprising administering an effective amount of a compound of formula (I).

A further aspect of the invention is the use of the compounds according to formula (I) for the treatment of lung cancer, particularly lung cancer harboring a mutant EGFR with in-frame deletions in exon 19 (such as EGFR E746_A750del) or point mutations in exon 21 (e.g. L858R), and/or metastases thereof.

A further aspect of the invention is the use of the compounds according to formula (I) for the treatment of lung cancer, particularly lung cancer harboring a mutant EGFR with a D770_N771insSVD C797S, E746_A750del C797S, or L858R C797S acquired resistance mutation, and/or metastases thereof.

A further aspect of the invention is the use of the compounds according to formula (I) for the treatment of lung cancer, particularly lung cancer harboring a mutant ERBB2 with exon 20 insertion mutations (such as ERBB2 A775_G776insYVMA), and/or metastases thereof. In accordance with an aspect of the present invention therefore the invention relates to a compound of general formula I, or an N-oxide, a salt, a tautomer or a stereoisomer of said compound, or a salt of said N-oxide, tautomer or stereoisomer particularly a pharmaceutically acceptable salt thereof, or a mixture of same, as described and defined herein, for use in the treatment or prophylaxis of a disease, especially for use in the treatment of a disease.

Another particular aspect of the present invention is therefore the use of a compound of general formula I, described supra, or a stereoisomer, a tautomer, an N-oxide, a hydrate, a solvate, or a salt thereof, particularly a pharmaceutically acceptable salt thereof, or a mixture of same, for the prophylaxis or treatment of hyperproliferative disorders or disorders responsive to induction of cell death, i.e., apoptosis.

By "hyperproliferative disease" is meant a disease, such as cancer, associated with inappropriately high levels of cell division, inappropriately low levels of apoptosis, or both. The term "inappropriate" within the context of the present invention, in particular in the context of "inappropriate cellular immune responses, or inappropriate cellular inflammatory responses", as used herein, is to be understood as generally meaning a response, which is less than, or greater than normal, and which is associated with, responsible for, or results in, the pathology of said diseases.

In particular embodiments, the use is in the treatment or prophylaxis of diseases, especially the treatment, wherein the diseases are haematological tumours, solid tumours and/or metastases thereof.

Another aspect is the use of a compound of formula (I) for the prophylaxis and/or treatment of lung cancer, particularly lung cancer harboring mutant EGFR with exon 20 insertion mutations, more particularly lung cancer harboring V769_770ins ASV and/or D770_N771ins SVD exon 20 insertions, and/or metastases thereof, especially preferred for the treatment thereof.

Another aspect of the present invention is the use of a compound of formula (I) or a stereoisomer, a tautomer, an N-oxide, a hydrate, a solvate, or a salt thereof, particularly a pharmaceutically acceptable salt thereof, or a mixture of same, as described herein, in the manufacture of a medicament for the treatment or prophylaxis of a disease, wherein such disease is a hyperproliferative disorder or a disorder responsive to induction of cell death e.g., apoptosis. In an embodiment the disease is a haematological tumour, a solid tumour and/or metastases thereof. In another embodiment the disease is lung cancer, particularly lung cancer harboring mutant EGFR with exon 20 insertion mutations, more particularly lung cancer harboring V769_770ins ASV and/or D770_N771ins SVD exon 20 insertions, and/or metastases thereof.

Method of Treating Hyper-Proliferative Disorders

The present invention relates to a method for using the compounds of the present invention and compositions thereof, to treat mammalian hyper-proliferative disorders. Compounds can be utilized to inhibit, block, reduce, decrease, etc., cell proliferation and/or cell division, and/or produce cell death e.g. apoptosis. This method comprises administering to a mammal in need thereof, including a human, an amount of a compound of this invention, or a pharmaceutically acceptable salt, isomer, polymorph, metabolite, hydrate, solvate or ester thereof; etc. which is effective to treat the disorder. Hyper-proliferative disorders include but are not limited, e.g., psoriasis, keloids, and other hyperplasias affecting the skin, benign prostate hyperplasia (BPH), solid tumours, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukaemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypothalmic glioma, cerebellar and cerebral astrocytoma, medulloblastoma, ependymoma, as well as neuroectodermal and pineal tumour.

Tumours of the male reproductive organs include, but are not limited to prostate and testicular cancer. Tumours of the female reproductive organs include, but are not limited to endometrial, cervical, ovarian, vaginal, and vulvar cancer, as well as sarcoma of the uterus.

Tumours of the digestive tract include, but are not limited to anal, colon, colorectal, oesophageal, gallbladder, gastric, pancreatic, rectal, small-intestine, and salivary gland cancers.

Tumours of the urinary tract include, but are not limited to bladder, penile, kidney, renal pelvis, ureter, urethral and human papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, inverted sinonasal papilloma, inverted sinonasal papilloma-associated sinonasal squamous cell carcinoma, Merkel cell skin cancer, and non-melanoma skin cancer.

Head-and-neck cancers include, but are not limited to laryngeal, hypopharyngeal, nasopharyngeal, oropharyngeal cancer, inverted sinonasal papilloma, inverted sinonasal papilloma-associated sinonasal squamous cell carcinoma, lip and oral cavity cancer and squamous cell. Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

These disorders have been well characterized in humans, but also exist with a similar etiology in other mammals, and can be treated by administering pharmaceutical compositions of the present invention.

The term "treating" or "treatment" as stated throughout this document is used conventionally, e.g., the management or care of a subject for the purpose of combating, alleviating, reducing, relieving, improving the condition of, etc., of a disease or disorder, such as a carcinoma.

The present invention relates to a method of treating cancer in a subject, the method comprising administering to the subject an effective amount of a compound of general formula (I) as defined herein.

The present invention relates to a method of treating cancer in a subject, wherein the cancer is or has acquired resistance to an anti-EGF receptor therapy, the method comprising administering to the subject an effective amount of a compound of general formula (I) as defined herein.

The present invention relates to a method of enhancing the efficacy of an anti-EGF-receptor therapy, the method comprising administering to the subject an anti-EGF receptor therapy in combination with a a compound of general formula (I) as defined herein.

In a further embodiment, the present invention relates to a method of treating cancer in a subject, wherein the cancer is selected from the group consisting of leukemia, myelodysplastic syndrome, malignant lymphoma, head and neck tumours, tumours of the thorax, gastrointestinal tumours, endocrine tumours, mammary and other gynaecological tumours, urological tumours, skin tumours, and sarcomas, the method comprising administering to the subject an effective amount of a compound of general formula (I) as defined herein.

In a further embodiment, the present invention relates to a method of treating cancer in a subject, wherein the cancer is selected from the group consisting of inverted sinonasal papilloma or inverted sinonasal papilloma associated sinanonasal squamous cell carcinoma, the method comprising administering to the subject an effective amount of a compound of general formula (I) as defined herein.

In a further embodiment, the present invention relates to a method of treating cancer in a subject, wherein the tumour of the thorax is non-small cell lung cancer, the method comprising administering to the subject an effective amount of a compound of general formula (I) as defined herein.

In a further embodiment, the present invention relates to a method of treating cancer in a subject, wherein the cancer is lung cancer, particularly lung cancer harboring a mutant EGFR with in-frame deletions in exon 19 (such as EGFR E746_A750del) or point mutations in exon 21 (e.g. L858R), and/or metastases thereof, the method comprising administering to the subject an effective amount of a compound of general formula (I) as defined herein.

In a further embodiment, the present invention relates to a a method of treating cancer in a subject, wherein the cancer is lung cancer, particularly lung cancer harboring a mutant EGFR with a D770_N771 insSVD C797S, E746_A750del C797S, or L858R C797S acquired resistance mutation, and/or metastases thereof, the method comprising administering to the subject an effective amount of a compound of general formula (I) as defined herein.

In a further embodiment, the present invention relates to a a method of treating cancer in a subject, wherein the cancer is lung cancer, particularly lung cancer harboring a mutant ERBB2 with exon 20 insertion mutations (such as ERBB2 A775_G776insYVMA), and/or metastases thereof, the method comprising administering to the subject an effective amount of a compound of general formula (I) as defined herein.

The present disclosure is also related to method of selecting a patient for cancer treatment with a compound of general formula (I) comprising detecting the presence of a mutation in exon 20 of the gene encoding the EGF-receptor in a biological sample of the subject, thereby determining that the patient should be treated with said compound. In some embodiments, the EGFR comprises aD770_N771insSVD C797S, E746_A750del C797S, or L858R C797S acquired resistance mutation, and/or metastases thereof. In some embodiments, the method of selecting a patient for cancer treatment with a compound of general formula (I) may comprise detecting the presence of in-frame deletions in exon 19 or point mutations in exon 21 of the gene encoding EGF-receptor in a biological sample of the subject, thereby determining that the patient should be treated with said compound. For example, the in-frame deletion in exon 19 may be EGFR E746_A750del or the point mutation in exon 21 may be L858R. In some embodiments, the method of selecting a patient for cancer treatment with a compound of general formula (I) may comprise detecting the presence of a mutation in exon 20 of the gene encoding ERBB2 in a biological sample of the subject, thereby determining that the patient should be treated with said compound. In some embodiments, the ERBB2 comprises an ERBB2 A775 or_G776insYVMA insertion mutation, and/or metastases thereof. Furthermore, methods of treating a patient with cancer may comprise administering to the subject a compound of general formula (I) (e.g., in combination with anti-EGF receptor therapy), wherein the subject is selected for therapy by detecting the presence of a mutation in EGFR in a biological sample of the subject. Detection of the presence of a mutation in exon 20 is within the skill of one of the art.

In some embodiments, the detection of a mutation (e.g., in an EGFR or a mutation in exon 20 of the gene encoding EGFR) may be performed by sequencing (e.g., Sanger, Next Generation Sequencing) or a method selected from the group consisting of immunoblotting, mass spectrometry, immunoprecipitation quantitative PCR, Northern Blot, microarray, enzyme-linked immunosorbent assay (ELISA), in situ hybridization, and combinations thereof.

Methods of Treating Kinase Disorders

The present invention also provides methods for the treatment of disorders associated with aberrant mitogen extracellular kinase activity, including, but not limited to stroke, heart failure, hepatomegaly, cardiomegaly, diabetes, Alzheimer's disease, cystic fibrosis, symptoms of xenograft rejections, septic shock or asthma.

Effective amounts of compounds of the present invention can be used to treat such disorders, including those diseases (e.g., cancer) mentioned in the Background section above. Nonetheless, such cancers and other diseases can be treated with compounds of the present invention, regardless of the mechanism of action and/or the relationship between the kinase and the disorder.

The phrase "aberrant kinase activity" or "aberrant tyrosine kinase activity," includes any abnormal expression or activity of the gene encoding the kinase or of the polypeptide it encodes. Examples of such aberrant activity, include, but are not limited to, over-expression of the gene or polypeptide; gene amplification; mutations which produce constitutively-active or hyperactive kinase activity; gene mutations, deletions, substitutions, additions, etc.

The present invention also provides for methods of inhibiting kinase activity, especially of mitogen extracellular kinase, comprising administering an effective amount of a compound of the present invention, including salts, polymorphs, metabolites, hydrates, solvates, prodrugs (e.g.: esters) thereof, and diastereoisomeric forms thereof. Kinase activity can be inhibited in cells (e.g., in vitro), or in the cells of a mammalian subject, especially a human patient in need of treatment.

Methods of Treating Angiogenic Disorders

The present invention also provides methods of treating disorders and diseases associated with excessive and/or abnormal angiogenesis.

Inappropriate and ectopic expression of angiogenesis can be deleterious to an organism. A number of pathological conditions are associated with the growth of extraneous blood vessels. These include, e.g., diabetic retinopathy, ischemic retinal-vein occlusion, and retinopathy of prematurity [Aiello et al. New Engl. J. Med. 1994, 331, 1480; Peer et al. Lab. Invest. 1995, 72, 638], age-related macular degeneration [AMD; see, Lopez et al. Invest. Opththalmol. Vis. Sci. 1996, 37, 855], neovascular glaucoma, psoriasis, retrolental fibroplasias, angiofibroma, inflammation, rheumatoid arthritis (RA), restenosis, in-stent restenosis, vascular graft restenosis, etc. In addition, the increased blood supply associated with cancerous and neoplastic tissue, encourages growth, leading to rapid tumour enlargement and metastasis. Moreover, the growth of new blood and lymph vessels in a tumour provides an escape route for renegade cells, encouraging metastasis and the consequence spread of the cancer. Thus, compounds of the present invention can be utilized to treat and/or prevent any of the aforementioned angiogenesis disorders, e.g., by inhibiting and/or reducing blood vessel formation; by inhibiting, blocking, reducing, decreasing, etc. endothelial cell proliferation or other types involved in angiogenesis, as well as causing cell death e.g. apoptosis of such cell types.

In various embodiments, the diseases of said method are haematological tumours, solid tumour and/or metastases thereof.

The compounds of the present invention can be used in particular in therapy and prevention i.e. prophylaxis, especially in therapy of tumour growth and metastases, especially in solid tumours of all indications and stages with or without pre-treatment of the tumour growth.

Pharmaceutical Compositions of the Compounds of the Invention

This invention also relates to pharmaceutical compositions containing one or more compounds of the present invention. These compositions can be utilised to achieve the desired pharmacological effect by administration to a patient in need thereof. A patient, for the purpose of this invention, is a mammal, including a human, in need of treatment for the particular condition, disorder, or disease.

Therefore, the present invention includes pharmaceutical compositions that are comprised of a pharmaceutically acceptable carrier or auxiliary and a pharmaceutically effective amount of a compound, or salt thereof, of the present invention.

Another aspect of the invention is a pharmaceutical composition comprising a pharmaceutically effective amount of a compound of formula (I) and a pharmaceutically acceptable auxiliary for the treatment of a disease mentioned supra, especially for the treatment of haematological tumours, solid tumours and/or metastases thereof.

A pharmaceutically acceptable carrier or auxiliary may be a carrier that is non-toxic and innocuous to a patient at concentrations consistent with effective activity of the active ingredient so that any side effects ascribable to the carrier do not vitiate the beneficial effects of the active ingredient. Carriers and auxiliaries are all kinds of additives assisting to the composition to be suitable for administration.

A pharmaceutically effective amount of compound may be that amount which produces a result or exerts the intended influence on the particular condition being treated.

The compounds of the present invention can be administered with pharmaceutically-acceptable carriers or auxiliaries well known in the art using any effective conventional dosage unit forms, including immediate, slow and timed release preparations, orally, parenterally, topically, nasally, ophthalmically, optically, sublingually, rectally, vaginally, and the like.

For oral administration, the compounds can be formulated into solid or liquid preparations such as capsules, pills, tablets, troches, lozenges, melts, powders, solutions, suspensions, or emulsions, and may be prepared according to methods known to the art for the manufacture of pharmaceutical compositions. The solid unit dosage forms can be a capsule that can be of the ordinary hard- or soft-shelled gelatine type containing auxiliaries, for example, surfactants, lubricants, and inert fillers such as lactose, sucrose, calcium phosphate, and corn starch.

In another embodiment, the compounds of this invention may be tableted with conventional tablet bases such as lactose, sucrose and cornstarch in combination with binders such as acacia, corn starch or gelatine, disintegrating agents intended to assist the break-up and dissolution of the tablet following administration, such as potato starch, alginic acid, corn starch, and guar gum, gum tragacanth, acacia, lubricants intended to improve the flow of tablet granulation and to prevent the adhesion of tablet material to the surfaces of the tablet dies and punches, for example talc, stearic acid, or magnesium, calcium or zinc stearate, dyes, colouring agents, and flavouring agents such as peppermint, oil of wintergreen, or cherry flavouring, intended to enhance the aesthetic qualities of the tablets and make them more acceptable to the patient. Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavouring and colouring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived from fatty acids and hexitol anhydrides, for example, sorbitan monooleate, (4) condensation products of said partial esters with ethylene oxide, for example, polyoxyethylene sorbitan monooleate. The emulsions may also contain sweetening and flavouring agents.

Oily suspensions may be formulated by suspending the active ingredient in a vegetable oil such as, for example, arachis oil, olive oil, sesame oil or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more colouring agents; one or more flavouring agents; and one or more sweetening agents such as sucrose or saccharin.

Syrups and elixirs may be formulated with sweetening agents such as, for example, glycerol, propylene glycol, sorbitol or sucrose. Such formulations may also contain a demulcent, and preservative, such as methyl and propyl parabens and flavouring and colouring agents.

The compounds of this invention may also be administered parenterally, that is, subcutaneously, intravenously, intraocularly, intrasynovially, intramuscularly, or interperitoneally, as injectable dosages of the compound in, for example, a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4-methanol, ethers such as poly(ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methycellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum and mineral oil. Suitable fatty acids include oleic acid, stearic acid, isostearic acid and myristic acid. Suitable fatty acid esters are, for example, ethyl oleate and isopropyl myristate. Suitable soaps include fatty acid alkali metal, ammonium, and triethanolamine salts and suitable detergents include cationic detergents, for example dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; non-ionic detergents, for example, fatty amine oxides, fatty acid alkanolamides, and poly(oxyethylene-oxypropylene)s or ethylene oxide or propylene oxide copolymers; and amphoteric detergents, for example, alkyl-beta-aminopropionates, and 2-alkylimidazoline quarternary ammonium salts, as well as mixtures.

The parenteral compositions of this invention will typically contain from about 0.5% to about 25% by weight of the active ingredient in solution. Preservatives and buffers may also be used advantageously. In order to minimise or eliminate irritation at the site of injection, such compositions may contain a non-ionic surfactant having a hydrophile-lipophile balance (HLB) in one embodiment of from about 12 to about 17. The quantity of surfactant in such formulation in one embodiment ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadeca-ethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

A composition of the invention may also be administered in the form of suppositories for rectal administration of the drug. These compositions can be prepared by mixing the drug with a suitable non-irritation excipient which is solid at ordinary temperatures but liquid at the rectal temperature and will therefore melt in the rectum to release the drug. Such materials are, for example, cocoa butter and polyethylene glycol.

Controlled release formulations for parenteral administration include liposomal, polymeric microsphere and polymeric gel formulations that are known in the art.

It may be desirable or necessary to introduce the pharmaceutical composition to the patient via a mechanical delivery device. The construction and use of mechanical delivery devices for the delivery of pharmaceutical agents is well known in the art. Direct techniques for administration, for example, administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, issued Apr. 30, 1991.

The compositions of the invention can also contain other conventional pharmaceutically acceptable compounding ingredients, generally referred to as carriers or diluents, as necessary or desired. Conventional procedures for preparing such compositions in appropriate dosage forms can be utilized.

Such ingredients and procedures include those described in the following references, each of which is incorporated herein by reference: Powell, M. F. et al., "Compendium of Excipients for Parenteral Formulations" PDA Journal of Pharmaceutical Science & Technology 1998, 52(5), 238-311; Strickley, R. G "Parenteral Formulations of Small Molecule Therapeutics Marketed in the United States (1999)-Part-1" PDA Journal of Pharmaceutical Science & Technology 1999, 53(6), 324-349; and Nema, S. et al., "Excipients and Their Use in Injectable Products" PDA Journal of Pharmaceutical Science & Technology 1997, 51(4), 166-171.

Commonly used pharmaceutical ingredients that can be used as appropriate to formulate the composition for its intended route of administration include:

- acidifying agents (examples include but are not limited to acetic acid, citric acid, fumaric acid, hydrochloric acid, nitric acid);
- alkalinizing agents (examples include but are not limited to ammonia solution, ammonium carbonate, diethanolamine, monoethanolamine, potassium hydroxide, sodium borate, sodium carbonate, sodium hydroxide, triethanolamine, trolamine);
- adsorbents (examples include but are not limited to powdered cellulose and activated charcoal);
- aerosol propellants (examples include but are not limited to carbon dioxide, $CCl_2F_2$, $F_2ClC—CClF_2$ and $CClF_3$);
- air displacement agents (examples include but are not limited to nitrogen and argon);
- antifungal preservatives (examples include but are not limited to benzoic acid, butylparaben, ethylparaben, methylparaben, propylparaben, sodium benzoate);
- antimicrobial preservatives (examples include but are not limited to benzalkonium chloride, benzethonium chloride, benzyl alcohol, cetylpyridinium chloride, chlorobutanol, phenol, phenylethyl alcohol, phenylmercuric nitrate and thimerosal);
- antioxidants (examples include but are not limited to ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite);
- binding materials (examples include but are not limited to block polymers, natural and synthetic rubber, polyacrylates, polyurethanes, silicones, polysiloxanes and styrene-butadiene copolymers);
- buffering agents (examples include but are not limited to potassium metaphosphate, dipotassium phosphate, sodium acetate, sodium citrate anhydrous and sodium citrate dihydrate);
- carrying agents (examples include but are not limited to acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection);
- chelating agents (examples include but are not limited to edetate disodium and edetic acid);
- colourants (examples include but are not limited to FD&C Red No. 3, FD&C Red No. 20, FD&C Yellow No. 6, FD&C Blue No. 2, D&C Green No. 5, D&C Orange No. 5, D&C Red No. 8, caramel and ferric oxide red);
- clarifying agents (examples include but are not limited to bentonite);
- emulsifying agents (examples include but are not limited to acacia, cetomacrogol, cetyl alcohol, glyceryl monostearate, lecithin, sorbitan monooleate, polyoxyethylene 50 monostearate);
- encapsulating agents (examples include but are not limited to gelatin and cellulose acetate phthalate);
- flavourants (examples include but are not limited to anise oil, cinnamon oil, cocoa, menthol, orange oil, peppermint oil and vanillin);
- humectants (examples include but are not limited to glycerol, propylene glycol and sorbitol);
- levigating agents (examples include but are not limited to mineral oil and glycerin);
- oils (examples include but are not limited to arachis oil, mineral oil, olive oil, peanut oil, sesame oil and vegetable oil);
- ointment bases (examples include but are not limited to lanolin, hydrophilic ointment, polyethylene glycol ointment, petrolatum, hydrophilic petrolatum, white ointment, yellow ointment, and rose water ointment);
- penetration enhancers (transdermal delivery) (examples include but are not limited to monohydroxy or polyhydroxy alcohols, mono- or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas);
- plasticizers (examples include but are not limited to diethyl phthalate and glycerol);
- solvents (examples include but are not limited to ethanol, corn oil, cottonseed oil, glycerol, isopropanol, mineral oil, oleic acid, peanut oil, purified water, water for injection, sterile water for injection and sterile water for irrigation);
- stiffening agents (examples include but are not limited to cetyl alcohol, cetyl esters wax, microcrystalline wax, paraffin, stearyl alcohol, white wax and yellow wax);
- suppository bases (examples include but are not limited to cocoa butter and polyethylene glycols (mixtures));
- surfactants (examples include but are not limited to benzalkonium chloride, nonoxynol 10, oxtoxynol 9, polysorbate 80, sodium lauryl sulfate and sorbitan monopalmitate);
- suspending agents (examples include but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum);
- sweetening agents (examples include but are not limited to aspartame, dextrose, glycerol, mannitol, propylene glycol, saccharin sodium, sorbitol and sucrose);
- tablet anti-adherents (examples include but are not limited to magnesium stearate and talc);
- tablet binders (examples include but are not limited to acacia, alginic acid, carboxymethylcellulose sodium, compressible sugar, ethylcellulose, gelatin, liquid glucose, methylcellulose, non-crosslinked polyvinyl pyrrolidone, and pregelatinized starch);
- tablet and capsule diluents (examples include but are not limited to dibasic calcium phosphate, kaolin, lactose, mannitol, microcrystalline cellulose, powdered cellulose, precipitated calcium carbonate, sodium carbonate, sodium phosphate, sorbitol and starch);
- tablet coating agents (examples include but are not limited to liquid glucose, hydroxyethyl cellulose, hydroxypropyl cellulose, hydroxypropyl methylcellulose, methylcellulose, ethylcellulose, cellulose acetate phthalate and shellac);

tablet direct compression excipients (examples include but are not limited to dibasic calcium phosphate);

tablet disintegrants (examples include but are not limited to alginic acid, carboxymethylcellulose calcium, microcrystalline cellulose, polacrillin potassium, cross-linked polyvinylpyrrolidone, sodium alginate, sodium starch glycollate and starch);

tablet glidants (examples include but are not limited to colloidal silica, corn starch and talc);

tablet lubricants (examples include but are not limited to calcium stearate, magnesium stearate, mineral oil, stearic acid and zinc stearate);

tablet/capsule opaquants (examples include but are not limited to titanium dioxide);

tablet polishing agents (examples include but are not limited to carnuba wax and white wax); thickening agents (examples include but are not limited to beeswax, cetyl alcohol and paraffin);

tonicity agents (examples include but are not limited to dextrose and sodium chloride);

viscosity increasing agents (examples include but are not limited to alginic acid, bentonite, carbomers, carboxymethylcellulose sodium, methylcellulose, polyvinyl pyrrolidone, sodium alginate and tragacanth); and wetting agents (examples include but are not limited to heptadecaethylene oxycetanol, lecithins, sorbitol monooleate, polyoxyethylene sorbitol monooleate, and polyoxyethylene stearate).

Pharmaceutical compositions according to the present invention can be illustrated as follows:

Sterile i.v. solution: A 5 mg/ml solution of the desired compound of this invention can be made using sterile, injectable water, and the pH is adjusted if necessary. The solution is diluted for administration to 1-2 mg/ml with sterile 5% dextrose and is administered as an i.v. infusion over about 60 minutes.

Lyophilised powder for i.v. administration: A sterile preparation can be prepared with (i) 100-1000 mg of the desired compound of this invention as a lyophilised powder, (ii) 32-327 mg/ml sodium citrate, and (iii) 300-3000 mg Dextran 40. The formulation is reconstituted with sterile, injectable saline or dextrose 5% to a concentration of 10 to 20 mg/ml, which is further diluted with saline or dextrose 5% to 0.2-0.4 mg/ml, and is administered either IV bolus or by IV infusion over 15-60 minutes.

Intramuscular suspension: The following solution or suspension can be prepared, for intramuscular injection:

50 mg/ml of the desired, water-insoluble compound of this invention 5 mg/ml sodium carboxymethylcellulose 4 mg/ml TWEEN 80

9 mg/ml sodium chloride 9 mg/ml benzyl alcohol

Hard Shell Capsules: A large number of unit capsules are prepared by filling standard two-piece hard galantine capsules each with 100 mg of powdered active ingredient, 150 mg of lactose, 50 mg of cellulose and 6 mg of magnesium stearate.

Soft Gelatin Capsules: A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets: A large number of tablets are prepared by conventional procedures so that the dosage unit is 100 mg of active ingredient, 0.2 mg. of colloidal silicon dioxide, 5 mg of magnesium stearate, 275 mg of microcrystalline cellulose, 11 mg. of starch, and 98.8 mg of lactose. Appropriate aqueous and non-aqueous coatings may be applied to increase palatability, improve elegance and stability or delay absorption.

Immediate Release Tablets/Capsules: These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Dose and Administration

Based upon standard laboratory techniques known to evaluate compounds useful for the treatment of hyper-proliferative disorders and angiogenic disorders, by standard toxicity tests and by standard pharmacological assays for the determination of treatment of the conditions identified above in mammals, and by comparison of these results with the results of known medicaments that are used to treat these conditions, the effective dosage of the compounds of this invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and in particular embodiments from about 0.01 mg/kg to about 20 mg/kg body weight per day. Clinically useful dosing schedules will range from one to three times a day dosing to once every four weeks dosing. In addition, "drug holidays" in which a patient is not dosed with a drug for a certain period of time, may be beneficial to the overall balance between pharmacological effect and tolerability. A unit dosage may contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will in other embodiments be from 0.01 to 200 mg/kg of total body weight. The average daily rectal dosage regimen will in particular embodiments be from 0.01 to 200 mg/kg of total body weight. The average daily vaginal dosage regimen will in other embodiments be from 0.01 to 200 mg/kg of total body weight. The average daily topical dosage regimen will in still other embodiments be from 0.1 to 200 mg administered between one to four times daily. The transdermal concentration will in other embodiments be that required to maintain a daily dose of from 0.01 to 200 mg/kg.

The average daily inhalation dosage regimen will in other embodiments be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

Combination Therapies

The compounds of this invention can be administered as the sole pharmaceutical agent or in combination with one or more other pharmaceutical agents where the combination causes no unacceptable adverse effects. Those combined pharmaceutical agents can be other agents having antiproliferative effects such as for example for the treatment of haematological tumours, solid tumours and/or metastases thereof and/or agents for the treatment of undesired side effects. The present invention relates also to such combinations.

Other anti-hyper-proliferative agents suitable for use with the composition of the invention include but are not limited to those compounds acknowledged to be used in the treatment of neoplastic diseases in Goodman and Gilman's The Pharmacological Basis of Therapeutics (Ninth Edition), editor Molinoff et al., publ. by McGraw-Hill, pages 1225-1287, (1996), which is hereby incorporated by reference, especially (chemotherapeutic) anti-cancer agents as defined supra. The combination can be a non-fixed combination or a fixed-dose combination as the case may be.

Methods of testing for a particular pharmacological or pharmaceutical property are well known to persons skilled in the art.

The example testing experiments described herein serve to illustrate the present invention and the invention is not limited to the examples given.

As will be appreciated by persons skilled in the art, the invention is not limited to the particular embodiments described herein, but covers all modifications of said embodiments that are within the spirit and scope of the invention as defined by the appended claims.

The following examples illustrate the invention in greater detail, without restricting it. Further compounds according to the invention, of which the preparation is not explicitly described, can be prepared in an analogous way.

The compounds, which are mentioned in the examples and the salts thereof represent preferred embodiments of the invention as well as a claim covering all subcombinations of the residues of the compound of formula (I) as disclosed by the specific examples.

The term "according to" within the experimental section is used in the sense that the procedure referred to is to be used "analogously to".

EXPERIMENTAL SECTION

Chemical names were generated using the ACD/Name software from ACD/Labs. In some cases generally accepted names of commercially available reagents were used in place of AC/Name generated names.

The following table 1 lists the abbreviations used in this paragraph and in the Examples section as far as they are not explained within the text body. Other abbreviations have their meanings customary per se to the skilled person.

TABLE 1

Abbreviations

| Abbreviation | Meaning |
|---|---|
| ACN | Acetonitrile |
| AcOH | Acetic acid |
| br | broad signal (NMR) |
| d | doublet (NMR) |
| DAD | Diode Array Detector |
| DAST | Diethylaminosulfur trifluoride |
| DBU | 1,8-Diazabicyclo(5.4.0)undec-7-ene |
| DCM | Dichloromethane |
| dd | doublet of doublet (NMR) |
| DIPEA | Diisopropylethylamine |
| DMA | N,N-dimethylacetamide |
| DMAP | 4-Dimethylaminopyridine |
| DMF | N,N-dimethylformamide |
| DMSO | Dimethylsulfoxide |
| EDC•HCl | N-(3-Dimethylaminopropyl)-N'-ethylcarbodiimide hydrochloride salt |
| ESI | electrospray (ES) ionization |
| EtOAc | Ethyl acetate |
| EtOH | Ethanol |
| h, hr (hrs) | hour(s) |
| HCI | hydrogen chloride, hydrochloric acid |
| HPLC | high performance liquid chromatography |
| LC-MS | liquid chromatography-mass spectrometry |
| m | multiplet (NMR) |
| MeCN | Acetonitrile |
| MeOH | Methanol |
| min | minute(s) |
| MS | mass spectrometry |
| MTBE | Methyl-tert-butylether |
| MWD | Multiple wavelength detector |
| NMR | Nuclear Magnetic Resonance spectroscopy: chemical shifts (δ) are given in ppm. The chemical shifts were corrected by setting the DMSO signal to 2.50 ppm using unless otherwise stated. |
| q | quartet (NMR) |
| Rt or RT | room temperature |
| $R_t$, Rt | retention time |
| s | singulet (NMR) |
| sat. | Saturated |
| SFC | Supercritical Fluid Chromatography |
| t | triplet (NMR) |
| td | triplet of doublet (NMR) |
| TEA | Triethylamine |
| TFA | Trifluoroacetic acid |
| THF | Tetrahydrofuran |
| δ | chemical shift |

Other abbreviations have their meanings customary per se to the skilled person.

The various aspects of the invention described in this application are illustrated by the following examples which are not meant to limit the invention in any way.

The example testing experiments described herein serve to illustrate the present invention and the invention is not limited to the examples given.

Experimental Section—General Part

All reagents, for which the synthesis is not described in the experimental part, are either commercially available, or are known compounds or may be formed from known compounds by known methods by a person skilled in the art.

The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallization. In some cases, impurities may be removed by trituration using a suitable solvent. In some cases, the compounds may be purified by chromatography, particularly flash column chromatography, using for example prepacked silica gel cartridges, e.g. Biotage SNAP cartridges KP-Sil® or KP-NH® in combination with a Biotage autopurifier system (SP4® or Isolera Four®) and eluents such as gradients of hexane/ethyl acetate or DCM/methanol. In flash column chromatography, unmodified ("regular") silica gel may be used as well as aminophase functionalized silica gel. If reference is made to flash column chromatography or to flash chromatography in the experimental section without specification of a stationary phase, regular silica gel was used.

In some cases, the compounds may be purified by preparative HPLC using for example a Waters autopurifier equipped with a diode array detector and/or on-line electrospray ionization mass spectrometer in combination with a suitable prepacked reverse phase column and eluents such as gradients of water and acetonitrile which may contain additives such as trifluoroacetic acid, formic acid or aqueous ammonia.

In some cases, purification methods as described above can provide those compounds of the present invention which possess a sufficiently basic or acidic functionality in the form of a salt, such as, in the case of a compound of the present invention which is sufficiently basic, a trifluoroacetate or formate salt for example, or, in the case of a compound of the present invention which is sufficiently acidic, an ammonium salt for example. A salt of this type can either be transformed into its free base or free acid form, respectively, by various methods known to the person skilled in the art, or be used as salts in subsequent biological assays. It is to be understood that the specific form (e.g. salt, free base etc.) of a compound of the present invention as isolated and as described herein is not necessarily the only form in which said compound can be applied to a biological assay in order to quantify the specific biological activity.

Analytical LC-MS Methods:

Method 1:

Instrument: Waters Acquity UPLCMS SingleQuad; Column: Acquity UPLC BEH C18 1.7 µm, 50×2.1 mm; eluent A: water+0.1 vol. % formic acid (99%), eluent B: acetonitrile; gradient: 0-1.6 min. 1-99% B, 1.6-2.0 min. 99% B; flow 0.8 ml/min; temperature: 60° C.; DAD scan: 210-400 nm.

Method 2:

Instrument: Waters Acquity UPLCMS SingleQuad; Column: Acquity UPLC BEH C18 1.7 µm, 50×2.1 mm; eluent A: water+0.2 vol. % aqueous ammonia (32%), eluent B: acetonitrile; gradient: 0-1.6 min. 1-99% B, 1.6-2.0 min. 99% B; flow 0.8 ml/min; temperature: 60° C.; DAD scan: 210-400 nm.

Method 3:

Instrument: Waters Acquity UPLC H-Class system; Column: Acquity CSH C18 1.7 µm 2.1×50 mm; eluent A: water+0.1 vol. % formic acid, eluent B: acetonitrile, eluent C: 2 vol. % ammonia (28%) in water, eluent D: 2 vol. % formic acid in water; gradient: 0-1.2 min 2-95% B with A and 5% D throughout, 1.2-1.4 min. 95% B; flow 0.8 ml/min; temperature: 40° C.; PDA: 215-350 nm.

Method 4:

Instrument: Waters Acquity UPLC H-Class system; Column: XBridge BEH C18 2.5 µm 2.1×50 mm; eluent A: water+0.1 vol % formic acid, eluent B: acetonitrile, eluent C: 2 vol % ammonia (28%) in water, eluent D: 2 vol % formic acid in water; gradient: 0-1.2 min 2-95% B with A and 5% C throughout, 1.2-1.4 min 95% B; flow 0.8 ml/min; temperature: 40° C.; PDA: 215-350 nm.

Method 5:

MS instrument: SHIMADZU LCMS-2020; HPLC instrument: LabSolution Version 5.72; Column: Kinetex@5 um EVO C18 30×2.1 mm; eluent A: 0.0375% TFA in water (v/v), eluent B: 0.01875% TFA in acetonitrile: gradient: 0.0 min 0% B→3.00 min 60% B→3.50 min 60% B→3.51 min 0% B→4.00 min 0% B; flow rate: 0.8 mL/mix; oven temperature: 50° C.; UV detection: 220 nm & 254 nm.

Method 6:

Instrument: Agilent 1290 UPLCMS 6230 TOF; Saule: BEH C 18 1.7 µm, 50×2.1 mm; Eluent A: Wasser+0.05% Ameisensaure (99%); Eluent B: Acetonitril+0.05% Ameisensaure (99%); Gradient: 0-1.7 2-90% B, 1.7-2.0 90% B; Fluss 1.2 ml/min; Temperatur: 60° C.; DAD scan: 190-400 nm.

Preparative LC-MS Methods:

Method 7:

Instrument: Waters Autopurification MS SingleQuad; Column: Waters XBrigde C18 5µ100×30 mm; eluent A: water+0.2 vol. % aqueous ammonia (32%), eluent B: acetonitrile; gradient: 0-5.5 min. 5-100% B; flow 70 ml/min; temperature: 25° C.; DAD scan: 210-400 nm Method 8:

Instrument: Waters Autopurification MS SingleQuad; Column: Waters XBrigde C18 5µ50×50 mm; eluent A: water+0.1 vol % formic acid, eluent B: methanol; gradient: 0-0.50 min. 20% B; flow 50 to 100 ml/min, 0.50-8.00 min. 20-60% B; flow 100 ml/min, temperature: 25° C.; DAD scan: 210-400 nm Method 9:

Instrument: Labomatic HD-5000, pump head HDK-280, gradient module NDB-1000, fraction collector Labomatic Labocol Vario 2000, Knauer UV detector Azura UVD 2.1S, Prepcon 5 software. Column: Chromatorex C18 10 µM 120×30 mm; Eluent A: water+0.1% formic acid; Eluent B: acetonitrile; gradient: given for intermediates and examples, rate 150 mL/min, temperature 25° C.; UV 220 nm Method 10:

Instrument: Labomatic HD-5000, pump head HDK-280, gradient module NDB-1000, fraction collector Labomatic Labocol Vario 2000, Knauer UV detector Azura UVD 2.1S, Prepcon 5 software. Column: Chromatorex C18 10 µM 120×30 mm; Eluent A: 0.1% ammonia in water; Eluent B: acetonitrile; gradient: given for intermediates and examples, rate 150 mL/min, temperature 25° C.; UV 250 nm Method 11:

Instrument: Labomatic HD-5000, pump head HDK-280, gradient module NDB-1000, fraction collector Labomatic Labocol Vario 2000, Knauer UV detector Azura UVD 2.1S, Prepcon 5 software. Column: Chromatorex $C_{18\ 10}$ µM 300×50 mm; Eluent A: 0.1% ammonia in water; Eluent B: acetonitrile; gradient: given for intermediates and examples, rate 250 mL/min, temperature 25° C.; UV 250 nm NMR Spectra:

The multiplicities of proton signals in $^1H$ NMR spectra given in the following paragraphs reflect the observed signal form and do not take into account any higher-order signal phenomena. As a rule, the chemical shift data refers to the center of the signal in question.

In the case of wide multiplets, a range is specified. Signals hidden by solvent or water were either assigned tentatively or are not listed. Strongly broadened signals—e.g. caused by rapid rotation of molecular moieties or by interchanging protons—have also been assigned tentatively (often referred to as a broad multiplet or broad singlet) or are not shown.

The $^{1}$H-NMR data of selected compounds are listed in the form of $^{1}$H-NMR peaklists. Therein, for each signal peak the 6 value in ppm is given, followed by the signal intensity, reported in round brackets. The 6 value-signal intensity pairs from different peaks are separated by commas. Therefore, a peaklist is described by the general form: $\delta_1$(intensity$_1$), $\delta_2$ (intensity$_2$), . . . , $\delta_1$ (intensity$_1$), . . . , $\delta_n$ (intensity$_n$).

The intensity of a sharp signal correlates with the height (in cm) of the signal in a printed NMR spectrum. When compared with other signals, this data can be correlated to the real ratios of the signal intensities. In the case of broad signals, more than one peak, or the center of the signal along with their relative intensity, compared to the most intense signal displayed in the spectrum, are shown. A $^{1}$H-NMR peaklist is similar to a classical $^{1}$H-NMR readout, and thus usually contains all the peaks listed in a classical NMR interpretation. Moreover, similar to classical $^{1}$H-NMR printouts, peaklists can show solvent signals, signals derived from stereoisomers of the particular target compound, peaks of impurities, $^{13}$C satellite peaks, and/or spinning sidebands. The peaks of stereoisomers, and/or peaks of impurities are typically displayed with a lower intensity compared to the peaks of the target compound (e.g., with a purity of >90%). Such stereoisomers and/or impurities may be typical for the particular manufacturing process, and therefore their peaks may help to identify a reproduction of the manufacturing process on the basis of "by-product fingerprints". An expert who calculates the peaks of the target compound by known methods (MestReC, ACD simulation, or by use of empirically evaluated expectation values), can isolate the peaks of the target compound as required, optionally using additional intensity filters. Such an operation would be similar to peak-picking in classical $^{1}$H-NMR interpretation. A detailed description of the reporting of NMR data in the form of peaklists can be found in the publication "Citation of NMR Peaklist Data within Patent Applications" (cf. http://www.researchdisclosure.com/searching-disclosures, Research Disclosure Database Number 605005, 2014, 1 Aug. 2014). In the peak picking routine, as described in the Research Disclosure Database Number 605005, the parameter "MinimumHeight" can be adjusted between 1% and 4%. However, depending on the chemical structure and/or depending on the concentration of the measured compound it may be reasonable to set the parameter "MinimumHeight"<1%.

Syntheses of Intermediate 1 Compounds

Intermediate 1-1

3-[(1,4-dioxan-2-yl)methoxy]pyridine-4-carbonitrile

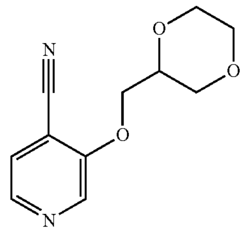 [SMILES: N#Cc1ccncc1OCC1COCCO1]

3-chloropyridine-4-carbonitrile (CAS 68325-15-5, 1.40 g, 10.1 mmol) and (1,4-dioxan-2-yl)methanol (CAS 143669-41-4, 1.31 g, 11.1 mmol) were dissolved in THF (45 ml). Potassium tert-butoxide (1.03 g, 9.14 mmol) was added and the mixture was stirred for 1 h at 0° C. The reaction mixture was diluted slowly with sat. ammonium chloride solution and extracted with EtOAc (3×). The organic phase was washed with brine and filtered over a water-repellent filter, concentrated under reduced pressure and purified by flash chromatography (silica, hexane/EtOAc gradient 0-100%; EtOAc/EtOH gradient 0-35%) to give 1.18 g of the title compound (53% yield).

$^{1}$H-NMR (400 MHz, DMSO-$d_6$): δ [ppm]=8.72 (s, 1H), 8.23-8.46 (m, 1H), 7.68-7.86 (m, 1H), 4.32 (d, 2H), 3.40-3.99 (m, 7H).

LC-MS (method 2): $R_t$=0.77 min; MS (ESipos): m/z=221 $[M+H]^+$

Intermediate 1-2

3-{[(3R)-4-methylmorpholin-3-yl]methoxy}pyridine-4-carbonitrile

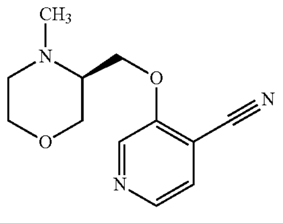 [SMILES: CN1CCOC[C@@H]1COc1cnccc1C#N]

To a solution of [(3S)-4-methylmorpholin-3-yl]methanol (CAS 1620510-50-0, 1.00 g, 7.62 mmol) in THF (20 ml) at 0° C. was slowly added sodium hydride (366 mg, 9.15 mmol, 60% purity). The reaction mixture was stirred for 3 hat RT. 3-chloropyridine-4-carbonitrile (CAS 68325-15-5, 1.06 g, 7.62 mmol) in THF (10 ml) was added and the mixture was stirred overnight. The reaction mixture was quenched with 1N HCl until pH=7. The suspension was filtered through a hydrophobic filter paper and the filter cake was washed with EtOAc. The filtrate was concentrated under reduced pressure and the residue was purified by flash chromatography (basic silica, hexane/EtOAc gradient 0-100%) to give 355 mg of the title compound (20% yield).

$^{1}$H-NMR (400 MHz, DMSO-$d_6$): δ [ppm]=8.75 (s, 1H), 8.40 (d, 1H), 7.78 (d, 1H), 4.44 (dd, 1H), 4.23 (dd, 1H), 3.87 (dd, 1H), 3.71 (dt, 1H), 3.50 (td, 1H), 3.35-3.41 (m, 1H), 2.65-2.71 (m, 1H), 2.45-2.49 (m, 1H), 2.29-2.35 (m, 3H), 2.24 (ddd, 1H).

LC-MS (method 2): $R_t$=0.72 min; MS (ESIpos): m/z=234.2 $[M+H]^+$

Intermediate 1-3

3-{[4-methylmorpholin-2-yl]methoxy}pyridine-4-carbonitrile

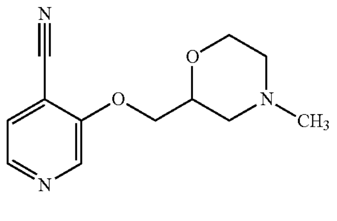 [SMILES: CN1CCOC(COc2cnccc2C#N)C1]

Using an analogous method as described for intermediate 1-1 with 3-chloropyridine-4-carbonitrile (CAS 68325-15-5, 764 mg, 5.51 mmol) and [4-methylmorpholin-2-yl]methanol (CAS 40987-46-0, 940 mg, 7.17 mmol) as the starting materials; 836 mg (90% purity, 59% yield) of the title compound were prepared.

$^1$H-NMR (400 MHz, DMSO-$d_6$): δ [ppm]=1.893 (0.97), 1.920 (1.44), 1.947 (1.07), 1.954 (0.50), 1.962 (0.54), 1.983 (1.01), 1.991 (1.03), 2.011 (0.58), 2.019 (0.52), 2.197 (16.00), 2.518 (0.41), 2.589 (0.80), 2.593 (0.82), 2.617 (0.73), 2.621 (0.74), 2.766 (0.66), 2.770 (0.95), 2.794 (0.63), 2.798 (0.89), 3.513 (0.60), 3.520 (0.73), 3.541 (1.36), 3.547 (1.39), 3.570 (0.80), 3.575 (0.67), 3.793 (0.74), 3.796 (1.10), 3.801 (1.12), 3.805 (0.92), 3.808 (0.85), 3.814 (0.79), 3.821 (1.18), 3.826 (1.18), 3.833 (1.27), 3.839 (0.66), 4.316 (5.03), 4.329 (4.72), 7.772 (2.40), 7.774 (2.63), 7.785 (2.49), 8.381 (3.41), 8.393 (3.28), 8.714 (4.32).

LC-MS (method 2): $R_t$=0.70 min; MS (ESIpos): m/z=234.2 [M+H]$^+$

Intermediate 1-4

3-{[(3S)-4-methylmorpholin-3-yl]methoxy}pyridine-4-carbonitrile

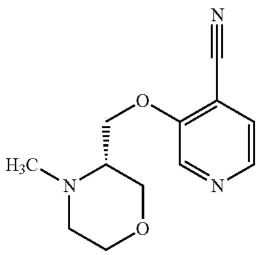 [SMILES: CN1CCOC[C@H]1COc1cnccc1C#N]

Using an analogous method as described for intermediate 1-2 with 3-chloropyridine-4-carbonitrile (CAS 68325-15-5, 1.00 g, 7.24 mmol) and [(3R)-4-methylmorpholin-3-yl]methanol (1.00 g, 95% purity, 7.24 mmol; CAS 1620510-51-1) as the starting materials; 823 mg (99% purity, 48% yield) of the title compound were prepared.

$^1$H-NMR (400 MHz, DMSO-$d_6$): δ [ppm]=2.211 (0.52), 2.219 (0.64), 2.236 (0.66), 2.240 (0.68), 2.245 (0.68), 2.249 (0.72), 2.266 (0.69), 2.274 (0.63), 2.306 (16.00), 2.472 (0.48), 2.475 (0.50), 2.518 (1.22), 2.522 (0.71), 2.658 (0.56), 2.664 (1.27), 2.671 (0.67), 2.687 (0.47), 2.694 (0.96), 2.701 (0.47), 3.356 (1.17), 3.378 (1.16), 3.384 (1.30), 3.406 (1.20), 3.472 (0.50), 3.478 (0.58), 3.499 (0.80), 3.506 (0.81), 3.525 (0.71), 3.532 (0.61), 3.685 (0.44), 3.692 (0.86), 3.698 (0.45), 3.720 (0.66), 3.856 (0.80), 3.864 (0.81), 3.884 (0.73), 3.892 (0.72), 4.209 (1.03), 4.223 (1.01), 4.234 (1.29), 4.249 (1.23), 4.417 (1.25), 4.429 (1.28), 4.443 (1.03), 4.454 (0.99), 7.778 (2.39), 7.780 (2.38), 7.790 (2.45), 7.792 (2.50), 8.391 (3.23), 8.403 (3.11), 8.745 (3.91).

LC-MS (method 2): Rt=0.70 min; MS (ESipos): m/z=234 [M+H]$^+$

Intermediate 1-5 tert-butyl (2S)-2-{[(4-cyanopyridin-3-yl)oxy]methyl}morpholine-4-carboxylate

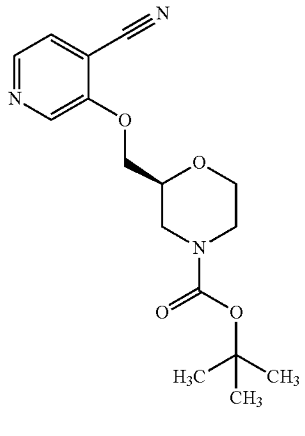 [SMILES: CC(C)(C)OC(=O)N1CCO[C@H](COc2cnccc2C#N)C1]

Using an analogous method as described for intermediate 1-1 with 3-chloropyridine-4-carbonitrile (CAS 68325-15-5, 2.55 g, 18.4 mmol) and tert-butyl (2S)-2-(hydroxymethyl)morpholine-4-carboxylate (CAS 135065-76-8, 4.00 g, 18.4 mmol) as the starting materials; 4.82 g (90% purity, 74% yield) of the title compound were prepared.

$^1$H-NMR (400 MHz, DMSO-$d_6$): δ [ppm]=1.41 (s, 9H), 2.72-3.05 (m, 2H), 3.46 (br d, 1H), 3.67-3.82 (m, 2H), 3.82-3.88 (m, 1H), 4.00 (s, 1H), 4.37 (br d, 2H), 7.79 (d, 1H), 8.40 (d, 1H), 8.73 (s, 1H).

LC-MS (method 2): $R_t$=1.06 min; MS (ESIpos): m/z=320 [M+H]$^+$

Intermediate 1-6

3-[2-(1,4-dioxan-2-yl)ethoxy]pyridine-4-carbonitrile

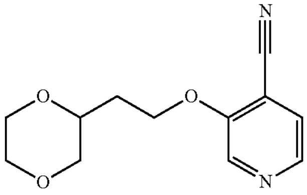 [SMILES: N#Cc1ccncc1OCCC1COCCO1]

Using an analogous method as described for intermediate 1-2 with 3-chloropyridine-4-carbonitrile (CAS 68325-15-5, 2.10 g, 15.1 mmol) and 2-(1,4-dioxan-2-yl)ethan-1-ol (CAS 151720-04-6, 2.00 g, 15.1 mmol) as the starting materials; 2.89 g (99% purity, 81% yield) of the title compound were prepared.

$^1$H-NMR (400 MHz, DMSO-$d_6$) δ [ppm]: 1.754 (0.63), 1.768 (1.37), 1.774 (0.82), 1.781 (0.98), 1.790 (2.18), 1.803 (3.39), 1.810 (2.10), 1.817 (1.93), 1.824 (3.23), 1.838 (2.78), 1.855 (2.41), 1.867 (2.45), 1.869 (2.40), 1.874 (2.53), 1.886 (2.23), 1.902 (0.99), 1.910 (0.87), 1.922 (0.67), 2.326 (0.72), 2.668 (0.69), 3.223 (4.26), 3.247 (5.57), 3.250 (5.62), 3.276 (5.26), 3.428 (1.77), 3.434 (1.89), 3.455 (4.59), 3.462 (4.80), 3.483 (3.76), 3.489 (3.97), 3.530 (3.36), 3.535 (3.38), 3.558 (4.71), 3.564 (5.40), 3.585 (1.93), 3.592 (3.08), 3.626 (4.58), 3.631 (4.33), 3.654 (3.70), 3.659 (4.02), 3.668 (1.98), 3.673 (1.97), 3.680 (2.77), 3.687 (2.85), 3.693 (2.89), 3.706 (6.98), 3.712 (6.06), 3.724 (1.75), 3.735 (3.40), 3.759 (4.77), 3.766

(4.02), 3.788 (4.04), 3.794 (3.73), 4.315 (0.93), 4.329 (1.18), 4.339 (3.54), 4.354 (6.92), 4.359 (5.21), 4.370 (6.49), 4.384 (3.79), 4.392 (1.47), 4.408 (0.68), 7.778 (9.22), 7.790 (9.58), 8.380 (10.88), 8.392 (10.45), 8.698 (16.00).

LC-MS (method 6): Rt=0.64 min; MS (ESIpos): m/z=235 $[M+H]^+$

Intermediate 1-7

3-[(5,5-dimethyl-1,4-dioxan-2-yl)methoxy]pyridine-4-carbonitrile

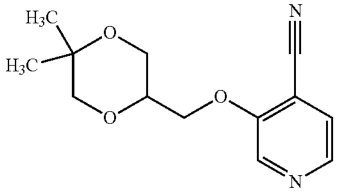 [SMILES: CC1(C)COC(COc2cnccc2C#N)CO1]

Using an analogous method as described for intermediate 1-2 with 3-chloropyridine-4-carbonitrile (CAS 68325-15-5, 948 mg, 6.84 mmol) and (5,5-dimethyl-1,4-dioxan-2-yl) methanol (1.00 g, 6.84 mmol; CAS 54321-57-2) as the starting materials; 1.31 g (95% purity, 73% yield) of the title compound were prepared.

$^1$H-NMR (400 MHz, DMSO-$d_6$): δ [ppm]=1.014 (0.69), 1.048 (16.00), 1.172 (0.55), 1.200 (0.51), 1.263 (13.01), 1.987 (0.92), 2.518 (0.62), 2.523 (0.43), 3.313 (1.67), 3.340 (2.27), 3.342 (2.21), 3.542 (2.95), 3.570 (2.39), 3.604 (1.50), 3.627 (1.97), 3.734 (1.24), 3.760 (3.08), 3.781 (2.25), 3.787 (2.73), 3.791 (1.58), 3.796 (0.77), 3.802 (0.63), 4.356 (3.63), 4.365 (4.41), 7.780 (3.42), 7.792 (3.63), 8.387 (4.49), 8.399 (4.29), 8.715 (5.54).

LC-MS (method 6): Rt=0.75 min; MS (ESIpos): m/z=249 $[M+H]^+$

Intermediate 1-8

3-{[(2S)-1,4-dioxan-2-yl]methoxy}pyridine-4-carbonitrile

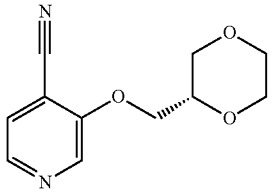 [SMILES: N#Cc1ccncc1OC[C@@H]1COCCO1]

Using an analogous method as described for intermediate 1-1 with 3-chloropyridine-4-carbonitrile (CAS 68325-15-5, 1.00 g, 7.22 mmol) and [(2R)-1,4-dioxan-2-yl]methanol (CAS406913-88-0, 938 mg, 7.94 mmol) as the starting materials; 490 mg (95% purity, 29% yield) of the title compound were prepared.

Optical rotation: $[\alpha]_D$=—1.68°+/−0.35° (c=7 mg/ml, methanol)

$^1$H-NMR (400 MHz, DMSO-$d_6$): δ ppm=3.41-3.53 (m, 2H), 3.59-3.72 (m, 2H), 3.75-3.81 (m, 1H), 3.82-3.87 (m, 1H), 3.87-3.95 (m, 1H), 4.27-4.37 (m, 2H), 7.77-7.80 (m, 1H), 8.38-8.41 (m, 1H), 8.71-8.73 (m, 1H).

Intermediate 1-9 tert-butyl (3R)-3-{[(4-cyanopyridin-3-yl)oxy]methyl}morpholine-4-carboxylate

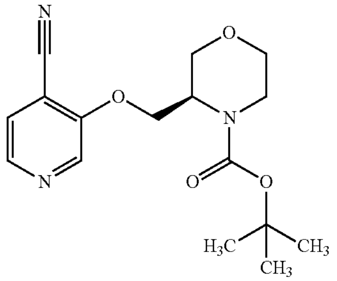 [SMILES: CC(C)(C)OC(=O)N1CCOC[C@@H]1COc1cnccc1C#N]

To a solution of tert-butyl (3S)-3-(hydroxymethyl)morpholine-4-carboxylate (4.30 g, 19.8 mmol) in THF (28 ml) at 0° C. was slowly added sodium hydride (1.55 g, 55% purity, 35.6 mmol). The reaction mixture was stirred for 1 h. 3-fluoropyridine-4-carbonitrile (CAS 113770-88-0, 2.42 g, 19.8 mmol) in THF (14 ml) was added and the mixture was stirred for 4 h at 0° C. The reaction mixture was quenched with 2N HCl until pH=6-7 and was extracted with EE. The organic layer was filtered through a water repellent filter paper and concentrated under reduced pressure. The residue was purified by flash chromatography (silica, DCM/EtOH gradient 0-7%) to give 4 g of the title compound (70% yield).

LC-MS (method 6): $R_t$=0.95 min; MS (ESIpos): m/z=264 $[M+H]^+$

Intermediate 1-10 tert-butyl (2R)-2-{[(4-cyanopyridin-3-yl)oxy]methyl}morpholine-4-carboxylate

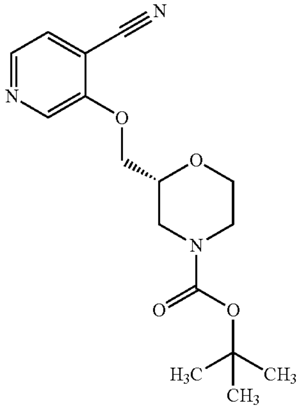 [SMILES: CC(C)(C)OC(=O)N1CCO[C@@H](COc2cnccc2C#N)C1]

Using an analogous method as described for intermediate 1-1 with 3-chloropyridine-4-carbonitrile (CAS 68325-15-5, 3.25 g, 23.5 mmol) and tert-butyl (2R)-2-(hydroxymethyl) morpholine-4-carboxylate (CAS 135065-71-3, 5.10 g, 23.5 mmol) as the starting materials; 6.92 g (90% purity, 83% yield) of the title compound were prepared.

$^1$H-NMR (400 MHz, DMSO-$d_6$): δ [ppm]=1.41 (s, 9H), 2.73-3.00 (m, 2H), 3.39-3.50 (m, 1H), 3.75 (m, 2H), 3.82-

3.89 (m, 1H), 3.95-4.00 (m, 1H), 4.37 (br d, 2H), 7.79 (d, 1H), 8.40 (d, 1H), 8.73 (s, 1H).

LC-MS (method 2): $R_t$=1.04 min; MS (ESIpos): m/z=320 $[M+H]^+$

Intermediate 1-11

3-[(1S)-1-(1,4-dioxan-2-yl)ethoxy]pyridine-4-carbonitrile

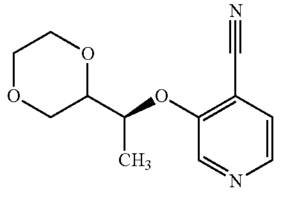 [SMILES: C[C@H](Oc1cnccc1C#N)C1COCCO1]

Using an analogous method as described for intermediate 1-9 with 3-fluoropyridine-4-carbonitrile (878 mg, 7.19 mmol) and (1S)-1-[1,4-dioxan-2-yl]ethan-1-ol (CAS 1372875-59-6, 950 mg, 7.19 mmol) as the starting materials; 1.68 g (95% purity, 95% yield) of the title compound were prepared.

$^1$H-NMR (400 MHz, DMSO-$d_6$): δ ppm=0.988 (0.85), 1.004 (0.92), 1.056 (0.59), 1.071 (0.60), 1.154 (4.47), 1.166 (0.63), 1.172 (9.29), 1.189 (4.59), 1.276 (12.44), 1.292 (12.55), 1.325 (11.08), 1.341 (11.16), 1.987 (16.00), 2.518 (1.63), 2.522 (1.05), 3.300 (0.46), 3.396 (1.81), 3.421 (2.99), 3.424 (2.99), 3.429 (1.78), 3.450 (5.06), 3.457 (3.42), 3.472 (1.97), 3.478 (1.62), 3.485 (2.38), 3.497 (2.19), 3.500 (1.91), 3.525 (2.26), 3.552 (1.16), 3.559 (1.31), 3.582 (2.48), 3.588 (2.91), 3.611 (1.70), 3.616 (2.62), 3.638 (4.15), 3.642 (3.63), 3.664 (3.89), 3.671 (4.01), 3.676 (1.93), 3.683 (1.76), 3.685 (1.80), 3.689 (1.79), 3.695 (1.76), 3.701 (1.17), 3.704 (1.27), 3.707 (1.26), 3.710 (1.28), 3.744 (1.82), 3.750 (3.32), 3.757 (1.01), 3.778 (3.94), 3.784 (2.19), 3.807 (1.47), 3.813 (1.33), 3.906 (1.40), 3.912 (1.35), 3.935 (1.24), 3.941 (1.18), 3.999 (1.24), 4.016 (3.72), 4.034 (3.66), 4.052 (1.20), 4.804 (0.41), 4.821 (1.95), 4.836 (3.43), 4.852 (2.64), 4.864 (1.34), 7.755 (3.58), 7.757 (3.60), 7.769 (4.33), 7.771 (3.80), 7.783 (3.28), 7.785 (3.20), 8.351 (4.95), 8.363 (4.90), 8.368 (4.48), 8.380 (4.17), 8.749 (6.40), 8.772 (5.46).

LC-MS (method 6): $R_t$=0.64 min; MS (ESipos): m/z=235 $[M+H]^+$

Intermediate 1-12

3-{(1R)-1-[1,4-dioxan-2-yl]ethoxy}pyridine-4-carbonitrile

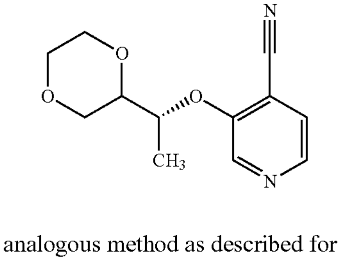

Using an analogous method as described for intermediate 1-9 with 3-fluoropyridine-4-carbonitrile (905 mg, 7.42 mmol) and (1R)-1-[1,4-dioxan-2-yl]ethan-1-ol (CAS 1372881-98-5, 980 mg, 7.42 mmol) as the starting materials; 1.39 g (95% purity, 76% yield) of the title compound were prepared.

$^1$H-NMR (400 MHz, DMSO-$d_6$): δ ppm=1.274 (0.82), 1.289 (0.87), 1.322 (16.00), 1.337 (15.97), 1.984 (0.48), 2.331 (0.56), 2.673 (0.57), 3.427 (2.95), 3.448 (3.45), 3.455 (3.30), 3.471 (3.27), 3.482 (2.59), 3.496 (3.79), 3.499 (3.36), 3.524 (3.41), 3.580 (1.59), 3.586 (1.80), 3.609 (2.32), 3.615 (2.92), 3.636 (5.12), 3.662 (3.60), 3.668 (3.70), 3.680 (2.08), 3.687 (1.49), 3.693 (1.53), 3.698 (1.52), 3.704 (1.41), 3.746 (3.19), 3.754 (1.74), 3.775 (2.26), 3.903 (2.52), 3.909 (2.44), 3.932 (2.24), 3.937 (2.13), 4.818 (0.65), 4.833 (2.08), 4.845 (2.30), 4.849 (2.22), 4.861 (2.00), 4.876 (0.57), 7.766 (5.15), 7.778 (5.29), 8.348 (0.42), 8.365 (6.23), 8.377 (6.01), 8.743 (0.51), 8.765 (9.13).

LC-MS (method 6): $R_t$=0.67 min; MS (ESIpos): m/z=235 $[M+H]^+$

Intermediate 1-71

3-[1-(4-methylmorpholin-2-yl)ethoxy]isonicotinonitrile

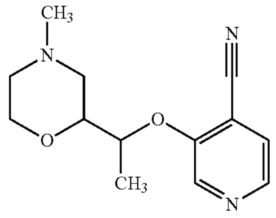 [SMILES: CC(Oc1cnccc1C#N)C1CN(C)CCO1]

Using an analogous method as described for intermediate 1-9 with 3-fluoropyridine-4-carbonitrile (824 mg, 6.75 mmol) and 1-(4-methylmorpholin-2-yl)ethanol (980 mg, 6.75 mmol, CAS 1540922-49-3) as the starting materials; 817 mg (99% purity, 48% yield) of the title compound were prepared after column chromatography using the Biotage Isolera.

$^1$H-NMR (400 MHz, DMSO-$d_6$) δ [ppm]: 1.285 (4.44), 1.300 (4.47), 1.318 (5.38), 1.333 (5.31), 1.848 (0.57), 1.874 (0.94), 1.901 (0.63), 1.927 (0.93), 1.933 (0.66), 1.953 (2.04), 1.961 (1.23), 1.981 (1.32), 1.990 (0.60), 2.188 (16.00), 2.518 (1.33), 2.522 (0.90), 2.572 (0.89), 2.600 (0.79), 2.718 (0.54), 2.746 (0.52), 2.839 (0.64), 2.867 (0.60), 3.485 (0.78), 3.488 (0.66), 3.491 (0.85), 3.516 (1.00), 3.522 (0.92), 3.544 (0.48), 3.550 (0.42), 3.562 (0.44), 3.568 (0.54), 3.573 (0.73), 3.578 (0.77), 3.587 (0.81), 3.593 (0.83), 3.598 (0.85), 3.604 (0.71), 3.772 (0.51), 3.777 (0.56), 3.781 (0.78), 3.786 (0.61), 3.789 (0.59), 3.794 (0.56), 3.800 (0.46), 3.805 (0.46), 3.809 (0.64), 3.814 (0.50), 3.817 (0.45), 4.818 (0.60), 4.833 (0.97), 4.848 (0.79), 4.858 (0.65), 4.862 (0.67), 4.874 (0.57), 7.746 (1.41), 7.760 (2.88), 7.772 (1.71), 8.341 (1.93), 8.355 (2.69), 8.368 (2.12), 8.745 (2.34), 8.766 (2.68).

LC-MS (method 6): $R_t$=0.32 min; MS (ESIpos): m/z=248 $[M+H]^+$

Syntheses of Intermediate 2 Compounds

Intermediate 2-1

1-{3-[(1,4-dioxan-2-yl)methoxy]pyridin-4-yl}methanamine

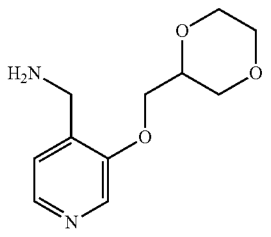 [SMILES: NCc1ccncc1OCC1COCCO1]

An autoclave was charged with 3-[(1,4-dioxan-2-yl)methoxy]pyridine-4-carbonitrile (intermediate 1-1, 1.17 g, 5.34 mmol), ammonia (19 ml, 7.0 M in methanol, 850 mmol) and Raney-Nickel (CAS 7440-02-0, 783 mg, 50% wetted) and the mixture was stirred under 25 bar hydrogen atmosphere at RT for 22 h. The mixture was filtered through a pad of celite, eluted with methanol and the combined filtrates were concentrated under reduced pressure. The residue was used directly in the next step without further purification (1.13 g, 94% yield).

$^1$H-NMR (400 MHz, DMSO-$d_6$): δ [ppm]=8.24 (s, 1H), 8.17 (d, 1H), 7.38 (d, 1H), 4.09 (d, 2H), 3.73-3.91 (m, 3H), 3.59-3.73 (m, 4H), 3.46-3.52 (m, 2H), 3.39-3.45 (m, 2H). 2.06 (br., 2H).

LC-MS (method 2): $R_t$=0.54 min; MS (ESipos): m/z=225 [M+H]$^+$

Intermediate 2-2

1-(3-{[(3R)-4-methylmorpholin-3-yl]methoxy}pyridin-4-yl)methanamine

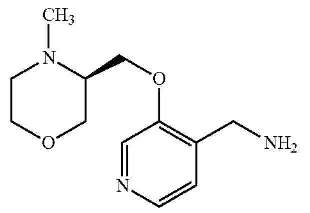 [SMILES: CN1CCOC[C@@H]1COc1cnccc1CN]

Using an analogous method as described for intermediate 2-1 with 3-{[(3R)-4-methylmorpholin-3-yl]methoxy}pyridine-4-carbonitrile (intermediate 1-2, 355 mg, 1.52 mmol) as the starting material; 350 mg of the title compound were prepared (89% yield).

$^1$H-NMR (400 MHz, DMSO-$d_6$): δ [ppm]=8.24-8.31 (m, 1H), 8.17 (d, 1H), 7.39 (d, 1H), 4.18-4.27 (m, 1H), 4.00 (dd, 1H), 3.86 (dd, 1H), 3.63-3.75 (m, 3H), 3.42-3.55 (m, 1H), 3.36-3.41 (m, 1H), 2.67 (dq, 1H), 2.40-2.47 (m, 1H), 2.19-2.31 (m, 4H), 1.63-2.19 (m, 2H).

Intermediate 2-3

1-(3-{[4-methylmorpholin-2-yl]methoxy}pyridin-4-yl)methanamine

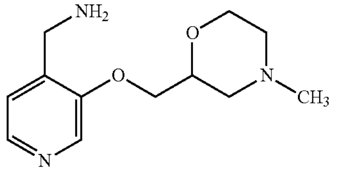 [SMILES: CN1CCOC(COc2cnccc2CN)C1]

Using an analogous method as described for intermediate 2-1 with 3-{[4-methylmorpholin-2-yl]methoxy}pyridine-4-carbonitrile (intermediate 1-3, 836 mg, 3.58 mmol) as the starting material; 860 mg (90% purity, 91% yield) of the title compound were prepared.

$^1$H-NMR (400 MHz, DMSO-$d_6$): δ [ppm]=1.68-1.84 (br s, 2H), 1.85-1.94 (t, 1H), 1.94-2.05 (td, 1H), 2.19 (s, 3H), 2.57-2.64 (d, 1H), 2.73-2.83 (d, 1H), 3.46-3.63 (t, 1H), 3.63-3.73 (s, 2H), 3.73-3.86 (m, 3H), 4.10 (br d, 2H), 7.34-7.44 (d, 1H), 8.10-8.20 (d, 1H), 8.21-8.30 (s, 1H).

LC-MS (method 2): $R_t$=0.56 min; MS (ESIpos): m/z=238 [M+H]$^+$

Intermediate 2-4

1-(3-{[(3S)-4-methylmorpholin-3-yl]methoxy}pyridin-4-yl)methanamine

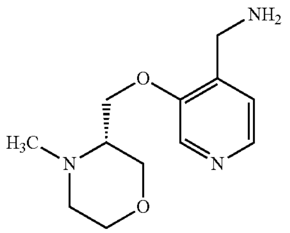 [SMILES: CN1CCOC[C@H]1COc1cnccc1CN]

Using an analogous method as described for intermediate 2-1 with 3-{[(3S)-4-methylmorpholin-3-yl]methoxy}pyridine-4-carbonitrile (intermediate 1-4, 823 mg, 3.53 mmol) as the starting material; 798 mg (90% purity, 86% yield) of the title compound were prepared.

$^1$H-NMR (400 MHz, DMSO-$d_6$): δ [ppm]=1.865 (0.49), 2.199 (0.64), 2.210 (1.08), 2.228 (0.99), 2.233 (0.96), 2.236 (0.96), 2.254 (0.85), 2.263 (0.81), 2.269 (0.55), 2.284 (16.00), 2.327 (0.53), 2.430 (0.78), 2.439 (0.81), 2.447 (0.65), 2.518 (2.11), 2.523 (1.42), 2.649 (0.75), 2.654 (1.38), 2.660 (0.91), 2.669 (0.65), 2.674 (0.60), 2.678 (0.83), 2.684 (1.22), 2.690 (0.66), 3.361 (1.52), 3.365 (1.53), 3.388 (1.10), 3.469 (0.59), 3.474 (0.65), 3.496 (1.15), 3.502 (1.16), 3.523 (0.75), 3.528 (0.68), 3.683 (2.49), 3.690 (2.42), 3.712 (0.79), 3.719 (1.11), 3.846 (1.01), 3.853 (1.04), 3.873 (0.94), 3.880 (0.91), 3.982 (0.79), 3.997 (0.86), 4.007 (1.03), 4.021 (0.96), 4.215 (1.01), 4.226 (1.09), 4.240 (0.86), 4.250 (0.84), 7.379 (0.99), 7.389 (1.01), 8.168 (1.06), 8.179 (1.11), 8.259 (1.53).

Intermediate 2-5 tert-butyl (2S)-2-({[4-(aminomethyl)pyridin-3-yl]oxy}methyl)morpholine-4-carboxylate

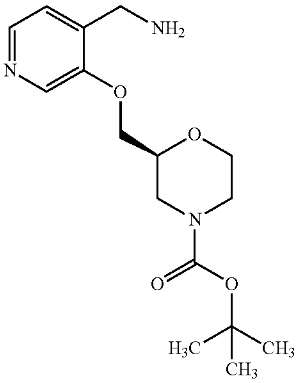 [SMILES: CC(C)(C)OC(=O)N1CCO[C@H](COc2cnccc2CN)C1]

Using an analogous method as described for intermediate 2-1 with tert-butyl (2S)-2-{[(4-cyanopyridin-3-yl)oxy]methyl}morpholine-4-carboxylate (intermediate 1-5, 5.75 g, 18.0 mmol) as the starting material; 6.00 g (95% purity, 98% yield) of the title compound were prepared.

1H-NMR (400 MHz, DMSO-$d_6$): δ [ppm]=1.41 (s, 9H), 3.16 (s, 2H), 3.39-3.49 (m, 2H), 3.66-3.79 (m, 5H), 3.79-3.98 (m, 3H), 4.07-4.20 (m, 3H), 7.39 (d, 1H), 8.19 (d, 1H), 8.27 (s, 1H).

LC-MS (method 2): $R_t$=0.84 min; MS (ESIpos): m/z=324 $[M+H]^+$

Intermediate 2-6

1-{3-[2-(1,4-dioxan-2-yl)ethoxy]pyridin-4-yl}methanamine

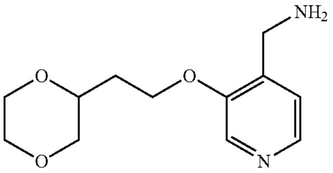 [SMILES: NCc1ccncc1OCCC1COCCO1]

Using an analogous method as described for intermediate 2-1 with 3-[2-(1,4-dioxan-2-yl)ethoxy]pyridine-4-carbonitrile (intermediate 1-6, 2.89 g, 12.3 mmol) as the starting material; 2.22 g (90% purity, 68% yield) of the title compound were prepared.

$^1$H-NMR (400 MHz, DMSO-$d_6$): δ [ppm]=1.536 (0.40), 1.729 (1.99), 1.751 (3.41), 1.765 (5.01), 1.785 (6.00), 1.804 (5.59), 1.817 (5.34), 1.834 (4.06), 1.852 (2.92), 1.870 (2.15), 2.326 (1.02), 2.669 (1.04), 3.159 (0.53), 3.208 (5.54), 3.235 (8.67), 3.261 (7.11), 3.424 (3.46), 3.430 (3.63), 3.451 (7.09), 3.457 (7.51), 3.479 (5.43), 3.485 (5.78), 3.528 (4.90), 3.534 (5.03), 3.557 (6.69), 3.563 (7.65), 3.584 (3.06), 3.590 (4.57), 3.622 (8.16), 3.653 (8.66), 3.688 (14.98), 3.697 (16.00), 3.731 (13.03), 3.759 (6.36), 4.136 (7.05), 4.152 (13.01), 4.167 (8.38), 7.385 (5.36), 7.394 (5.58), 8.163 (5.21), 8.172 (5.56), 8.224 (7.44).

Intermediate 2-7

1-{3-[(5,5-dimethyl-1,4-dioxan-2-yl)methoxy]pyridin-4-yl}methanamine

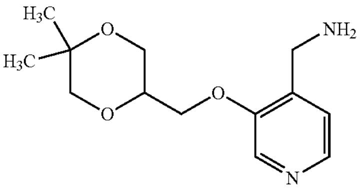 [SMILES: CC1(C)COC(COc2cnccc2CN)CO1]

Using an analogous method as described for intermediate 2-1 with 3-[(5,5-dimethyl-1,4-dioxan-2-yl)methoxy]pyridine-4-carbonitrile (intermediate 1-7, 1.30 g, 5.24 mmol) as the starting material; 1.26 g (90% purity, 86% yield) of the title compound were prepared. $^1$H-NMR (400 MHz, DMSO-$d_6$) δ [ppm]: 1.014 (0.96), 1.049 (16.00), 1.201 (0.72), 1.262 (13.58), 1.751 (0.48), 2.518 (2.17), 2.523 (1.47), 3.308 (2.76), 3.539 (2.43), 3.567 (1.99), 3.601 (1.13), 3.623 (1.75), 3.694 (1.97), 3.720 (2.07), 3.746 (2.38), 3.783 (0.46), 4.128 (3.01), 4.136 (2.80), 7.386 (0.85), 8.181 (0.83), 8.237 (0.96).

Intermediate 2-8

1-(3-{[(2S)-1,4-dioxan-2-yl]methoxy}pyridin-4-yl)methanamine

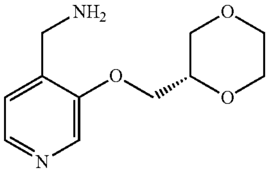 [SMILES: NCc1ccncc1OC[C@@H]1COCCO1]

Using an analogous method as described for intermediate 2-1 with 3-{[(2S)-1,4-dioxan-2-yl]methoxy}pyridine-4-carbonitrile (intermediate 1-8, 1.24 g, 5.63 mmol) as the starting material; 1.56 g (80% purity, 99% yield) of the title compound were prepared.

$^1$H-NMR (400 MHz, DMSO-$d_6$): δ [ppm]=1.232 (0.52), 1.845 (1.06), 2.518 (2.37), 2.523 (1.54), 3.159 (14.24), 3.171 (14.33), 3.376 (0.69), 3.379 (0.65), 3.404 (2.41), 3.419 (0.41), 3.428 (3.79), 3.431 (3.86), 3.439 (0.59), 3.447 (0.69), 3.455 (2.71), 3.465 (1.97), 3.474 (0.57), 3.486 (2.71), 3.493 (2.97), 3.508 (1.01), 3.520 (2.61), 3.592 (0.45), 3.601 (1.92), 3.608 (2.10), 3.630 (2.77), 3.636 (3.65), 3.659 (5.73), 3.661 (5.45), 3.683 (16.00), 3.700 (1.95), 3.754 (3.49), 3.762 (2.18), 3.784 (2.51), 3.794 (0.57), 3.812 (0.61), 3.823 (2.48), 3.829 (3.16), 3.842 (0.81), 3.849 (2.07), 3.856 (6.45), 3.868 (1.93), 3.874 (1.37), 3.880 (1.69), 3.887 (1.30), 3.892 (1.13), 3.899 (0.89), 4.087 (11.44), 4.099 (10.46), 4.111 (2.62), 4.125 (1.15), 7.380 (4.02), 7.391 (4.11), 7.411 (0.67), 7.423 (0.67), 8.168 (6.28), 8.179 (6.26), 8.184 (1.58), 8.196 (1.02), 8.230 (10.21), 8.274 (1.76).

Intermediate 2-9 tert-butyl (3R)-3-({[4-(aminomethyl)pyridin-3-yl]oxy}methyl)morpholine-4-carboxylate

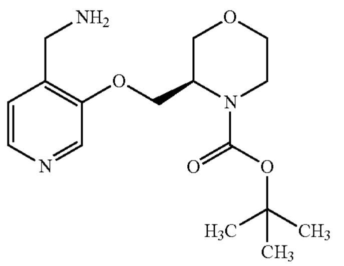 [SMILES: CC(C)(C)OC(=O)N1CCOC[C@@H]1COc1cnccc1CN]

Using an analogous method as described for intermediate 2-1 with tert-butyl (3R)-3-{[(4-cyanopyridin-3-yl)oxy]methyl}morpholine-4-carboxylate (intermediate 1-9, 4.00 g, 12.5 mmol) as the starting material; 3.65 g of the title compound were prepared (86% yield).

$^1$H-NMR (400 MHz, DMSO-$d_6$): δ [ppm]=1.038 (0.41), 1.055 (0.77), 1.073 (0.44), 1.363 (10.92), 1.754 (6.47), 2.200 (1.02), 2.325 (1.05), 2.330 (1.42), 2.334 (1.05), 2.521 (5.72), 2.526 (3.72), 2.667 (0.88), 2.672 (1.22), 2.676 (0.89), 3.057 (1.02), 3.068 (1.10), 3.087 (1.65), 3.090 (1.62), 3.097 (1.89), 3.101 (1.73), 3.120 (2.21), 3.130 (2.39), 3.168 (16.00), 3.210 (1.86), 3.235 (0.59), 3.240 (1.07), 3.258 (1.25), 3.265 (1.40), 3.286 (1.75), 3.294 (2.07), 3.316 (3.15), 3.365 (3.67), 3.372 (3.73), 3.395 (1.88), 3.402 (1.68), 3.462 (1.41), 3.470 (1.43), 3.503 (3.53), 3.534 (2.78), 3.682 (7.14), 3.764 (1.68), 3.774 (1.81), 3.792 (3.17), 3.802 (2.81), 3.820 (1.93), 3.855 (0.89), 3.859 (1.19), 3.865 (1.80), 3.869 (2.32), 3.873 (3.62), 3.882 (2.64), 3.886 (3.02), 3.889 (2.79), 3.893 (4.31), 3.899 (3.39), 3.902 (2.87), 3.927 (2.09), 4.111 (1.76), 4.227 (3.64), 4.303 (0.96), 4.315 (1.37), 4.329 (3.71), 4.331 (3.43), 4.338 (1.95), 4.345 (2.50), 7.401 (2.60), 8.192 (2.81), 8.337 (2.91).

LC-MS (method 1): $R_t$=0.49 min; MS (ESipos): m/z=324 $[M+H]^+$

Intermediate 2-10 tert-butyl (2R)-2-({[4-(aminomethyl)pyridin-3-yl]oxy}methyl)morpholine-4-carboxylate

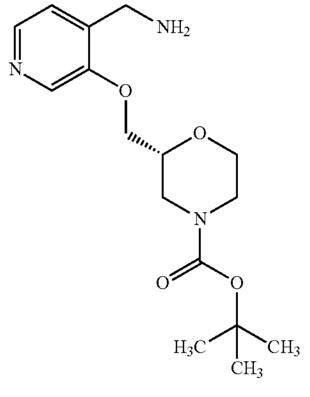 [SMILES: CC(C)(C)OC(=O)N1CCO[C@@H](COc2cnccc2CN)C1]

Using an analogous method as described for intermediate 2-1 with tert-butyl (2R)-2-{[(4-cyanopyridin-3-yl)oxy]methyl}morpholine-4-carboxylate (intermediate 1-10, 6.92 g, 21.7 mmol) as the starting material; 6.95 g of the title compound were prepared (90% purity, 89% yield).

$^1$H-NMR (400 MHz, DMSO-$d_6$): δ [ppm]=1.41 (s, 9H), 2.70-3.01 (m, 2H), 3.17 (d, 3H), 3.41-3.52 (m, 1H), 3.63-3.70 (m, 2H), 3.70-3.81 (m, 2H), 3.82-4.00 (m, 2H), 4.08-4.18 (m, 3H), 7.39 (d, 1H), 8.18 (d, 1H), 8.25 (s, 1H).

LC-MS (method 2): $R_t$=0.84 min; MS (ESIpos): m/z=324 $[M+H]^+$

Intermediate 2-11

1-{3-[(1 S)-1-(1,4-dioxan-2-yl)ethoxy]pyridin-4-yl}methanamine

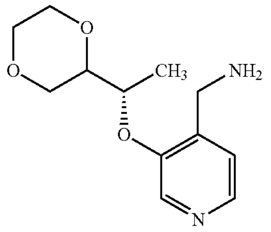 [SMILES: C[C@H](Oc1cnccc1CN)C1COCCO1]

Using an analogous method as described for intermediate 2-1 with 3-[(1 S)-1-(1,4-dioxan-2-yl)ethoxy]pyridine-4-carbonitrile (intermediate 1-11, 1.68 g, 7.17 mmol) as the starting material; 1.49 g (90% purity, 78% yield) of the title compound were prepared.

LC-MS (method 6): $R_t$=0.2 min; MS (ESIpos): m/z=239 $[M+H]^+$ $^1$H-NMR (400 MHz, DMSO-$d_6$) δ [ppm]: 0.990 (0.87), 1.006 (0.89), 1.058 (0.73), 1.073 (0.73), 1.165 (0.76), 1.216 (15.68), 1.232 (16.00), 1.256 (14.15), 1.272 (13.96), 1.755 (9.46), 1.917 (0.88), 3.240 (0.43), 3.265 (0.46), 3.276 (0.41), 3.293 (0.54), 3.302 (0.81), 3.325 (0.68), 3.338 (0.50), 3.350 (0.56), 3.371 (0.56), 3.378 (0.58), 3.400 (2.78), 3.412 (2.79), 3.426 (5.84), 3.438 (5.24), 3.453 (6.52), 3.459 (6.28), 3.466 (5.96), 3.479 (2.46), 3.486 (3.26), 3.493 (2.78), 3.521 (0.49), 3.529 (0.67), 3.535 (0.58), 3.564 (2.05), 3.572 (2.72), 3.580 (2.41), 3.600 (6.11), 3.609 (5.52), 3.617 (4.09), 3.634 (11.25), 3.637 (11.05), 3.756 (8.08), 3.785 (6.75), 3.889 (2.49), 3.894 (2.48), 3.917 (2.26), 3.922 (2.16), 4.540 (1.04), 4.555 (3.05), 4.569 (4.27), 4.580 (2.83), 4.584 (2.84), 7.369 (3.21), 7.379 (4.91), 8.135 (3.33), 8.146 (5.23), 8.157 (3.20), 8.261 (4.69), 8.275 (4.23).

Intermediate 2-12

1-{3-[(1R)-1-(1,4-dioxan-2-yl)ethoxy]pyridin-4-yl}methanamine

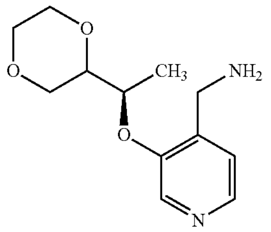 [SMILES: C[C@@H](Oc1cnccc1CN)C1COCCO1]

Using an analogous method as described for intermediate 2-1 with 3-{(1R)-1-[1,4-dioxan-2-yl]ethoxy}pyridine-4-carbonitrile (intermediate 1-12, 1.39 g, 5.93 mmol) as the starting material; 1.36 g (95% purity, 91% yield) of the title compound were prepared.

$^1$H-NMR (400 MHz, DMSO-$d_6$) δ [ppm]: 1.216 (0.81), 1.232 (0.99), 1.255 (15.91), 1.271 (16.00), 1.753 (0.71), 3.290 (0.44), 3.399 (0.54), 3.412 (2.42), 3.424 (0.71), 3.437 (3.81), 3.440 (3.42), 3.453 (0.77), 3.459 (2.72), 3.465 (5.00), 3.485 (1.48), 3.494 (2.02), 3.573 (1.45), 3.580 (1.70), 3.598 (2.00), 3.603 (3.43), 3.609 (3.84), 3.616 (2.24), 3.622 (2.04), 3.628 (1.97), 3.634 (4.41), 3.638 (4.68), 3.645 (2.04), 3.662 (5.32), 3.672 (6.05), 3.713 (0.63), 3.757 (2.28), 3.764 (2.39), 3.787 (1.75), 3.790 (1.84), 3.887 (2.14), 3.894 (2.12), 3.916 (1.94), 3.922 (1.85), 4.535 (0.53), 4.550 (1.85), 4.564 (2.15), 4.566 (2.17), 4.579 (1.80), 4.595 (0.50), 7.381 (3.18), 7.393 (3.14), 8.144 (4.36), 8.156 (4.13), 8.257 (0.50), 8.272 (6.58).

LC-MS (method 6): $R_t$=0.21 min; MS (ESIpos): m/z=239 $[M+H]^+$

Intermediate 2-71

1-{3-[1-(4-methylmorpholin-2-yl)ethoxy]pyridin-4-yl}methanamine

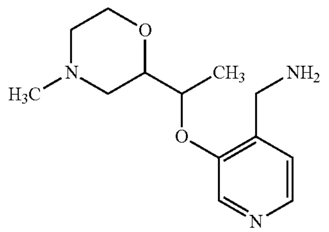 [SMILES: CC(Oc1cnccc1CN)C1CN(C)CCO1]

Using an analogous method as described for intermediate 2-1 with 3-({1-[4-methylmorpholin-2-yl]ethyl}oxy)pyridine-4-carbonitrile (intermediate 1-71, 815 mg, 3.30 mmol) as the starting material; 810 mg (99% purity, 97% yield) of the title compound were prepared.

1H-NMR (400 MHz, DMSO-$d_6$) δ [ppm]: 1.227 (3.82), 1.242 (3.97), 1.254 (4.80), 1.270 (4.60), 1.850 (1.08), 1.862 (1.12), 1.876 (1.43), 1.888 (1.42), 1.903 (0.90), 1.915 (1.07), 1.928 (0.67), 1.937 (0.65), 1.945 (0.81), 1.957 (1.14), 1.965 (0.95), 1.973 (0.53), 1.985 (0.64), 1.993 (0.48), 2.152 (0.51), 2.183 (16.00), 2.332 (0.45), 2.518 (2.14), 2.522 (1.29), 2.575 (1.38), 2.602 (1.24), 2.673 (0.44), 2.692 (0.68), 2.720 (0.63), 2.834 (0.79), 2.862 (0.75), 3.475 (0.48), 3.480 (0.56), 3.487 (0.60), 3.504 (1.27), 3.508 (1.56), 3.514 (1.44), 3.536 (1.04), 3.542 (1.01), 3.563 (0.49), 3.568 (0.50), 3.575 (0.48), 3.588 (0.47), 3.667 (1.61), 3.793 (1.27), 3.821 (1.05), 4.561 (0.97), 7.374 (1.24), 8.138 (1.27), 8.267 (1.31).

LC-MS (method 6): $R_t$=0.11 min; MS (ESipos): m/z=252 $[M+H]^+$

Syntheses of Intermediate 3 Compounds

Intermediate 3-1

1-chloro-3-isothiocyanato-2-methoxybenzene

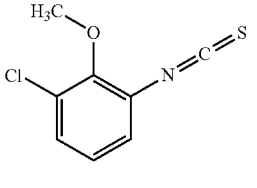

3-chloro-2-methoxyaniline (CAS 51114-68-2, 8.4 ml, 63 mmol) was solved in DCM (100 ml) and sat. sodium bicarbonate solution (100 ml) was added. To the ice cooled mixture was slowly added thiophosgene (5.4 ml, 70 mmol). The reaction was stirred at 0° C. for 2 h. At RT the DCM layer was separated and washed with sat. sodium bicarbonate solution, filtered through a hydrophobic filter and concentrated under reduced pressure to give the title compound (12.97 g, 100% yield) which was used directly in the next step.

$^1$H-NMR (400 MHz, DMSO-$d_6$): δ [ppm]=7.51 (dd, 1H), 7.35 (dd, 1H), 7.20 (t, 1H), 3.85-3.91 (m, 3H).

Intermediate 3-4

1-fluoro-3-isothiocyanato-2-methoxybenzene

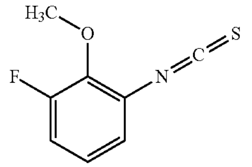

Using an analogous method as described for intermediate 3-1; 3-fluoro-2-methoxyaniline (CAS 437-83-2, 5.00 g, 35.4 mmol) as the starting material; 6.24 g of the title compound were prepared (96% yield).

$^1$H-NMR (400 MHz, DMSO-$d_6$): δ [ppm]=7.32 (m, 1H), 7.10-7.19 (m, 2H), 3.96 (d, 3H).

Intermediate 3-18

1-chloro-5-fluoro-3-isothiocyanato-2-methoxybenzene

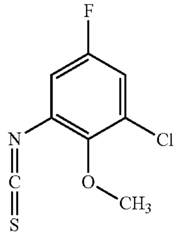

Using an analogous method as described for intermediate 3-1 with 3-chloro-5-fluoro-2-methoxyaniline (1.00 g, 5.70 mmol) as the starting material; 1.17 g of the title compound were prepared (95% purity, 90% yield).

1H NMR (400 MHz, DMSO-$d_6$): δ [ppm]=3.86 (s, 3H) 7.38 (dd, 1H) 7.58 (dd, 1H).

Intermediate 3-29

1-chloro-2-ethyl-3-isothiocyanatobenzene

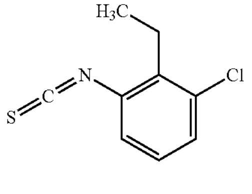

Using an analogous method as described for intermediate 3-1; 3-chloro-2-ethylaniline (5.00 g, 85% purity, 27.3 mmol) as the starting material, the title compound was prepared 6.29 g (85% purity, 99% yield).

$^1$H-NMR (400 MHz, DMSO-$d_6$): δ [ppm]=1.009 (7.50), 1.027 (16.00), 1.046 (7.55), 1.090 (0.44), 1.109 (0.89), 1.128 (0.44), 2.590 (2.26), 2.608 (6.71), 2.627 (6.58), 2.646 (2.00), 5.199 (6.39), 6.533 (4.44), 6.539 (4.27), 6.553 (5.20), 6.559 (4.97), 6.821 (3.47), 6.841 (5.70), 6.861 (2.75), 7.056 (0.43), 7.060 (0.52).

Intermediate 3-65

2-ethyl-1-fluoro-3-isothiocyanatobenzene

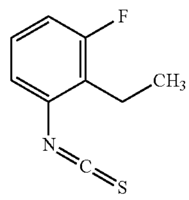

Using an analogous method as described for intermediate 3-1; 2-ethyl-3-fluoroaniline (2.50 g, 18.0 mmol, CAS 1139437-61-8) as the starting material, the title compound was prepared 3.0 g (90% purity, 83% yield).

$^1$H-NMR (400 MHz, DMSO-$d_6$) δ [ppm]: 1.108 (7.13), 1.127 (16.00), 1.146 (7.13), 2.462 (0.95), 2.483 (1.27), 2.517 (0.79), 2.522 (0.48), 2.637 (0.95), 2.641 (1.11), 2.655 (3.17), 2.659 (3.17), 2.674 (3.17), 2.678 (3.17), 2.693 (0.95), 2.697 (0.95), 3.461 (0.48), 3.477 (0.63), 3.484 (0.63), 3.506 (1.11), 3.528 (2.06), 3.537 (2.69), 3.625 (3.01), 3.648 (1.11), 3.663 (0.63), 3.669 (0.63), 7.185 (1.11), 7.189 (1.11), 7.205 (1.58), 7.209 (2.53), 7.212 (1.27), 7.229 (1.43), 7.233 (1.74), 7.243 (1.27), 7.246 (1.43), 7.263 (3.80), 7.266 (2.38), 7.282 (2.53), 7.296 (2.38), 7.301 (2.38), 7.317 (2.53), 7.322 (0.79), 7.337 (0.79).

Syntheses of Intermediate 4 Compounds

Intermediate 4-1 tert-butyl 5-[(3-chloro-2-methoxyphenyl)carbamothioyl]-4-hydroxy-6-oxo-3,6-dihydropyridine-1(2H)-carboxylate

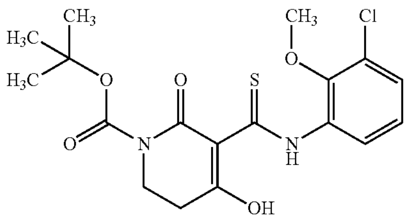 [SMILES: COc1c(Cl)cccc1NC(=S)C1=C(O)CCN(C(=O)OC(C)(C)C)C1=O]

To an ice-cooled solution of 1-chloro-3-isothiocyanato-2-methoxybenzene (intermediate 3-1, 4.00 g, 20.0 mmol) and tert-butyl 2,4-dioxopiperidine-1-carboxylate (CAS 845267-78-9, 4.27 g, 20.0 mmol) in acetonitrile (92 ml) was added dropwise DBU (4.5 ml, 30 mmol). The reaction was stirred at RT overnight. To the reaction mixture was added ice-water (200 mL) and conc. HCl (2 mL). The mixture was stirred for 20 min. and extracted with DCM. The organic phase was filtered over a water-repellent filter, concentrated under reduced pressure and purified by flash chromatography (silica, hexane/EtOAc gradient 0-50%) to give 6.54 g of the title compound (71% yield).

$^1$H-NMR (400 MHz, DMSO-$d_6$): δ [ppm]=13.36 (br s, 1H), 7.73 (d, 1H), 7.47 (dd, 1H), 7.22 (t, 1H), 3.76-3.82 (m, 5H), 2.88 (t, 2H), 1.48 (s, 9H).

LC-MS (method 1): $R_t$=1.49 min; MS (ESIpos): m/z=413.1 $[M+H]^+$

Intermediate 4-4 tert-butyl 5-[(3-fluoro-2-methoxyphenyl)carbamothioyl]-4-hydroxy-6-oxo-3,6-dihydropyridine-1(2H)-carboxylate

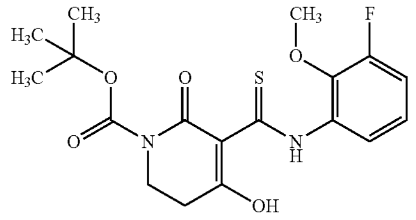 [SMILES: COc1c(F)cccc1NC(=S)C1=C(O)CCN(C(=O)OC(C)(C)C)C1=O]

Using an analogous method as described for Intermediate 4-1 with tert-butyl 2,4-dioxopiperidine-1-carboxylate (CAS 845267-78-9, 7.26 g, 34.1 mmol) and 1-fluoro-3-isothiocyanato-2-methoxybenzene (intermediate 3-4, 6.24 g, 34.1 mmol) as the starting materials; 9.49 g of the title compound were prepared (67% yield) after stirring the product in MeOH, filtration and drying of the precipitate in vacuo.

$^1$H-NMR (400 MHz, DMSO-$d_6$): δ [ppm]=13.37 (br s, 1H), 7.58 (br d, 1H), 7.23-7.30 (m, 1H), 7.09-7.21 (m, 1H), 4.10 (br s, 1H), 3.78 (t, 2H), 3.17 (s, 3H), 2.88 (br t, 2H), 1.48 (s, 9H).

LC-MS (method 2): $R_t$=0.66 min; MS (ESIpos): m/z=397.3 $[M+H]^+$

Intermediate 4-7 tert-butyl 5-[(2,3-dichlorophenyl)carbamothioyl]-4-hydroxy-6-oxo-3,6-dihydropyridine-1(2H)-carboxylate

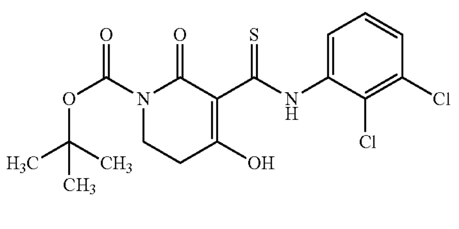 [SMILES: CC(C)(C)OC(=O)N1CCC(O)=C(C(=S)Nc2cccc(Cl)c2Cl)C1=O]

1,2-Dichloro-3-isothiocyanatobenzene (CAS 6590-97-2, 5.00 g, 24.5 mmol) and tert-butyl 2,4-dioxopiperidine-1-carboxylate (CAS 845267-78-9, 5.22 g, 24.5 mmol) were solubilised in acetonitrile (55 ml), DBU (5.5 ml, 37 mmol) was added carefully at 0° C. under argon atmosphere and the mixture was stirred overnight at RT. The reaction mixture was diluted with HCl (200 ml, 1 N in water) and stirred for 30 min. at RT. The resulting solid was filtered off, the filter cake was washed with water and dried at 50° C. in vacuo oven overnight to give 9.40 g of the title compound (92% yield).

$^1$H-NMR (400 MHz, DMSO-$d_6$): δ [ppm]=1.467 (16.00), 1.484 (0.56), 1.622 (0.34), 1.644 (0.25), 1.661 (0.20), 1.674 (0.17), 1.898 (0.19), 1.913 (0.31), 1.927 (0.19), 2.075 (0.20), 2.327 (0.18), 2.518 (0.60), 2.523 (0.39), 2.621 (0.30), 2.647 (0.32), 2.665 (0.24), 2.669 (0.29), 2.673 (0.25), 3.249 (0.25), 3.459 (0.23), 3.473 (0.39), 3.487 (0.22), 3.538 (0.28), 3.561 (0.29), 3.727 (0.50), 7.357 (0.17), 7.377 (0.36), 7.383 (0.28), 7.397 (0.28), 7.544 (0.27), 7.547 (0.33), 7.560 (0.29), 7.564 (0.31), 7.568 (0.25), 7.580 (0.18).

LC-MS (method 2): $R_t$=0.70 min; MS (ESIpos): m/z=416 $[M-H]^-$

Intermediate 4-10 tert-butyl 5-[(3-chloro-2-methylphenyl)carbamothioyl]-4-hydroxy-6-oxo-3,6-dihydropyridine-1(2H)-carboxylate

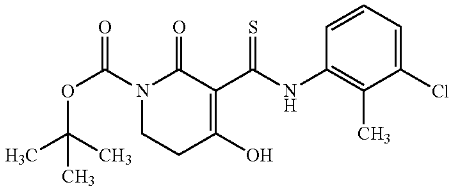 [SMILES: Cc1c(Cl)cccc1NC(=S)C1=C(O)CCN(C(=O)OC(C)(C)C)C1=O]

According to the method described for intermediate 4-1; 1-chloro-3-isothiocyanato-2-methylbenzene (CAS 19241-35-1; 2.50 g, 13.6 mmol) and tert-butyl 2,4-dioxopiperidine-1-carboxylate (CAS 845267-78-9, 2.9 g, 13.6 mmol) as the starting materials; 4.68 g of the title compound were prepared (78% yield), after addition of HCl filtration, and drying of the precipitate in vacuo.

$^1$H-NMR (400 MHz, DMSO-$d_6$): δ [ppm]=15.73 (s, 1H), 12.77 (br s, 1H), 7.45 (d, 1H), 7.30 (t, 1H), 7.19 (d, 1H), 3.78 (t, 2H), 2.85 (t, 2H), 2.20 (s, 3H), 1.48 (s, 9H).

LC-MS (method 2): $R_t$=0.72 min; MS (ESIpos): m/z=397.3 $[M+H]^+$

Intermediate 4-18 tert-butyl 5-[(3-chloro-5-fluoro-2-methoxyphenyl)carbamothioyl]-4-hydroxy-6-oxo-3,6-dihydropyridine-1(2H)-carboxylate

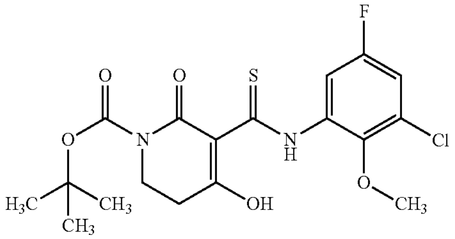 [SMILES: COc1c(Cl)cc(F)cc1NC(=S)C1=C(O)CCN(C(=O)OC(C)(C)C)C1=O]

Using an analogous method as described for Intermediate 4-1 with tert-butyl 2,4-dioxopiperidine-1-carboxylate (CAS 845267-78-9, 1.15 g, 5.38 mmol) and 1-chloro-5-fluoro-3-isothiocyanato-2-methoxybenzene (intermediate 3-18, 1.17 g, 5.38 mmol) as the starting materials; 1.42 g of the title compound were prepared (75% purity, 46% yield).

$^1$H-NMR (400 MHz, DMSO-$d_6$): δ [ppm]=1.154 (0.88), 1.172 (1.70), 1.189 (0.80), 1.484 (16.00), 1.987 (3.28), 2.518 (0.89), 2.522 (0.61), 2.883 (0.73), 2.899 (0.40), 3.359 (0.69), 3.644 (4.46), 3.760 (7.94), 3.774 (0.44), 3.782 (1.03), 3.798 (0.53), 4.017 (0.69), 4.035 (0.69), 6.400 (0.60), 6.405 (0.53), 6.427 (1.00), 7.498 (0.41).

LC-MS (method 2): $R_t$=0.73 min; MS (ESIpos): m/z=431 $[M+H]^+$

Intermediate 4-29 tert-butyl 5-[(3-chloro-2-ethylphenyl)carbamothioyl]-4-hydroxy-6-oxo-3,6-dihydropyridine-1(2H)-carboxylate

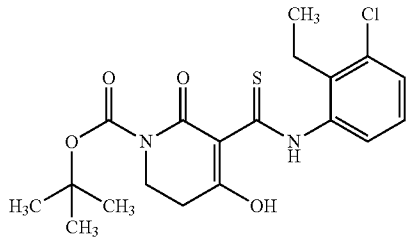 [SMILES: CCc1c(Cl)cccc1NC(=S)C1=C(O)CCN(C(=O)OC(C)(C)C)C1=O]

Using an analogous method as described for Intermediate 4-1 with tert-butyl 2,4-dioxopiperidine-1-carboxylate (CAS 845267-78-9, 5.77 g, 27.0 mmol) and 2-chloro-1-ethyl-3-isothiocyanatobenzene (intermediate 3-29, 6.29 g, 85% purity, 27.0 mmol) as the starting materials; 6.35 g of the title compound were prepared (85% purity, 49% yield).

$^1$H-NMR (400 MHz, DMSO-$d_6$): δ [ppm]=1.063 (0.89), 1.082 (2.14), 1.100 (0.95), 1.362 (0.65), 1.478 (16.00), 1.486 (1.29), 2.518 (0.64), 2.523 (0.44), 2.631 (0.70), 2.650 (0.69), 2.850 (0.41), 2.866 (0.78), 2.883 (0.43), 3.775 (0.51), 3.791 (0.90), 3.807 (0.46), 7.212 (0.46), 7.214 (0.44), 7.232 (0.62), 7.234 (0.61), 7.293 (0.62), 7.313 (1.08), 7.332 (0.53), 7.440 (0.61), 7.443 (0.62), 7.460 (0.49), 7.463 (0.45).

Intermediate 4-38 tert-butyl 5-[(3-fluoro-2-methylphenyl)carbamothioyl]-4-hydroxy-6-oxo-3,6-dihydropyridine-1(2H)-carboxylate

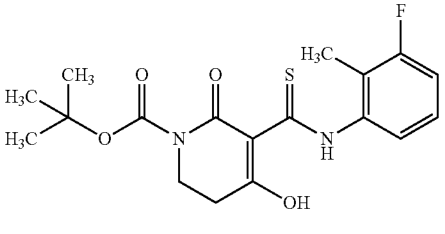 [SMILES: Cc1c(F)cccc1NC(=S)C1=C(O)CCN(C(=O)OC(C)(C)C)C1=O]

Using an analogous method as described for Intermediate 4-1 with tert-butyl 2,4-dioxopiperidine-1-carboxylate (CAS 845267-78-9, 8.19 g, 38.4 mmol) and 1-fluoro-3-isothiocyanato-2-methylbenzene (CAS 363179-58-2, 6.42 g, 38.4 mmol) as the starting materials; 11.1 g of the title compound were prepared (95% purity, 72% yield) after stirring the product in MeOH, filtration and drying of the precipitate in vacuo.

$^1$H-NMR (400 MHz, DMSO-$d_6$): δ [ppm]=1.479 (16.00), 2.084 (2.80), 2.088 (2.74), 2.834 (0.58), 2.850 (1.12), 2.866 (0.61), 3.768 (0.64), 3.784 (1.16), 3.800 (0.59), 7.073 (0.61), 7.093 (0.71), 7.186 (0.59), 7.299 (0.45), 7.316 (0.42).

Intermediate 4-40 tert-butyl 5-{[2-(2,2-difluoroethyl)-3-fluorophenyl] carbamothioyl}-4-hydroxy-6-oxo-3,6-dihydropyridine-1(2H)-carboxylate

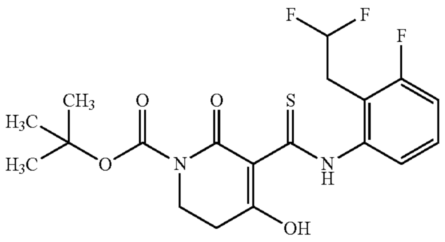 [SMILES: CC(C)(C)OC(=O)N1CCC(O)=C(C(=S)Nc2cccc(F)c2CC(F)F)C1=O]

Using an analogous method as described for Intermediate 4-1 with tert-butyl 2,4-dioxopiperidine-1-carboxylate (CAS 845267-78-9, 7.85 g, 36.8 mmol) and 2-(2,2-difluoroethyl)-1-fluoro-3-isothiocyanatobenzene (CAS 2311902-79-9, 8.00 g, 36.8 mmol) as the starting materials; 12.1 g of the title compound were prepared (95% purity, 72% yield).

$^1$H-NMR (400 MHz, DMSO-$d_6$): δ [ppm]=1.471 (16.00), 2.518 (0.65), 2.523 (0.43), 2.788 (0.47), 2.804 (0.87), 2.820 (0.50), 3.166 (3.72), 3.754 (0.60), 3.770 (1.08), 3.786 (0.57), 7.149 (0.62), 7.169 (0.70), 7.271 (0.58), 7.446 (0.46), 7.462 (0.43).

Intermediate 4-65 tert-butyl 5-[(2-ethyl-3-fluorophenyl)carbamothioyl]-4-hydroxy-6-oxo-3,6-dihydropyridine-1(2H)-carboxylate

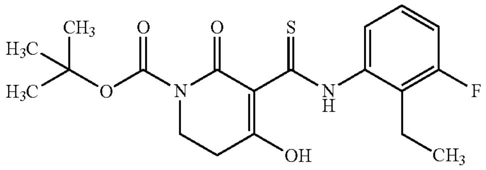 [SMILES: CCc1c(F)cccc1NC(=S)C1=C(O)CCN(C(=O)OC(C)(C)C)C1=O]

Using an analogous method as described for Intermediate 4-1 with tert-butyl 2,4-dioxopiperidine-1-carboxylate (CAS 845267-78-9, 7.85 g, 36.8 mmol) and 2-ethyl-1-fluoro-3-isothiocyanatobenzene (intermediate 3-65, 3.00 g, 16.6 mmol) as the starting materials; 5.46 g of the title compound were prepared (95% purity, 79% yield).

$^1$H-NMR (400 MHz, DMSO-$d_6$) δ [ppm]: 1.066 (1.02), 1.085 (2.41), 1.104 (1.06), 1.477 (16.00), 1.486 (1.04), 2.074 (0.65), 2.518 (1.12), 2.522 (0.92), 2.538 (0.61), 2.858 (0.69), 3.771 (0.55), 3.787 (0.98), 3.803 (0.50), 7.092 (0.50), 7.112 (0.55), 7.186 (0.45), 7.311 (0.44), 7.327 (0.41). LC-MS (method 2): $R_t$=0.72 min; MS (ESIpos): m/z=395 [M+H]$^+$ Syntheses of Intermediate 5 Compounds Intermediate 5-1

N-(3-chloro-2-methoxyphenyl)-4-hydroxy-2-oxo-1,2,5,6-tetrahydropyridine-3-carbothioamide

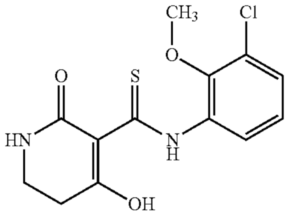 [SMILES: COc1c(Cl)cccc1NC(=S)C1=C(O)CCNC1=O]

To a solution of tert-butyl 5-[(3-chloro-2-methoxyphenyl) carbamothioyl]-4-hydroxy-6-oxo-3,6-dihydropyridine-1 (2H)-carboxylate (intermediate 4-1, 6.54 g, 15.8 mmol) in dichloromethane (94 ml) was added TFA (12 ml, 160 mmol) and the mixture was stirred 1.5 h at RT. The reaction mixture was concentrated under reduced pressure and the residue was solved in EtOAc and washed with sat. sodium bicarbonate solution and brine. The organic layer was filtered through a hydrophobic filter and the filtrate was dried to dryness. The residue was purified by flash chromatography (silica, hexane/EtOAc gradient 20-100%) to give 4.06 g of the title compound (78% yield).

$^1$H-NMR (400 MHz, DMSO-$d_6$): δ [ppm]=16.45 (d, 1H), 14.69 (s, 1H), 14.33 (s, 1H), 9.37 (br s, 1H), 8.18 (br s, 1H), 7.76-7.87 (m, 1H), 7.37-7.45 (m, 1H), 7.15-7.23 (m, 1H), 3.73-3.76 (m, 3H), 3.43 (td, 1H), 3.27-3.32 (m, 1H), 2.79 (t, 1H), 2.59-2.69 (m, 1H).

LC-MS (method 1): $R_t$=1.19 min; MS (ESIpos): m/z=313 [M+H]$^+$

Intermediate 5-4

N-(3-fluoro-2-methoxyphenyl)-4-hydroxy-2-oxo-1,2,5,6-tetrahydropyridine-3-carbothioamide

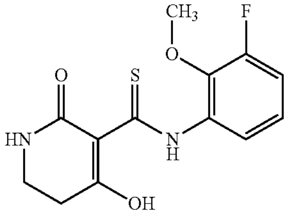 [SMILES: COc1c(F)cccc1NC(=S)C1=C(O)CCNC1=O]

Using an analogous method as described for intermediate 5-1 with tert-butyl 5-[(3-fluoro-2-methoxyphenyl)carbamothioyl]-4-hydroxy-6-oxo-3,6-dihydropyridine-1(2H)-carboxylate (intermediate 4-4, 9.49 g, 23.9 mmol) as the starting material, 6.98 g of the title compound was prepared (89% yield) after 15 min of stirring and used in the next steps without further purification.

$^1$H-NMR (400 MHz, DMSO-$d_6$): δ [ppm]=16.48 (d, 1H), 14.63 (s, 0.5H), 14.28 (s, 0.5H), 9.34 (br s, 0.5H), 8.16 (br s, 0.5H), 7.65 (t, 1H), 6.97-7.37 (m, 2H), 3.79-3.85 (m, 3H), 3.35-3.46 (m, 1H), 3.26-3.32 (m, 1H), 2.78 (t, 1H), 2.63 (t, 1H).

LC-MS (method 2): $R_t$=0.46 min; MS (ESIpos): m/z=297.1 [M+H]$^+$

Intermediate 5-7

N-(2,3-dichlorophenyl)-4-hydroxy-2-oxo-1,2,5,6-tetrahydropyridine-3-carbothioamide

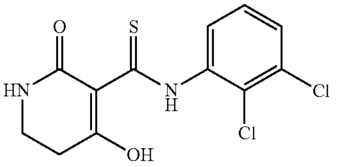 [SMILES: O=C1NCCC(O)=C1C(=S)Nc1cccc(Cl)c1Cl]

Using an analogous method as described for intermediate 5-1 with tert-butyl 5-[(2,3-dichlorophenyl)carbamothioyl]-4-hydroxy-6-oxo-3,6-dihydropyridine-1(2H)-carboxylate (intermediate 4-7, 9.40 g, 22.5 mmol) as the starting material; 5.71 g of the title compound were prepared (62% yield) after stirring overnight.

$^1$H-NMR (400 MHz, DMSO-$d_6$): δ [ppm]=1.018 (1.18), 1.050 (1.33), 1.072 (0.81), 1.102 (0.59), 1.132 (0.81), 1.154 (1.84), 1.172 (3.17), 1.189 (1.84), 1.199 (0.88), 1.231 (1.92), 1.259 (1.40), 1.486 (0.66), 1.593 (1.33), 1.626 (1.18), 1.695 (1.25), 1.727 (1.18), 1.907 (2.14), 1.987 (5.97), 2.322 (3.17), 2.326 (4.28), 2.331 (3.17), 2.518 (15.85), 2.522 (9.44), 2.638 (11.06), 2.664 (7.82), 2.669 (7.52), 2.673 (5.53), 2.798 (8.11), 3.436 (9.81), 4.017 (1.18), 4.035 (1.11), 5.560 (1.33), 5.579 (1.25), 7.392 (4.42), 7.410 (10.03), 7.430 (9.22), 7.565 (12.24), 7.585 (16.00), 7.605 (9.51), 8.134 (0.74), 8.197 (4.35), 9.418 (3.91), 14.273 (6.93), 14.665 (6.64), 16.114 (1.03), 16.295 (9.95), 16.352 (5.82), 16.503 (1.11).

LC-MS (method 2): $R_t$=0.55 min; MS (ESipos): m/z=316 $[M-H]^-$.

Intermediate 5-10

N-(3-chloro-2-methylphenyl)-4-hydroxy-2-oxo-1,2,5,6-tetrahydropyridine-3-carbothioamide

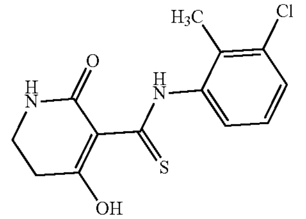 [SMILES: Cc1c(Cl)cccc1NC(=S)C1=C(O)CCNC1=O]

Using an analogous method as described for intermediate 5-1 with tert-butyl 5-[(3-chloro-2-methylphenyl)carbamothioyl]-4-hydroxy-6-oxo-3,6-dihydropyridine-1(2H)-carboxylate (intermediate 4-10, 4.67 g, 11.8 mmol) as the starting material, 3.54 g of the title compound were prepared (91% yield) after 3 h and used in the next steps without further purification.

$^1$H-NMR (400 MHz, DMSO-$d_6$): δ [ppm]=16.42 (d, 1H), 14.01-14.37 (m, 1H), 8.14-9.40 (m, 1H), 7.43 (br t, 1H), 7.16-7.32 (m, 2H), 3.42-3.48 (m, 1H), 3.26-3.34 (m, 1H), 2.78 (t, 1H), 2.60-2.68 (m, 1H), 2.12-2.21 (m, 3H).

LC-MS (method 2): $R_t$=0.60 min; MS (ESIpos): m/z=297.4 $[M+H]^+$.

Intermediate 5-18

N-(3-chloro-5-fluoro-2-methoxyphenyl)-4-hydroxy-2-oxo-1,2,5,6-tetrahydropyridine-3-carbothioamide

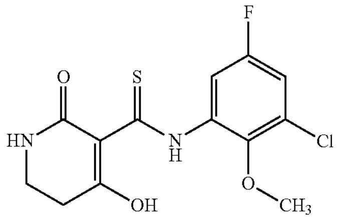 [SMILES: COc1c(Cl)cc(F)cc1NC(=S)C1=C(O)CCNC1=O]

Using an analogous method as described for intermediate 5-1 with tert-butyl 5-[(3-chloro-5-fluoro-2-methoxyphenyl)carbamothioyl]-4-hydroxy-6-oxo-3,6-dihydropyridine-1(2H)-carboxylate (intermediate 4-18, 1.42 g, 3.30 mmol) as the starting material; 690 mg of the title compound were prepared (95% purity, 60% yield).

$^1$H-NMR (400 MHz, DMSO-$d_6$): δ [ppm]=2.61-2.70 (m, 1H), 2.80 (m, 1H), 3.25-3.32 (m, 1H), 3.38-3.47 (m, 1H), 3.74 (s, 3H), 7.39-7.62 (m, 1H), 7.83-8.02 (m, 1H), 8.20-8.33 (s, 0.5H), 9.33-9.57 (s, 0.5H), 14.53 (s, 0.5H), 14.93 (s, 0.5H), 16.29 (s, 0.5H), 16.36 (s, 0.5H).

LC-MS (method 2): $R_t$=0.57 min; MS (ESIneg): m/z=329 $[M-H]^-$.

Intermediate 5-29

N-(3-chloro-2-ethylphenyl)-4-hydroxy-2-oxo-1,2,5,6-tetrahydropyridine-3-carbothioamide

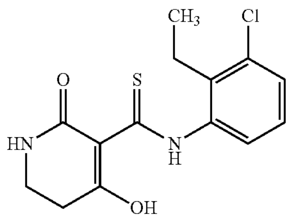 [SMILES: CCc1c(Cl)cccc1NC(=S)C1=C(O)CCNC1=O]

Using an analogous method as described for intermediate 5-1 with tert-butyl 5-[(3-chloro-2-ethylphenyl)carbamothioyl]-4-hydroxy-6-oxo-3,6-dihydropyridine-1(2H)-carboxylate (intermediate 4-29, 2.35 g, 75% purity, 4.29 mmol) as the starting material; 1.22 g of the title compound were prepared (95% purity, 87% yield).

$^1$H-NMR (400 MHz, DMSO-$d_6$): δ [ppm]=1.048 (7.06), 1.067 (16.00), 1.086 (7.43), 1.107 (1.58), 1.124 (1.32), 1.143 (0.50), 1.154 (1.34), 1.172 (2.43), 1.190 (1.24), 1.232 (0.50), 1.988 (4.56), 2.318 (0.47), 2.323 (1.05), 2.327 (1.56), 2.332 (1.11), 2.336 (0.47), 2.518 (5.61), 2.523 (4.03), 2.581 (2.03), 2.600 (6.41), 2.619 (6.62), 2.642 (4.59), 2.661 (2.69), 2.669 (1.90), 2.673 (1.27), 2.678 (0.58), 2.771 (2.35), 2.789 (4.82), 2.807 (2.58), 3.287 (1.61), 3.294 (1.79), 3.305 (3.11), 3.312 (3.14), 3.323 (2.06), 3.330 (2.35), 3.415 (1.53), 3.422 (1.66), 3.433 (2.56), 3.441 (2.45), 3.452 (1.40), 3.459 (1.24), 4.017 (1.03), 4.035 (1.00), 7.166 (0.95), 7.176 (0.58), 7.179 (0.58), 7.248 (0.71), 7.259 (6.30), 7.268 (3.58), 7.275 (4.43), 7.287 (7.20), 7.294 (3.90), 7.303 (3.56), 7.324 (0.87), 7.392 (1.85), 7.400 (1.37), 7.407 (1.85), 7.415 (1.74), 7.419 (2.40), 7.426 (1.77), 7.436 (1.77), 7.443 (1.45), 8.174 (1.77), 9.335 (1.42), 14.111 (2.98), 14.452 (2.74), 16.428 (7.88), 16.441 (7.38).

LC-MS (method 6): Rt=1.28 min; MS (ESIpos): m/z=311 $[M+H]^+$.

Intermediate 5-38 N-(3-fluoro-2-methylphenyl)-4-hydroxy-2-oxo-1,2,5,6-tetrahydropyridine-3-carbothioamide

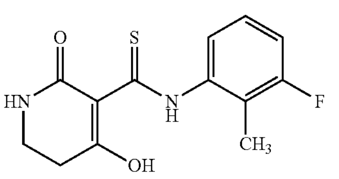 [SMILES: Cc1c(F)cccc1NC(=S)C1=C(O)CCNC1=O]

Using an analogous method as described for intermediate 5-1 with tert-butyl 5-[(3-fluoro-2-methylphenyl)carbamothioyl]-4-hydroxy-6-oxo-3,6-dihydropyridine-1(2H)-carboxylate (intermediate 4-38, 11.1 g, 29.1 mmol) as the starting material, 7.25 g of the title compound was prepared (84% yield) after 15 min of stirring and used in the next steps without further purification.

$^1$H-NMR (400 MHz, DMSO-$d_6$): δ [ppm]=1.172 (0.55), 1.987 (1.05), 2.063 (16.00), 2.518 (1.49), 2.523 (1.01), 2.612 (1.94), 2.631 (3.67), 2.649 (2.11), 2.761 (1.99), 2.779 (4.22), 2.798 (2.26), 3.280 (1.36), 3.287 (1.47), 3.298 (2.58), 3.305 (2.57), 3.315 (1.39), 3.322 (1.33), 3.410 (1.40), 3.417 (1.48), 3.428 (2.27), 3.435 (2.22), 3.446 (1.27), 3.454 (1.15), 7.112 (1.56), 7.119 (0.96), 7.132 (2.25), 7.141 (3.30), 7.161 (2.66), 7.168 (2.15), 7.192 (1.12), 7.243 (0.73), 7.262 (1.15), 7.272 (0.99), 7.279 (1.25), 7.292 (1.27), 7.308 (1.21), 7.328 (0.45), 8.150 (1.43), 9.317 (1.16), 14.003 (2.32), 14.321 (2.05), 16.439 (5.35), 16.468 (4.62).

LC-MS (method 2): $R_t$=0.47 min; MS (ESIpos): m/z=281 $[M+H]^+$.

Intermediate 5-40

N-[2-(2,2-difluoroethyl)-3-fluorophenyl]-4-hydroxy-2-oxo-1,2,5,6-tetrahydropyridine-3-carbothioamide

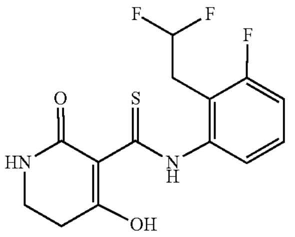 [SMILES: O=C1NCCC(O)=C1C(=S)Nc1cccc(F)c1CC(F)F]

Using an analogous method as described for intermediate 5-1 with tert-butyl 5-{[2-(2,2-difluoroethyl)-3-fluorophenyl]carbamothioyl}-4-hydroxy-6-oxo-3,6-dihydropyridine-1(2H)-carboxylate (intermediate 4-40, 12.1 g, 28.0 mmol) as the starting material; 8.81 g of the title compound were prepared (95% purity, 90% yield).

$^1$H-NMR (400 MHz, DMSO-$d_6$): δ [ppm]=1.145 (0.50), 1.154 (1.98), 1.172 (3.87), 1.190 (1.88), 1.441 (0.60), 1.987 (7.01), 2.323 (1.39), 2.327 (1.98), 2.332 (1.39), 2.518 (8.20), 2.523 (5.52), 2.617 (6.21), 2.635 (11.74), 2.653 (7.04), 2.665 (3.21), 2.669 (3.14), 2.673 (2.21), 2.769 (5.92), 2.786 (10.81), 2.803 (6.18), 3.059 (7.57), 3.067 (7.93), 3.104 (15.40), 3.111 (15.40), 3.148 (7.93), 3.307 (9.36), 3.434 (8.96), 4.000 (0.56), 4.017 (1.65), 4.035 (1.65), 4.053 (0.53), 6.057 (3.27), 6.067 (6.55), 6.077 (2.98), 6.198 (6.18), 6.208 (13.09), 6.217 (6.12), 6.339 (2.81), 6.348 (6.12), 6.358 (3.01), 7.165 (5.62), 7.185 (7.24), 7.207 (6.64), 7.227 (8.53), 7.242 (9.39), 7.265 (9.26), 7.288 (3.31), 7.393 (2.38), 7.413 (5.55), 7.430 (6.51), 7.459 (4.53), 7.479 (1.45), 8.152 (5.29), 9.352 (4.96), 14.013 (9.02), 14.389 (7.90), 16.346 (15.47), 16.353 (16.00).

LC-MS (method 2): $R_t$=0.48 min; MS (ESIpos): m/z=331.1 $[M+H]^+$.

Intermediate 5-65

N-(2-ethyl-3-fluorophenyl)-4-hydroxy-2-oxo-1,2,5,6-tetrahydropyridine-3-carbothioamide

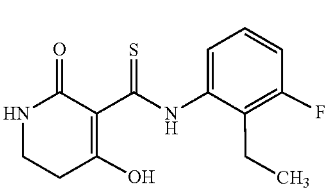 [SMILES: CCc1c(F)cccc1NC(=S)C1=C(O)CCNC1=O]

Using an analogous method as described for intermediate 5-1 with tert-butyl 5-[(2-ethyl-3-fluorophenyl)carbamothioyl]-4-hydroxy-6-oxo-3,6-dihydropyridine-1(2H)-carboxylate (intermediate 4-65, 5.46 g, 71% purity, 9.83 mmol) as the starting material; 4.0 g of the title compound were prepared (70% purity, 97% yield).

$^1$H-NMR (400 MHz, DMSO-$d_6$) delta [ppm]: 1.052 (6.61), 1.071 (16.00), 1.089 (6.75), 1.116 (0.56), 1.224 (4.60), 1.734 (1.58), 2.326 (0.43), 2.472 (1.56), 2.518 (2.10), 2.523 (1.69), 2.647 (0.85), 2.659 (0.85), 2.664 (0.98), 2.668 (1.03), 2.673 (0.80), 2.782 (0.89), 3.423 (0.82), 4.037 (0.62), 7.160 (2.35), 7.288 (0.98), 8.170 (0.48), 14.073 (0.46), 14.414 (0.52).

LC-MS (method 6): $R_t$=1.18 min; MS (ESIpos): m/z=295 $[M+H]^+$.

Syntheses of Intermediate 6 Compounds

Intermediate 6-1

N-(3-chloro-2-methoxyphenyl)-4-[({3-[(1,4-dioxan-2-yl)methoxy]pyridin-4-yl}methyl)amino]-2-oxo-1,2,5,6-tetrahydropyridine-3-carbothioamide

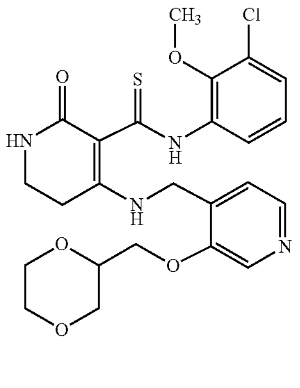 [SMILES: COc1c(Cl)cccc1NC(=S)C1=C(NCc2ccncc2OCC2COCCO2)CCNC1=O]

A mixture of N-(3-chloro-2-methoxyphenyl)-4-hydroxy-2-oxo-1,2,5,6-tetrahydropyridine-3-carbothioamide (intermediate 5-1, 498 mg, 1.59 mmol) and 1-{3-[(1,4-dioxan-2-yl)methoxy]pyridin-4-yl}methanamine (intermediate 2-1, 0.5 g, 2.23 mmol) was stirred for 4 h at 120° C. The reaction mixture was purified by flash chromatography (silica, DCM/EtOH gradient 0-30%) to give 325 mg of the title compound (39% yield).

$^1$H-NMR (400 MHz, DMSO-$d_6$): δ [ppm]=14.79 (s, 1H), 13.69 (t, 1H), 8.39 (s, 1H), 8.24 (d, 1H), 7.81 (dd, 1H), 7.73 (s, 1H), 7.26-7.33 (m, 2H), 7.11 (t, 1H), 4.67 (d, 2H), 4.16 (t, 2H), 3.84-3.95 (m, 2H), 3.74-3.79 (m, 1H), 3.71 (s, 3H), 3.59-3.70 (m, 2H), 3.45-3.54 (m, 2H), 3.11-3.20 (m, 2H), 2.78 (t, 2H).

LC-MS (method 2): $R_t$=1.07 min; MS (ESIpos): m/z=519.2 $[M+H]^+$.

Intermediate 6-2

N-(3-chloro-2-methoxyphenyl)-4-{[(3-{[(2S)-1,4-dioxan-2-yl]methoxy}pyridin-4-yl)methyl]amino}-2-oxo-1,2,5,6-tetrahydropyridine-3-carbothioamide

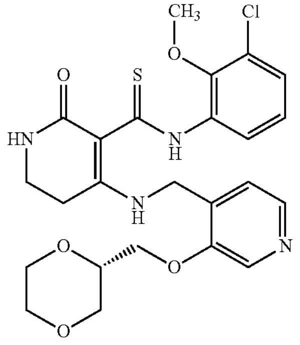 [SMILES: COc1c(Cl)cccc1NC(=S)C1=C(NCc2ccncc2OC[C@@H]2COCCO2)CCNC1=O]

A mixture of N-(3-chloro-2-methoxyphenyl)-4-hydroxy-2-oxo-1,2,5,6-tetrahydropyridine-3-carbothioamide (intermediate 5-1, 866 mg, 2.77 mmol) and 1-(3-{[(2S)-1,4-dioxan-2-yl]methoxy}pyridin-4-yl)methanamine (intermediate 2-8, 776 mg, 80% purity, 2.77 mmol) in ACN (22 ml) was treated with N,O-bis(trimethylsilyl)acetamide (2.05 ml, 8.6 mmol, CAS 10416-59-8) and stirred at 80° C. for 4 h. The reaction mixture was concentrated under reduced pressure and purified by flash chromatography (silica, DCM/EtOH gradient 0-20%) to give 1.23 g (95% purity, 81% yield) of the title compound.

$^1$H-NMR (400 MHz, DMSO-$d_6$): δ [ppm]=2.78 (t, 2H), 3.16 (td, 2H), 3.40-3.54 (m, 3H), 3.59-3.69 (m, 2H), 3.71 (s, 3H), 3.73-3.79 (m, 1H), 3.83-3.95 (m, 2H), 4.16 (t, 2H), 4.67 (d, 2H), 7.11 (t, 1H), 7.27-7.33 (m, 2H), 7.73 (br s, 1H), 7.81 (dd, 1H), 8.24 (d, 1H), 8.39 (s, 1H), 13.69 (s, 1H), 14.79 (s, 1H).

LC-MS (method 2): $R_t$=1.09 min; MS (ESIpos): m/z=519 $[M+H]^+$

Intermediate 6-4

4-[({3-[(1,4-dioxan-2-yl)methoxy]pyridin-4-yl}methyl)amino]-N-(3-fluoro-2-methoxyphenyl)-2-oxo-1,2,5,6-tetrahydropyridine-3-carbothioamide

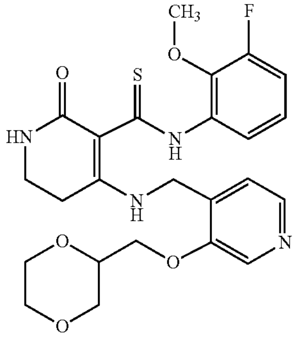 [SMILES: COc1c(F)cccc1NC(=S)C1=C(NCc2ccncc2OCC2COCCO2)CCNC1=O]

Using an analogous method as described for intermediate 6-1 with N-(3-fluoro-2-methoxyphenyl)-4-hydroxy-2-oxo-1,2,5,6-tetrahydropyridine-3-carbothioamide (intermediate 5-4, 179 mg, 604 μmol) and 1-{3-[(1,4-dioxan-2-yl)methoxy]pyridin-4-yl}methanamine (intermediate 2-1, 190 mg, 845 μmol) as the starting materials; 120 mg of the title compound were prepared (34% yield) after heating for 2 h and purification by flash chromatography (amino phase silica, DCM/EtOH gradient 0-10%).

$^1$H-NMR (400 MHz, DMSO-$d_6$): δ [ppm]=14.74 (s, 1H), 13.70 (br t, 1H), 8.39 (s, 1H), 8.24 (d, 1H), 7.64-7.73 (m, 2H), 7.30 (d, 1H), 7.02-7.14 (m, 2H), 4.67 (d, 2H), 4.13-4.21 (m, 2H), 3.84-3.95 (m, 2H), 3.59-3.77 (m, 4H), 3.40-3.53 (m, 2H), 3.13-3.22 (m, 2H), 2.68-2.80 (m, 2H), 1.59 (br s, 1H), 0.93-1.39 (m, 1H).

LC-MS (method 2): $R_t$=1.01 min; MS (ESIpos): m/z=503 $[M+H]^+$.

Intermediate 6-7

N-(2,3-dichlorophenyl)-4-[({3-[(1,4-dioxan-2-yl)methoxy]pyridin-4-yl}methyl)amino)]-2-oxo-1,2,5,6-tetrahydropyridine-3-carbothioamide

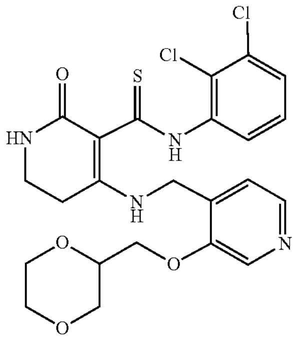 [SMILES: O=C1NCCC(NCc2ccncc2OCC2COCCO2)=C1C(=S)Nc1cccc(Cl)c1Cl]

Using an analogous method as described for intermediate 6-1 with N-(2,3-dichlorophenyl)-4-hydroxy-2-oxo-1,2,5,6-tetrahydropyridine-3-carbothioamide (intermediate 5-7, 160 mg, 504 μmol) and 1-{3-[(1,4-dioxan-2-yl)methoxy]pyridin-4-yl}methanamine (intermediate 2-1, 158 mg, 706 μmol) as the starting materials; 110 mg of the title compound were prepared (35% yield) after and heating for 2 h and purification by flash chromatography (amino phase silica, DCM/EtOH gradient 0-10%).

$^1$H-NMR (400 MHz, DMSO-$d_6$): δ [ppm]=14.90 (s, 1H), 13.66 (t, 1H), 8.39 (s, 1H), 8.24 (d, 1H), 7.75 (br s, 1H), 7.55 (dd, 1H), 7.51 (dd, 1H), 7.28-7.38 (m, 3H), 4.68 (d, 3H), 4.14-4.21 (m, 2H), 3.87-3.90 (m, 1H), 3.72-3.76 (m, 1H), 3.64-3.67 (m, 1H), 3.58-3.63 (m, 1H), 3.35-3.53 (m, 3H), 2.79 (t, 2H).

LC-MS (method 2): $R_t$=1.08 min; MS (ESIpos): m/z=523 [M+H]$^+$.

Intermediate 6-10

N-(3-chloro-2-methylphenyl)-4-[({3-[(1,4-dioxan-2-yl)methoxy]pyridin-4-yl}methyl)amino]-2-oxo-1,2,5,6-tetrahydropyridine-3-carbothioamide

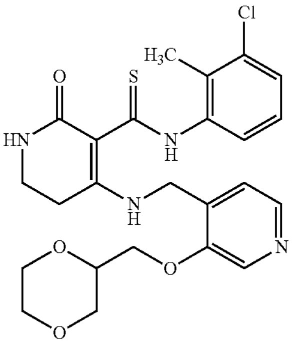 [SMILES: Cc1c(Cl)cccc1NC(=S)C1=C(NCc2ccncc2OCC2COCCO2)CCNC1=O]

Using an analogous method as described for intermediate 6-1; N-(3-chloro-2-methylphenyl)-4-hydroxy-2-oxo-1,2,5,6-tetrahydropyridine-3-carbothioamide (intermediate 5-10, 189 mg, 637 μmol) and 1-{3-[(1,4-dioxan-2-yl)methoxy]pyridin-4-yl}methanamine (intermediate 2-1, 200 mg, 892 μmol) as the starting materials; 180 mg of the title compound were prepared (56% yield) after heating for 2 h and purification by flash chromatography (amino phase silica, DCM/EtOH gradient 0-10%).

$^1$H-NMR (400 MHz, DMSO-$d_6$): δ [ppm]=14.54 (s, 1H), 13.64 (br t, 1H), 8.38 (s, 1H), 8.24 (d, 1H), 7.69 (br s, 1H), 7.28-7.37 (m, 2H), 7.13-7.26 (m, 2H), 4.65 (d, 2H), 4.14-4.20 (m, 2H), 3.74-3.88 (m, 3H), 3.63-3.71 (m, 2H), 3.42-3.53 (m, 2H), 3.14-3.31 (m, 2H), 2.77 (t, 2H), 2.16 (s, 3H).

LC-MS (method 2): $R_t$=1.09 min; MS (ESIpos): m/z=501 [M+H]$^+$.

Intermediate 6-11

N-(3-chloro-2-methoxyphenyl)-4-{[(3-{[(3R)-4-methylmorpholin-3-yl]methoxy}pyridin-4-yl)methyl]amino}-2-oxo-1,2,5,6-tetrahydropyridine-3-carbothioamide

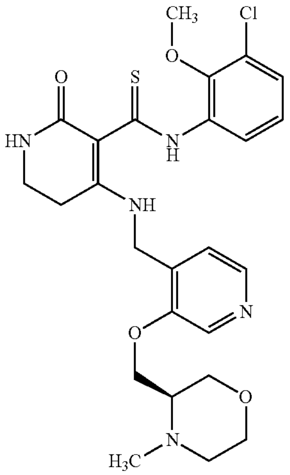 [SMILES: COc1c(Cl)cccc1NC(=S)C1=C(NCc2ccncc2OC[C@H]2COCCN2C)CCNC1=O]

Using an analogous method as described for intermediate 6-1 with N-(3-chloro-2-methoxyphenyl)-4-hydroxy-2-oxo-1,2,5,6-tetrahydropyridine-3-carbothioamide (intermediate 5-1, 142 mg, 407 μmol) and 1-(3-{[(3R)-4-methylmorpholin-3-yl]methoxy}pyridin-4-yl)methanamine (intermediate 2-2, 116 mg, 489 μmol) as the starting materials; 85.6 mg of the title compound were prepared (36% yield) after heating for 3 h and purification by preparative HPLC (method 10, gradient: 0.00-0.50 min 30% B, 0.50-6.00 min 30-70% B).

$^1$H-NMR (400 MHz, DMSO-$d_6$): δ [ppm]=14.79 (s, 1H), 13.67 (br t, 1H), 8.41 (s, 1H), 8.24 (d, 1H), 7.81 (dd, 1H), 7.73 (br s, 1H), 7.28-7.33 (m, 2H), 7.11 (t, 1H), 4.67 (br d, 2H), 4.31 (dd, 1H), 4.05 (dd, 1H), 3.90 (dd, 1H), 3.67-3.73 (m, 4H), 3.50 (td, 1H), 3.34-3.40 (m, 1H), 3.13-3.21 (m, 2H), 2.79 (t, 2H), 2.63-2.70 (m, 1H), 2.19-2.33 (m, 4H), 1.46-1.76 (m, 1H).

LC-MS (method 2): $R_t$=1.08 min; MS (ESIpos): m/z=532.5 [M+H]$^+$

Intermediate 6-12

N-(3-fluoro-2-methoxyphenyl)-4-(((3-hydroxypyridin-4-yl)methyl)amino)-2-oxo-1,2,5,6-tetrahydropyridine-3-carbothioamide

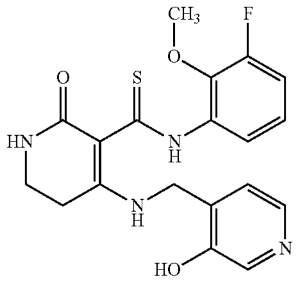 [SMILES: COc1c(F)cccc1NC(=S)C1=C(NCc2ccncc2O)CCNC1=O]

A mixture of 4-(aminomethyl)pyridin-3-ol (CAS 20485-35-2, 75 g, 0.604 mol) and N-(3-fluoro-2-methoxyphenyl)-4-hydroxy-2-oxo-1,2,5,6-tetrahydropyridine-3-carbothioamide (intermediate 5-4, 150 g, 0.506 mol) in DMA (1.2 L) was stirred at 120° C. for 2.5 h under nitrogen. The mixture was concentrated in vacuum to remove most of the solvent. The dark brown solution was slowly added to EtOAc (8 L) with stirring. The resulting mixture was washed with water (2.5 L) and brine (2.5 L×2). The organic phase was dried over sodium sulphate, filtered and concentrated in vacuum. The residue was slurried with EtOAc (300 mL) and filtered. The filter cake was dried in vacuum to afford the title compound (87 g, 47% yield) as a yellow solid.

$^1$H NMR (400 MHz, DMSO-$d_6$): δ [ppm]=14.73 (s, 1H), 13.69 (t, 1H), 10.28 (s, 1H), 8.21-8.13 (m, 2H), 7.67-7.66 (m, 2H), 7.10 (br.s, 1H), 7.09-7.04 (m, 2H), 4.61 (d, 2H), 3.79 (s, 3H), 3.16 (t, 2H), 2.77 (t, 2H).

Intermediate 6-15

N-(3-chloro-2-methoxyphenyl)-4-[({3-[(4-methylmorpholin-2-yl)methoxy]pyridin-4-yl}methyl)amino]-2-oxo-1,2,5,6-tetrahydropyridine-3-carbothioamide

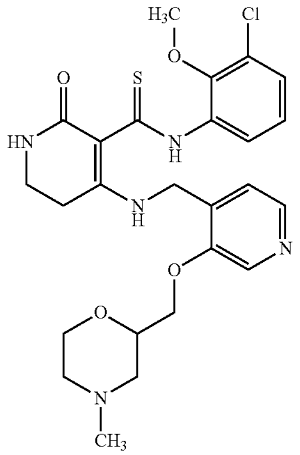 [SMILES: COc1c(Cl)cccc1NC(=S)C1=C(NCc2ccncc2OCC2CN(C)CCO2)CCNC1=O]

Using an analogous method as described for intermediate 6-1 with N-(3-fluoro-2-methoxyphenyl)-4-hydroxy-2-oxo-1,2,5,6-tetrahydropyridine-3-carbothioamide (intermediate 5-4, 100 mg, 320 μmol) and 1-(3-{[4-methylmorpholin-2-yl]methoxy}pyridin-4-yl)methanamine (intermediate 2-3, 114 mg, 480 μmol) as the starting materials; 74.3 mg (80% purity, 35% yield) of the title compound were prepared after heating for 4 h and purification by flash chromatography (amino phase silica, DCM/EtOH gradient 0-10%).

$^1$H-NMR (400 MHz, DMSO-$d_6$) δ [ppm]: 1.880 (0.45), 2.176 (4.07), 2.186 (0.73), 2.191 (0.45), 2.518 (1.66), 2.523 (1.13), 2.787 (0.65), 2.799 (0.61), 3.162 (0.56), 3.169 (0.54), 3.533 (0.46), 3.539 (0.45), 3.711 (9.24), 3.819 (0.47), 3.823 (0.40), 4.149 (0.65), 4.161 (1.12), 4.176 (0.61), 4.655 (0.80), 4.670 (0.82), 5.759 (16.00), 7.086 (0.63), 7.107 (1.27), 7.127 (0.73), 7.283 (0.77), 7.287 (0.81), 7.302 (0.77), 7.306 (1.39), 7.318 (0.80), 7.723 (0.53), 7.803 (0.59), 7.806 (0.60), 7.823 (0.57), 7.827 (0.53), 8.234 (1.27), 8.246 (1.26), 8.392 (1.87), 14.791 (1.01).

LC-MS (method 2): $R_t$=0.84 min; MS (ESipos): m/z=532 $[M+H]^+$

Intermediate 6-18

N-(3-chloro-5-fluoro-2-methoxyphenyl)-4-[({3-[(4-methylmorpholin-2-yl)methoxy]pyridin-4-yl}methyl)amino]-2-oxo-1,2,5,6-tetrahydropyridine-3-carbothioamide

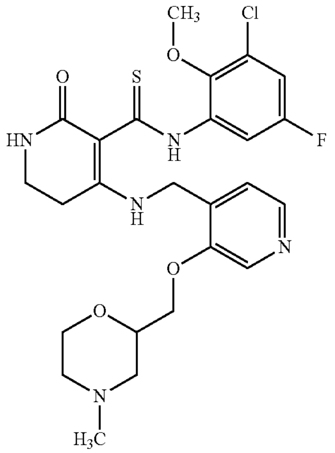 [SMILES: COc1c(Cl)cc(F)cc1NC(=S)C1=C(NCc2ccncc2OCC2CN(C)CCO2)CCNC1=O]

Using an analogous method as described for intermediate 6-1 with N-(3-chloro-5-fluoro-2-methoxyphenyl)-4-hydroxy-2-oxo-1,2,5,6-tetrahydropyridine-3-carbothioamide (intermediate 5-18, 100 mg, 302 μmol) and 1-(3-{[4-methylmorpholin-2-yl]methoxy}pyridin-4-yl)methanamine (intermediate 2-3, 108 mg, 453 μmol) as the starting materials; 166 mg (70% purity, 70% yield) of the title compound were prepared after purification by flash chromatography (amino phase silica, DCM/EtOH gradient 0-10%).

$^1$H-NMR (400 MHz, DMSO-$d_6$): δ [ppm]=1.881 (0.59), 1.908 (0.51), 1.984 (0.51), 1.991 (0.55), 2.174 (5.75), 2.185 (0.88), 2.191 (2.53), 2.518 (2.46), 2.523 (1.65), 2.581 (0.55), 2.609 (0.49), 2.785 (0.52), 2.798 (0.96), 2.815 (0.60), 3.096 (0.44), 3.161 (0.55), 3.168 (0.51), 3.387 (0.97), 3.535 (0.57), 3.542 (0.68), 3.700 (7.75), 3.786 (0.69), 3.791 (0.73), 3.795 (0.71), 3.810 (0.63), 3.815 (0.70), 3.823 (0.75), 4.115 (0.52), 4.119 (0.55), 4.128 (0.53), 4.154 (0.77), 4.166 (0.94), 4.181 (0.60), 4.672 (0.76), 4.687 (0.77), 5.759 (16.00), 7.267 (0.58), 7.275 (0.65), 7.287 (0.58), 7.295 (0.63), 7.313 (0.77), 7.325 (0.74), 7.792 (0.49), 8.046 (0.50), 8.053 (0.50), 8.073 (0.47), 8.080 (0.47), 8.238 (1.20), 8.250 (1.12), 8.267 (0.55), 8.279 (0.66), 8.399 (1.72), 15.080 (0.94).

LC-MS (method 2): $R_t$=1.11 min; MS (ESipos): m/z=550 $[M+H]^+$

Intermediate 6-19

N-(3-chloro-5-fluoro-2-methoxyphenyl)-4-[({3-[(1,4-dioxan-2-yl)methoxy]pyridin-4-yl}methyl)amino]-2-oxo-1,2,5,6-tetrahydropyridine-3-carbothioamide

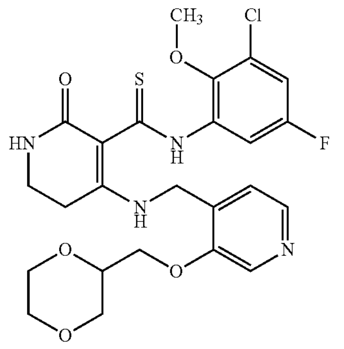 [SMILES: COc1c(Cl)cc(F)cc1NC(=S)C1=C(NCc2ccncc2OCC2COCCO2)CCNC1=O]

Using an analogous method as described for intermediate 6-1 with N-(3-chloro-5-fluoro-2-methoxyphenyl)-4-hydroxy-2-oxo-1,2,5,6-tetrahydropyridine-3-carbothioamide (intermediate 5-18, 100 mg, 302 μmol) and 1-(3-{[1,4-dioxan-2-yl]methoxy}pyridin-4-yl)methanamine (intermediate 2-1, 94.9 mg, 423 μmol) as the starting materials, 160 mg (90% purity, 89% yield) of the title compound were prepared after purification by flash chromatography (silica, DCM/EtOH gradient 0-30%).

$^1$H-NMR (400 MHz, DMSO-$d_6$) δ [ppm]: 0.821 (0.41), 0.904 (0.45), 1.035 (8.84), 1.052 (16.00), 1.070 (9.56), 1.154 (1.90), 1.172 (3.66), 1.189 (1.72), 1.987 (6.85), 2.518 (1.36), 2.522 (0.92), 2.790 (0.61), 3.157 (0.42), 3.404 (1.39), 3.417 (1.49), 3.421 (4.01), 3.434 (4.35), 3.439 (4.40), 3.452 (4.43), 3.457 (1.21), 3.461 (0.53), 3.469 (1.28), 3.501 (0.40), 3.652 (0.66), 3.655 (0.65), 3.702 (7.42), 3.750 (0.43), 3.785 (0.67), 3.788 (0.43), 3.890 (0.58), 3.999 (0.46), 4.017 (1.36), 4.035 (1.39), 4.053 (0.47), 4.156 (0.56), 4.165 (0.77), 4.179 (0.54), 4.343 (2.52), 4.356 (4.91), 4.368 (2.35), 4.683 (0.68), 4.697 (0.68), 7.272 (0.48), 7.280 (0.60), 7.293 (0.51), 7.300 (0.64), 7.305 (0.63), 7.317 (0.62), 7.800 (0.42), 8.032 (0.40), 8.040 (0.42), 8.059 (0.41), 8.066 (0.40), 8.242 (0.98), 8.254 (0.94), 8.394 (1.43), 15.078 (0.82).

LC-MS (method 2): $R_t$=1.14 min; MS (ESipos): m/z=537 $[M+H]^+$

Intermediate 6-20

N-(3-fluoro-2-methoxyphenyl)-4-{[(3-{[(3S)-4-methylmorpholin-3-yl]methoxy}pyridin-4-yl)methyl]amino}-2-oxo-1,2,5,6-tetrahydropyridine-3-carbothioamide

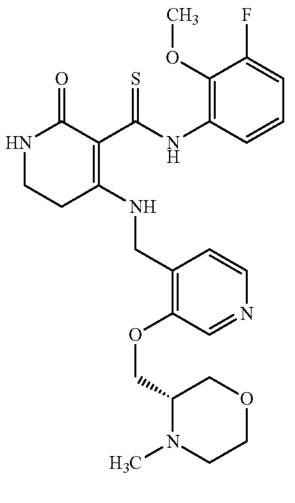 [SMILES: COc1c(F)cccc1NC(=S)C1=C(NCc2ccncc2OC[C@@H]2COCCN2C)CCNC1=O]

Using an analogous method as described for intermediate 6-1 with N-(3-fluoro-2-methoxyphenyl)-4-hydroxy-2-oxo-1,2,5,6-tetrahydropyridine-3-carbothioamide (intermediate 5-4, 200 mg, 675 μmol) and 1-(3-{[(3S)-4-methylmorpholin-3-yl]methoxy}pyridin-4-yl)methanamine (intermediate 2-4, 208 mg, 877 μmol) as the starting materials, 105 mg (99% purity, 30% yield) of the title compound were prepared after heating for 3 h and purification by preparative HPLC (method 10, gradient: 0.00-0.50 min 15% B, 0.50-6.00 min 15-55% B).

$^1$H-NMR (400 MHz, DMSO-$d_6$): δ [ppm]=2.195 (0.50), 2.203 (0.62), 2.221 (0.73), 2.224 (0.80), 2.229 (0.79), 2.232 (0.77), 2.250 (0.69), 2.258 (0.63), 2.287 (16.00), 2.322 (0.48), 2.326 (0.65), 2.331 (0.46), 2.518 (2.86), 2.522 (1.80), 2.645 (0.60), 2.651 (1.24), 2.658 (0.75), 2.664 (0.58), 2.668 (0.75), 2.673 (0.96), 2.680 (1.16), 2.687 (0.56), 2.760 (1.14), 2.776 (2.31), 2.793 (1.34), 3.134 (0.86), 3.142 (0.98), 3.152 (1.59), 3.158 (1.51), 3.167 (0.87), 3.175 (0.73), 3.347 (1.31), 3.371 (1.26), 3.375 (1.37), 3.398 (1.19), 3.473 (0.50), 3.480 (0.60), 3.501 (0.98), 3.507 (0.98), 3.527 (0.72), 3.533 (0.60), 3.677 (0.56), 3.683 (1.07), 3.690 (0.58), 3.704 (0.46), 3.711 (0.82), 3.718 (0.41), 3.780 (13.85), 3.783 (13.72), 3.884 (0.99), 3.892 (0.99), 3.912 (0.89), 3.920 (0.88), 4.029 (0.98), 4.044 (1.01), 4.054 (1.17), 4.070 (1.12), 4.291 (1.18), 4.302 (1.21), 4.317 (1.03), 4.327 (0.97), 4.658 (1.87), 4.674 (1.89), 7.044 (0.58), 7.049 (1.31), 7.065 (1.59), 7.069 (2.63), 7.075 (1.64), 7.085 (1.41), 7.090 (0.58), 7.096 (1.44), 7.101 (1.44), 7.117 (0.56), 7.122 (0.41), 7.296 (2.20), 7.308 (2.24), 7.653 (1.44), 7.658 (0.89), 7.670 (1.15), 7.676 (0.86), 7.704 (1.58), 8.236 (3.27), 8.247 (3.17), 8.411 (4.92), 13.661 (0.56), 13.676 (1.10), 13.690 (0.53), 14.736 (2.92).

LC-MS (method 6): Rt=0.62 min; MS (ESipos): m/z=516 $[M+H]^+$

Intermediate 6-21

N-(3-chloro-2-methoxyphenyl)-4-{[(3-{[(3S)-4-methylmorpholin-3-yl]methoxy}pyridin-4-yl)methyl]amino}-2-oxo-1,2,5,6-tetrahydropyridine-3-carbothioamide

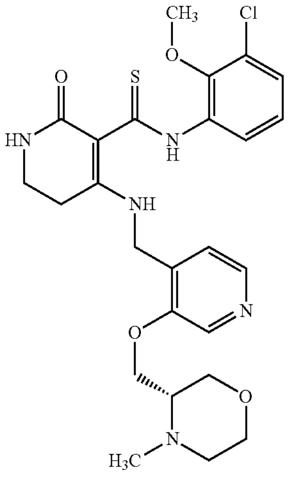 [SMILES: COc1c(Cl)cccc1NC(=S)C1=C(NCc2ccncc2OC[C@@H]2COCCN2C)CCNC1=O]

Using an analogous method as described for intermediate 6-1 with N-(3-chloro-2-methoxyphenyl)-4-hydroxy-2-oxo-1,2,5,6-tetrahydropyridine-3-carbothioamide (intermediate 5-1, 200 mg, 639 μmol) and 1-(3-{[(3S)-4-methylmorpholin-3-yl]methoxy}pyridin-4-yl)methanamine (intermediate 2-4, 197 mg, 831 μmol) as the starting materials 102 mg (99% purity, 30% yield) of the title compound were prepared after heating for 3 h at 120° C. and purification by preparative HPLC (method 10, gradient: 0.00-0.50 min 15% B, 0.50-6.00 min 15-55% B).

$^1$H-NMR (400 MHz, DMSO-$d_6$) δ [ppm]: 2.288 (3.78), 2.327 (0.47), 2.518 (1.87), 2.523 (1.27), 2.651 (0.43), 2.665 (0.45), 2.669 (0.59), 2.673 (0.55), 2.679 (0.47), 2.769 (0.69), 2.786 (1.40), 2.803 (0.81), 3.141 (0.53), 3.148 (0.61), 3.157 (0.97), 3.164 (0.93), 3.174 (0.53), 3.181 (0.44), 3.346 (0.55), 3.372 (0.52), 3.506 (0.45), 3.684 (0.50), 3.712 (16.00), 3.883 (0.44), 3.891 (0.53), 3.912 (0.42), 4.293 (0.54), 4.304 (0.56), 4.319 (0.47), 4.329 (0.44), 4.663 (1.08), 4.679 (1.10), 7.088 (1.04), 7.108 (2.24), 7.128 (1.28), 7.285 (1.42), 7.289 (1.49), 7.301 (1.47), 7.305 (1.46), 7.309 (1.44), 7.312 (1.47), 7.726 (0.92), 7.794 (1.07), 7.797 (1.08), 7.814 (1.02), 7.818 (0.96), 8.238 (1.81), 8.250 (1.65), 8.413 (3.11), 13.667 (0.68), 14.787 (1.82).

LC-MS (method 6): Rt=0.68 min; MS (ESipos): m/z=532 [M+H]$^+$

Intermediate 6-22 tert-butyl (2S)-2-[({4-[({5-[(3-fluoro-2-methoxyphenyl) carbamothioyl]-6-oxo-1,2,3,6-tetrahydropyridin-4-yl}amino)methyl]pyridin-3-yl}oxy)methyl]morpholine-4-carboxylate

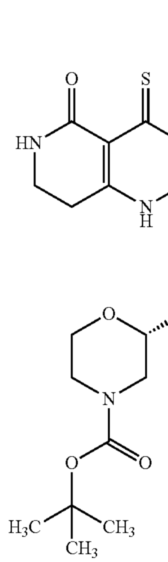

Using an analogous method as described for intermediate 6-1 with N-(3-fluoro-2-methoxyphenyl)-4-hydroxy-2-oxo-1,2,5,6-tetrahydropyridine-3-carbothioamide (intermediate 5-4, 1.00 g, 3.37 mmol) and tert-butyl (2S)-2-({[4-(aminomethyl)pyridin-3-yl]oxy}methyl)morpholine-4-carboxylate (intermediate 2-5, 1.53 g, 4.72 mmol) as the starting materials; 1.43 g (70% purity, 49% yield) of the title compound were prepared after heating for 6 h and purification by flash chromatography (silica, DCM/EtOH gradient 0-20%).

$^1$H-NMR (400 MHz, DMSO-$d_6$): δ [ppm]=1.035 (6.69), 1.052 (16.00), 1.070 (7.70), 1.394 (4.63), 1.401 (2.39), 1.405 (3.46), 2.331 (0.41), 2.518 (1.92), 2.523 (1.41), 2.673 (0.42), 3.404 (1.10), 3.417 (1.21), 3.422 (3.66), 3.435 (3.78), 3.440 (3.26), 3.452 (3.33), 3.457 (1.19), 3.469 (1.18), 3.780 (2.11), 3.782 (2.08), 3.797 (0.42), 3.857 (0.84), 3.860 (0.83), 4.219 (0.41), 4.231 (0.42), 4.344 (2.52), 4.356 (4.87), 4.369 (2.35), 8.241 (0.54), 8.253 (0.53), 8.402 (0.81), 14.735 (0.40).

LC-MS (method 2): $R_t$=1.19 min; MS (ESIpos): m/z=602 [M+H]$^+$

Intermediate 6-24

N-(3-chloro-2-methoxyphenyl)-4-[({3-[2-(1,4-dioxan-2-yl)ethoxy]pyridin-4-yl}methyl)amino]-2-oxo-1,2,5,6-tetrahydropyridine-3-carbothioamide

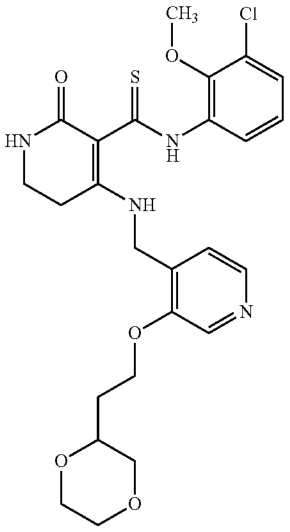 [SMILES: COc1c(Cl)cccc1NC(=S)C1=C(NCc2ccncc2OCCC2COCCO2)CCNC1=O]

Using an analogous method as described for intermediate 6-1 with N-(3-chloro-2-methoxyphenyl)-4-hydroxy-2-oxo-1,2,5,6-tetrahydropyridine-3-carbothioamide (intermediate 5-1, 200 mg, 639 μmol) and 1-(3-{2-[1,4-dioxan-2-yl] ethoxy}pyridin-4-yl)methanamine (intermediate 2-6, 198 mg, 831 μmol) as the starting materials, 110 mg (96% purity, 31% yield) of the title compound were prepared after heating for 3 h at 130° C. and purification by preparative HPLC (method 10, gradient: 0.00-0.50 min 15% B, 0.50-6.00 min 15-55% B).

$^1$H-NMR (400 MHz, DMSO-$d_6$) δ [ppm]: 1.792 (0.45), 1.812 (0.43), 1.838 (0.40), 1.850 (0.42), 2.518 (1.13), 2.523 (0.78), 2.763 (0.87), 2.771 (0.86), 2.780 (0.52), 2.786 (0.47), 3.140 (0.51), 3.148 (0.57), 3.156 (0.97), 3.164 (0.96), 3.173 (0.50), 3.181 (0.43), 3.197 (0.60), 3.224 (0.94), 3.227 (0.95), 3.253 (0.64), 3.445 (0.75), 3.452 (0.83), 3.471 (0.48), 3.480 (0.60), 3.545 (0.45), 3.551 (0.53), 3.573 (0.70), 3.580 (0.81), 3.605 (0.86), 3.611 (1.14), 3.617 (0.53), 3.638 (0.55), 3.644 (0.47), 3.689 (0.92), 3.697 (1.10), 3.712 (16.00), 3.718 (2.12), 3.744 (0.88), 3.749 (0.65), 4.203 (0.84), 4.219 (1.35), 4.232 (0.58), 4.238 (0.56), 4.656 (1.44), 4.670 (1.43), 7.089 (1.01), 7.110 (2.16), 7.130 (1.25), 7.286 (1.37), 7.289 (1.46), 7.306 (2.13), 7.310 (1.42), 7.317 (1.10), 7.726 (0.93), 7.802 (1.03), 7.806 (1.05), 7.823 (0.99), 7.826 (0.93), 8.225 (1.23), 8.237 (1.18), 8.373 (1.98), 13.695 (0.65), 14.792 (1.75).

LC-MS (method 6): Rt=0.90 min; MS (ESipos): m/z=533 [M+H]$^+$

Intermediate 6-27 tert-butyl (2S)-2-[({4-[({5-[(3-chloro-5-fluoro-2-methoxyphenyl)carbamothioyl]-6-oxo-1,2,3,6-tetrahydro-pyridin-4-yl}amino)methyl]pyridin-3-yl}oxy)methyl]morpholine-4-carboxylate

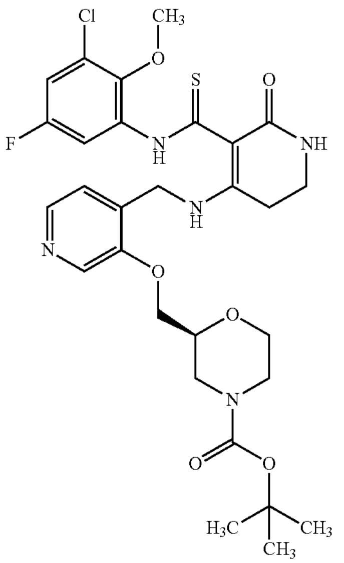 [SMILES: COc1c(Cl)cc(F)cc1NC(=S)C1=C(NCc2ccncc2OC[C@@H]2CN(C(=O)OC(C)(C)C)CCO2)CCNC1=O]

Using an analogous method as described for intermediate 6-1 with N-(3-chloro-5-fluoro-2-methoxyphenyl)-4-hydroxy-2-oxo-1,2,5,6-tetrahydropyridine-3-carbothioamide (intermediate 5-18, 225 mg, 680 μmol) and tert-butyl (2S)-2-({[4-(aminomethyl)pyridin-3-yl]oxy}methyl)morpholine-4-carboxylate (intermediate 2-5, 308 mg, 952 μmol) as the starting materials; 150 mg (80% purity, 28% yield) of the title compound were prepared after heating for 6 h and purification by flash chromatography (silica, DCM/EtOH gradient 0-20%).

$^1$H-NMR (400 MHz, DMSO-$d_6$) δ [ppm]: 1.035 (2.70), 1.052 (5.86), 1.070 (3.02), 1.232 (0.46), 1.389 (16.00), 1.405 (6.16), 1.419 (1.21), 2.331 (0.75), 2.430 (0.47), 2.447 (0.51), 2.518 (3.46), 2.523 (2.53), 2.673 (0.75), 2.772 (0.61), 2.789 (1.14), 2.805 (0.74), 3.137 (0.46), 3.145 (0.53), 3.154 (0.79), 3.161 (0.75), 3.405 (0.58), 3.417 (0.72), 3.422 (1.54), 3.435 (1.70), 3.440 (1.70), 3.445 (0.63), 3.452 (1.56), 3.457 (0.61), 3.469 (0.63), 3.655 (0.79), 3.699 (12.68), 3.719 (0.53), 3.732 (0.75), 3.738 (0.84), 3.757 (0.49), 3.764 (0.44), 3.787 (2.07), 3.821 (0.49), 3.842 (0.93), 3.870 (0.40), 4.225 (1.58), 4.237 (1.60), 4.344 (0.84), 4.357 (1.63), 4.370 (0.82), 4.681 (1.14), 4.696 (1.11), 5.759 (0.75), 7.267 (0.93), 7.275 (1.12), 7.287 (0.96), 7.295 (1.05), 7.311 (0.79), 7.323 (0.79), 7.799 (0.77), 8.031 (0.67), 8.038 (0.68), 8.057 (0.67), 8.065 (0.63), 8.245 (1.81), 8.257 (1.63), 8.290 (0.54), 8.410 (2.60), 13.671 (0.58), 15.074 (1.58).

LC-MS (method 2): $R_t$=1.30 min; MS (ESIpos): m/z=636 [M+H]$^+$

Intermediate 6-29

N-(3-chloro-2-ethylphenyl)-4-[({3-[(4-methylmorpholin-2-yl)methoxy]pyridin-4-yl}methyl)amino]-2-oxo-1,2,5,6-tetrahydropyridine-3-carbothioamide

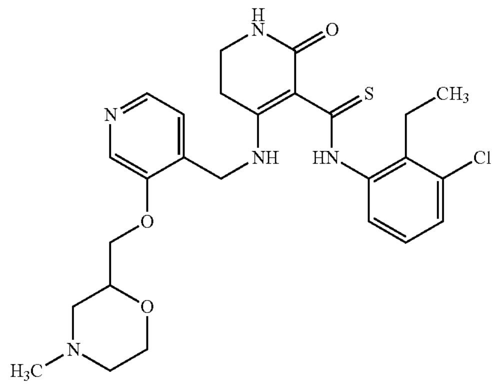 [SMILES: CCc1c(Cl)cccc1NC(=S)C1=C(NCc2ccncc2OCC2CN(C)CCO2)CCNC1=O]

Using an analogous method as described for intermediate 6-1 with N-(3-chloro-2-ethylphenyl)-4-hydroxy-2-oxo-1,2,5,6-tetrahydropyridine-3-carbothioamide (intermediate 5-29, 300 mg, 965 μmol) and 1-(3-{[4-methylmorpholin-2-yl]methoxy}pyridin-4-yl)methanamine (intermediate 2-3, 321 mg, 1.35 mmol) as the starting materials; 300 mg (80% purity, 47% yield) of the title compound were prepared after heating for 6 h and purification by flash chromatography (silica, DCM/EtOH gradient 0-20%).

$^1$H-NMR (400 MHz, DMSO-$d_6$): δ [ppm]=0.798 (0.84), 0.814 (0.93), 0.821 (0.93), 0.840 (0.43), 0.886 (0.53), 0.904 (1.07), 0.922 (0.50), 1.035 (9.51), 1.052 (16.00), 1.066 (1.09), 1.070 (9.08), 1.073 (1.50), 1.232 (0.45), 1.874 (0.59), 1.901 (0.47), 1.907 (0.59), 1.983 (0.41), 1.990 (0.52), 2.178 (5.56), 2.195 (1.38), 2.202 (0.47), 2.331 (0.74), 2.518 (3.86), 2.522 (2.50), 2.580 (0.57), 2.591 (1.05), 2.610 (1.21), 2.673 (0.95), 2.784 (0.95), 2.817 (0.50), 3.162 (0.41), 3.172 (0.69), 3.179 (0.65), 3.404 (1.33), 3.417 (1.38), 3.421 (3.41), 3.434 (3.43), 3.439 (3.91), 3.452 (4.01), 3.457 (1.15), 3.469 (1.19), 3.529 (0.57), 3.535 (0.57), 3.735 (0.55), 3.784 (0.47), 3.788 (0.47), 3.792 (0.47), 3.812 (0.64), 3.816 (0.62), 4.111 (0.41), 4.123 (0.48), 4.138 (0.83), 4.149 (0.83), 4.154 (0.88), 4.168 (0.74), 4.343 (2.64), 4.356 (5.06), 4.368 (2.39), 4.636 (0.93), 4.651 (0.93), 7.205 (1.50), 7.208 (1.38), 7.218 (2.69), 7.296 (1.02), 7.305 (1.02), 7.308 (1.05), 7.315 (1.17), 7.327 (0.55), 7.701 (0.64), 8.228 (1.50), 8.240 (1.38), 8.282 (0.47), 8.385 (2.07), 13.654 (0.43), 14.636 (1.17).

LC-MS (method 2): $R_t$=1.14 min; MS (ESIpos): m/z=530 [M+H]$^+$

Intermediate 6-30

N-(3-chloro-2-methoxyphenyl)-4-[({3-[(5,5-dimethyl-1,4-dioxan-2-yl)methoxy]pyridin-4-yl}methyl)amino]-2-oxo-1,2,5,6-tetrahydropyridine-3-carbothioamide

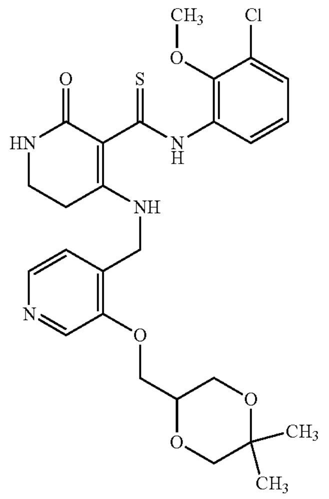 [SMILES: COc1c(Cl)cccc1NC(=S)C1=C(NCc2ccncc2OCC2COC(C)(C)CO2)CCNC1=O]

Using an analogous method as described for intermediate 6-1 with N-(3-chloro-2-methoxyphenyl)-4-hydroxy-2-oxo-1,2,5,6-tetrahydropyridine-3-carbothioamide (intermediate 5-1, 200 mg, 639 μmol) and 1-{3-[(5,5-dimethyl-1,4-dioxan-2-yl)methoxy]pyridin-4-yl}methanamine (intermediate 2-7, 210 mg, 831 μmol) as the starting materials; 55.0 mg (98% purity, 15% yield) of the title compound were prepared after heating for 3 h at 130° C. and purification by preparative HPLC (method 10, gradient: 0.00-0.50 min 15% B, 0.50-6.00 min 15-55% B).

$^1$H-NMR (400 MHz, DMSO-$d_6$): δ [ppm]=1.042 (9.29), 1.249 (8.31), 2.518 (2.85), 2.523 (1.83), 2.752 (0.79), 2.768 (1.57), 2.785 (0.95), 3.147 (0.74), 3.156 (1.18), 3.164 (1.13), 3.299 (1.11), 3.533 (1.90), 3.562 (1.50), 3.628 (0.50), 3.648 (1.21), 3.658 (1.28), 3.667 (1.26), 3.691 (1.55), 3.713 (16.00), 3.720 (1.14), 3.795 (0.51), 3.806 (0.64), 3.817 (0.52), 4.154 (0.42), 4.164 (0.43), 4.180 (1.25), 4.191 (1.23), 4.198 (1.31), 4.212 (1.18), 4.225 (0.43), 4.663 (1.86), 4.678 (1.86), 7.088 (1.13), 7.108 (2.42), 7.128 (1.39), 7.286 (1.58), 7.290 (1.68), 7.305 (2.17), 7.310 (1.58), 7.316 (1.59), 7.729 (1.16), 7.799 (1.26), 7.803 (1.27), 7.819 (1.18), 7.823 (1.14), 8.241 (1.91), 8.253 (1.81), 8.397 (3.02), 13.669 (0.43), 13.683 (0.81), 14.792 (2.17).

LC-MS (method 6): Rt=1.04 min; MS (ESIpos): m/z=547 $[M+H]^+$

Intermediate 6-33

4-[({3-[(5,5-dimethyl-1,4-dioxan-2-yl)methoxy]pyridin-4-yl}methyl)amino]-N-(3-fluoro-2-methoxyphenyl)-2-oxo-1,2,5,6-tetrahydropyridine-3-carbothioamide

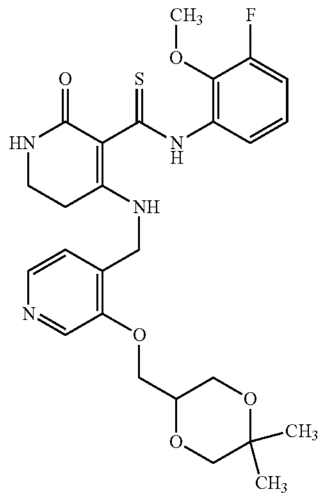 [SMILES: COc1c(F)cccc1NC(=S)C1=C(NCc2ccncc2OCC2COC(C)(C)CO2)CCNC1=O]

Using an analogous method as described for intermediate 6-1; N-(3-fluoro-2-methoxyphenyl)-4-hydroxy-2-oxo-1,2,5,6-tetrahydropyridine-3-carbothioamide (intermediate 5-1, 200 mg, 675 μmol) and 1-{3-[(5,5-dimethyl-1,4-dioxan-2-yl)methoxy]pyridin-4-yl}methanamine (intermediate 2-7, 221 mg, 877 μmol) as the starting materials, 130 mg (96% purity, 35% yield) of the title compound were prepared after heating for 2 h at 130° C. and purification by preparative HPLC (method 10, gradient: 0.00-0.50 min 15% B, 0.50-6.00 min 15-55% B).

$^1$H-NMR (400 MHz, DMSO-$d_6$) δ [ppm]: 1.043 (15.59), 1.251 (13.74), 2.518 (2.60), 2.523 (1.78), 2.742 (1.25), 2.759 (2.52), 2.775 (1.52), 3.134 (1.00), 3.142 (1.15), 3.152 (1.86), 3.158 (1.79), 3.167 (1.02), 3.175 (0.86), 3.300 (1.91), 3.535 (3.14), 3.563 (2.56), 3.622 (0.60), 3.630 (0.81), 3.650 (1.97), 3.659 (2.07), 3.668 (2.14), 3.692 (2.45), 3.722 (1.19), 3.782 (15.81), 3.785 (16.00), 3.796 (0.91), 3.808 (1.03), 3.819 (0.82), 3.832 (0.62), 4.155 (0.57), 4.165 (0.61), 4.181 (1.80), 4.192 (1.83), 4.198 (1.91), 4.212 (1.68), 4.225 (0.61), 4.238 (0.55), 4.658 (2.20), 4.672 (2.17), 7.029 (0.54), 7.045 (0.69), 7.050 (1.65), 7.065 (1.84), 7.069 (2.29), 7.071 (2.14), 7.077 (2.06), 7.085 (1.65), 7.093 (0.69), 7.098 (1.72), 7.103 (1.74), 7.119 (0.69), 7.124 (0.54), 7.307 (0.94), 7.317 (0.99), 7.657 (1.74), 7.662 (1.08), 7.676 (1.36), 7.681 (1.03), 7.708 (1.84), 8.254 (0.72), 8.404 (0.81), 13.678 (0.65), 13.693 (1.25), 13.707 (0.60), 14.741 (3.47).

LC-MS (method 6): Rt=0.94 min; MS (ESIpos): m/z=531 $[M+H]^+$

Intermediate 6-35

4-{[(3-{2-[1,4-dioxan-2-yl]ethoxy}pyridin-4-yl) methyl]amino}-N-(3-fluoro-2-methoxyphenyl)-2-oxo-1,2,5,6-tetrahydropyridine-3-carbothioamide

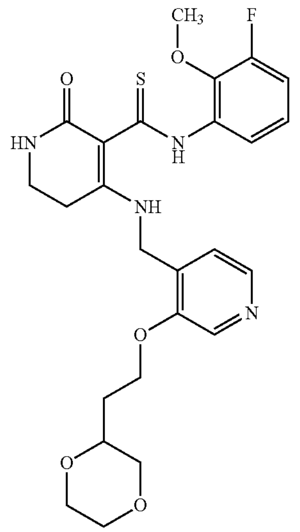 [SMILES: COc1c(F)cccc1NC(=S)C1=C(NCc2ccncc2OCCC2COCCO2)CCNC1=O]

Using an analogous method as described for intermediate 6-1; N-(3-fluoro-2-methoxyphenyl)-4-hydroxy-2-oxo-1,2,5,6-tetrahydropyridine-3-carbothioamide (intermediate 5-4, 200 mg, 675 μmol) and 1-(3-{2-[1,4-dioxan-2-yl] ethoxy}pyridin-4-yl)methanamine (intermediate 2-6, 209 mg, 877 μmol) as the starting materials, 137 mg (96% purity, 38% yield) of the title compound were prepared.

LC-MS (method 6): Rt=0.83 min; MS (ESIpos): m/z=517 $[M+H]^+$ $^1$H-NMR (400 MHz, DMSO-$d_6$) δ [ppm]: 1.757 (0.42), 1.778 (0.61), 1.793 (0.89), 1.813 (0.86), 1.822 (0.55), 1.826 (0.49), 1.833 (0.54), 1.840 (0.80), 1.852 (0.85), 1.857 (0.64), 1.868 (0.60), 2.518 (2.52), 2.523 (1.61), 2.674 (0.45), 2.735 (0.74), 2.752 (1.68), 2.761 (1.69), 2.769 (1.02), 2.777 (0.89), 3.134 (1.00), 3.142 (1.11), 3.151 (1.92), 3.159 (1.89), 3.168 (0.98), 3.175 (0.85), 3.198 (1.19), 3.224 (1.91), 3.228 (1.91), 3.254 (1.24), 3.421 (0.47), 3.425 (0.68), 3.446 (1.52), 3.453 (1.67), 3.472 (0.99), 3.481 (1.19), 3.545 (0.92), 3.552 (1.09), 3.574 (1.39), 3.580 (1.60), 3.606 (1.73), 3.612 (2.26), 3.618 (1.04), 3.639 (1.07), 3.645 (0.93), 3.690 (1.77), 3.697 (2.11), 3.709 (0.79), 3.719 (3.54), 3.728 (1.41), 3.735 (0.73), 3.744 (1.71), 3.751 (1.33), 3.782 (15.79), 3.784 (16.00), 4.203 (1.78), 4.219 (2.73), 4.232 (1.20), 4.237 (1.18), 4.653 (2.89), 4.667 (2.88), 7.030 (0.49), 7.046 (0.68), 7.051 (1.63), 7.067 (1.82), 7.070 (3.31), 7.077 (2.11), 7.086 (1.65), 7.092 (0.71), 7.098 (1.72), 7.103 (1.73), 7.119 (0.68), 7.124 (0.52), 7.303 (1.99), 7.314 (2.03), 7.660 (1.68), 7.665 (1.06), 7.677 (1.35), 7.683 (1.07), 7.703 (1.84), 8.226 (1.84), 8.237 (1.79), 8.373 (2.98), 13.689 (0.64), 13.704 (1.28), 13.718 (0.60), 14.740 (3.42).

Intermediate 6-37

N-(3-fluoro-2-methoxyphenyl)-4-{[(3-{[(3R)-4-methylmorpholin-3-yl]methoxy}pyridin-4-yl) methyl]amino}-2-oxo-1,2,5,6-tetrahydropyridine-3-carbothioamide

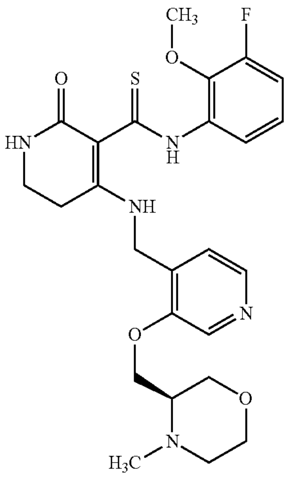 [SMILES: COc1c(F)cccc1NC(=S)C1=C(NCc2ccncc2OC[C@H]2COCCN2C)CCNC1=O]

Using an analogous method as described for intermediate 6-1 with N-(3-fluoro-2-methoxyphenyl)-4-hydroxy-2-oxo-1,2,5,6-tetrahydropyridine-3-carbothioamide (intermediate 5-4, 200 mg, 675 μmol) and 1-(3-{[(3R)-4-methylmorpholin-3-yl]methoxy}pyridin-4-yl)methanamine (intermediate 2-2, 224 mg, 945 μmol) as the starting materials; 134 mg of the title compound were prepared (38% yield) after heating for 1 h at 124° C. and purification by preparative HPLC (method 10, gradient: 0.00-0.50 min 15% B, 0.50-6.00 min 15-55% B).

$^1$H-NMR (400 MHz, DMSO-$d_6$): δ [ppm]=2.205 (0.86), 2.226 (1.57), 2.254 (1.23), 2.290 (15.27), 2.327 (1.28), 2.654 (2.07), 2.681 (1.95), 2.762 (2.11), 2.779 (3.81), 2.795 (2.41), 3.155 (3.13), 3.374 (3.80), 3.401 (2.16), 3.482 (0.97), 3.504 (1.80), 3.531 (1.16), 3.686 (1.75), 3.714 (1.51), 3.784 (16.00), 3.888 (1.65), 3.916 (1.59), 4.031 (1.27), 4.047 (1.48), 4.057 (1.61), 4.073 (1.47), 4.294 (1.53), 4.304 (1.57), 4.320 (1.45), 4.328 (1.29), 4.661 (3.52), 4.675 (3.54), 7.031 (0.48), 7.052 (1.50), 7.070 (3.26), 7.087 (1.82), 7.099 (1.95), 7.122 (0.79), 7.299 (2.83), 7.311 (2.84), 7.655 (2.12), 7.672 (2.11), 7.706 (2.52), 8.239 (3.08), 8.250 (2.98), 8.414 (5.21), 13.678 (1.85), 14.738 (3.80).

LC-MS (method 6): $R_t$=0.64 min; MS (ESIpos): m/z=516 $[M+H]^+$

Intermediate 6-38

4-[[3-[(5,5-dimethyl-1,4-dioxan-2-yl)methoxy]-4-pyridyl]methylamino]-N-(3-fluoro-2-methyl-phenyl)-6-oxo-2,3-dihydro-1H-pyridine-5-carbothioamide

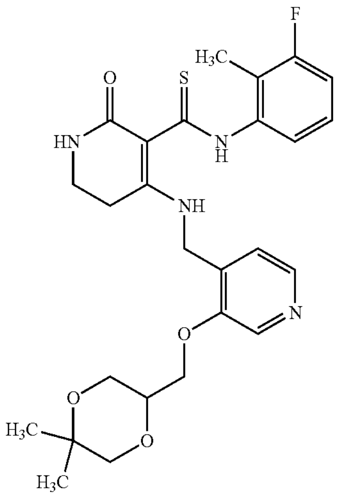 [SMILES: Cc1c(F)cccc1NC(=S)C1=C(NCc2ccncc2OCC2COC(C)(C)CO2)CCNC1=O]

Using an analogous method as described for intermediate 6-1 with N-(3-fluoro-2-methylphenyl)-4-hydroxy-2-oxo-1,2,5,6-tetrahydropyridine-3-carbothioamide (intermediate 5-38, 350 mg, 1.25 mmol) and 1-{3-[(5,5-dimethyl-1,4-dioxan-2-yl)methoxy]pyridin-4-yl}methanamine (intermediate 2-7, 315 mg, 1.25 mmol) as the starting materials; 192 mg of the title compound were prepared (27% yield) after heating for 3 h at 120° C. and purification by preparative HPLC (method 11, gradient: 0.00-2.00 min 30% B, 2.00-14.00 min 30-70% B).

$^1$H-NMR (400 MHz, DMSO-$d_6$): δ [ppm]=1.046 (16.00), 1.253 (14.02), 2.045 (8.35), 2.050 (8.21), 2.063 (1.09), 2.521 (2.37), 2.525 (1.62), 2.741 (1.29), 2.757 (2.61), 2.774 (1.60), 3.145 (1.01), 3.152 (1.15), 3.161 (1.90), 3.168 (1.80), 3.178 (0.99), 3.185 (0.85), 3.298 (1.92), 3.534 (3.17), 3.562 (2.60), 3.617 (0.65), 3.626 (0.83), 3.647 (2.00), 3.656 (2.10), 3.666 (2.13), 3.690 (2.57), 3.719 (1.29), 3.780 (0.43), 3.793 (0.82), 3.803 (1.04), 3.814 (0.83), 3.828 (0.60), 4.148 (0.72), 4.159 (0.78), 4.174 (2.17), 4.186 (2.01), 4.194 (2.14), 4.208 (2.03), 4.220 (0.76), 4.234 (0.69), 4.647 (3.08), 4.662 (3.06), 7.040 (0.87), 7.061 (1.78), 7.074 (1.74), 7.085 (1.37), 7.094 (2.40), 7.189 (0.89), 7.208 (1.38), 7.225 (1.30), 7.244 (0.54), 7.295 (2.49), 7.307 (2.52), 7.686 (1.77), 8.237 (2.54), 8.249 (2.42), 8.393 (3.97), 13.662 (1.07), 14.520 (2.54).

LC-MS (method 6): $R_t$=0.98 min; MS (ESIpos): m/z=515 [M+H]$^+$

Intermediate 6-40

N-[2-(2,2-difluoroethyl)-3-fluoro-phenyl]-4-[[3-(1,4-dioxan-2-ylmethoxy)-4-pyridyl]methylamino]-6-oxo-2,3-dihydro-1H-pyridine-5-carbothioamide

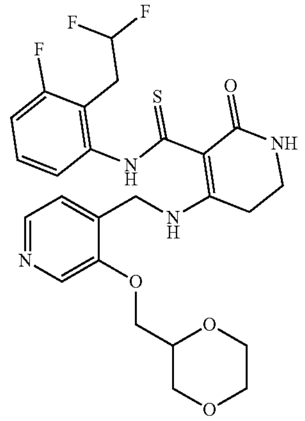 [SMILES: O=C1NCCC(NCc2ccncc2OCC2COCCO2)=C1C(=S)Nc1cccc(F)c1CC(F)F]

Using an analogous method as described for intermediate 6-1 with N-[2-(2,2-difluoroethyl)-3-fluorophenyl]-4-hydroxy-2-oxo-1,2,5,6-tetrahydropyridine-3-carbothioamide (intermediate 5-40, 100 mg, 303 μmol) and 1-{3-[(1,4-dioxan-2-yl)methoxy]pyridin-4-yl}methanamine (intermediate 2-1, 95.0 mg, 424 μmol) as the starting materials; 19.5 mg of the title compound were prepared (10% yield) after purification by flash chromatography (silica, DCM/EtOH gradient 0-10%).

LC-MS (method 2): $R_t$=1.07 min; MS (ESIpos): m/z=537 [M+H]$^+$

Intermediate 6-41 tert-butyl (2S)-2-{[(4-{[(5-{[2-(2,2-difluoroethyl)-3-fluorophenyl]carbamothioyl}-6-oxo-1,2,3,6-tetrahydropyridin-4-yl)amino]methyl}pyridin-3-yl)oxy]methyl}morpholine-4-carboxylate

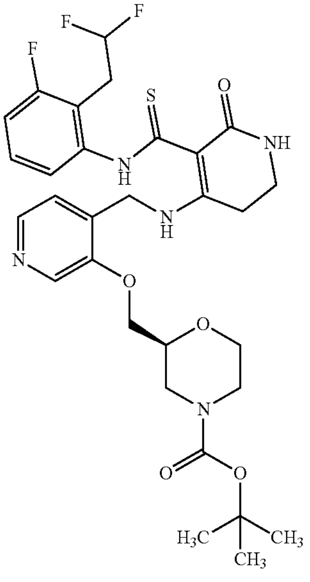 [SMILES: CC(C)(C)OC(=O)N1CCO[C@H](COc2cnccc2CNC2=C(C(=S)Nc3cccc(F)c3CC(F)F)C(=O)NCC2)C1]

A mixture of N-[2-(2,2-difluoroethyl)-3-fluorophenyl]-4-hydroxy-2-oxo-1,2,5,6-tetrahydropyridine-3-carbothioamide (intermediate 5-40, 200 mg, 605 μmol) and tert-butyl (2S)-2-({[4-(aminomethyl)pyridin-3-yl]oxy}methyl)morpholine-4-carboxylate (intermediate 2-5, 274 mg, 848 μmol) in ACN (2.5 ml) was treatet with N,O-bis-(trimethylsiliyl) acetamide (111 μl, 0.6 mmol, CAS 10416-59-8) and stirred at 80° C. for 5 h. The reaction was treated with another equivalent (111 μl, 0.6 mmol) of N,O-bis-(trimethylsiliyl) acetamide and stirred at 80° C. overnight. The reaction mixture was diluted in DCM and purified by flash chromatography (silica, DCM/EtOH gradient 0-20%) to give 255 mg (45% yield) of the title compound.

LC-MS (method 2): $R_t$=1.25 min; MS (ESIpos): m/z=636 $[M+H]^+$

Intermediate 6-42 tert-butyl (2S)-2-[({4-[({5-[(3-chloro-2-methylphenyl)carbamothioyl]-6-oxo-1,2,3,6-tetrahydropyridin-4-yl}amino)methyl]pyridin-3-yl}oxy)methyl]morpholine-4-carboxylate

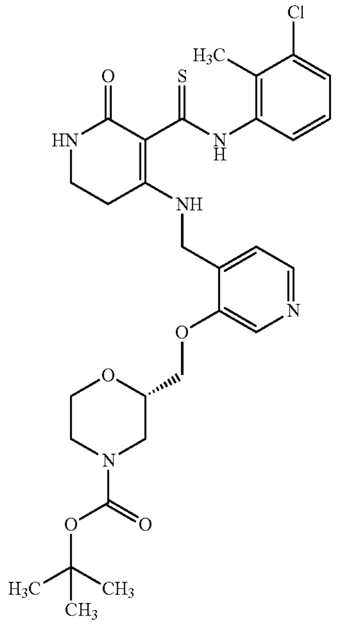 [SMILES: Cc1c(Cl)cccc1NC(=S)C1=C(NCc2ccncc2OC[C@@H]2CN(C(=O)OC(C)(C)C)CCO2)CCNC1=O]

Using an analogous method as described for intermediate 6-1 with N-(3-chloro-2-methylphenyl)-4-hydroxy-2-oxo-1,2,5,6-tetrahydropyridine-3-carbothioamide (intermediate 5-10, 350 mg, 1.18 mmol) and tert-butyl (2S)-2-({[4-(aminomethyl)pyridin-3-yl]oxy}methyl)morpholine-4-carboxylate (intermediate 2-5, 381 mg, 1.18 mmol) as the starting materials; 208 mg of the title compound were prepared (99% purity, 29% yield) after heating for 3 h and purification by preparative HPLC (method 11, 0.00-1.00 min 30% B, 1.00-12.74 min 30-68.9% B, 12.74-14.19 min 68.9 B, 14.19-14.45 min 68.9-70% B)

$^1$H-NMR (400 MHz, DMSO-$d_6$): δ [ppm]=1.396 (16.00), 2.077 (0.96), 2.158 (7.73), 2.520 (2.53), 2.525 (1.63), 2.542 (0.50), 2.747 (0.68), 2.763 (1.35), 2.780 (0.85), 3.146 (0.53), 3.153 (0.62), 3.162 (0.99), 3.169 (0.96), 3.434 (0.57), 3.441 (0.60), 3.710 (0.46), 3.723 (0.54), 3.730 (0.70), 3.737 (0.68), 3.749 (0.56), 3.756 (0.45), 3.837 (0.42), 4.213 (1.89), 4.225 (1.86), 4.648 (1.39), 4.663 (1.40), 7.153 (0.57), 7.170 (1.15), 7.196 (0.92), 7.216 (1.36), 7.236 (0.59), 7.294 (0.89), 7.306 (0.92), 7.326 (1.13), 7.329 (1.10), 7.346 (0.85), 7.349 (0.79), 7.691 (0.91), 8.237 (2.11), 8.249 (1.94), 8.399 (3.05), 13.653 (0.59), 14.540 (1.38).

LC-MS (method 6): Rt=1.17 min; MS (ESIpos): m/z=602 $[M+H]^+$

Intermediate 6-43 tert-butyl (3R)-3-[({4-[({5-[(3-chloro-2-methylphenyl)carbamothioyl]-6-oxo-1,2,3,6-tetrahydropyridin-4-yl}amino)methyl]pyridin-3-yl}oxy)methyl]morpholine-4-carboxylate

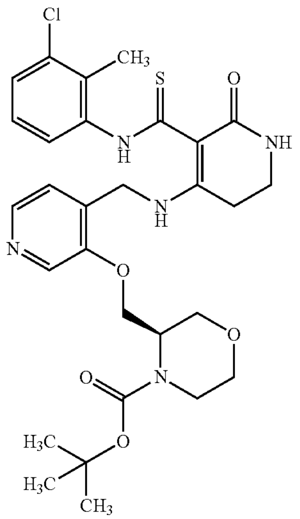 [SMILES: Cc1c(Cl)cccc1NC(=S)C1=C(NCc2ccncc2OC[C@H]2COCCN2C(=O)OC(C)(C)C)CCNC1=O]

Using an analogous method as described for intermediate 6-1 with N-(3-chloro-2-methylphenyl)-4-hydroxy-2-oxo-1,2,5,6-tetrahydropyridine-3-carbothioamide (intermediate 5-10, 350 mg, 1.18 mmol) and tert-butyl (3R)-3-({[4-(aminomethyl)pyridin-3-yl]oxy}methyl)morpholine-4-carboxylate (intermediate 2-9, 381 mg, 1.18 mmol) as the starting materials; 184 mg of the title compound were prepared (99% purity, 26% yield) after heating for 3 h and by preparative HPLC (method 11, 0.00-1.00 min 30% B, 1.00-12.74 min 30-68.9% B, 12.74-14.19 min 68.9 B, 14.19-14.45 min 68.9-70% B)

$^1$H-NMR (400 MHz, DMSO-$d_6$): δ [ppm]=1.339 (2.92), 2.087 (1.31), 2.161 (16.00), 2.521 (1.63), 2.525 (1.08), 2.676 (0.52), 2.708 (0.66), 2.725 (1.74), 2.742 (1.82), 2.757 (0.75), 3.140 (1.42), 3.147 (1.59), 3.156 (2.44), 3.163 (2.41), 3.319 (0.58), 3.365 (1.06), 3.372 (1.25), 3.395 (0.56), 3.402 (0.54), 3.478 (0.92), 3.507 (1.00), 3.651 (0.51), 3.797 (0.72), 3.821 (0.64), 3.957 (0.67), 3.985 (0.59), 4.236 (1.53), 4.415 (0.46), 4.441 (0.83), 4.625 (2.12), 4.639 (2.15), 7.160 (1.07), 7.178 (2.26), 7.200 (2.08), 7.220 (3.03), 7.239 (1.27), 7.291 (1.19), 7.301 (1.19), 7.329 (2.50), 7.332 (2.34), 7.349 (1.83), 7.352 (1.71), 7.691 (1.99), 8.240 (3.22), 8.252 (3.11), 8.489 (2.72), 13.669 (0.94), 14.536 (3.05).

LC-MS (method 6): Rt=1.17 min; MS (ESIpos): m/z=602 $[M+H]^+$

Intermediate 6-44

N-(3-chloro-2-methyl-phenyl)-4-[[3-[(5,5-dimethyl-1,4-dioxan-2-yl)methoxy]-4-pyridyl]methylamino]-6-oxo-2,3-dihydro-1H-pyridine-5-carbothioamide

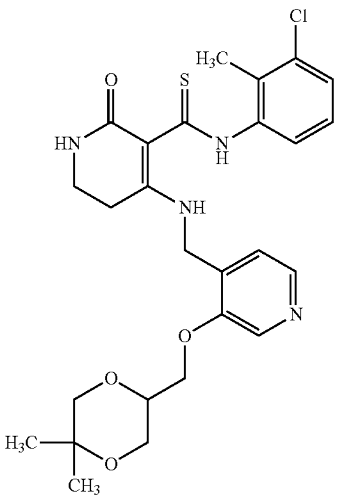 [SMILES: Cc1c(Cl)cccc1NC(=S)C1=C(NCc2ccncc2OCC2COC(C)(C)CO2)CCNC1=O]

Using an analogous method as described for intermediate 6-41 with N-(3-chloro-2-methylphenyl)-4-hydroxy-2-oxo-1,2,5,6-tetrahydropyridine-3-carbothioamide (intermediate 5-10, 200 mg, 674 μmol) and 1-{3-[(5,5-dimethyl-1,4-dioxan-2-yl)methoxy]pyridin-4-yl}methanamine (intermediate 2-7, 200 mg, 85% purity, 674 μmol) as the starting materials; 328 mg of the title compound were prepared (97% purity, 89% yield).

$^1$H-NMR (400 MHz, DMSO-$d_6$): δ [ppm]=1.047 (14.25), 1.253 (12.85), 2.077 (16.00), 2.162 (14.45), 2.520 (1.87), 2.525 (1.19), 2.742 (1.21), 2.759 (2.44), 2.775 (1.45), 3.147 (0.98), 3.154 (1.11), 3.163 (1.80), 3.170 (1.74), 3.180 (0.98), 3.186 (0.82), 3.297 (1.66), 3.327 (2.92), 3.533 (2.87), 3.561 (2.30), 3.617 (0.55), 3.626 (0.77), 3.646 (1.84), 3.655 (1.96), 3.664 (1.91), 3.689 (2.20), 3.718 (1.12), 3.791 (0.79), 3.802 (0.97), 3.812 (0.78), 3.826 (0.56), 4.147 (0.62), 4.158 (0.66), 4.173 (1.85), 4.184 (1.77), 4.193 (1.88), 4.206 (1.73), 4.220 (0.66), 4.233 (0.60), 4.644 (2.79), 4.659 (2.74), 7.158 (1.13), 7.175 (2.37), 7.200 (1.72), 7.220 (2.58), 7.239 (1.09), 7.298 (1.31), 7.310 (1.39), 7.328 (2.08), 7.332 (2.01), 7.348 (1.56), 7.351 (1.42), 7.689 (1.69), 8.245 (0.80), 8.399 (1.03), 13.621 (0.57), 13.635 (1.07), 14.542 (2.54).

LC-MS (method 6): Rt=1.06 min; MS (ESIpos): m/z=531 $[M+H]^+$

Intermediate 6-47

4-[[3-(1,4-dioxan-2-ylmethoxy)-4-pyridyl]methyl-amino]-N-(3-fluoro-2-methyl-phenyl)-6-oxo-2,3-dihydro-1H-pyridine-5-carbothioamide

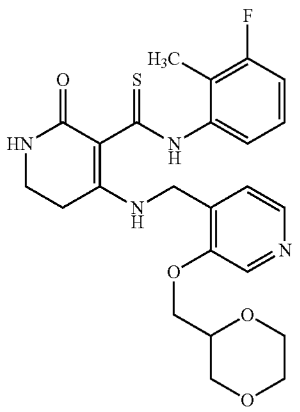 [SMILES: Cc1c(F)cccc1NC(=S)C1=C(NCc2ccncc2OCC2COCCO2)CCNC1=O]

Using an analogous method as described for intermediate 6-41 with N-(3-fluoro-2-methylphenyl)-4-hydroxy-2-oxo-1,2,5,6-tetrahydropyridine-3-carbothioamide (intermediate 5-38, 300 mg, 1.07 mmol) and 1-{3-[(1,4-dioxan-2-yl)methoxy]pyridin-4-yl}methanamine (intermediate 2-1, 240 mg, 1.07 mmol) as the starting materials; 156.3 mg of the title compound were prepared (93% purity, 71% yield).

$^1$H-NMR (400 MHz, DMSO-$d_6$): δ [ppm]=0.000 (0.70), 1.998 (0.55), 2.033 (16.00), 2.038 (15.45), 2.064 (3.23), 2.508 (3.78), 2.513 (2.36), 2.737 (2.61), 2.754 (5.23), 2.771 (2.96), 3.142 (2.39), 3.151 (3.71), 3.158 (3.53), 3.168 (2.07), 3.393 (2.34), 3.418 (3.51), 3.421 (3.41), 3.446 (3.16), 3.461 (1.34), 3.482 (2.56), 3.488 (2.76), 3.506 (1.42), 3.516 (2.71), 3.579 (1.64), 3.585 (1.94), 3.608 (2.49), 3.614 (2.79), 3.641 (5.03), 3.670 (1.97), 3.735 (2.71), 3.744 (2.66), 3.769 (2.09), 3.837 (2.39), 3.844 (2.81), 3.871 (4.35), 3.883 (1.72), 3.890 (1.32), 3.895 (1.57), 3.902 (1.32), 3.907 (1.44), 3.914 (1.14), 3.926 (0.62), 4.108 (0.85), 4.120 (0.95), 4.134 (3.73), 4.145 (6.69), 4.158 (3.48), 4.171 (0.87), 4.184 (0.75), 4.624 (4.75), 4.639 (4.68), 7.028 (1.64), 7.050 (3.46), 7.062 (3.48), 7.073 (2.79), 7.081 (4.60), 7.179 (1.62), 7.198 (2.71), 7.215 (2.51), 7.235 (1.00), 7.333 (1.12), 7.676 (3.41), 8.321 (0.42), 13.651 (2.04), 14.509 (4.80).

LC-MS (method 6): Rt=0.85 min; MS (ESipos): m/z=487 $[M+H]^+$

Intermediate 6-50

N-(3-chloro-2-methyl-phenyl)-4-[[3-(1,4-dioxan-2-ylmethoxy)-4-pyridyl]methylamino]-6-oxo-2,3-dihydro-1H-pyridine-5-carbothioamide

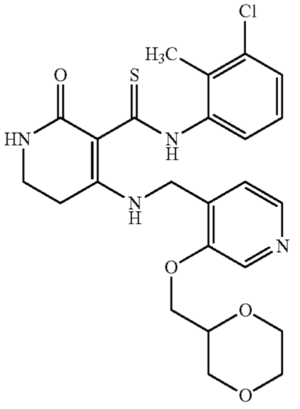 [SMILES: Cc1c(Cl)cccc1NC(=S)C1=C(NCc2ccncc2OCC2COCCO2)CCNC1=O]

Using an analogous method as described for intermediate 6-41 with N-(3-chloro-2-methylphenyl)-4-hydroxy-2-oxo-1,2,5,6-tetrahydropyridine-3-carbothioamide (intermediate 5-10, 200 mg, 674 μmol) and 1-{3-[(1,4-dioxan-2-yl)methoxy]pyridin-4-yl}methanamine (intermediate 2-1, 151 mg, 674 μmol) as the starting materials; 150.0 mg of the title compound were prepared (96% purity, 42% yield).

$^{1}$H-NMR (400 MHz, DMSO-$d_6$): δ [ppm]=2.077 (1.64), 2.162 (16.00), 2.520 (2.60), 2.525 (1.64), 2.751 (1.41), 2.768 (2.82), 2.784 (1.63), 3.156 (1.22), 3.165 (1.94), 3.172 (1.87), 3.404 (1.32), 3.429 (1.94), 3.432 (1.93), 3.457 (1.81), 3.472 (0.72), 3.493 (1.40), 3.500 (1.50), 3.518 (0.79), 3.528 (1.45), 3.591 (0.91), 3.597 (1.05), 3.619 (1.35), 3.626 (1.54), 3.650 (2.14), 3.653 (2.65), 3.660 (0.95), 3.682 (1.04), 3.748 (1.44), 3.756 (1.54), 3.781 (1.16), 3.849 (1.30), 3.855 (1.59), 3.883 (2.54), 3.894 (0.99), 3.901 (0.68), 3.906 (0.89), 3.913 (0.76), 3.918 (0.79), 3.925 (0.62), 3.930 (0.51), 4.118 (0.55), 4.129 (0.59), 4.144 (2.26), 4.155 (4.42), 4.168 (2.30), 4.181 (0.52), 4.194 (0.48), 4.648 (3.19), 4.663 (3.19), 7.159 (1.24), 7.176 (2.55), 7.203 (1.84), 7.222 (2.83), 7.242 (1.22), 7.290 (2.72), 7.302 (2.78), 7.330 (2.22), 7.333 (2.19), 7.349 (1.69), 7.353 (1.54), 7.691 (1.83), 8.233 (4.07), 8.245 (3.96), 8.383 (6.40), 13.623 (0.61), 13.637 (1.14), 14.544 (2.74).

LC-MS (method 6): Rt=0.94 min; MS (ESipos): m/z=503 $[M+H]^+$

Intermediate 6-52

N-(3-chloro-2-ethyl-phenyl)-4-[[3-(1,4-dioxan-2-ylmethoxy)-4-pyridyl]methylamino]-6-oxo-2,3-dihydro-1H-pyridine-5-carbothioamide

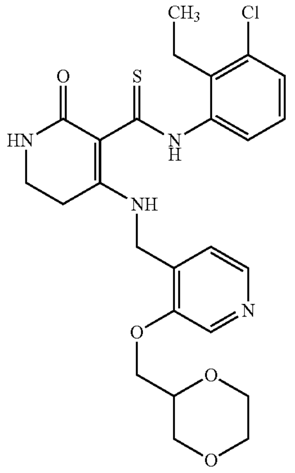 [SMILES: CCc1c(Cl)cccc1NC(=S)C1=C(NCc2ccncc2OCC2COCCO2)CCNC1=O]

Using an analogous method as described for intermediate 6-41 with N-(3-chloro-2-ethylphenyl)-4-hydroxy-2-oxo-1,2,5,6-tetrahydropyridine-3-carbothioamide (intermediate 5-29, 150 mg, 483 μmol) and 1-{3-[(1,4-dioxan-2-yl)methoxy]pyridin-4-yl}methanamine (intermediate 2-1, 108 mg, 483 μmol) as the starting materials; 150.0 mg of the title compound were prepared (90% purity, 54% yield) by using flash chromatography (silica, DCM/EtOH gradient 1-13%).

$^{1}$H-NMR (400 MHz, DMSO-$d_6$): δ ppm=1.01-1.11 (m, 4H), 2.56-2.65 (m, 2H), 2.73-2.81 (m, 2H), 3.12-3.22 (m, 2H), 3.39-3.54 (m, 3H), 3.58-3.69 (m, 2H), 3.73-3.80 (m, 1H), 3.88 (s, 2H), 4.09-4.23 (m, 2H), 4.11-4.15 (m, 1H), 4.57-4.71 (m, 2H), 7.16-7.25 (m, 2H), 7.28-7.36 (m, 2H), 7.32 (s, 1H), 7.66-7.75 (m, 1H), 8.07-8.11 (m, 1H), 8.21-8.26 (m, 1H), 8.33-8.43 (m, 1H), 13.60-13.70 (m, 1H), 14.59-14.67 (m, 1H).

LC-MS (method 2): $R_t$=1.15 min; MS (ESIpos): m/z=517 $[M+H]^+$

Intermediate 6-53

N-(3-chloro-2-ethylphenyl)-4-{[(3-{[(2S)-1,4-dioxan-2-yl]methoxy}pyridin-4-yl)methyl]amino}-2-oxo-1,2,5,6-tetrahydropyridine-3-carbothioamide

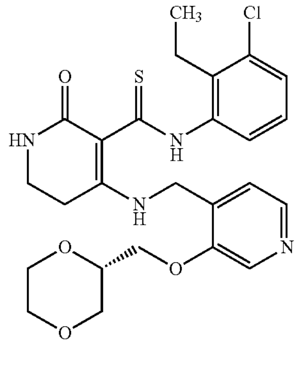 [SMILES: CCc1c(Cl)cccc1NC(=S)C1=C(NCc2ccncc2OC[C@@H]2COCCO2)CCNC1=O]

Using an analogous method as described for intermediate 6-41 with N-(3-chloro-2-ethylphenyl)-4-hydroxy-2-oxo-1,2, 5,6-tetrahydropyridine-3-carbothioamide (intermediate 5-29, 210 mg, 676 μmol) and 1-(3-{[(2S)-1,4-dioxan-2-yl]methoxy}pyridin-4-yl)methanamine (intermediate 2-8, 185 mg, 90% purity, 743 μmol) as the starting materials; 320.0 mg of the title compound were prepared (86% yield) by using flash chromatography (silica, DCM/EtOH gradient 1-15%).

$^1$H-NMR (400 MHz, DMSO-$d_6$): δ [ppm]=1.036 (8.39), 1.040 (4.03), 1.053 (16.00), 1.059 (9.01), 1.071 (8.71), 1.078 (3.84), 2.066 (0.41), 2.518 (1.19), 2.523 (0.81), 2.577 (0.95), 2.596 (2.98), 2.614 (2.87), 2.632 (0.86), 2.757 (1.69), 2.774 (3.38), 2.790 (1.92), 3.152 (1.31), 3.159 (1.49), 3.169 (2.36), 3.174 (2.23), 3.185 (1.26), 3.403 (1.67), 3.405 (1.77), 3.418 (1.45), 3.423 (4.19), 3.427 (2.48), 3.430 (2.54), 3.435 (4.26), 3.440 (3.60), 3.453 (4.76), 3.457 (2.12), 3.470 (1.96), 3.492 (1.59), 3.498 (1.73), 3.516 (0.85), 3.526 (1.70), 3.589 (1.03), 3.594 (1.21), 3.617 (1.57), 3.623 (1.85), 3.651 (3.24), 3.679 (1.31), 3.745 (1.75), 3.754 (1.70), 3.779 (2.03), 3.847 (1.59), 3.853 (1.84), 3.880 (2.81), 3.893 (1.13), 3.900 (0.84), 3.905 (1.04), 3.912 (0.89), 3.917 (0.95), 3.924 (0.75), 3.929 (0.59), 3.936 (0.44), 4.116 (0.64), 4.127 (0.69), 4.142 (2.65), 4.154 (5.01), 4.167 (2.53), 4.180 (0.60), 4.193 (0.55), 4.343 (2.64), 4.356 (5.10), 4.369 (2.52), 4.647 (3.70), 4.662 (3.66), 7.209 (5.05), 7.211 (4.85), 7.222 (8.23), 7.231 (0.55), 7.293 (2.86), 7.307 (4.24), 7.319 (3.43), 7.331 (1.67), 7.706 (2.31), 8.234 (3.16), 8.246 (3.01), 8.383 (5.19), 13.642 (0.84), 13.657 (1.55), 13.672 (0.72), 14.639 (4.11).

LC-MS (method 2): Rt=1.17 min; MS (ESIpos): m/z=517 [M+H]$^+$

Intermediate 6-55 tert-butyl (2R)-2-[({4-[({5-[(3-chloro-2-ethylphenyl)carbamothioyl]-6-oxo-1,2,3,6-tetrahydropyridin-4-yl}amino)methyl]pyridin-3-yl}oxy)methyl]morpholine-4-carboxylate

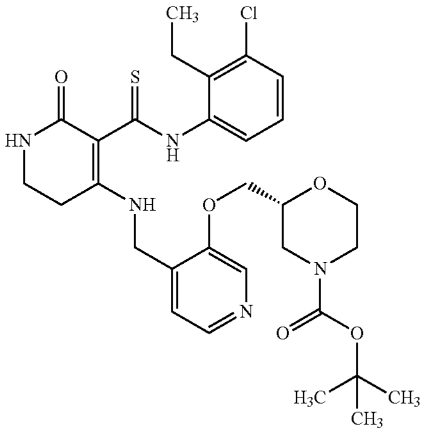 [SMILES: CCc1c(Cl)cccc1NC(=S)C1=C(NCc2ccncc2OC[C@H]2CN(C(=O)OC(C)(C)C)CCO2)CCNC1=O]

Using an analogous method as described for intermediate 6-41 with N-(3-chloro-2-ethylphenyl)-4-hydroxy-2-oxo-1,2,5,6-tetrahydropyridine-3-carbothioamide (intermediate 5-29, 300 mg, 965 μmol) and tert-butyl (2R)-2-({[4-(aminomethyl)pyridin-3-yl]oxy}methyl)morpholine-4-carboxylate (intermediate 2-10, 312 mg, 965 μmol) as the starting materials; 476.0 mg of the title compound were prepared (95% purity, 76% yield) by using flash chromatography (silica, DCM/EtOH gradient 1-10%).

$^1$H-NMR (400 MHz, DMSO-$d_6$): δ [ppm]=1.036 (1.51), 1.055 (3.57), 1.073 (1.55), 1.393 (16.00), 2.518 (1.71), 2.523 (1.10), 2.590 (1.19), 2.609 (1.16), 2.751 (0.68), 2.769 (1.33), 2.785 (0.84), 3.165 (0.96), 3.171 (0.92), 3.431 (0.55), 3.438 (0.59), 3.729 (0.71), 3.749 (0.48), 3.756 (0.41), 3.835 (0.41), 4.210 (1.81), 4.222 (1.76), 4.646 (1.35), 4.662 (1.35), 5.758 (7.84), 7.202 (2.06), 7.214 (2.99), 7.296 (1.00), 7.304 (1.58), 7.316 (1.60), 7.328 (0.75), 7.703 (0.94), 8.236 (1.90), 8.248 (1.81), 8.398 (2.84), 13.671 (0.64), 14.632 (1.67).

LC-MS (method 2): $R_t$=1.32 min; MS (ESipos): m/z=616 [M+H]$^+$

Intermediate 6-56 tert-butyl (2S)-2-[({4-[({5-[(3-chloro-2-ethylphenyl)carbamothioyl]-6-oxo-1,2,3,6-tetrahydropyridin-4-yl}amino)methyl]pyridin-3-yl}oxy)methyl]morpholine-4-carboxylate

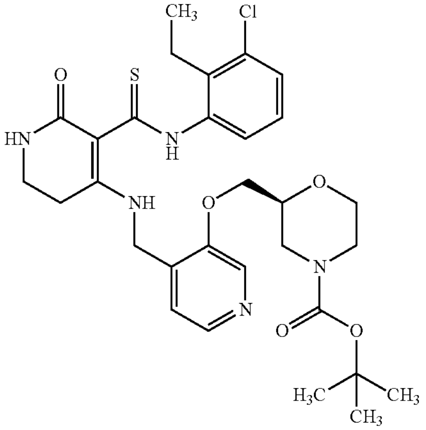 [SMILES: CCc1c(Cl)cccc1NC(=S)C1=C(NCc2ccncc2OC[C@@H]2CN(C(=O)OC(C)(C)C)CCO2)CCNC1=O]

Using an analogous method as described for intermediate 6-41 with N-(3-chloro-2-ethylphenyl)-4-hydroxy-2-oxo-1,2,5,6-tetrahydropyridine-3-carbothioamide (intermediate 5-29, 300 mg, 965 μmol) and tert-butyl(2S)-2-({[4-(aminomethyl)pyridin-3-yl]oxy}methyl) morpholine-4-carboxylate (intermediate 2-5, 312 mg, 965 μmol) as the starting materials; 479.0 mg of the title compound were prepared (95% purity, 77% yield) after purification by flash chromatography (silica, DCM/EtOH gradient 1-10%).

$^1$H-NMR (400 MHz, DMSO-$d_6$): δ [ppm]=14.55-14.67 (m, 1H), 13.60-13.72 (m, 1H), 8.40 (s, 1H), 8.24 (d, 1H), 7.70 (br s, 1H), 7.16-7.36 (m, 4H), 5.70-5.80 (m, 1H), 5.66-5.81 (m, 1H), 4.59-4.73 (m, 2H), 4.12-4.27 (m, 2H), 3.80-3.99 (m, 2H), 3.65-3.78 (m, 2H), 3.37-3.50 (m, 1H), 3.10-3.22 (m, 2H), 2.70-2.99 (m, 4H), 2.55-2.64 (m, 2H), 1.30-1.46 (m, 9H), 1.01-1.12 (m, 3H).

LC-MS (method 2): $R_t$=1.32 min; MS (ESipos): m/z=616 [M+H]$^+$

Intermediate 6-57

N-(3-chloro-2-methoxyphenyl)-4-([{3-[(1 S)-1-(1,4-dioxan-2-yl)ethoxy]pyridin-4-yl}methyl)amino]-2-oxo-1,2,5,6-tetrahydropyridine-3-carbothioamide

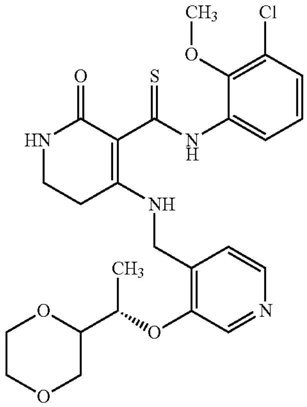 [SMILES: COc1c(Cl)cccc1NC(=S)C1=C(NCc2ccncc2O[C@@H](C)C2COCCO2)CCNC1=O]

Using an analogous method as described for intermediate 6-41 with N-(3-chloro-2-methoxyphenyl)-4-hydroxy-2-oxo-1,2,5,6-tetrahydropyridine-3-carbothioamide (intermediate 5-1, 300 mg, 959 μmol) and 1-{3-[(1S)-1-(1,4-dioxan-2-yl) ethoxy]pyridin-4-yl}methanamine (intermediate 2-11, 251 mg, 1.06 mmol) as the starting materials; 384 mg of the title compound were prepared (99% purity, 74% yield) as mixture of diastereomers.

$^1$H-NMR (400 MHz, DMSO-$d_6$): δ [ppm]=0.064 (0.95), 1.239 (2.82), 1.255 (2.83), 1.279 (2.06), 1.295 (2.09), 2.518 (1.11), 2.523 (0.82), 2.761 (0.76), 2.777 (0.86), 3.141 (0.52), 3.148 (0.60), 3.157 (1.00), 3.164 (0.99), 3.181 (0.43), 3.417 (0.87), 3.443 (0.88), 3.455 (0.44), 3.462 (0.47), 3.470 (0.68), 3.476 (0.41), 3.591 (0.40), 3.597 (0.65), 3.620 (0.88), 3.632 (0.76), 3.639 (0.41), 3.647 (0.54), 3.653 (0.56), 3.672 (0.40), 3.678 (0.44), 3.711 (16.00), 3.732 (0.56), 3.766 (0.89), 3.772 (0.52), 3.794 (0.57), 4.651 (1.27), 4.665 (1.31), 4.682 (0.58), 7.090 (0.70), 7.110 (1.53), 7.131 (0.88), 7.287 (1.67), 7.289 (1.87), 7.300 (1.26), 7.305 (1.12), 7.309 (1.02), 7.314 (0.67), 7.726 (0.98), 7.791 (0.95), 7.794 (0.96), 7.811 (0.90), 7.815 (0.85), 8.198 (1.34), 8.211 (1.99), 8.223 (0.91), 8.416 (1.88), 8.432 (1.35), 13.666 (0.43), 13.675 (0.50), 14.790 (1.61).

LC-MS (method 6): $R_t$=0.96 min and $R_t$=0.98 min; MS (ESipos): m/z=533.2 [M+H]$^+$ Intermediate 6-60

N-(3-chloro-2-methoxyphenyl)-4-{[(3-{(1R)-1-[1,4-dioxan-2-yl]ethoxy}pyridin-4-yl)methyl]amino}-2-oxo-1,2,5,6-tetrahydropyridine-3-carbothioamide

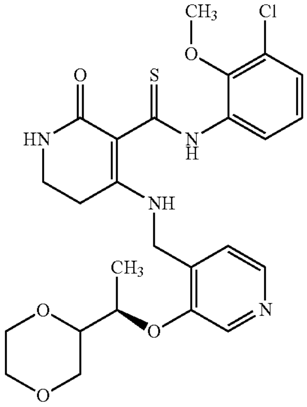 [SMILES: COc1c(Cl)cccc1NC(=S)C1=C(NCc2ccncc2O[C@H](C)C2COCCO2)CCNC1=O]

Using an analogous method as described for intermediate 6-41 with N-(3-chloro-2-methoxyphenyl)-4-hydroxy-2-oxo-1,2,5,6-tetrahydropyridine-3-carbothioamide (intermediate 5-1, 300 mg, 959 μmol) and 1-{3-[(1R)-1-(1,4-dioxan-2-yl) ethoxy]pyridin-4-yl}methanamine (intermediate 2-12, 251 mg, 1.06 mmol) as the starting materials; 346 mg (99% purity, 67% yield) of the title compound were prepared.

$^1$H-NMR (400 MHz, DMSO-$d_6$): δ [ppm]=1.278 (5.25), 1.294 (5.21), 2.073 (0.98), 2.331 (0.40), 2.518 (2.02), 2.522 (1.36), 2.673 (0.42), 2.749 (0.74), 2.765 (0.56), 2.775 (0.83), 2.792 (0.42), 3.140 (0.62), 3.147 (0.73), 3.156 (1.17), 3.164 (1.16), 3.417 (0.81), 3.441 (1.16), 3.445 (1.15), 3.469 (1.68), 3.475 (0.85), 3.503 (0.74), 3.570 (0.47), 3.576 (0.55), 3.598 (0.72), 3.604 (0.82), 3.631 (1.87), 3.638 (0.97), 3.646 (0.63), 3.652 (0.78), 3.657 (1.02), 3.663 (0.93), 3.670 (0.52), 3.677 (0.47), 3.710 (16.00), 3.758 (0.87), 3.767 (0.74), 3.790 (0.67), 3.920 (0.78), 3.926 (0.76), 3.949 (0.72), 3.955 (0.66), 4.646 (1.57), 4.653 (1.48), 4.662 (1.63), 4.682 (0.73), 7.092 (1.08), 7.112 (2.33), 7.133 (1.33), 7.287 (1.60), 7.290 (1.60), 7.302 (1.73), 7.306 (1.61), 7.310 (1.69), 7.314 (1.68), 7.725 (1.16), 7.791 (1.23), 7.794 (1.22), 7.811 (1.17), 7.814 (1.08), 8.210 (2.42), 8.222 (2.24), 8.430 (3.36), 13.651 (0.41), 13.665 (0.79), 14.786 (2.12).

LC-MS (method 6): $R_t$=0.96 min; MS (ESipos): m/z=533 [M+H]$^+$

Intermediate 6-62

N-(3-fluoro-2-methylphenyl)-4-{[(3-{[(2S)-4-methylmorpholin-2-yl]methoxy}pyridin-4-yl)methyl]amino}-2-oxo-1,2,5,6-tetrahydropyridine-3-carbothioamide

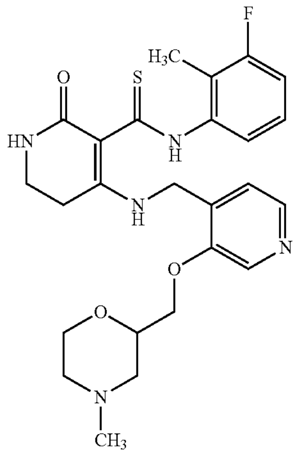 [SMILES: Cc1c(F)cccc1NC(=S)C1=C(NCc2ccncc2OCC2CN(C)CCO2)CCNC1=O]

Using an analogous method as described for intermediate 6-41 with N-(3-fluoro-2-methylphenyl)-4-hydroxy-2-oxo-1,2,5,6-tetrahydropyridine-3-carbothioamide (intermediate 5-38, 197 mg, 704 μmol) and 1-(3-{[-4-methylmorpholin-2-yl]methoxy}pyridin-4-yl)methanamine (intermediate 2-3, 167 mg, 704 μmol) as the starting materials; 170 mg of the title compound were prepared (93% purity, 45% yield) after purification by reversed phase HPLC (basic).

$^1$H-NMR (400 MHz, DMSO-$d_6$): δ [ppm]=1.035 (0.65), 1.053 (1.08), 1.070 (0.68), 1.848 (1.00), 1.876 (1.47), 1.901 (1.11), 1.953 (0.45), 1.962 (0.59), 1.982 (1.04), 1.990 (1.08), 2.010 (0.69), 2.019 (0.57), 2.040 (7.36), 2.044 (6.91), 2.177 (16.00), 2.518 (1.64), 2.522 (1.10), 2.578 (0.88), 2.607 (0.81), 2.756 (0.84), 2.770 (1.72), 2.789 (2.10), 2.817 (1.02), 3.149 (0.83), 3.156 (0.97), 3.166 (1.67), 3.173 (1.63), 3.182 (0.94), 3.318 (0.50), 3.501 (0.55), 3.507 (0.70), 3.529 (1.25), 3.535 (1.29), 3.557 (0.76), 3.563 (0.62), 3.784 (0.93), 3.788 (0.90), 3.791 (0.76), 3.812 (1.29), 3.815 (1.26), 3.829 (0.63), 3.837 (0.57), 4.112 (0.53), 4.124 (0.56), 4.138 (1.82), 4.150 (1.97), 4.154 (2.08), 4.168 (1.68), 4.180 (0.56), 4.194 (0.52), 4.636 (2.30), 4.651 (2.34), 7.034 (0.71), 7.055 (1.49), 7.070 (1.47), 7.079 (1.12), 7.089 (1.98), 7.185 (0.72), 7.204 (1.19), 7.221 (1.13), 7.241 (0.44), 7.295 (2.26), 7.306 (2.30), 7.679 (1.46), 8.227 (3.76), 8.239 (3.55), 8.383 (5.45), 13.662 (0.88), 14.516 (2.06).

LC-MS (method 6): $R_t$=0.62 min; MS (ESipos): m/z=500 [M+H]$^+$

Intermediate 6-65

4-{[(3-{[1,4-dioxan-2-yl]methoxy}pyridin-4-yl)methyl]amino}-N-(2-ethyl-3-fluorophenyl)-2-oxo-1,2,5,6-tetrahydropyridine-3-carbothioamide

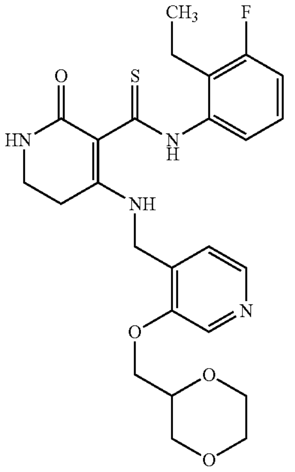 [SMILES: CCc1c(F)cccc1NC(=S)C1=C(NCc2ccncc2OCC2COCCO2)CCNC1=O]

Using an analogous method as described for intermediate 6-41 with N-(2-ethyl-3-fluorophenyl)-4-hydroxy-2-oxo-1,2,5,6-tetrahydropyridine-3-carbothioamide (300 mg, 1.02 mmol) and 1-(3-{[1,4-dioxan-2-yl]methoxy}pyridin-4-yl)methanamine (229 mg, 1.02 mmol) as the starting materials; 218 mg of the title compound were prepared (90% purity, 38% yield) after evaporation of the solvent, filtration and washing of the solid with ACN.

$^1$H-NMR (400 MHz, DMSO-$d_6$) δ [ppm]: 0.057 (1.12), 1.042 (7.32), 1.061 (16.00), 1.080 (7.29), 1.231 (0.88), 1.751 (0.58), 2.074 (6.86), 2.522 (5.66), 2.753 (3.09), 2.770 (6.11), 2.787 (3.52), 3.156 (2.86), 3.166 (4.42), 3.172 (4.30), 3.181 (2.51), 3.402 (2.65), 3.427 (3.92), 3.430 (3.92), 3.455 (3.70), 3.471 (1.62), 3.491 (2.84), 3.498 (3.08), 3.516 (1.51), 3.526 (2.87), 3.589 (1.80), 3.594 (1.99), 3.617 (2.79), 3.623 (3.19), 3.650 (5.74), 3.679 (2.35), 3.745 (3.17), 3.754 (3.06), 3.778 (2.46), 3.846 (2.80), 3.853 (3.24), 3.881 (4.78), 3.893 (1.98), 3.900 (1.58), 3.905 (1.80), 3.911 (1.59), 3.918 (1.69), 3.925 (1.36), 3.936 (0.73), 4.117 (1.01), 4.129 (1.14), 4.143 (4.20), 4.155 (7.71), 4.168 (3.95), 4.181 (1.08), 4.194 (0.91), 4.632 (5.48), 4.646 (5.40), 7.029 (2.23), 7.051 (3.97), 7.074 (2.84), 7.091 (3.92), 7.110 (5.33), 7.191 (2.31), 7.207 (2.86), 7.211 (3.55), 7.228 (3.42), 7.248 (1.35), 7.351 (1.30), 7.701 (4.14), 8.329 (0.48), 8.476 (0.42), 13.662 (1.51), 13.676 (2.76), 13.691 (1.37), 14.588 (6.37).

LC-MS (method 6): $R_t$=0.92 min; MS (ESipos): m/z=501 [M+H]$^+$

Intermediate 6-68

4-{[(3-{[5,5-dimethyl-1,4-dioxan-2-yl]methoxy}pyridin-4-yl)methyl]amino}-N-(2-ethyl-3-fluorophenyl)-2-oxo-1,2,5,6-tetrahydropyridine-3-carbothioamide

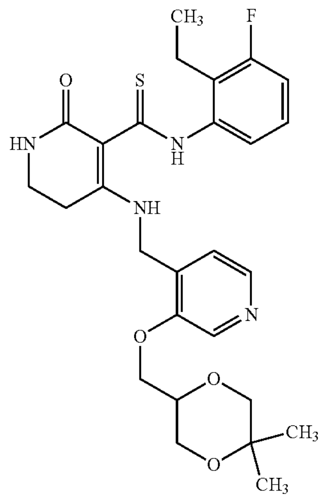 [SMILES: CCc1c(F)cccc1NC(=S)C1=C(NCc2ccncc2OCC2COC(C)(C)CO2)CCNC1=O]

Using an analogous method as described for intermediate 6-41 with N-(2-ethyl-3-fluorophenyl)-4-hydroxy-2-oxo-1,2,5,6-tetrahydropyridine-3-carbothioamide (300 mg, 1.02 mmol) and 1-(3-{[5,5-dimethyl-1,4-dioxan-2-yl]methoxy}pyridin-4-yl)methanamine (257 mg, 1.02 mmol) as the starting materials; 360 mg of the title compound were prepared (93% purity, 62% yield) after purification by column chromatography.

$^1$H-NMR (400 MHz, DMSO-$d_6$) δ [ppm]: 1.014 (0.69), 1.044 (16.00), 1.061 (7.08), 1.080 (3.30), 1.172 (0.52), 1.200 (0.60), 1.251 (13.22), 1.987 (0.87), 2.745 (1.36), 2.761 (2.65), 2.779 (1.61), 3.164 (2.11), 3.170 (2.09), 3.295 (1.79), 3.532 (2.73), 3.560 (2.19), 3.615 (0.59), 3.624 (0.79), 3.644 (1.91), 3.653 (2.05), 3.664 (1.79), 3.688 (2.07), 3.718 (1.01), 3.778 (0.45), 3.789 (0.91), 3.801 (1.07), 3.812 (0.86), 3.824 (0.63), 4.145 (0.65), 4.156 (0.71), 4.172 (1.96), 4.182 (1.95), 4.191 (2.02), 4.205 (1.76), 4.218 (0.69), 4.231 (0.59), 4.644 (3.11), 4.658 (3.10), 7.029 (0.86), 7.050 (1.63), 7.074 (1.12), 7.091 (1.71), 7.111 (2.37), 7.189 (0.89), 7.208 (1.52), 7.225 (1.39), 7.245 (0.52), 7.295 (2.40), 7.306 (2.41), 7.700 (1.92), 8.235 (3.11), 8.247 (2.98), 8.389 (5.24), 13.661 (0.71), 13.675 (1.32), 13.688 (0.68), 14.587 (3.04).

LC-MS (method 6): $R_t$=1.03 min; MS (ESipos): m/z=529 $[M+H]^+$

Intermediate 6-71

N-(3-chloro-2-methoxyphenyl)-4-({[3-({1-[4-methylmorpholin-2-yl]ethyl}oxy)pyridin-4-yl]methyl}amino)-2-oxo-1,2,5,6-tetrahydropyridine-3-carbothioamide

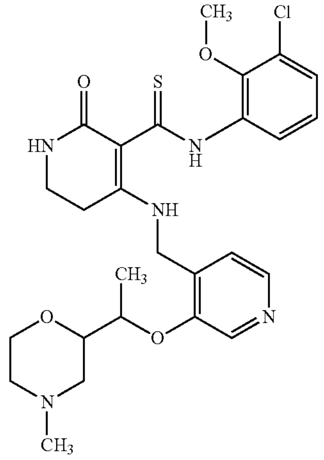 [SMILES: COc1c(Cl)cccc1NC(=S)C1=C(NCc2ccncc2OC(C)C2CN(C)CCO2)CCNC1=O]

Using an analogous method as described for intermediate 6-41 with N-(3-chloro-2-methoxyphenyl)-4-hydroxy-2-oxo-1,2,5,6-tetrahydropyridine-3-carbothioamide (intermediate 5-1, 300 mg, 959 μmol) and 1-[3-({1-[4-methylmorpholin-2-yl]ethyl}oxy)pyridin-4-yl]methanamine (intermediate 2-71, 265 mg, 1.06 mmol) as the starting materials; 360 mg of the title compound were prepared (93% purity, 62% yield) after purification by column chromatography.

$^1$H-NMR (400 MHz, DMSO-$d_6$) δ [ppm]: 1.014 (0.69), 1.044 (16.00), 1.061 (7.08), 1.080 (3.30), 1.172 (0.52), 1.200 (0.60), 1.251 (13.22), 1.987 (0.87), 2.745 (1.36), 2.761 (2.65), 2.779 (1.61), 3.164 (2.11), 3.170 (2.09), 3.295 (1.79), 3.532 (2.73), 3.560 (2.19), 3.615 (0.59), 3.624 (0.79), 3.644 (1.91), 3.653 (2.05), 3.664 (1.79), 3.688 (2.07), 3.718 (1.01), 3.778 (0.45), 3.789 (0.91), 3.801 (1.07), 3.812 (0.86), 3.824 (0.63), 4.145 (0.65), 4.156 (0.71), 4.172 (1.96), 4.182 (1.95), 4.191 (2.02), 4.205 (1.76), 4.218 (0.69), 4.231 (0.59), 4.644 (3.11), 4.658 (3.10), 7.029 (0.86), 7.050 (1.63), 7.074 (1.12), 7.091 (1.71), 7.111 (2.37), 7.189 (0.89), 7.208 (1.52), 7.225 (1.39), 7.245 (0.52), 7.295 (2.40), 7.306 (2.41), 7.700 (1.92), 8.235 (3.11), 8.247 (2.98), 8.389 (5.24), 13.661 (0.71), 13.675 (1.32), 13.688 (0.68), 14.587 (3.04).

LC-MS (method 6): $R_t$=1.03 min; MS (ESipos): m/z=529 $[M+H]^+$

Intermediate 12

3-((3-fluoro-2-methoxyphenyl)amino)-2-(3-hydroxy-pyridin-4-yl)-6,7-dihydro-1H-pyrrolo[3,2-c]pyridin-4(5H)-one

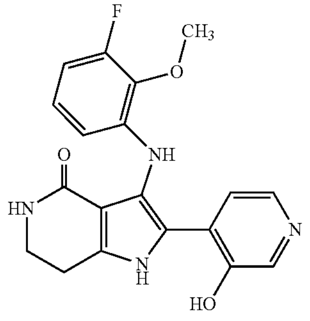 [SMILES: COc1c(F)cccc1Nc1c(-c2ccncc2O)[nH]c2c1C(=O)NCC2]

To a suspension of N-(3-fluoro-2-methoxyphenyl)-4-(((3-hydroxypyridin-4-yl)methyl)amino)-2-oxo-1,2,5,6-tetrahydropyridine-3-carbothioamide (intermediate 6-12, 41 g, 101.88 mmol) in MeOH (410 mL) was added TFA (0.75 mL, 10.13 mmol), followed by hydrogen peroxide (18 mL, 30% in water). The mixture was heated to 60° C. and stirred for 16 h. Additional TFA (6.8 mL, 91.84 mmol) and hydrogen peroxide (1.5 mL, 30% in water) were added. The suspension was stirred at 60° C. for further 3 h. The mixture was cooled to room temperature and stand overnight. The suspension was combined with a second batch that was generated identically. The combined suspension was filtered and the cake was washed with water (250 mL) and MeOH (150 mL), and then slurried in MeOH (150 mL). The suspension was filtered. The cake was washed with MeOH (75 mL) and dried in vacuum to afford the title compound (25.4 g, 33.8% yield) as a yellow solid.

$^1$H NMR (400 MHz, DMSO-$d_6$): δ=11.45 (s, 1H), 8.18 (s, 1H), 7.98 (d, 1H), 7.39 (d, 1H), 7.18 (s, 1H), 6.67 (t, 1H), 6.54 (t, 1H), 6.04 (d, 1H), 3.92 (s, 3H), 3.40 (t, 2H), 2.90 (t, 2H).

LC-MS (method 5): $R_t$=1.851 min; m/z=369.0 $(M+H)^+$

Intermediate 22-1 tert-butyl (2S)-2-[({4-[3-(3-fluoro-2-methoxyanilino)-4-oxo-4,5,6,7-tetrahydro-1H-pyrrolo[3,2-c]pyridin-2-yl]pyridin-3-yl}oxy)methyl]morpholine-4-carboxylate

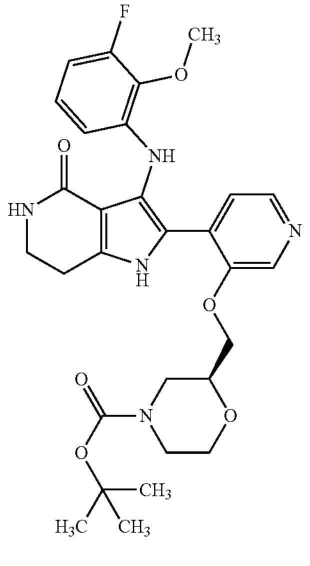 [SMILES: COc1c(F)cccc1Nc1c(-c2ccncc2OC[C@@H]2CN(C(=O)OC(C)(C)C)CCO2)[nH]c2c1C(=O)NCC2]

Using an analogous method as described for example 1 with tert-butyl (2S)-2-[({4-[({5-[(3-fluoro-2-methoxyphenyl)carbamothioyl]-6-oxo-1,2,3,6-tetrahydropyridin-4-yl}amino)methyl]pyridin-3-yl}oxy)methyl]morpholine-4-carboxylate (intermediate 6-22, 1.43 g, 2.38 mmol) as the starting material; 572 mg (80% purity, 34% yield) of the title compound were prepared after purification by flash chromatography (silica, DCM/EtOH gradient 0-10%).

$^1$H-NMR (400 MHz, DMSO-$d_6$) δ [ppm]: 1.035 (0.86), 1.053 (1.99), 1.071 (0.88), 1.380 (0.83), 1.401 (6.79), 1.409 (16.00), 2.518 (1.63), 2.523 (1.18), 2.842 (0.65), 2.859 (1.16), 2.877 (0.76), 3.178 (0.95), 3.301 (0.60), 3.398 (0.50), 3.404 (0.61), 3.415 (0.94), 3.418 (0.82), 3.422 (1.10), 3.435 (0.77), 3.440 (0.72), 3.452 (0.50), 3.553 (0.42), 3.560 (0.43), 3.750 (0.64), 3.760 (0.40), 3.851 (0.50), 3.858 (0.40), 3.873 (0.46), 3.906 (6.63), 3.936 (0.57), 3.939 (0.59), 3.950 (0.46), 4.343 (0.56), 4.356 (0.65), 5.759 (1.09), 5.993 (0.75), 6.013 (0.76), 6.485 (0.50), 6.489 (0.49), 6.492 (0.42), 6.513 (0.45), 6.516 (0.42), 6.627 (0.54), 6.642 (0.52), 7.147 (0.86), 7.280 (1.09), 7.293 (1.13), 7.509 (0.98), 8.025 (1.38), 8.038 (1.27), 8.401 (2.10), 11.020 (0.61).

LC-MS (method 2): $R_t$=1.12 min; MS (ESIpos): m/z=568 $[M+H]^+$

Intermediate 22-2

3-(3-fluoro-2-methoxyanilino)-2-(3-{[(2S)-morpholin-2-yl]methoxy}pyridin-4-yl)-1,5,6,7-tetrahydro-4H-pyrrolo[3,2-c]pyridin-4-one

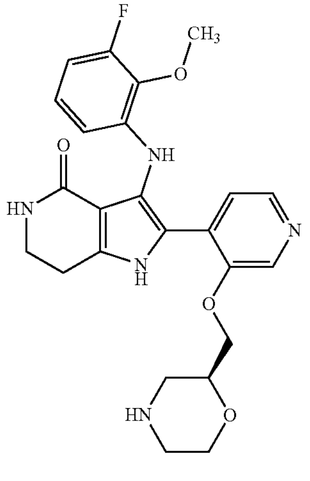 [SMILES: COc1c(F)cccc1Nc1c(-c2ccncc2OC[C@@H]2CNCCO2)[nH]c2c1C(=O)NCC2]

Tert-butyl (2S)-2-[({4-[3-(3-fluoro-2-methoxyanilino)-4-oxo-4,5,6,7-tetrahydro-1H-pyrrolo[3,2-c]pyridin-2-yl]pyridin-3-yl}oxy)methyl]morpholine-4-carboxylate (intermediate 22-1, 572 mg, 1.01 mmol) was solubilised in dichloromethane (7.2 ml) and TFA (780 μl, 10 mmol) was added. The mixture was stirred for 2 h at RT. The mixture was evaporated and purified by flash chromatography (amino phase silica, DCM/EtOH gradient 0-20%) to give 352 mg (95% purity, 71% yield) of the title compound.

$^1$H-NMR (400 MHz, DMSO-$d_6$): δ [ppm]=2.53-2.78 (m, 4H), 2.80-2.90 (m, 3H), 3.38-3.47 (m, 3H), 3.55-3.66 (m, 1H), 3.83-3.90 (m, 1H), 3.91-3.95 (s, 3H), 4.07-4.16 (m, 1H), 4.29-4.39 (m, 1H), 6.01 (d, 1H), 6.44-6.56 (m, 1H), 6.65 (dt, 1H), 7.17 (s, 1H), 7.29 (d, 1H), 7.53 (s, 1H), 8.01 (d, 1H), 8.39 (s, 1H), 11.10 (s, 1H).

LC-MS (method 2): $R_t$=0.84 min; MS (ESIpos): m/z=468 $[M+H]^+$

Intermediate 27-1 tert-butyl (2S)-2-[({4-[3-(3-chloro-5-fluoro-2-methoxyanilino)-4-oxo-4,5,6,7-tetrahydro-1H-pyrrolo[3,2-c]pyridin-2-yl]pyridin-3-yl}oxy)methyl]morpholine-4-carboxylate

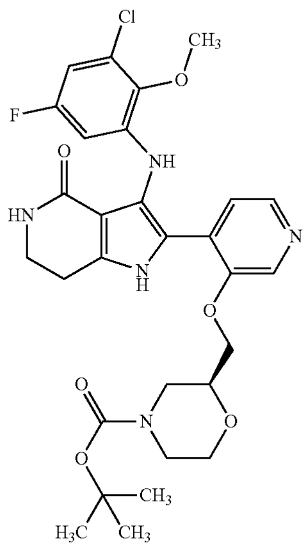 [SMILES: COc1c(Cl)cc(F)cc1Nc1c(-c2ccncc2OC[C@@H]2CN(C(=O)OC(C)(C)C)CCO2)[nH]c2c1C(=O)NCC2]

Using an analogous method as described for example 1 with tert-butyl (2S)-2-[({4-[({5-[(3-chloro-5-fluoro-2-methoxyphenyl)carbamothioyl]-6-oxo-1,2,3,6-tetrahydropyridin-4-yl}amino)methyl]pyridin-3-yl}oxy)methyl]morpholine-4-carboxylate (intermediate 6-27, 150 mg, 236 μmol) as the starting material, 73.5 mg (90% purity, 47% yield) of the title compound were prepared.

1H-NMR (400 MHz, DMSO-d6): δ [ppm]=1.40 (s, 9H), 2.52-2.53 (m, 2H), 2.70-3.03 (m, 1H), 2.87 (br t, 2H), 3.42 (td, 2H), 3.46-3.61 (m, 1H), 3.71-3.79 (m, 1H), 3.82 (s, 4H), 3.93 (br d, 1H), 4.20 (m, 1H), 4.27-4.33 (dd, 1H), 5.85 (dd, 1H), 6.55 (dd, 1H), 7.11 (s, 1H), 7.32 (d, 1H), 7.60 (s, 1H), 8.10 (d, 1H), 8.44 (s, 1H), 11.17 (s, 1H).

LC-MS (method 2): $R_t$=1.19 min; MS (ESIpos): m/z=602 $[M+H]^+$

Intermediate 27-2

3-(3-chloro-5-fluoro-2-methoxyanilino)-2-(3-{[(2S)-morpholin-2-yl]methoxy}pyridin-4-yl)-1,5,6,7-tetrahydro-4H-pyrrolo[3,2-c]pyridin-4-one

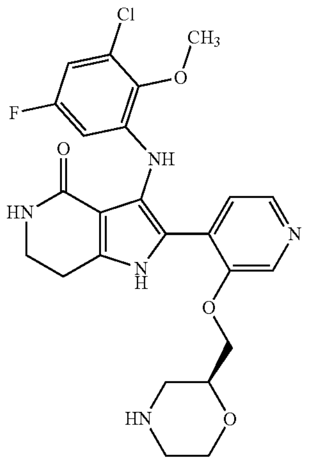 [SMILES: COc1c(Cl)cc(F)cc1Nc1c(-c2ccncc2OC[C@@H]2CNCCO2)[nH]c2c1C(=O)NCC2]

Using an analogous method as described for intermediate 22-2 with tert-butyl (2S)-2-[({4-[3-(3-chloro-5-fluoro-2-methoxyanilino)-4-oxo-4,5,6,7-tetrahydro-1H-pyrrolo[3,2-c]pyridin-2-yl]pyridin-3-yl}oxy)methyl]morpholine-4-carboxylate (intermediate 27-1, 73.0 mg, 121 μmol) as the starting material; 56.3 mg (95% purity, 88% yield) of the title compound were prepared after purification by flash chromatography (amino phase silica, DCM/EtOH gradient 0-15%).

$^1$H-NMR (400 MHz, DMSO-$d_6$): δ [ppm]=2.51-2.58 (m, 2H), 2.61-2.75 (m, 2H), 2.77-2.94 (m, 3H), 3.38-3.48 (m, 1H), 3.56 (td, 1H), 3.76-3.92 (m, 2H), 3.84 (s, 3H), 4.10 (dd, 1H), 4.29 (dd, 1H), 5.85 (dd, 1H), 6.57 (dd, 1H), 7.13 (s, 1H), 7.32 (d, 1H), 7.64 (d, 1H), 8.09 (d, 1H), 8.43 (s, 1H), 11.22 (s, 1H).

LC-MS (method 2): $R_t$=0.93 min; MS (ESIpos): m/z=502 $[M+H]^+$.

Intermediate 41-1 tert-butyl (2S)-2-{[(4-{3-[2-(2,2-difluoroethyl)-3-fluoroanilino]-4-oxo-4,5,6,7-tetrahydro-1H-pyrrolo[3,2-c]pyridin-2-yl}pyridin-3-yl)oxy]methyl}morpholine-4-carboxylate

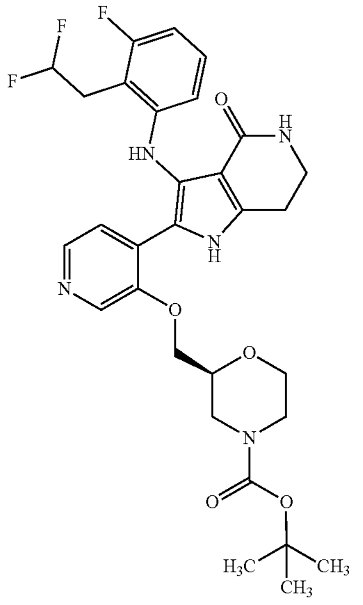 [SMILES: CC(C)(C)OC(=O)N1CCO[C@H](COc2cnccc2-c2[nH]c3c(c2Nc2cccc(F)c2CC(F)F)C(=O)NCC3)C1]

Using an analogous method as described for example 1 with tert-butyl (2S)-2-{[(4-{[(5-{[2-(2,2-difluoroethyl)-3-fluorophenyl]carbamothioyl}-6-oxo-1,2,3,6-tetrahydropyridin-4-yl)amino]methyl}pyridin-3-yl)oxy]methyl}morpholine-4-carboxylate (intermediate 6-41, 266 mg, 418 μmol) as the starting material; 33.0 mg (65% purity, 9% yield) of the title compound were prepared after purification by preparative HPLC (method 10, gradient: 0.00-0.50 min 30% B, 0.50-6.00 min 30-70% B).

LC-MS (method 2): $R_t$=1.16 min; MS (ESIneg): m/z=600 $[M-H]^-$

Intermediate 41-2

3-[2-(2,2-difluoroethyl)-3-fluoroanilino]-2-(3-{[(2S)-morpholin-2-yl]methoxy}pyridin-4-yl)-1,5,6,7-tetrahydro-4H-pyrrolo[3,2-c]pyridin-4-one

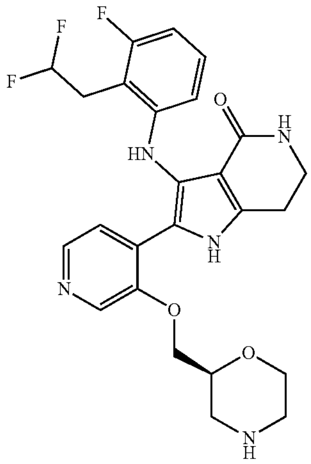 [SMILES: O=C1NCCc2[nH]c(-c3ccncc3OC[C@@H]3CNCCO3)c(Nc3cccc(F)c3CC(F)F)c21]

Using an analogous method as described for intermediate 22-2 with tert-butyl (2S)-2-{[(4-{3-[2-(2,2-difluoroethyl)-3-fluoroanilino]-4-oxo-4,5,6,7-tetrahydro-1H-pyrrolo[3,2-c]pyridin-2-yl}pyridin-3-yl)oxy]methyl}morpholine-4-carboxylate (intermediate 41-1, 33.0 mg, 54.9 μmol) as the starting material; 22.0 mg (65% purity, 52% yield) of the title compound were prepared after purification by flash chromatography (amino phase silica, DCM/EtOH gradient 0-10%).

LC-MS (method 2): $R_t$=0.92 min; MS (ESIneg): m/z=500 $[M-H]^-$

Intermediate 42-1 tert-butyl (2S)-2-[({4-[3-(3-chloro-2-methylanilino)-4-oxo-4,5,6,7-tetrahydro-1H-pyrrolo[3,2-c]pyridin-2-yl]pyridin-3-yl}oxy)methyl]morpholine-4-carboxylate

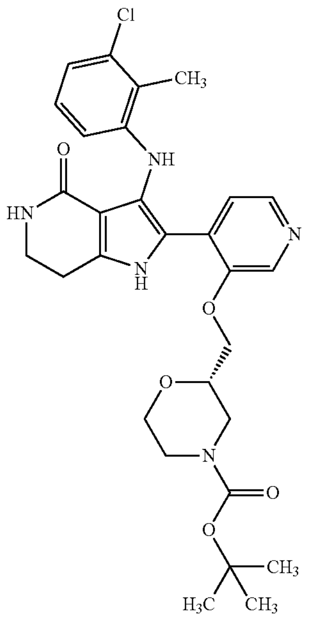 [SMILES: Cc1c(Cl)cccc1Nc1c(-c2ccncc2OC[C@@H]2CN(C(=O)OC(C)(C)C)CCO2)[nH]c2c1C(=O)NCC2]

Using an analogous method as described for example 1 with tert-butyl (2S)-2-[({4-[({5-[(3-chloro-2-methylphenyl)carbamothioyl]-6-oxo-1,2,3,6-tetrahydropyridin-4-yl}amino)methyl]pyridin-3-yl}oxy)methyl]morpholine-4-carboxylate (intermediate 6-42, 207 mg, 344 μmol) as the starting material; 27.8 mg (90% purity, 13% yield) of the title compound were prepared after purification by preparative HPLC (method 9, gradient: 0.00-0.50 min 15% B, 0.50-4.65 min 15-44.9% B, 4.65-5.94 min 44.9% B, 5.94-7.29 min 44.9-55% B).

$^1$H-NMR (400 MHz, DMSO-$d_6$): δ [ppm]=1.414 (16.00), 2.349 (5.99), 2.520 (0.82), 2.525 (0.50), 2.853 (0.68), 2.870 (1.29), 2.887 (0.75), 3.405 (0.49), 3.410 (0.53), 3.422 (0.95), 3.428 (0.93), 3.439 (0.48), 3.445 (0.43), 3.554 (0.43), 3.560 (0.45), 4.294 (0.43), 4.304 (0.45), 6.191 (0.69), 6.195 (0.66), 6.211 (0.71), 6.214 (0.69), 6.719 (0.48), 6.735 (1.31), 6.738 (1.11), 6.747 (0.85), 6.767 (0.82), 7.175 (0.83), 7.232 (0.92), 7.245 (0.92), 7.351 (0.48), 7.998 (1.24), 8.010 (1.16), 8.378 (1.84), 11.016 (0.78).

LC-MS (method 6): Rt=0.92 min; MS (ESIpos): m/z=568 $[M+H]^+$

Intermediate 42-2

3-(3-chloro-2-methylanilino)-2-(3-{[(2S)-morpholin-2-yl]methoxy}pyridin-4-yl)-1,5,6,7-tetrahydro-4H-pyrrolo[3,2-c]pyridin-4-one

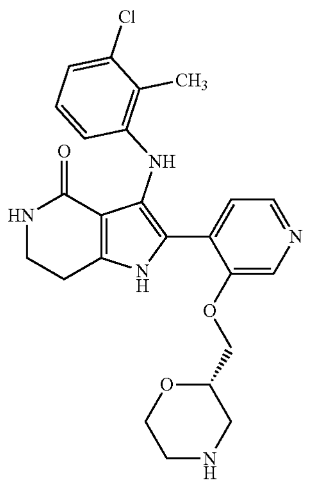 [SMILES: Cc1c(Cl)cccc1Nc1c(-c2ccncc2OC[C@@H]2CNCCO2)[nH]c2c1C(=O)NCC2]

Using an analogous method as described for intermediate 22-2 with tert-butyl (2S)-2-[({4-[3-(3-chloro-2-methyl-anilino)-4-oxo-4,5,6,7-tetrahydro-1H-pyrrolo[3,2-c]pyridin-2-yl]pyridin-3-yl}oxy)methyl]morpholine-4-carboxylate (intermediate 42-1, 30.0 mg, 52.8 μmol) as the starting material, 19.0 mg (92% purity, 71% yield) of the title compound were prepared after filtration through a SCX-2 column (MeOH wash followed by eluation with 1M ammonia in MeOH).

$^1$H-NMR (400 MHz, DMSO-$d_6$): δ [ppm]=1.235 (1.09), 2.334 (1.58), 2.338 (0.84), 2.362 (16.00), 2.520 (7.24), 2.525 (4.55), 2.545 (1.21), 2.570 (1.33), 2.575 (1.40), 2.601 (1.20), 2.676 (1.83), 2.680 (1.06), 2.705 (1.02), 2.713 (0.99), 2.732 (1.01), 2.740 (0.93), 2.758 (1.50), 2.787 (0.62), 2.846 (1.74), 2.863 (4.52), 2.880 (2.07), 2.894 (1.12), 3.300 (4.30), 3.410 (1.44), 3.416 (1.55), 3.427 (2.54), 3.433 (2.52), 3.445 (1.29), 3.585 (0.65), 3.593 (0.77), 3.612 (1.20), 3.620 (1.22), 3.640 (0.69), 3.646 (0.62), 3.851 (0.59), 3.868 (0.92), 3.875 (0.91), 3.902 (1.40), 3.930 (1.00), 4.073 (1.20), 4.090 (1.18), 4.098 (1.63), 4.116 (1.39), 4.274 (1.41), 4.282 (1.45), 4.299 (1.18), 4.307 (1.08), 5.528 (0.41), 6.196 (1.85), 6.200 (1.81), 6.215 (2.00), 6.219 (1.86), 6.726 (1.04), 6.730 (1.33), 6.746 (3.44), 6.750 (2.92), 6.761 (2.53), 6.780 (2.58), 6.800 (0.88), 7.192 (2.31), 7.231 (3.82), 7.244 (3.92), 7.364 (4.42), 7.980 (4.81), 7.993 (4.51), 8.370 (6.73), 8.397 (0.45), 11.102 (2.40).

LC-MS (method 6): Rt=0.52 min; MS (ESIpos): m/z=468 $[M+H]^+$

Intermediate 43-1 tert-butyl (3R)-3-[({4-[3-(3-chloro-2-methylanilino)-4-oxo-4,5,6,7-tetrahydro-1H-pyrrolo[3,2-c]pyridin-2-yl]pyridin-3-yl}oxy)methyl]morpholine-4-carboxylate

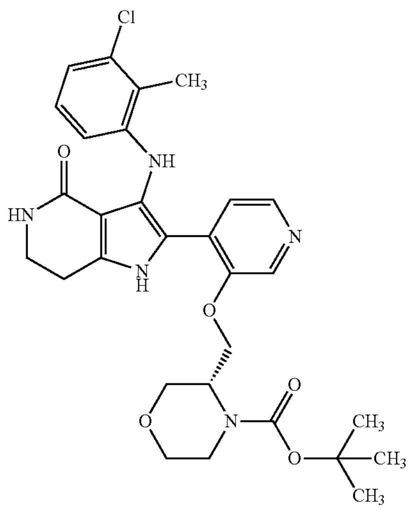 [SMILES: Cc1c(Cl)cccc1Nc1c(-c2ccncc2OC[C@H]2COCCN2C(=O)OC(C)(C)C)[nH]c2c1C(=O)NCC2]

Using an analogous method as described for example 1 with tert-butyl (3R)-3-[({4-[({5-[(3-chloro-2-methylphenyl)carbamothioyl]-6-oxo-1,2,3,6-tetrahydropyridin-4-yl}amino)methyl]pyridin-3-yl}oxy)methyl]morpholine-4-carboxylate (180 mg, 299 μmol) as the starting material; 35.1 mg (90% purity, 19% yield) of the title compound were prepared after purification by preparative HPLC (method 9, gradient: 0.00-0.50 min 15% B, 0.50-4.23 min 15-41.9% B, 4.23-5.60 min 41.9% B, 5.60-7.37 min 41.9-55% B).

$^1$H-NMR (400 MHz, DMSO-$d_6$): δ [ppm]=1.344 (16.00), 2.357 (14.22), 2.520 (2.49), 2.525 (1.70), 2.891 (0.42), 2.923 (1.43), 3.384 (1.03), 3.405 (2.12), 3.412 (2.73), 3.417 (2.74), 3.435 (1.48), 3.555 (0.76), 3.577 (0.85), 3.680 (1.24), 3.709 (1.06), 3.840 (1.02), 3.860 (0.92), 3.952 (1.42), 3.982 (1.23), 4.301 (0.62), 6.161 (1.64), 6.165 (1.44), 6.179 (1.77), 6.184 (1.67), 6.725 (0.94), 6.740 (3.11), 6.745 (3.77), 6.765 (1.40), 6.785 (0.46), 7.187 (1.94), 7.309 (2.75), 7.322 (2.75), 7.351 (4.78), 7.971 (1.97), 7.983 (1.88), 8.445 (5.01), 11.063 (1.60).

LC-MS (method 6): $R_t$=0.92 min; MS (ESIpos): m/z=568 $[M+H]^+$

Intermediate 43-2

3-(3-chloro-2-methylanilino)-2-(3-{[(3R)-morpholin-3-yl]methoxy}pyridin-4-yl)-1,5,6,7-tetrahydro-4H-pyrrolo[3,2-c]pyridin-4-one

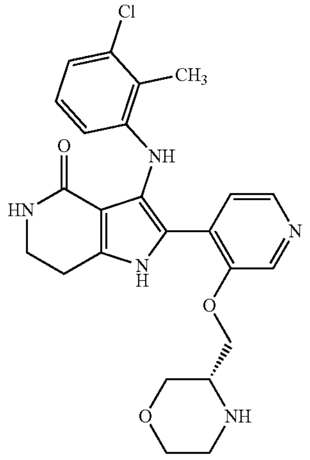 [SMILES: Cc1c(Cl)cccc1Nc1c(-c2ccncc2OC[C@H]2COCCN2)[nH]c2c1C(=O)NCC2]

Using an analogous method as described for intermediate 22-2 with tert-butyl (3R)-3-[({4-[3-(3-chloro-2-methylanilino)-4-oxo-4,5,6,7-tetrahydro-1H-pyrrolo[3,2-c]pyridin-2-yl]pyridin-3-yl}oxy)methyl]morpholine-4-carboxylate (intermediate 43-1, 30.0 mg, 52.8 μmol) as the starting material 25.3 mg (97% purity, 99% yield) of the title compound were prepared after filtration through a SCX-2 column (MeOH wash followed by eluation with 1M ammonia in MeOH).

$^1$H-NMR (400 MHz, DMSO-$d_6$): δ [ppm]=1.235 (0.47), 2.334 (1.10), 2.338 (0.53), 2.367 (16.00), 2.383 (0.45), 2.520 (5.15), 2.525 (3.36), 2.676 (1.09), 2.680 (0.50), 2.825 (1.81), 2.842 (3.79), 2.860 (2.41), 2.888 (0.56), 2.945 (0.90), 2.976 (0.54), 3.155 (0.67), 3.371 (1.08), 3.398 (1.36), 3.416 (2.04), 3.426 (3.16), 3.433 (2.75), 3.444 (2.06), 3.450 (1.95), 3.471 (0.57), 3.720 (1.01), 3.747 (0.86), 3.794 (1.03), 3.816 (0.90), 4.192 (0.59), 4.208 (0.66), 4.218 (1.25), 4.232 (1.21), 4.252 (1.38), 4.261 (1.46), 4.277 (0.69), 4.286 (0.59), 6.222 (1.82), 6.225 (1.83), 6.241 (1.98), 6.245 (1.89), 6.731 (1.15), 6.735 (1.43), 6.751 (3.26), 6.754 (2.74), 6.769 (2.24), 6.790 (2.51), 6.809 (0.87), 7.172 (2.36), 7.217 (2.75), 7.230 (2.77), 7.391 (4.55), 7.941 (1.75), 7.953 (1.66), 8.359 (2.93), 12.612 (0.40).

LC-MS (method 6): $R_t$=0.53 min; MS (ESIpos): m/z=468 $[M+H]^+$

Intermediate 55-1 tert-butyl (2R)-2-[({4-[3-(3-chloro-2-ethylanilino)-4-oxo-4,5,6,7-tetrahydro-1H-pyrrolo[3,2-c]pyridin-2-yl]pyridin-3-yl}oxy)methyl]morpholine-4-carboxylate

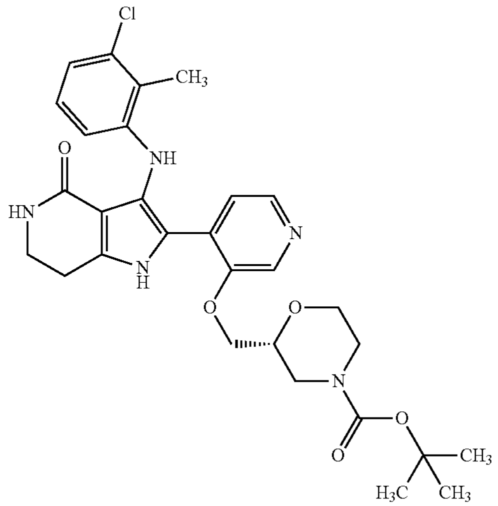 [SMILES: Cc1c(Cl)cccc1Nc1c(-c2ccncc2OC[C@H]2CN(C(=O)OC(C)(C)C)CCO2)[nH]c2c1C(=O)NCC2]

Using an analogous method as described for example 1 with tert-butyl (2R)-2-[({4-[({5-[(3-chloro-2-ethylphenyl)carbamothioyl]-6-oxo-1,2,3,6-tetrahydropyridin-4-yl}amino)methyl]pyridin-3-yl}oxy)methyl]morpholine-4-carboxylate (intermediate 6-55, 473 mg, 768 μmol) as the starting material; 57.0 mg (95% purity, 12% yield) of the title compound were prepared after purification by preparative HPLC (method 10, gradient: 0.00-0.50 min 10% B, 0.50-11.05 min 10-34.4% B, 11.05-12.46 min 34.4% B, 12.46-24.12 min 34.4-60% B) followed by flash chromatography (silica, DCM/EtOH gradient 0-12%).

LC-MS (method 2): $R_t$=1.26 min; MS (ESIpos): m/z=582 $[M+H]^+$

Intermediate 55-2

3-(3-chloro-2-ethylanilino)-2-(3-{[(2R)-morpholin-2-yl]methoxy}pyridin-4-yl)-1,5,6,7-tetrahydro-4H-pyrrolo[3,2-c]pyridin-4-one

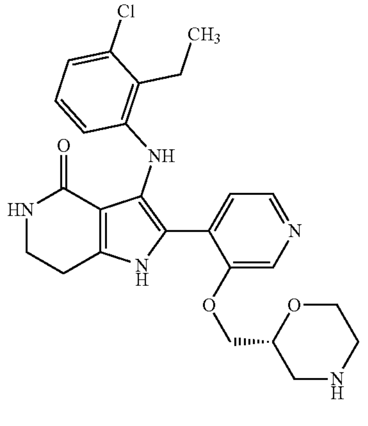 [SMILES: CCc1c(Cl)cccc1Nc1c(-c2ccncc2OC[C@H]2CNCCO2)[nH]c2c1C(=O)NCC2]

Using an analogous method as described for intermediate 22-2 with tert-butyl (2R)-2-[({4-[3-(3-chloro-2-ethylanilino)-4-oxo-4,5,6,7-tetrahydro-1H-pyrrolo[3,2-c]pyridin-2-yl]pyridin-3-yl}oxy)methyl]morpholine-4-carboxylate (intermediate 55-1, 70.4 mg, 121 μmol) as the starting material; 58.0 mg (95% purity, 95% yield) of the title compound were prepared after purification by flash chromatography (silica, DCM/EtOH+triethylamine gradient 1-40%).

$^1$H-NMR (400 MHz, DMSO-$d_6$): δ [ppm]=10.96-11.17 (m, 1H), 8.36 (s, 1H), 7.69-8.02 (m, 1H), 7.37-7.51 (m, 1H), 7.19 (s, 2H), 6.65-6.86 (m, 2H), 6.15-6.24 (m, 1H), 6.12-6.31 (m, 1H), 4.26-4.36 (m, 1H), 4.06-4.14 (m, 1H), 3.85-3.96 (m, 2H), 3.58-3.67 (m, 1H), 3.40-3.46 (m, 2H), 3.35-3.39 (m, 1H), 2.69-2.96 (m, 7H), 2.56-2.64 (m, 1H), 1.19-1.27 (m, 6H).

LC-MS (method 2): $R_t$=0.99 min; MS (ESIneg): m/z=480 $[M-H]^-$

Intermediate 56-1 tert-butyl (2S)-2-[({4-[3-(3-chloro-2-ethylanilino)-4-oxo-4,5,6,7-tetrahydro-1H-pyrrolo[3,2-c]pyridin-2-yl]pyridin-3-yl}oxy)methyl]morpholine-4-carboxylate

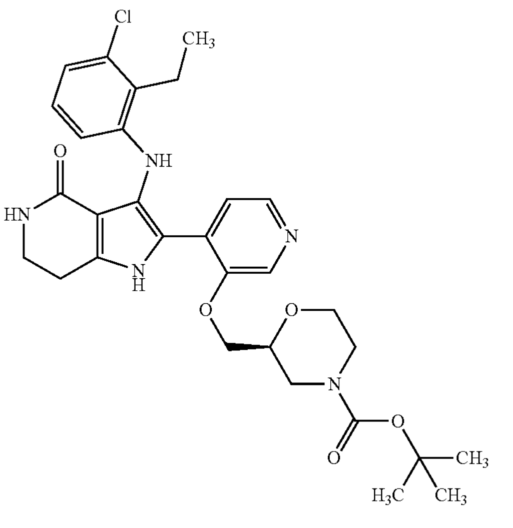 [SMILES: CCc1c(Cl)cccc1Nc1c(-c2ccncc2OC[C@@H]2CN(C(=O)OC(C)(C)C)CCO2)[nH]c2c1C(=O)NCC2]

Using an analogous method as described for example 1 with tert-butyl (2S)-2-[({4-[({5-[(3-chloro-2-ethylphenyl) carbamothioyl]-6-oxo-1,2,3,6-tetrahydropyridin-4-yl}amino)methyl]pyridin-3-yl}oxy)methyl]morpholine-4-carboxylate (intermediate 6-56, 476 mg, 772 μmol) as the starting material; 68.0 mg (95% purity, 14% yield) of the title compound were prepared after purification by preparative HPLC (method 10, gradient: 0.00-0.50 min 20% B, 0.50-12.99 min 20-40% B, 12.99-15.46 min 40% B, 15.46-24.12 min 40-55% B) followed by flash chromatography (silica, DCM/EtOH gradient 0-12%).

LC-MS (method 2): $R_t$=1.26 min; MS (ESIpos): m/z=582 $[M+H]^+$

Intermediate 56-2

3-(3-chloro-2-ethylanilino)-2-(3-{[(2S)-morpholin-2-yl]methoxy}pyridin-4-yl)-1,5,6,7-tetrahydro-4H-pyrrolo[3,2-c]pyridin-4-one

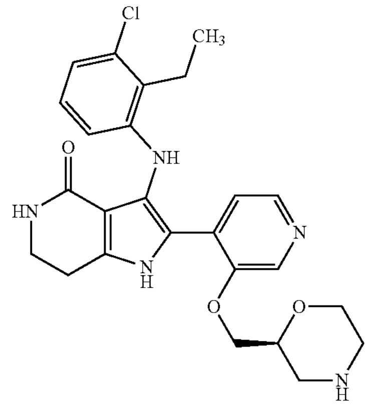 [SMILES: CCc1c(Cl)cccc1Nc1c(-c2ccncc2OC[C@@H]2CNCCO2)[nH]c2c1C(=O)NCC2]

Using an analogous method as described for intermediate 22-2 with tert-butyl (2S)-2-[({4-[3-(3-chloro-2-ethylanilino)-4-oxo-4,5,6,7-tetrahydro-1H-pyrrolo[3,2-c]pyridin-2-yl]pyridin-3-yl}oxy)methyl]morpholine-4-carboxylate (intermediate 56-1, 70.4 mg, 121 μmol) as the starting material; 46.9 mg (95% purity, 78% yield) of the title compound were prepared after purification by flash chromatography (amino phase silica, DCM/EtOH gradient 1-35%).

$^1$H-NMR (400 MHz, DMSO-$d_6$): δ [ppm]=11.09 (s, 1H), 8.36 (s, 1H), 7.96 (d, 1H), 7.46 (s, 1H), 7.19 (d, 2H), 6.68-6.84 (m, 2H), 6.23 (dd, 1H), 4.24-4.34 (m, 1H), 4.03-4.16 (m, 1H), 3.82-3.96 (m, 2H), 3.57-3.65 (m, 1H), 3.39-3.48 (m, 2H), 2.82-2.94 (m, 5H), 2.64-2.79 (m, 2H), 2.54-2.60 (m, 1H), 1.23 (t, 3H).

LC-MS (method 2): $R_t$=0.99 min; MS (ESIneg): m/z=480 $[M-H]^-$

EXAMPLES

Example 1

3-(3-chloro-2-methoxyanilino)-2-{3-[(1,4-dioxan-2-yl)methoxy]pyridin-4-yl}-1,5,6,7-tetrahydro-4H-pyrrolo[3,2-c]pyridin-4-one

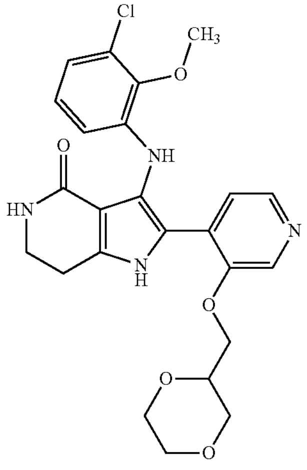 [SMILES: COc1c(Cl)cccc1Nc1c(-c2ccncc2OCC2COCCO2)[nH]c2c1C(=O)NCC2]

To a suspension of N-(3-chloro-2-methoxyphenyl)-4-[({3-[(1,4-dioxan-2-yl)methoxy]pyridin-4-yl}methyl)amino]-2-oxo-1,2,5,6-tetrahydropyridine-3-carbothioamide (intermediate 6-1, 140 mg, 240 μmol) in MeOH (2.7 ml) was added TFA (42 μl, 540 μmol) followed by aqueous hydrogen peroxide (94 μl, 35% purity, 1.08 mmol) and the mixture was heated at 50° C. for 17 h. The reaction mixture was allowed to cool down to RT and concentrated under reduced pressure. The residue was purified by preparative HPLC (method 10, gradient: 0.00-0.50 min 15% B, 0.50-6.00 min 15-55% B) to give 70 mg of the title compound (51% yield).

$^1$H-NMR (400 MHz, DMSO-$d_6$): δ [ppm]=2.86 (t, 2H), 3.37-3.57 (m, 4H), 3.70-3.90 (m, 4H), 3.88 (s, 3H), 3.92-4.08 (m, 1H), 4.10-4.20 (m, 1H), 4.28 (dd, 1H), 6.15 (t, 1H), 6.68 (d, 2H), 7.16 (br s, 1H), 7.28 (d, 1H), 7.52 (s, 1H), 8.04 (d, 1H), 8.39 (s, 1H), 11.07 (s, 1H).

LC-MS (method 2): $R_t$=0.98 min; MS (ESIpos): m/z=485 $[M+H]^+$

Example 2

3-(3-chloro-2-methoxyanilino)-2-(3-{[(2S)-1,4-dioxan-2-yl]methoxy}pyridin-4-yl)-1,5,6,7-tetrahydro-4H-pyrrolo[3,2-c]pyridin-4-one (Stereoisomer 1)

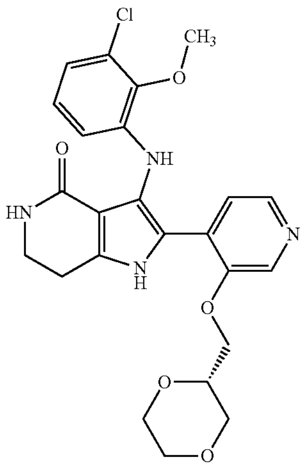 [SMILES: COc1c(Cl)cccc1Nc1c(-c2ccncc2OC[C@@H]2COCCO2)[nH]c2c1C(=O)NCC2]

The title compound from example 1 (140 mg) was separated into enantiomers by preparative chiral HPLC to give title compound (enantiomer 1, 27 mg at Rt=14.0-17.0 min) and enantiomer 2 (25 mg at $R_t$=20.0-24.8 min, see example 3).

Preparative Chiral HPLC Method:

Instrument: Labomatic HD5000, Labocord-5000; Gilson GX-241, Labcol Vario 4000; column: Cellulose SB 5μ, 250×30 mm; eluent A: hexane+0.1 vol. % diethylamine (99%); eluent B: 2-propanol; isocratic: 50% A+50% B; flow 50 ml/min; UV: 254 nm.

Analytical Chiral HPLC Method:

Instrument: Agilent HPLC 1260; column: Cellulose SB 3μ, 100×4.6 mm; eluent A: hexane+0.1 vol. % diethylamine (99%); eluent B: 2-propanol; isocratic: 50% A+50% B, flow 1.4 ml/min; temperature: 25° C.; UV: 254 nm Analytical chiral HPLC: $R_t$=4.49 min.

Optical rotation: $[\alpha]_D$=1.7°+/−0.98° (c=3.6 mg/2 ml, methanol)

Enantioselective synthesis confirmed the title compound as 3-(3-chloro-2-methoxyanilino)-2-(3-{[(2S)-1,4-dioxan-2-yl]methoxy}pyridin-4-yl)-1,5,6,7-tetrahydro-4H-pyrrolo[3,2-c]pyridin-4-one. 872 mg (95% purity, 72% yield) of the title compound were prepared in analogy to example 1 using N-(3-chloro-2-methoxyphenyl)-4-{[(3-{[(2S)-1,4-dioxan-2-yl]methoxy}pyridin-4-yl)methyl]amino}-2-oxo-1,2,5,6-tetrahydropyridine-3-carbothioamide (intermediate 6-2, 1.23 g, 2.36 mmol) as starting material, followed by purification with preparative HPLC (method 10, gradient: 0.00-0.50 min 15% B, 0.50-6.00 min 15-55% B).

$^1$H-NMR (400 MHz, DMSO-$d_6$): δ [ppm]=2.86 (t, 2H), 3.38-3.47 (m, 3H), 3.53 (td, 1H), 3.69-3.78 (m, 2H), 3.83 (dd, 1H), 3.88 (s, 3H), 3.90 (m, 1H), 3.98-4.08 (m, 1H), 4.12-4.18 (m, 1H), 4.28 (dd, 1H), 6.12-6.17 (quin, 1H), 6.66-6.71 (m, 2H), 7.16 (s, 1H), 7.28 (d, 1H), 7.52 (s, 1H), 8.04 (d, 1H), 8.39 (s, 1H), 11.07 (s, 1H).

Analytical chiral HPLC: $R_t$=4.46 min.

Optical rotation: $[\alpha]_D$=−12.5°+/−0.52° (c=5.6 mg/ml, chloroform)

Example 3

3-(3-chloro-2-methoxyanilino)-2-(3-{[(2R)-1,4-dioxan-2-yl]methoxy}pyridin-4-yl)-1,5,6,7-tetrahydro-4H-pyrrolo[3,2-c]pyridin-4-one (Stereoisomer 2)

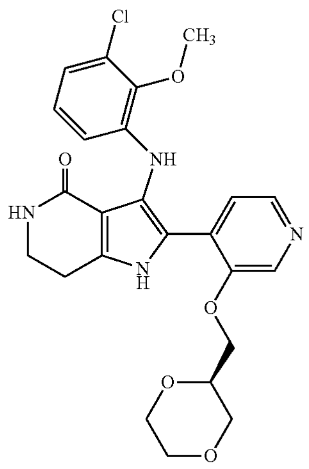 [SMILES: COc1c(Cl)cccc1Nc1c(-c2ccncc2OC[C@H]2COCCO2)[nH]c2c1C(=O)NCC2]

For the preparation of the racemic title compound see example 1. Separation of enantiomers by preparative chiral HPLC (method see example 2) gave 25 mg of the title compound (at $R_t$=20.0-24.8 min).

Analytical chiral HPLC (method see example 2): $R_t$=6.56 min.

Optical rotation: $[\alpha]_D$=−3.0°+/−1.03° (c=3.2 mg/2 ml, methanol)

Optical rotation: $[\alpha]_D$=22.8°+/−6.1° (c=6.3 mg/ml, chloroform)

Example 4

2-{3-[(1,4-dioxan-2-yl)methoxy]pyridin-4-yl}-3-(3-fluoro-2-methoxyanilino)-1,5,6,7-tetrahydro-4H-pyrrolo[3,2-c]pyridin-4-one

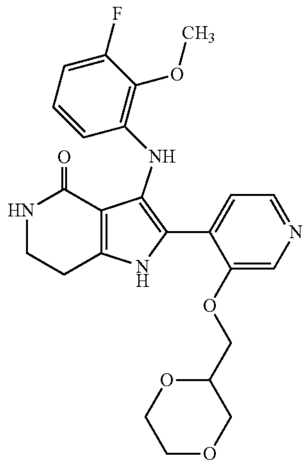 [SMILES: COc1c(F)cccc1Nc1c(-c2ccncc2OCC2COCCO2)[nH]c2c1C(=O)NCC2]

In analogy to example 1 4-[({3-[(1,4-dioxan-2-yl)methoxy]pyridin-4-yl}methyl)amino]-N-(3-fluoro-2-methoxyphenyl)-2-oxo-1,2,5,6-tetrahydropyridine-3-carbothioamide (intermediate 6-4, 120 mg, 239 μmol) was used to prepare 25.7 mg of the title compound (21% yield) after heating for 25 hours and purification by preparative HPLC (method 10, gradient: 0.00-0.50 min 15% B, 0.50-6.00 min 15-55% B).

$^1$H-NMR (400 MHz, DMSO-$d_6$): δ [ppm]=2.86 (t, 2H), 3.37-3.57 (m, 4H), 3.66-3.89 (m, 4H), 3.91 (s, 3H), 3.98-4.09 (m, 1H), 4.09-4.20 (m, 1H), 4.28 (dd, 1H), 6.00 (d, 1H), 6.45-6.54 (m, 1H), 6.64 (m, 1H), 7.16 (br s, 1H), 7.29 (d, 1H), 7.53 (s, 1H), 8.04 (d, 1H), 8.39 (s, 1H), 11.05 (s, 1H).

LC-MS (method 2): $R_t$=0.92 min; MS (ESIpos): m/z=469 $[M+H]^+$

Example 5

2-{3-[(1,4-dioxan-2-yl)methoxy]pyridin-4-yl}-3-(3-fluoro-2-methoxyanilino)-1,5,6,7-tetrahydro-4H-pyrrolo[3,2-c]pyridin-4-one (stereoisomer 1)

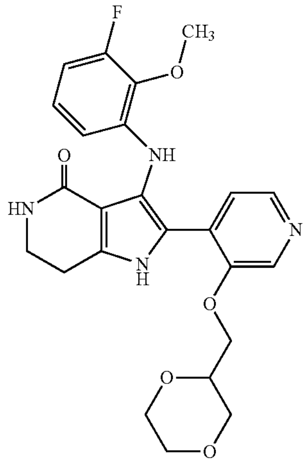 [SMILES: COc1c(F)cccc1Nc1c(-c2ccncc2OCC2COCCO2)[nH]c2c1C(=O)NCC2]

The title compound from example 4 (26 mg) was separated into enantiomers by preparative chiral HPLC to give title compound (enantiomer 1, 11 mg, at $R_t$=8.2-9.1 min, 10% yield) and enantiomer 2 (12 mg, at $R_t$=9.7-10.7 min, see example 6).

Preparative Chiral HPLC Method:

Instrument: Labomatic HD5000, Labocord-5000; Gilson GX-241, Labcol Vario 4000; column: Cellulose SB 5μ, 250×30 mm; eluent A: MTBE+0.1 vol. % diethylamine (99%); eluent B: acetonitrile; gradient: 2-60% B in 20 min; flow 50 ml/min; UV: 280 nm Analytical Chiral HPLC Method:

Instrument: Agilent HPLC 1260; column: Cellulose SB 3μ, 100×4.6 mm; eluent A: MTBE+0.1 vol. % diethylamine (99%); eluent B: acetonitrile; gradient: 2-60% B in 7 min, flow 1.4 ml/min; temperature: 25° C.; UV: 280 nm Analytical chiral HPLC: $R_t$=4.34 min.

Optical rotation: $[\alpha]_D$=−0.5°+/−0.87° (c=7.5 mg/2 ml, methanol)

Example 6

2-{3-[(1,4-dioxan-2-yl)methoxy]pyridin-4-yl}-3-(3-fluoro-2-methoxyanilino)-1,5,6,7-tetrahydro-4H-pyrrolo[3,2-c]pyridin-4-one (stereoisomer 2)

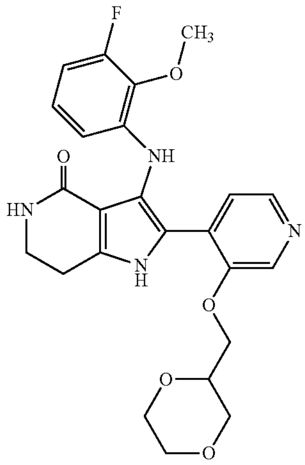 [SMILES: COc1c(F)cccc1Nc1c(-c2ccncc2OCC2COCCO2)[nH]c2c1C(=O)NCC2]

For the preparation of the racemic title compound see example 4. Separation of enantiomers by preparative chiral HPLC (method see example 5) to give 12 mg of the title compound (at $R_t$=9.7-10.7 min, 11% yield).

Analytical chiral HPLC (method see example 5): $R_t$=5.11 min.

Optical rotation: $[\alpha]_D$=−0.1°+/−0.89° (c=6.3 mg/3 ml, methanol)

Example 7

3-(2,3-dichloroanilino)-2-{3-[(1,4-dioxan-2-yl)methoxy]pyridin-4-yl}-1,5,6,7-tetrahydro-4H-pyrrolo[3,2-c]pyridin-4-one

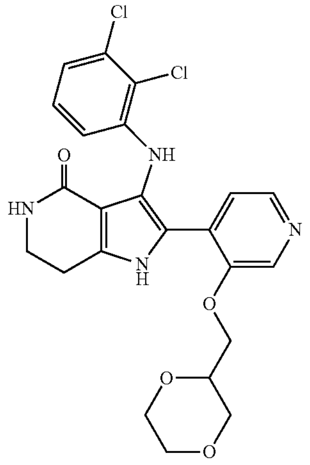 [SMILES: O=C1NCCc2[nH]c(-c3ccncc3OCC3COCCO3)c(Nc3cccc(Cl)c3Cl)c21]

In analogy to example 1 N-(2,3-dichlorophenyl)-4-[({3-[(1,4-dioxan-2-yl)methoxy]pyridin-4-yl}methyl)amino]-2-oxo-1,2,5,6-tetrahydropyridine-3-carbothioamide (intermediate 6-7, 110 mg, 210 μmol) was used to prepare 34.6 mg of the title compound (32% yield) after heating for 25 hours and purification by preparative HPLC (method 10, gradient: 0.00-0.50 min 15% B, 0.50-6.00 min 15-55% B).

$^1$H-NMR (400 MHz, DMSO-$d_6$): δ [ppm]=2.86 (brt, 2H), 3.35-3.45 (m, 3H), 3.47-3.56 (m, 1H), 3.65-3.75 (m, 2H), 3.75-3.88 (m, 2H), 3.93-4.04 (m, 1H), 4.06-4.20 (m, 2H), 6.27 (dd, 1H), 6.83-6.91 (m, 2H), 7.17 (br s, 1H), 7.26 (d, 1H), 7.66 (s, 1H), 8.08 (d, 1H), 8.38 (s, 1H), 11.21 (s, 1H).

LC-MS (method 2): $R_t$=1.01 min; MS (ESIpos): m/z=489 $[M+H]^+$

Example 8

3-(2,3-dichloroanilino)-2-{3-[(1,4-dioxan-2-yl)methoxy]pyridin-4-yl}-1,5,6,7-tetrahydro-4H-pyrrolo[3,2-c]pyridin-4-one (stereoisomer 1)

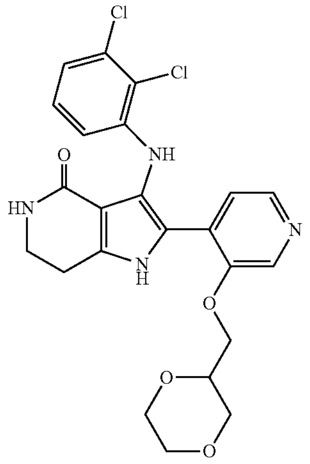 [SMILES: O=C1NCCc2[nH]c(-c3ccncc3OCC3COCCO3)c(Nc3cccc(Cl)c3Cl)c21]

The title compound from example 7 (27 mg) was separated into enantiomers by preparative chiral HPLC to give title compound (enantiomer 1, 10 mg) and enantiomer 2 (12 mg, see example 9).

Preparative Chiral HPLC Method:

Instrument: Labomatic HD5000, Labocord-5000; Gilson GX-241, Labcol Vario 4000; column: Cellulose SB 5μ, 250×30 mm; eluent A: MTBE+0.1 vol. % diethylamine (99%); eluent B: acetonitrile; gradient: 2-60% B in 20 min; flow 50 ml/min; UV: 280 nm Analytical Chiral HPLC Method:

Instrument: Agilent HPLC 1260; column: Cellulose SB 3μ, 100×4.6 mm; eluent A: MTBE+0.1 vol. % diethylamine (99%); eluent B: acetonitrile; gradient: 2-60% B in 7 min, flow 1.4 ml/min; temperature: 25° C.; UV: 280 nm Analytical chiral HPLC: Rt=5.11 min.

Optical rotation: $[\alpha]_D$=1.4°+/−0.69° (c=5.8 mg/2 ml, methanol)

Example 9

3-(2,3-Dichloroanilino)-2-{3-[(1,4-dioxan-2-yl)methoxy]pyridin-4-yl}-1,5,6,7-tetrahydro-4H-pyrrolo[3,2-c]pyridin-4-one (stereoisomer 2)

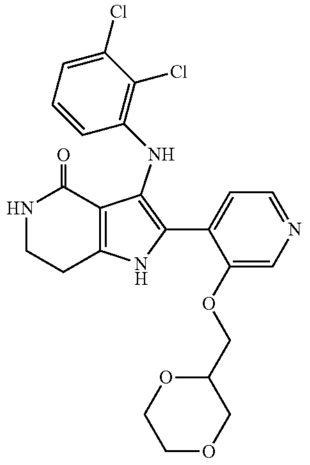 [SMILES: O=C1NCCc2[nH]c(-c3ccncc3OCC3COCCO3)c(Nc3cccc(Cl)c3Cl)c21]

For the preparation of the racemic title compound see example 7. Separation of enantiomers by preparative chiral HPLC (method see example 8) to gave 12 mg of the title compound.

Analytical chiral HPLC (method see example 8): $R_t$=6.74 min.

Optical rotation: $[\alpha]_D$=−14.9°+/−3.16° (c=5.6 mg/ml, methanol)

Example 10

3-(3-chloro-2-methylanilino)-2-{3-[(1,4-dioxan-2-yl)methoxy]pyridin-4-yl}-1,5,6,7-tetrahydro-4H-pyrrolo[3,2-c]pyridin-4-one

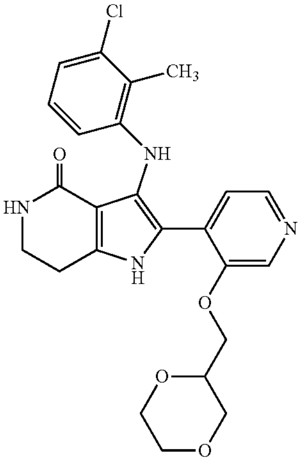 [SMILES: Cc1c(Cl)cccc1Nc1c(-c2ccncc2OCC2COCCO2)[nH]c2c1C(=O)NCC2]

In analogy to example 1 N-(3-chloro-2-methylphenyl)-4-[({3-[(1,4-dioxan-2-yl)methoxy]pyridin-4-yl}methyl)amino]-2-oxo-1,2,5,6-tetrahydropyridine-3-carbothioamide (intermediate 6-10, 180 mg, 358 μmol) was used to prepare 12.1 mg of the title compound (7% yield) after heating for 25 hours and purification by preparative HPLC (method 10, gradient: 0.00-0.50 min 15% B, 0.50-6.00 min 15-55% B).

$^1$H-NMR (400 MHz, DMSO-$d_6$): δ [ppm]=2.35 (s, 3H), 2.86 (br t, 2H), 3.37-3.47 (m, 3H), 3.55 (br dd, 1H), 3.67-3.85 (m, 3H), 3.89 (br d, 1H), 4.01 (br dd, 1H), 4.08-4.18 (m, 1H), 4.24 (dd, 1H), 6.20 (d, 1H), 6.71-6.80 (m, 2H), 7.19 (br s, 1H), 7.24 (d, 1H), 7.37 (s, 1H), 8.01 (d, 1H), 8.37 (s, 1H), 11.05 (s, 1H).

LC-MS (method 2): $R_t$=1.02 min; MS (ESipos): m/z=469 $[M+H]^+$

Example 11

3-(3-chloro-2-methoxyanilino)-2-(3-{[(3R)-4-methylmorpholin-3-yl]methoxy}pyridin-4-yl)-1,5,6,7-tetrahydro-4H-pyrrolo[3,2-c]pyridin-4-one

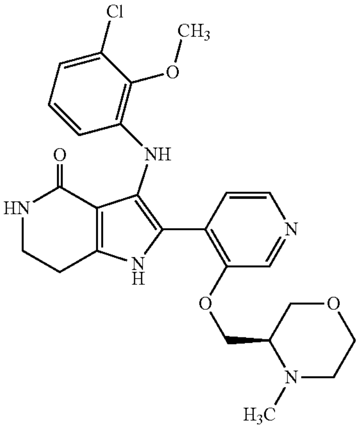 [SMILES: COc1c(Cl)cccc1Nc1c(-c2ccncc2OC[C@H]2COCCN2C)[nH]c2c1C(=O)NCC2]

In analogy to example 1 N-(3-chloro-2-methoxyphenyl)-4-{[(3-{[(3R)-4-methylmorpholin-3-yl]methoxy}pyridin-4-yl)methyl]amino}-2-oxo-1,2,5,6-tetrahydropyridine-3-carbothioamide (intermediate 6-11, 82 mg, 139 μmol) was used to prepare 11 mg of the title compound (15% yield) after heating for 17 hours and purification by preparative HPLC (method 10, gradient: 0.00-0.50 min 15% B, 0.50-6.00 min 15-55% B).

$^1$H-NMR (400 MHz, DMSO-$d_6$): δ [ppm]=11.51-12.57 (m, 1H), 8.40 (br s, 1H), 8.04 (br s, 1H), 7.62 (br s, 1H), 7.32 (d, 1H), 7.19 (br s, 1H), 6.71 (br d, 2H), 6.15 (dd, 1H), 4.40 (br s, 2H), 3.90 (s, 4H), 3.85 (br s, 1H), 3.60 (br d, 3H), 3.40-3.51 (m, 3H), 3.01 (br s, 1H), 2.74-2.96 (m, 3H), 2.22-2.43 (m, 2H).

LC-MS (method 6): $R_t$=0.55 min; MS (ESipos): m/z=498.2 $[M+H]^+$

Optical rotation: $[\alpha]_D$=−82.0°+/−0.41° (c=5.8 mg/ml, methanol)

Example 12

3-(3-fluoro-2-methoxyanilino)-2-{3-[(4-methylmorpholin-2-yl)methoxy]pyridin-4-yl}-1,5,6,7-tetrahydro-4H-pyrrolo[3,2-c]pyridin-4-one

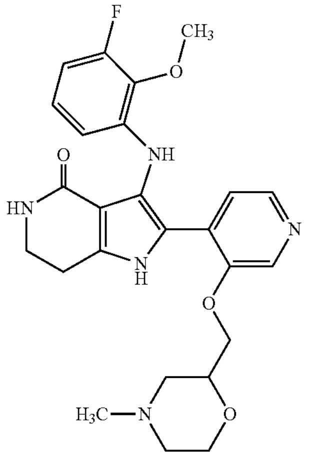 [SMILES: COc1c(F)cccc1Nc1c(-c2ccncc2OCC2CN(C)CCO2)[nH]c2c1C(=O)NCC2]

3-(3-Fluoro-2-methoxyanilino)-2-(3-hydroxypyridin-4-yl)-1,5,6,7-tetrahydro-4H-pyrrolo[3,2-c]pyridin-4-one (intermediate 12, 150 mg, 407 μmol) was solved in dioxane (4.8 ml). The reaction mixture was degassed with argon. Then (tributylphosphanylidene)acetonitrile (384 μl, 1.5 mmol, CAS 157141-27-0) and (4-methylmorpholin-2-yl)methanol (CAS 40987-46-0, 80.0 mg, 610 μmol) were added and the mixture was stirred at 50° C. for 30 h. The mixture was concentrated under reduced pressure and sat. sodium bicarbonate solution was added. The mixture was extracted with DCM. The organic phase was filtered over a water-repellent filter, concentrated under reduced pressure and purified by preparative HPLC (method 10, gradient: 0.00-0.50 min 1% B, 0.50-27.40 min 1-50% B) to give 16.2 mg of the title compound (8% yield).

$^1$H-NMR (400 MHz, DMSO-$d_6$): δ [ppm]=11.05 (s, 1H), 8.40 (s, 1H), 8.02 (d, 1H), 7.52 (s, 1H), 7.29 (d, 1H), 7.16 (s, 1H), 6.64 (td, 1H), 6.50 (ddd, 1H), 6.01 (d, 1H), 4.34 (dd, 1H), 4.15 (dd, 1H), 3.88-4.00 (m, 5H), 3.67 (td, 1H), 3.37-3.47 (m, 2H), 2.85 (t, 2H), 2.77 (br d, 1H), 2.66-2.70 (m, 1H), 2.20 (s, 3H), 2.04 (td, 1H), 1.91 (t, 1H).

LC-MS (method 2): $R_t$=0.92 min; MS (ESIpos): m/z=482.3 $[M+H]^+$

Example 13

3-(3-fluoro-2-methoxyanilino)-2-{3-[(4-methylmorpholin-2-yl)methoxy]pyridin-4-yl}-1,5,6,7-tetrahydro-4H-pyrrolo[3,2-c]pyridin-4-one (stereoisomer 1)

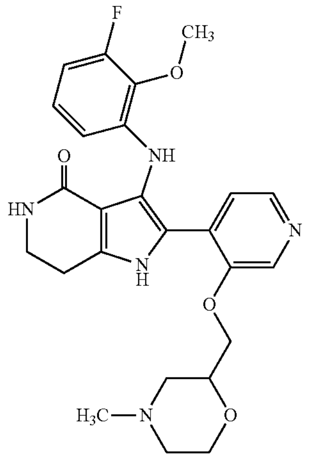 [SMILES: COc1c(F)cccc1Nc1c(-c2ccncc2OCC2CN(C)CCO2)[nH]c2c1C(=O)NCC2]

The title compound from example 12 (19 mg) was separated into enantiomers by preparative chiral HPLC to give title compound (enantiomer 1, 6 mg, at $R_t$=6.7-8.7 min, 3% yield) and enantiomer 2 (7 mg, at $R_t$=8.9-11.9 min, see example 14).

Preparative Chiral HPLC Method:

Instrument: PrepCon Labomatic HPLC; column: Chiralcel OD-H 5μ, 250×20; eluent A: acetonitrile+0.1 vol. % diethylamine (99%); eluent B: ethanol; isocratic: 93% A+7% B; flow 20 ml/min; temperature: 25° C.; UV: 254 nm Analytical Chiral HPLC Method:

Instrument: Waters Alliance 2695; column: Chiralcel OD-H 5μ, 100×4.6; eluent A: ethanol+0.1 vol. % diethylamine (99%); eluent B: ethanol; isocratic: 90% A+10% B, flow 1.4 ml/min; temperature: 25° C.; UV: 254 nm Analytical chiral HPLC: $R_t$=2.91 min.

$^1$H-NMR (400 MHz, DMSO-$d_6$): δ [ppm]=11.05 (s, 1H), 8.40 (s, 1H), 8.02 (d, 1H), 7.53 (s, 1H), 7.29 (d, 1H), 7.16 (s, 1H), 6.64 (td, 1H), 6.50 (t, 1H), 6.01 (d, 1H), 4.34 (dd, 1H), 4.15 (dd, 1H), 3.89-3.99 (m, 5H), 3.67 (td, 1H), 3.38-3.46 (m, 2H), 2.85 (t, 2H), 2.77 (br d, 1H), 2.61-2.71 (m, 1H), 2.20 (s, 3H), 1.98-2.16 (m, 1H), 1.91 (t, 1H).

Example 14

3-(3-fluoro-2-methoxyanilino)-2-{3-[(4-methylmorpholin-2-yl)methoxy]pyridin-4-yl}-1,5,6,7-tetrahydro-4H-pyrrolo[3,2-c]pyridin-4-one (stereoisomer 2)

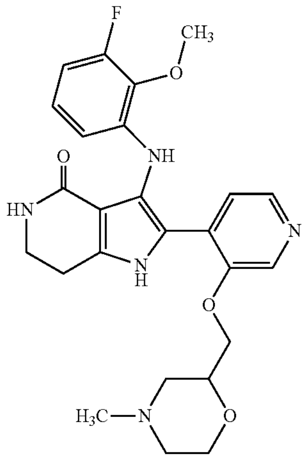 [SMILES: COc1c(F)cccc1Nc1c(-c2ccncc2OCC2CN(C)CCO2)[nH]c2c1C(=O)NCC2]

For the preparation of the racemic title compound see example 12. Separation of enantiomers by preparative chiral HPLC (method see example 13) to give 7 mg of the title compound (at $R_t$=8.9-11.9 min, 3% yield).

Analytical chiral HPLC (method see example 13): $R_t$=3.70 min.

$^1$H-NMR (400 MHz, DMSO-$d_6$): δ [ppm]=11.05 (s, 1H), 8.40 (s, 1H), 8.02 (br d, 1H), 7.53 (s, 1H), 7.29 (d, 1H), 7.16 (br s, 1H), 6.59-6.70 (m, 1H), 6.50 (br t, 1H), 6.01 (br d, 1H), 4.34 (br dd, 1H), 4.15 (br dd, 1H), 3.86-4.00 (m, 5H), 3.60-3.74 (m, 1H), 3.40-3.48 (m, 2H), 2.85 (br t, 2H), 2.77 (br d, 1H), 2.63-2.70 (m, 1H), 2.20 (s, 3H), 1.99-2.09 (m, 1H), 1.91 (br t, 1H).

Example 15

3-(3-chloro-2-methoxyanilino)-2-{3-[(4-methylmorpholin-2-yl)methoxy]pyridin-4-yl}-1,5,6,7-tetrahydro-4H-pyrrolo[3,2-c]pyridin-4-one

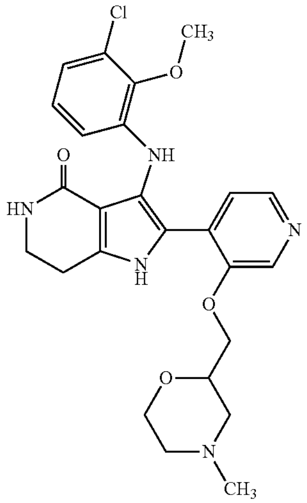 [SMILES: COc1c(Cl)cccc1Nc1c(-c2ccncc2OCC2CN(C)CCO2)[nH]c2c1C(=O)NCC2]

In analogy to example 1 N-(3-chloro-2-methoxyphenyl)-4-[({3-[(4-methylmorpholin-2-yl)methoxy]pyridin-4-yl}methyl)amino]-2-oxo-1,2,5,6-tetrahydropyridine-3-carbothioamide (intermediate 6-15, 74.0 mg, 139 μmol) was used to prepare 24.1 mg (90% purity, 31% yield) of the title compound after heating for 18 hours and purification by preparative HPLC (method 10, gradient: 0.00-0.50 min 15% B, 0.50-6.00 min 15-55% B).

$^1$H-NMR (400 MHz, DMSO-$d_6$): δ [ppm]=1.86-1.95 (t, 1H), 2.00-2.09 (td, 1H), 2.20 (s, 3H), 2.66 (br d, 1H), 2.73-2.81 (br d, 1H), 2.86 (t, 2H), 3.42 (td, 2H), 3.61-3.73 (td, 1H), 3.88 (s, 3H), 3.91-4.02 (m, 2H), 4.16 (dd, 1H), 4.33 (dd, 1H), 6.15 (t, 1H), 6.69 (d, 2H), 7.16 (s, 1H), 7.28 (d, 1H), 7.53 (s, 1H), 8.03 (d, 1H), 8.40 (s, 1H), 11.07 (s, 1H).

LC-MS (method 2): $R_t$=0.97 min; MS (ESIpos): m/z=498 $[M+H]^+$

Example 16

3-(3-chloro-2-methoxyanilino)-2-(3-{[4-methylmorpholin-2-yl]methoxy}pyridin-4-yl)-1,5,6,7-tetrahydro-4H-pyrrolo[3,2-c]pyridin-4-one (stereoisomer 1)

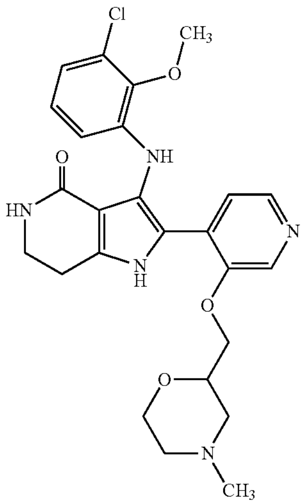 [SMILES: COc1c(Cl)cccc1Nc1c(-c2ccncc2OCC2CN(C)CCO2)[nH]c2c1C(=O)NCC2]

The title compound from example 15 (24.1 mg) was separated into enantiomers by preparative chiral HPLC to give title compound (enantiomer 1, 8 mg, at $R_t$=17.4-21.8, 11% yield) and enantiomer 2 (7 mg, at $R_t$=12.5-14.5 min, see example 17).

Preparative Chiral HPLC Method:

Instrument: PrepCon Labomatic HPLC; Column: Chiralpak IF 5μ, 250×30; eluent A: hexane+0.1 vol % diethylamine; eluent B: ethanol+0.1 vol % diethylamine; isocratic: 50% A+50% B; flow: 40 ml/min; temperature: 25° C.; UV: 280 nm Analytical Chiral HPLC Method:

Instrument: Waters Alliance 2695; Column: Chiralpak IF 3μ, 100×4.6; eluent A: hexane+0.1 vol % diethylamine; eluent B: ethanol; isocratic: 50% A+50% B; flow: 1.4 ml/min; temperature: 25° C.; UV: 280 nm Analytical chiral HPLC: $R_t$=4.55 min.

$^1$H-NMR (400 MHz, DMSO-$d_6$): δ [ppm]=1.232 (1.95), 1.259 (0.49), 1.888 (0.59), 1.914 (1.04), 1.941 (0.65), 2.016 (0.40), 2.037 (0.73), 2.045 (0.70), 2.065 (0.49), 2.206 (9.36), 2.327 (0.42), 2.518 (1.60), 2.523 (1.15), 2.540 (16.00), 2.646 (0.75), 2.670 (0.96), 2.673 (0.98), 2.758 (0.81), 2.787 (0.77), 2.841 (1.13), 2.858 (2.36), 2.876 (1.27), 3.405 (0.89), 3.410 (0.98), 3.422 (1.69), 3.428 (1.67), 3.439 (0.85), 3.445 (0.77), 3.638 (0.41), 3.644 (0.49), 3.666 (0.89), 3.672 (0.89), 3.694 (0.54), 3.700 (0.52), 3.883 (15.90), 3.933 (0.86), 3.952 (0.89), 3.960 (1.15), 3.976 (0.47), 3.983 (0.40), 4.137 (0.82), 4.154 (0.74), 4.163 (1.02), 4.179 (0.84), 4.315 (0.97), 4.324 (1.01), 4.341 (0.80), 4.349 (0.72), 6.139 (1.35), 6.151 (2.23), 6.163 (1.38), 6.681 (4.49), 6.692 (3.40), 6.694 (3.35), 7.163 (1.58), 7.274 (1.81), 7.287 (1.83), 7.533 (3.41), 8.021 (1.20), 8.034 (1.14), 8.402 (1.87), 11.066 (1.70).

Example 17

3-(3-chloro-2-methoxyanilino)-2-(3-{[4-methylmorpholin-2-yl]methoxy}pyridin-4-yl)-1,5,6,7-tetrahydro-4H-pyrrolo[3,2-c]pyridin-4-one (stereoisomer 2)

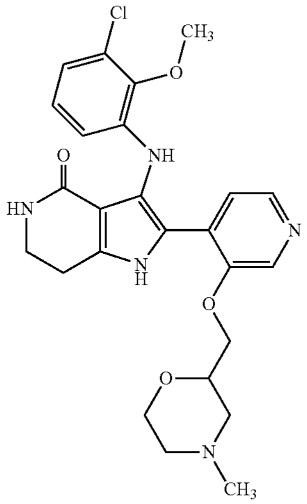 [SMILES: COc1c(Cl)cccc1Nc1c(-c2ccncc2OCC2CN(C)CCO2)[nH]c2c1C(=O)NCC2]

For the preparation of the racemic title compound see example 15. Separation of enantiomers by preparative chiral HPLC (method see example 16) to give 7 mg of the title compound (at $R_t$=12.5-14.5 min).

Analytical chiral HPLC (method see example 16): $R_t$=2.93 min.

Example 18

3-(3-chloro-5-fluoro-2-methoxyanilino)-2-(3-{[4-methylmorpholin-2-yl]methoxy}pyridin-4-yl)-1,5,6,7-tetrahydro-4H-pyrrolo[3,2-c]pyridin-4-one

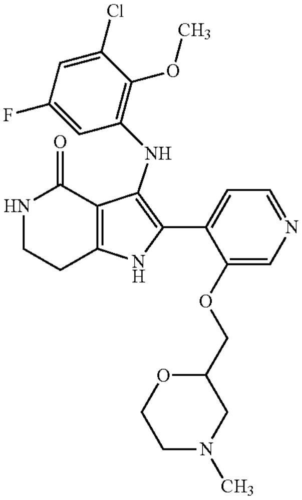 [SMILES: COc1c(Cl)cc(F)cc1Nc1c(-c2ccncc2OCC2CN(C)CCO2)[nH]c2c1C(=O)NCC2]

Using an analogous method as described for example 1 with N-(3-chloro-5-fluoro-2-methoxyphenyl)-4-[({3-[(4-methylmorpholin-2-yl)methoxy]pyridin-4-yl}methyl)amino]-2-oxo-1,2,5,6-tetrahydropyridine-3-carbothioamide (intermediate 6-18, 166 mg, 302 μmol) as the starting material; 13.0 mg (95% purity, 8% yield) of the title compound were prepared after purification by preparative HPLC (method 10, gradient: 0.00-0.50 min 15% B, 0.50-6.00 min 15-55% B).

$^1$H-NMR (400 MHz, DMSO-$d_6$): δ [ppm]=1.88 (t, 1H), 1.93-2.05 (dt, 1H), 2.19 (s, 3H), 2.60-2.66 (d, 1H), 2.70-2.77 (d, 1H), 2.86 (t, 2H), 3.37-3.48 (m, 2H), 3.56-3.68 (m, 1H), 3.83 (s, 3H), 3.90 (br d, 2H), 4.15 (m, 1H), 4.27 (dd, 1H), 5.85 (dd, 1H), 6.56 (dd, 1H), 7.13 (s, 1H), 7.33 (d, 1H), 7.64 (s, 1H), 8.10 (d, 1H), 8.43 (s, 1H), 11.18 (s, 1H).

LC-MS (method 2): $R_t$=1.00 min; MS (ESIpos): m/z=516 $[M+H]^+$

Example 19

3-(3-chloro-5-fluoro-2-methoxyanilino)-2-(3-{[1,4-dioxan-2-yl]methoxy}pyridin-4-yl)-1,5,6,7-tetrahydro-4H-pyrrolo[3,2-c]pyridin-4-one

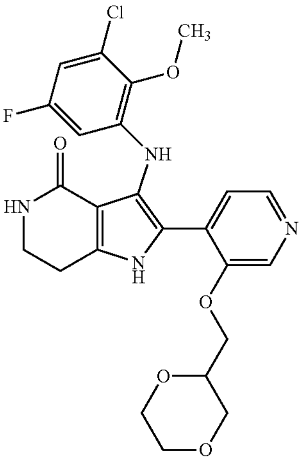 [SMILES: COc1c(Cl)cc(F)cc1Nc1c(-c2ccncc2OCC2COCCO2)[nH]c2c1C(=O)NCC2]

Using an analogous method as described for example 1 with N-(3-chloro-5-fluoro-2-methoxyphenyl)-4-[({3-[(1,4-dioxan-2-yl)methoxy]pyridin-4-yl}methyl)amino]-2-oxo-1,2,5,6-tetrahydropyridine-3-carbothioamide (intermediate 6-19, 160 mg, 298 μmol) as the starting material; 3.90 mg (90% purity, 2% yield) of the title compound were prepared after purification by preparative HPLC (method 10, gradient: 0.00-0.50 min 15% B, 0.50-6.00 min 15-55% B).

$^1$H-NMR (400 MHz, DMSO-$d_6$): δ [ppm]=2.86 (t, 2H), 3.37-3.45 (m, 3H), 3.47-3.61 (m, 1H), 3.62-3.77 (m, 3H), 3.77-3.87 (m, 6H), 3.94-4.01 (m, 1H), 4.07-4.20 (m, 1H), 4.24 (dd, 1H), 5.85 (dd, 1H), 6.56 (dd, 1H), 7.13 (s, 1H), 7.33 (d, 1H), 7.60-7.66 (d, 1H), 8.11 (br d, 1H), 8.42 (s, 1H), 11.19 (s, 1H).

LC-MS (method 2): $R_t$=1.01 min; MS (ESIpos): m/z=503 $[M+H]^+$

Example 20

3-(3-fluoro-2-methoxyanilino)-2-(3-{[(3S)-4-methylmorpholin-3-yl]methoxy}pyridin-4-yl)-1,5,6,7-tetrahydro-4H-pyrrolo[3,2-c]pyridin-4-one

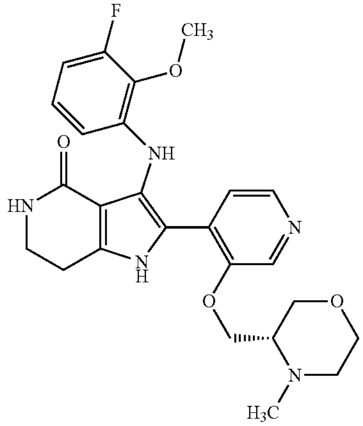

Using an analogous method as described for example 1 with N-(3-fluoro-2-methoxyphenyl)-4-{[(3-{[(3S)-4-methylmorpholin-3-yl]methoxy}pyridin-4-yl)methyl]amino}-2-oxo-1,2,5,6-tetrahydropyridine-3-carbothioamide (intermediate 6-20, 102 mg, 197 μmol) as the starting material; 27.9 mg (90% purity, 26% yield) of the title compound were prepared after purification by preparative HPLC (method 10, gradient: 0.00-0.50 min 10% B, 0.50-6.00 min 10-50% B).

LC-MS (method 6): Rt=0.51 min; MS (ESIpos): m/z=482 $[M+H]^+$ $^1$H-NMR (400 MHz, DMSO-$d_6$) δ [ppm]: 2.274 (13.29), 2.304 (1.76), 2.318 (0.55), 2.404 (0.46), 2.426 (0.88), 2.434 (0.91), 2.449 (0.43), 2.454 (0.88), 2.458 (1.03), 2.463 (1.43), 2.468 (1.37), 2.473 (1.55), 2.518 (5.99), 2.523 (4.32), 2.775 (0.40), 2.798 (0.70), 2.815 (1.49), 2.822 (0.88), 2.832 (0.91), 2.841 (1.16), 2.858 (0.79), 2.908 (1.13), 2.938 (1.00), 3.294 (0.43), 3.406 (0.64), 3.423 (1.46), 3.429 (1.19), 3.438 (1.37), 3.453 (0.58), 3.459 (0.55), 3.546 (1.13), 3.573 (1.76), 3.589 (1.13), 3.594 (1.22), 3.600 (1.28), 3.618 (0.61), 3.816 (0.94), 3.840 (1.83), 3.847 (1.95), 3.868 (1.06), 3.875 (0.97), 3.938 (16.00), 3.951 (2.07), 4.374 (1.67), 4.386 (2.71), 4.414 (0.46), 6.011 (1.89), 6.031 (1.89), 6.514 (1.03), 6.518 (0.97), 6.535 (1.28), 6.539 (1.34), 6.541 (1.19), 6.545 (0.94), 6.562 (1.19), 6.565 (1.06), 6.655 (0.97), 6.670 (1.03), 6.675 (1.70), 6.691 (1.55), 6.696 (0.82), 6.711 (0.67), 7.176 (2.07), 7.310 (3.71), 7.323 (3.68), 7.514 (0.43), 7.527 (0.52), 7.533 (0.58), 7.601 (4.56), 7.977 (5.29), 7.990 (4.50), 8.067 (0.61), 8.080 (0.55), 8.358 (6.27), 8.439 (0.73), 12.011 (2.13).

Example 21

3-(3-chloro-2-methoxyanilino)-2-(3-{[(3S)-4-methylmorpholin-3-yl]methoxy}pyridin-4-yl)-1,5,6,7-tetrahydro-4H-pyrrolo[3,2-c]pyridin-4-one

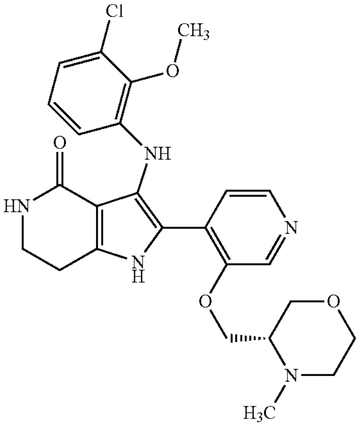 [SMILES: COc1c(Cl)cccc1Nc1c(-c2ccncc2OC[C@@H]2COCCN2C)[nH]c2c1C(=O)NCC2]

Using an analogous method as described for example 1 with N-(3-chloro-2-methoxyphenyl)-4-{[(3-{[(3S)-4-methylmorpholin-3-yl]methoxy}pyridin-4-yl)methyl]amino}-2-oxo-1,2,5,6-tetrahydropyridine-3-carbothioamide (intermediate 6-21, 99.5 mg, 187 μmol) as the starting material; 4.70 mg (98% purity, 5% yield) of the title compound were prepared after purification by preparative HPLC (method 10, gradient: 0.00-0.50 min 10% B, 0.50-6.00 min 10-50% B).

$^1$H-NMR (400 MHz, DMSO-$d_6$): δ [ppm]=1.232 (0.45), 2.276 (9.36), 2.426 (0.63), 2.434 (0.67), 2.456 (0.51), 2.464 (0.76), 2.472 (0.79), 2.518 (1.95), 2.523 (1.26), 2.539 (9.95), 2.806 (0.54), 2.823 (1.37), 2.841 (1.19), 2.860 (0.60), 2.910 (0.85), 2.940 (0.76), 3.408 (0.49), 3.425 (1.12), 3.431 (0.95), 3.441 (1.04), 3.454 (0.49), 3.460 (0.44), 3.544 (0.71), 3.572 (1.31), 3.588 (0.84), 3.594 (0.92), 3.599 (0.96), 3.617 (0.47), 3.817 (0.72), 3.841 (1.23), 3.847 (1.34), 3.868 (0.69), 3.875 (0.63), 3.912 (16.00), 3.924 (0.49), 4.376 (1.24), 4.387 (2.11), 6.151 (1.35), 6.162 (2.22), 6.175 (1.39), 6.718 (3.50), 6.720 (3.93), 6.731 (4.23), 7.179 (1.54), 7.299 (2.18), 7.312 (2.21), 7.614 (3.34), 7.983 (1.76), 7.995 (1.68), 8.362 (2.68), 12.027 (1.61).

LC-MS (method 6): Rt=0.54 min; MS (ESIpos): m/z=498 $[M+H]^+$

Example 22

2-(3-{[(2S)-4-(2,2-difluoroethyl)morpholin-2-yl]methoxy}pyridin-4-yl)-3-(3-fluoro-2-methoxyanilino)-1,5,6,7-tetrahydro-4H-pyrrolo[3,2-c]pyridin-4-one

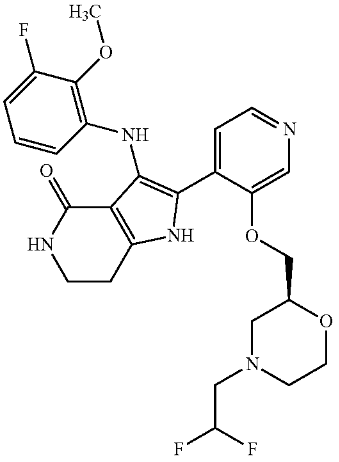 [SMILES: COc1c(F)cccc1Nc1c(-c2ccncc2OC[C@@H]2CN(CC(F)F)CCO2)[nH]c2c1C(=O)NCC2]

3-(3-Fluoro-2-methoxyanilino)-2-(3-{[(2S)-morpholin-2-yl]methoxy}pyridin-4-yl)-1,5,6,7-tetrahydro-4H-pyrrolo[3,2-c]pyridin-4-one (intermediate 22, 50.0 mg, 107 μmol) was solubilized in DMF (1.6 ml), triethylamine (89 μl, 640 μmol) and 2,2-difluoroethyl trifluoromethanesulfonate (64 μl, 480 μmol) were added and the mixture was stirred for 1 h at RT. The mixture was purified by preparative HPLC (method 10, gradient: 0.00-0.50 min 15% B, 0.50-6.00 min 15-55% B) to give 11.3 mg (90% purity, 18% yield) of the target compound.

$^1$H-NMR (400 MHz, DMSO-$d_6$): δ [ppm]=2.24 (t, 1H), 2.34-2.40 (dd, 1H), 2.78 (m, 1H), 2.78-2.81 (m, 1H), 2.83 (m, 1H), 2.85-2.90 (t, 2H), 2.90-2.97 (d, 1H), 3.38-3.47 (m, 2H), 3.68 (dt, 1H), 3.89-3.92 (s, 3H), 3.92-4.03 (m, 2H), 4.17 (dd, 1H), 4.29 (dd, 1H), 5.97-6.02 (d, 1H), 6.02-6.34 (tt, 1H), 6.47-6.54 (m, 1H), 6.64 (td, 1H), 7.16 (s, 1H), 7.29 (d, 1H), 7.54 (s, 1H), 8.02 (d, 1H), 8.40 (s, 1H), 11.03 (s, 1H).

LC-MS (method 2): $R_t$=1.04 min; MS (ESIpos): m/z=532 $[M+H]^+$

Example 23

3-(3-fluoro-2-methoxyanilino)-2-(3-{[(2S)-4-(2,2,2-trifluoroethyl)morpholin-2-yl]methoxy}pyridin-4-yl)-1,5,6,7-tetrahydro-4H-pyrrolo[3,2-c]pyridin-4-one

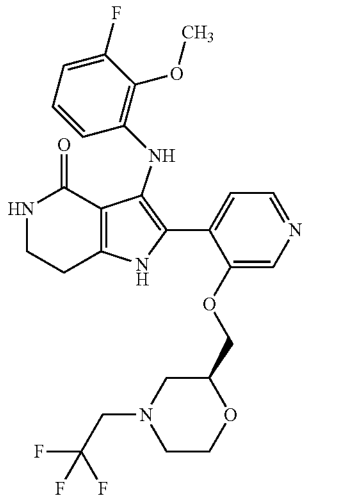 [SMILES: COc1c(F)cccc1Nc1c(-c2ccncc2OC[C@@H]2CN(CC(F)(F)F)CCO2)[nH]c2c1C(=O)NCC2]

Using an analogous method as described for example 22 with 3-(3-fluoro-2-methoxyanilino)-2-(3-{[(2S)-morpholin-2-yl]methoxy}pyridin-4-yl)-1,5,6,7-tetrahydro-4H-pyrrolo[3,2-c]pyridin-4-one (intermediate 22, 35.0 mg, 74.9 μmol) and 2,2,2-trifluoroethyl trifluoromethanesulfonate (CAS 6226-25-1, 16 μl, 110 μmol) as the starting materials; 11.9 mg (95% purity, 27% yield) of the title compound were prepared after preparative HPLC (method 10, gradient: 0.00-0.50 min 30% B, 0.50-6.00 min 30-70% B).

$^1$H-NMR (400 MHz, DMSO-$d_6$): δ [ppm]=1.231 (0.47), 1.264 (0.47), 2.326 (2.22), 2.331 (1.58), 2.359 (0.93), 2.387 (1.69), 2.414 (1.15), 2.518 (7.61), 2.522 (5.31), 2.668 (2.30), 2.673 (1.58), 2.805 (1.18), 2.836 (2.55), 2.853 (3.44), 2.870 (1.79), 2.936 (1.26), 2.964 (1.11), 3.196 (0.54), 3.205 (0.61), 3.221 (1.54), 3.230 (1.58), 3.247 (1.51), 3.255 (1.47), 3.271 (0.61), 3.281 (0.54), 3.400 (1.26), 3.406 (1.33), 3.417 (2.37), 3.423 (2.26), 3.434 (1.15), 3.440 (1.08), 3.654 (0.54), 3.660 (0.65), 3.674 (0.72), 3.683 (1.18), 3.688 (1.15), 3.711 (0.68), 3.912 (16.00), 3.934 (1.11), 3.966 (1.11), 3.983 (0.72), 3.999 (0.75), 4.008 (0.65), 4.157 (1.04), 4.174 (1.00), 4.183 (1.51), 4.199 (1.22), 4.277 (1.40), 4.286 (1.36), 4.303 (1.04), 4.312 (0.86), 5.989 (1.94), 6.010 (1.97), 6.472 (0.86), 6.475 (0.86), 6.493 (1.26), 6.497 (1.26), 6.502 (0.93), 6.520 (1.18), 6.523 (1.04), 6.611 (0.90), 6.626 (1.04), 6.632 (1.54), 6.647 (1.51), 6.652 (0.75), 6.668 (0.65), 7.161 (2.22), 7.278 (3.52), 7.291 (3.55), 7.535 (4.77), 8.018 (4.38), 8.030 (4.02), 8.391 (6.17), 11.018 (2.48).

LC-MS (method 2): $R_t$=1.09 min; MS (ESIpos): m/z=550 $[M+H]^+$

Example 24

3-(3-chloro-2-methoxyanilino)-2-{3-[2-(4-dioxan-2-yl)ethoxy]pyridin-4-yl}-1,5,6,7-tetrahydro-4H-pyrrolo[3,2-c]pyridin-4-one

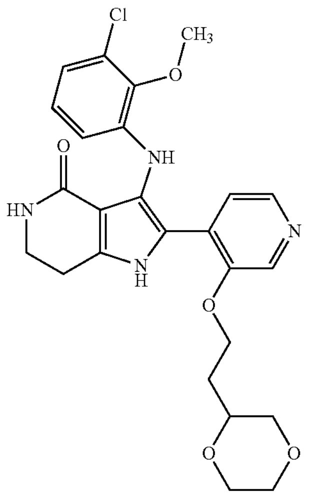 [SMILES: COc1c(Cl)cccc1Nc1c(-c2ccncc2OCCC2COCCO2)[nH]c2c1C(=O)NCC2]

Using an analogous method as described for example 1 with N-(3-chloro-2-methoxyphenyl)-4-[({3-[2-(1,4-dioxan-2-yl)ethoxy]pyridin-4-yl}methyl)amino]-2-oxo-1,2,5,6-tetrahydropyridine-3-carbothioamide (intermediate 6-24, 105 mg, 197 μmol) as the starting material; 43.5 mg (95% purity, 42% yield) of the title compound were prepared after preparative HPLC (method 7).

$^1$H-NMR (400 MHz, DMSO-$d_6$): δ [ppm]=1.817 (0.39), 1.834 (1.18), 1.849 (1.57), 1.861 (1.08), 1.876 (0.49), 2.518 (3.04), 2.522 (2.06), 2.673 (0.59), 2.833 (0.88), 2.846 (1.87), 2.863 (0.98), 3.204 (0.88), 3.231 (1.47), 3.260 (1.08), 3.312 (1.28), 3.396 (1.67), 3.408 (2.16), 3.413 (2.16), 3.426 (1.28), 3.456 (1.18), 3.462 (1.08), 3.484 (0.98), 3.490 (0.98), 3.521 (0.79), 3.525 (0.88), 3.549 (1.08), 3.554 (1.18), 3.582 (0.69), 3.625 (1.28), 3.648 (1.37), 3.668 (2.45), 3.678 (0.98), 3.693 (1.37), 3.716 (1.28), 3.745 (0.98), 3.858 (16.00), 4.226 (1.37), 4.241 (2.94), 4.257 (1.37), 6.103 (1.47), 6.115 (2.06), 6.127 (1.47), 6.640 (5.60), 6.650 (3.63), 7.108 (1.77), 7.287 (2.65), 7.299 (2.75), 7.458 (3.93), 8.020 (3.04), 8.033 (2.85), 8.350 (4.32), 11.191 (1.96).

LC-MS (method 6): Rt=0.68 min; MS (ESIpos): m/z=499 $[M+H]^+$

Example 25

3-(3-chloro-2-methoxyanilino)-2-{3-[2-(4-dioxan-2-yl)ethoxy]pyridin-4-yl}-1,5,6,7-tetrahydro-4H-pyrrolo[3,2-c]pyridin-4-one (stereoisomer 1)

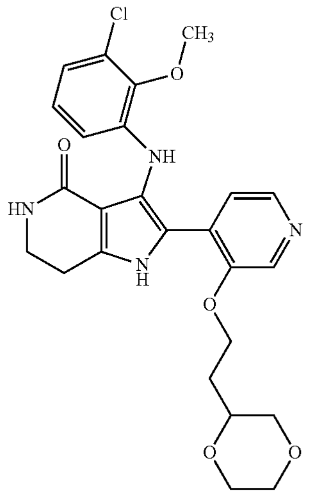 [SMILES: COc1c(Cl)cccc1Nc1c(-c2ccncc2OCCC2COCCO2)[nH]c2c1C(=O)NCC2]

The title compound from example 24 (40 mg) was separated into enantiomers by preparative chiral HPLC to give title compound (enantiomer 1, 18.0 mg, at $R_t$=18.8-21.3 min, 96% purity) and enantiomer 2 (17 mg, at $R_t$=21.7-24.5 min, see example 26).

Preparative Chiral HPLC Method:

Instrument: PrepCon Labomatic HPLC; Column: YMC Cellulose SB 5µ, 250x30; eluent A: methyl tert-butyl ether+0.1 vol % diethylamine; eluent B: acetonitrile+0.1 vol % diethylamine; gradient: 0-20 min 2-60% B; flow: 40 ml/min; temperature: 25° C.; UV: 280 nm Analytical Chiral HPLC Method:

Instrument: Waters Alliance 2695; Column: YMC Cellulose SB 3µ, 100x4.6; eluent A: methyl tert-butyl ether+0.1 vol % diethylamine; eluent B: acetonitrile; gradient: 0-7 min 2-60% B; flow: 1.4 ml/min; temperature: 25° C.; UV: 280 nm Analytical chiral HPLC: $R_t$=4.94 min.

Optical rotation: $[\alpha]_D$=−1.6°+/−1.63° (c=2.8 mg/ml in methanol)

$^1$H-NMR (400 MHz, DMSO-$d_6$) δ [ppm]=1.835 (1.01), 1.851 (1.31), 1.862 (0.93), 1.877 (0.41), 2.518 (1.52), 2.522 (0.99), 2.834 (0.77), 2.846 (1.61), 2.852 (1.47), 2.864 (0.82), 2.869 (0.80), 3.205 (0.76), 3.231 (1.30), 3.235 (1.27), 3.261 (0.85), 3.391 (0.83), 3.397 (0.91), 3.408 (1.57), 3.415 (1.62), 3.430 (0.98), 3.457 (0.99), 3.463 (1.01), 3.485 (0.84), 3.491 (0.79), 3.522 (0.72), 3.527 (0.76), 3.551 (0.96), 3.556 (1.07), 3.584 (0.57), 3.624 (1.00), 3.649 (1.11), 3.654 (1.11), 3.671 (1.96), 3.680 (0.81), 3.687 (0.53), 3.695 (1.23), 3.718 (1.09), 3.723 (1.01), 3.747 (0.79), 3.859 (16.00), 4.227 (1.22), 4.242 (2.58), 4.258 (1.21), 6.105 (1.40), 6.118 (1.81), 6.129 (1.46), 6.641 (5.45), 6.651 (3.33), 6.654 (3.12), 7.110 (1.60), 7.288 (2.35), 7.300 (2.36), 7.306 (0.49), 7.462 (3.57), 8.023 (2.38), 8.035 (2.27), 8.353 (3.43), 11.186 (1.77).

Example 26

3-(3-chloro-2-methoxyanilino)-2-{3-[2-(4-dioxan-2-yl)ethoxy]pyridin-4-yl}-1,5,6,7-tetrahydro-4H-pyrrolo[3,2-c]pyridin-4-one (Stereoisomer 2)

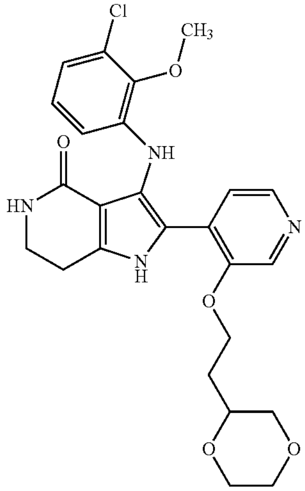 [SMILES: COc1c(Cl)cccc1Nc1c(-c2ccncc2OCCC2COCCO2)[nH]c2c1C(=O)NCC2]

For the preparation of the racemic title compound see example 24. Separation of enantiomers by preparative chiral HPLC (method see example 25) to give 25 mg of the title compound (at $R_t$=21.7-24.5 min, 19% yield).

Analytical chiral HPLC (method see example 25): $R_t$=5.49 min.

Optical rotation: $[\alpha]_D$=2.5°+/−1.93° (c=2.7 mg/ml in methanol)

Example 27

3-(3-chloro-5-fluoro-2-methoxyanilino)-2-(3-{[(2S)-4-methylmorpholin-2-yl]methoxy}pyridin-4-yl)-1,5,6,7-tetrahydro-4H-pyrrolo[3,2-c]pyridin-4-one

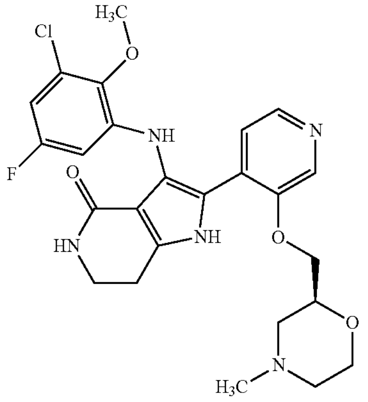 [SMILES: COc1c(Cl)cc(F)cc1Nc1c(-c2ccncc2OC[C@@H]2CN(C)CCO2)[nH]c2c1C(=O)NCC2]

3-(3-Chloro-5-fluoro-2-methoxyanilino)-2-(3-{[(2S)-morpholin-2-yl]methoxy}pyridin-4-yl)-1,5,6,7-tetrahydro-4H-pyrrolo[3,2-c]pyridin-4-one (intermediate 27, 24.0 mg, 47.8 µmol) was solubilized in methanol (650 µl), formaldehyde (7.2 µl, 37% purity, 96 µmol) and acetic acid (2.7 µl, 48 μmol) were added and the mixture was stirred for 15 min at RT. Sodium triacetoxyborohydride (15.2 mg, 71.7 μmol) was added and the mixture was stirred for 1 h at RT. The mixture was diluted with methanol, filtered through a SCX column and washed with methanol and ammonia (7 M in methanol). The filtrate was evaporated and purified by preparative HPLC (method 9, gradient: 0.00-0.50 min 15% B, 0.50-6.00 min 15-55% B) to yield 17.3 mg (95% purity, 61% yield) of the title compound as its formate salt.

LC-MS (method 2): Rt=1.01 min; MS (ESIpos): m/z=516 $[M+H]^+$ $^1$H-NMR (400 MHz, DMSO-$d_6$) δ [ppm]: 2.189 (13.49), 2.330 (5.06), 2.729 (5.60), 2.861 (7.86), 3.348 (16.00), 3.419 (15.57), 3.624 (4.81), 3.830 (14.46), 3.908 (6.49), 7.633 (4.30), 8.098 (4.59), 8.146 (8.39).

3-(3-chloro-5-fluoro-2-methoxy-anilino)-2-[3-[[(2S)-4-methylmorpholin-4-ium-2-yl]methoxy]-4-pyridyl]-1,5,6,7-tetrahydropyrrolo[3,2-c]pyridin-4-one; formate were solubilized in DCM and washed saturated aqueous $NaHCO_3$ and brine to yield 9.00 mg (90% purity, 33% yield) of the target compound as its free base.

$^1$H-NMR (400 MHz, DMSO-$d_6$): δ [ppm]=1.79-1.96 (t, 1H), 1.97-2.05 (td, 1H), 2.19 (s, 3H), 2.63 (br d, 1H), 2.71-2.82 (br d, 1H), 2.86 (t, 2H), 3.43 (td, 2H), 3.58-3.67 (m, 1H), 3.83 (s, 3H), 3.87-4.01 (m, 2H), 4.14 (dd, 1H), 4.29 (dd, 1H), 5.85 (dd, 1H), 6.56 (dd, 1H), 7.13 (s, 1H), 7.33 (d, 1H), 7.64 (d, 1H), 8.07-8.12 (d, 1H), 8.43 (s, 1H), 11.18 (s, 1H).

Example 28

3-(3-chloro-5-fluoro-2-methoxyanilino)-2-(3-{[(2S)-4-(2,2,2-trifluoroethyl)morpholin-2-yl]methoxy}pyridin-4-yl)-1,5,6,7-tetrahydro-4H-pyrrolo[3,2-c]pyridin-4-one

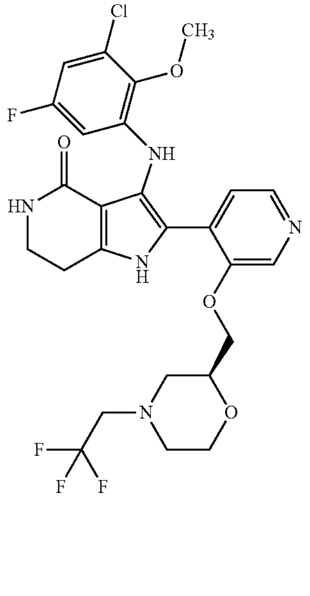

Using an analogous method as described for example 22 with 3-(3-chloro-5-fluoro-2-methoxyanilino)-2-(3-{[(2S)-morpholin-2-yl]methoxy}pyridin-4-yl)-1,5,6,7-tetrahydro-4H-pyrrolo[3,2-c]pyridin-4-one (intermediate 27, 25.0 mg, 49.8 μmol) and 2,2,2-trifluoroethyl trifluoromethanesulfonate (CAS 6226-25-1, 11 μl, 75 μmol) as the starting materials; 15.1 mg (95% purity, 49% yield) of the title compound were prepared after preparative HPLC (method 10, gradient: 0.00-0.50 min 30% B, 0.50-6.00 min 30-70% B).

$^1$H-NMR (400 MHz, DMSO-$d_6$): δ [ppm]=2.35 (t, 1H), 2.77-2.95 (m, 4H), 3.21 (dd, 2H), 3.42 (td, 2H), 3.60-3.69 (m, 1H), 3.83 (s, 3H), 3.88-4.01 (m, 2H), 4.14-4.28 (m, 2H), 5.84 (dd, 1H), 6.56 (dd, 1H), 7.13 (s, 1H), 7.32 (d, 1H), 7.62-7.66 (m, 1H), 8.10 (d, 1H), 8.43 (s, 1H), 11.16 (s, 1H).

LC-MS (method 2): $R_t$=1.19 min; MS (ESIpos): m/z=584 $[M+H]^+$

Example 29

3-(3-chloro-2-ethylanilino)-2-{3-[(4-methylmorpholin-2-yl)methoxy]pyridin-4-yl}-1,5,6,7-tetrahydro-4H-pyrrolo[3,2-c]pyridin-4-one

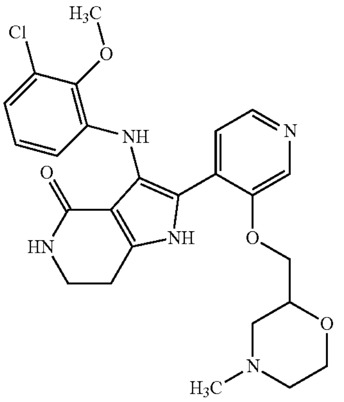 [SMILES: COc1c(Cl)cccc1Nc1c(-c2ccncc2OCC2CN(C)CCO2)[nH]c2c1C(=O)NCC2]

Using an analogous method as described for example 1 with N-(3-chloro-2-ethylphenyl)-4-[({3-[(4-methylmorpholin-2-yl)methoxy]pyridin-4-yl}methyl)amino]-2-oxo-1,2,5,6-tetrahydropyridine-3-carbothioamide (intermediate 6-29, 300 mg, 566 μmol) as the starting material; 3.00 mg (85% purity, 1% yield) of the title compound were prepared after preparative HPLC (method 10, gradient: 0.00-0.50 min 30% B, 0.50-6.00 min 30-70% B).

$^1$H-NMR (400 MHz, DMSO-$d_6$): δ [ppm]=0.851 (0.47), 1.210 (0.41), 1.230 (2.24), 1.352 (0.41), 2.206 (1.49), 2.331 (2.92), 2.336 (1.36), 2.518 (16.00), 2.522 (10.31), 2.539 (1.02), 2.673 (3.05), 2.678 (1.42), 2.864 (0.41), 6.728 (0.41), 6.735 (0.47), 7.188 (0.47), 7.201 (0.47), 7.962 (0.54), 7.975 (0.47), 8.365 (0.68).

LC-MS (method 2): $R_t$=1.07 min; MS (ESIpos): m/z=496 $[M+H]^+$

Example 30

3-(3-chloro-2-methoxyanilino)-2-{3-[(5,5-dimethyl-1,4-dioxan-2-yl)methoxy]pyridin-4-yl}-1,5,6,7-tetrahydro-4H-pyrrolo[3,2-c]pyridin-4-one

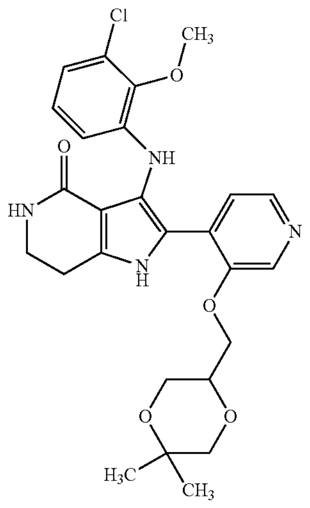 [SMILES: COc1c(Cl)cccc1Nc1c(-c2ccncc2OCC2COC(C)(C)CO2)[nH]c2c1C(=O)NCC2]

Using an analogous method as described for example 1 with N-(3-chloro-2-methoxyphenyl)-4-[({3-[(5,5-dimethyl-1,4-dioxan-2-yl)methoxy]pyridin-4-yl}methyl)amino]-2-oxo-1,2,5,6-tetrahydropyridine-3-carbothioamide (intermediate 6-30, 55.0 mg, 101 μmol) as the starting material; 28.00 mg (98% purity, 53% yield) of the title compound were prepared after purification by preparative HPLC (method 10, gradient: 0.00-0.50 min 30% B, 0.50-6.00 min 30-70% B).

$^1$H-NMR (400 MHz, DMSO-$d_6$): δ [ppm]=1.066 (9.57), 1.234 (8.81), 2.074 (0.42), 2.326 (1.06), 2.331 (0.74), 2.518 (3.90), 2.522 (2.65), 2.668 (1.04), 2.673 (0.76), 2.819 (1.08), 2.837 (2.21), 2.853 (1.18), 3.398 (1.96), 3.409 (1.62), 3.416 (1.61), 3.427 (2.05), 3.580 (0.57), 3.588 (0.65), 3.609 (1.17), 3.618 (1.13), 3.629 (1.85), 3.654 (1.43), 3.657 (1.70), 3.679 (1.32), 3.709 (0.74), 3.868 (16.00), 3.894 (0.49), 3.902 (0.53), 3.910 (0.64), 3.918 (0.58), 3.927 (0.42), 4.155 (0.76), 4.171 (0.72), 4.181 (1.01), 4.198 (0.88), 4.295 (0.97), 4.304 (0.99), 4.322 (0.76), 4.330 (0.67), 6.143 (1.40), 6.155 (1.71), 6.167 (1.40), 6.653 (0.46), 6.663 (5.26), 6.673 (3.14), 6.676 (2.88), 7.138 (1.48), 7.270 (2.51), 7.283 (2.51), 7.475 (3.39), 8.033 (3.36), 8.045 (2.98), 8.404 (4.26), 11.073 (1.66).

LC-MS (method 6): Rt=0.80 min; MS (ESIpos): m/z=513 $[M+H]^+$

Example 31

3-(3-chloro-2-methoxyanilino)-2-{3-[(5,5-dimethyl-1,4-dioxan-2-yl)methoxy]pyridin-4-yl}-1,5,6,7-tetrahydro-4H-pyrrolo[3,2-c]pyridin-4-one (Stereoisomer 1)

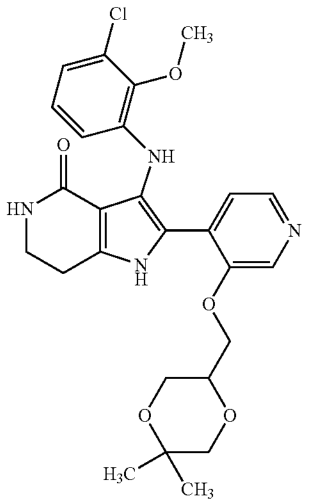 [SMILES: COc1c(Cl)cccc1Nc1c(-c2ccncc2OCC2COC(C)(C)CO2)[nH]c2c1C(=O)NCC2]

The title compound from example 30 (26.3 mg) was separated into enantiomers by preparative chiral HPLC to give title compound (enantiomer 1, 11.00 mg, at Rt=10.7-13.4 min) and enantiomer 2 (10 mg, at $R_t$=14.0-19.9 min, see example 32).

Preparative Chiral HPLC Method:

Instrument: PrepCon Labomatic HPLC; Column: Chiralcel OD-H 5μ, 250×20; eluent A: hexane+0.1 vol % diethylamine; eluent B: ethanol+0.1 vol % diethylamine; isocratic: 70% A+30% B; flow: 20 ml/min; temperature: 25° C.; UV: 280 nm Analytical Chiral HPLC Method:

Instrument: Waters Alliance 2695; Column: Chiralcel OD-H 5μ, 100×4.6; eluent A: hexane+0.1 vol % diethylamine; eluent B: ethanol; isocratic: 70% A+30% B; flow: 1.4 ml/min; temperature: 25° C.; UV: 280 nm Analytical chiral HPLC: $R_t$=6.72 min.

Example 32

3-(3-chloro-2-methoxyanilino)-2-{3-[(5,5-dimethyl-1,4-dioxan-2-yl)methoxy]pyridin-4-yl}-1,5,6,7-tetrahydro-4H-pyrrolo[3,2-c]pyridin-4-one (Stereoisomer 2)

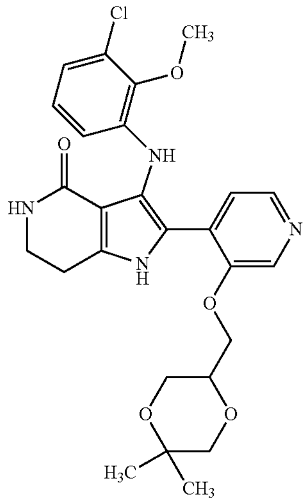 [SMILES: COc1c(Cl)cccc1Nc1c(-c2ccncc2OCC2COC(C)(C)CO2)[nH]c2c1C(=O)NCC2]

For the preparation of the racemic title compound see example 30. Separation of enantiomers by preparative chiral HPLC (method see example 31) to give 10 mg of the title compound (at $R_t$=14.0-19.9 min).

Analytical chiral HPLC (method see example 31): $R_t$=10.04 min.

Example 33

2-(3-{[5,5-dimethyl-1,4-dioxan-2-yl]methoxy}pyridin-4-yl)-3-(3-fluoro-2-methoxyanilino)-1,5,6,7-tetrahydro-4H-pyrrolo[3,2-c]pyridin-4-one

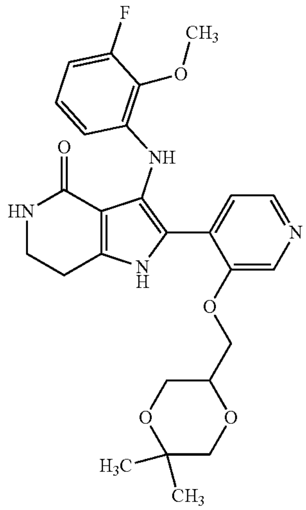 [SMILES: COc1c(F)cccc1Nc1c(-c2ccncc2OCC2COC(C)(C)CO2)[nH]c2c1C(=O)NCC2]

Using an analogous method as described for example 1; 4-{[(3-{[5,5-dimethyl-1,4-dioxan-2-yl]methoxy}pyridin-4-yl)methyl]amino}-N-(3-fluoro-2-methoxyphenyl)-2-oxo-1,2,5,6-tetrahydropyridine-3-carbothioamide (intermediate 6-33, 125 mg, 236 μmol) as the starting material, 15.00 mg (80% purity, 10% yield) of the title compound were prepared after preparative HPLC (method 7).

$^1$H-NMR (400 MHz, DMSO-$d_6$) δ [ppm]: 1.068 (15.53), 1.236 (15.37), 2.517 (2.98), 2.522 (2.00), 2.817 (1.52), 2.834 (3.10), 2.851 (1.65), 2.903 (0.47), 2.921 (0.89), 2.936 (0.48), 3.402 (2.87), 3.408 (2.55), 3.415 (2.29), 3.431 (3.39), 3.580 (0.97), 3.588 (1.12), 3.609 (2.52), 3.618 (2.17), 3.633 (3.03), 3.651 (2.10), 3.661 (2.34), 3.677 (2.32), 3.706 (1.26), 3.900 (16.00), 3.917 (5.39), 3.933 (0.80), 3.942 (0.71), 4.147 (1.18), 4.163 (1.12), 4.173 (1.56), 4.189 (1.34), 4.294 (1.63), 4.302 (1.37), 4.320 (1.26), 4.329 (0.93), 4.769 (0.55), 4.780 (0.55), 4.787 (0.58), 4.797 (0.52), 5.696 (0.85), 5.759 (1.92), 5.985 (0.55), 6.000 (1.88), 6.020 (1.84), 6.455 (0.97), 6.476 (1.43), 6.479 (1.49), 6.503 (1.30), 6.597 (0.86), 6.612 (1.11), 6.618 (1.49), 6.625 (0.60), 6.633 (1.47), 6.638 (0.71), 6.653 (0.62), 7.141 (2.11), 7.277 (3.15), 7.289 (3.21), 7.297 (1.00), 7.479 (4.43), 7.531 (1.26), 8.030 (3.74), 8.042 (3.54), 8.399 (6.35), 11.053 (2.30), 11.085 (0.73).

LC-MS (method 6): Rt=0.71 min; MS (ESipos): m/z=497 $[M+H]^+$ 2-(3-{[5,5-dimethyl-1,4-dioxan-2-yl]methoxy}pyridin-4-yl)-3-(3-fluoro-2-methoxyanilino)-1,5,6,7-tetrahydro-4H-pyrrolo[3,2-c]pyridin-4-one (Stereoisomer 1)

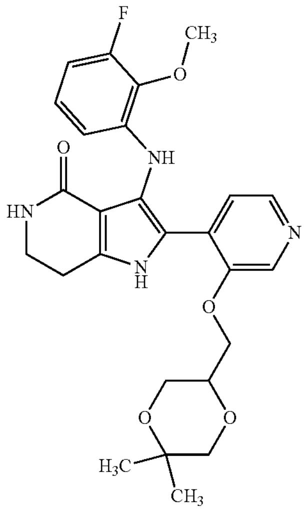 [SMILES: COc1c(F)cccc1Nc1c(-c2ccncc2OCC2COC(C)(C)CO2)[nH]c2c1C(=O)NCC2]

The title compound from example 33 (15.0 mg) was separated into enantiomers by preparative chiral HPLC to give title compound (enantiomer 1, 5.00 mg, at Rt=10.9-13.1 min, 32% yield) and enantiomer 2 (4 mg, at $R_t$=13.5-18.3 min, see example 34).

Preparative Chiral HPLC Method:

Instrument: PrepCon Labomatic HPLC; Column: Chiralcel OD-H 5μ, 250×20; eluent A: hexane+0.1 vol % diethylamine; eluent B: ethanol; isocratic: 70% A+30% B; flow: 20 ml/min; temperature: 25° C.; UV: 280 nm Analytical Chiral HPLC Method:

Instrument: Waters Alliance 2695; Column: Chiralcel OD-H 5μ, 100×4.6; eluent A: hexane+0.1 vol % diethylamine; eluent B: ethanol; isocratic: 70% A+30% B; flow: 1.4 ml/min; temperature: 25° C.; UV: 280 nm Analytical chiral HPLC: $R_t$=6.58 min.

Optical rotation: $[\alpha]_D$=2.6°+/−1.66° (c=2.3 mg/ml in methanol)

Example 34

2-(3-{[5,5-dimethyl-1,4-dioxan-2-yl]methoxy}pyridin-4-yl)-3-(3-fluoro-2-methoxyanilino)-1,5,6,7-tetrahydro-4H-pyrrolo[3,2-c]pyridin-4-one (stereoisomer 2)

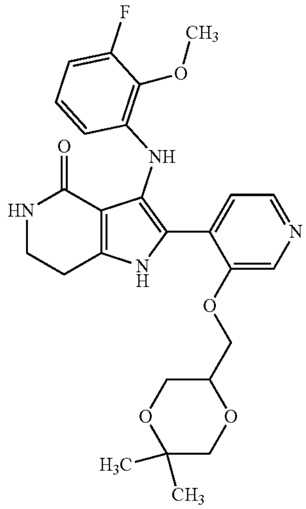 [SMILES: COc1c(F)cccc1Nc1c(-c2ccncc2OCC2COC(C)(C)CO2)[nH]c2c1C(=O)NCC2]

For the preparation of the racemic title compound see example 33. Separation of enantiomers by preparative chiral HPLC (method see example 33) to give 4 mg of the title compound (at $R_t$=13.5-18.3 min, 24% yield).

Analytical chiral HPLC (method see example 33): $R_t$=9.21 min. $^1$H-NMR (400 MHz, DMSO-$d_6$) δ [ppm]: 1.046 (0.67), 1.068 (13.52), 1.108 (0.86), 1.185 (0.55), 1.236 (13.07), 1.259 (0.64), 2.084 (0.44), 2.331 (0.49), 2.518 (2.88), 2.523 (1.93), 2.673 (0.47), 2.817 (1.52), 2.834 (3.11), 2.851 (1.67), 3.403 (2.57), 3.409 (2.57), 3.416 (2.39), 3.431 (2.89), 3.581 (0.83), 3.589 (0.95), 3.611 (1.68), 3.618 (1.66), 3.633 (2.61), 3.652 (1.72), 3.661 (2.23), 3.678 (1.86), 3.707 (1.00), 3.901 (16.00), 3.917 (1.07), 3.926 (0.91), 3.934 (0.65), 3.943 (0.58), 4.148 (1.01), 4.165 (0.96), 4.174 (1.36), 4.190 (1.18), 4.294 (1.36), 4.303 (1.36), 4.320 (1.03), 4.329 (0.91), 6.000 (1.83), 6.021 (1.91), 6.455 (0.83), 6.459 (0.87), 6.476 (1.19), 6.480 (1.27), 6.486 (0.94), 6.503 (1.10), 6.506 (1.01), 6.597 (0.86), 6.612 (1.01), 6.618 (1.47), 6.633 (1.44), 6.638 (0.75), 6.654 (0.61), 7.141 (2.15), 7.277 (2.70), 7.290 (2.68), 7.479 (4.53), 8.030 (2.67), 8.043 (2.48), 8.400 (4.07), 11.054 (2.33).

Example 35

2-(3-{2-[1,4-dioxan-2-yl]ethoxy}pyridin-4-yl)-3-(3-fluoro-2-methoxyanilino)-1,5,6,7-tetrahydro-4H-pyrrolo[3,2-c]pyridin-4-one (stereoisomer 1)

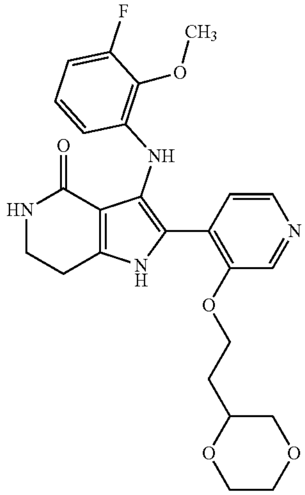 [SMILES: COc1c(F)cccc1Nc1c(-c2ccncc2OCCC2COCCO2)[nH]c2c1C(=O)NCC2]

Using an analogous method as described for example 1 with 4-{[(3-{2-[1,4-dioxan-2-yl]ethoxy}pyridin-4-yl)methyl]amino}-N-(3-fluoro-2-methoxyphenyl)-2-oxo-1,2,5,6-tetrahydropyridine-3-carbothioamide (intermediate 6-35, 130 mg, 252 μmol) as the starting material, 30.0 mg (90% purity, 22% yield) of the racemic title compound were prepared after preparative HPLC (method 7).

$^1$H-NMR (400 MHz, DMSO-$d_6$): δ [ppm]=1.229 (0.48), 1.827 (0.71), 1.843 (1.74), 1.859 (2.06), 1.869 (1.50), 1.885 (0.63), 2.331 (0.40), 2.517 (2.30), 2.522 (1.50), 2.539 (4.51), 2.669 (0.55), 2.673 (0.48), 2.831 (1.19), 2.842 (2.22), 2.848 (2.06), 2.858 (1.19), 2.865 (1.11), 3.162 (1.27), 3.174 (0.71), 3.207 (1.35), 3.233 (2.14), 3.236 (2.14), 3.262 (1.58), 3.406 (4.44), 3.412 (3.88), 3.428 (2.22), 3.456 (1.90), 3.462 (1.82), 3.484 (1.50), 3.490 (1.50), 3.522 (1.27), 3.527 (1.35), 3.550 (1.66), 3.556 (1.90), 3.578 (0.95), 3.583 (1.27), 3.624 (2.22), 3.651 (2.14), 3.671 (3.25), 3.681 (1.50), 3.695 (2.22), 3.700 (1.98), 3.716 (2.06), 3.721 (1.98), 3.728 (1.35), 3.745 (1.50), 3.780 (0.71), 3.862 (0.95), 3.889 (16.00), 3.906 (1.19), 4.074 (0.71), 4.222 (2.14), 4.238 (3.96), 4.253 (1.82), 4.754 (0.55), 5.960 (1.98), 5.981 (1.98), 6.430 (0.95), 6.433 (0.95), 6.451 (1.43), 6.455 (1.43), 6.461 (0.95), 6.478 (1.19), 6.482 (1.11), 6.572 (0.95), 6.587 (1.11), 6.593 (1.58), 6.608 (1.58), 6.613 (0.79), 6.628 (0.63), 7.108 (2.30), 7.292 (2.77), 7.305 (2.77), 7.455 (4.67), 8.017 (2.61), 8.030 (2.46), 8.344 (4.04), 11.175 (2.46).

LC-MS (method 6): $R_t$=0.63 min; MS (ESIpos): m/z=483 $[M+H]^+$

Racemic 2-(3-{2-[1,4-dioxan-2-yl]ethoxy}pyridin-4-yl)-3-(3-fluoro-2-methoxyanilino)-1,5,6,7-tetrahydro-4H-pyrrolo[3,2-c]pyridin-4-one (25.0 mg) was separated into enantiomers by preparative chiral HPLC to give title compound (enantiomer 1, 12.00 mg, at Rt=15.1-17.0 min,) and enantiomer 2 (4 mg, at $R_t$=19.8-26.8 min, see example 36).

Preparative Chiral HPLC Method:

Instrument: PrepCon Labomatic HPLC; Column: Chiralpak IF 5μ, 250×30; eluent A: hexane+0.1 vol % diethylamine; eluent B: ethanol+0.1 vol % diethylamine; isocratic: 70% A+30% B; flow: 50 ml/min; temperature: 25° C.; UV: 280 nm Analytical Chiral HPLC Method:

Instrument: Waters Alliance 2695; Column: Chiralpak IF 3μ, 100×4.6; eluent A: hexane+0.1 vol % diethylamine;

eluent B: ethanol; isocratic: 70% A+30% B; flow: 1.4 ml/min; temperature: 25° C.; UV: 280 nm Analytical chiral HPLC: $R_t$=4.68 min.

Optical rotation: $[\alpha]_D$=−12.9°+/−1.72° (c=1.4 mg/ml in methanol)

Example 36

2-(3-{2-[1,4-dioxan-2-yl]ethoxy}pyridin-4-yl)-3-(3-fluoro-2-methoxyanilino)-1,5,6,7-tetrahydro-4H-pyrrolo[3,2-c]pyridin-4-one (Stereoisomer 2)

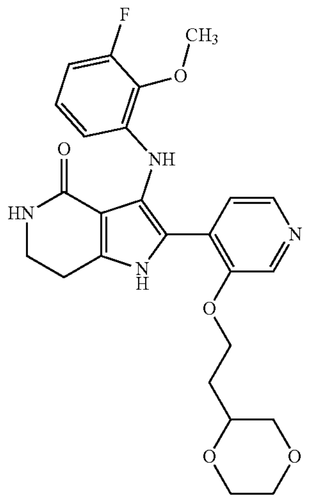 [SMILES: COc1c(F)cccc1Nc1c(-c2ccncc2OCCC2COCCO2)[nH]c2c1C(=O)NCC2]

For the preparation of the racemic title compound see example 35. Separation of enantiomers by preparative chiral HPLC (method see example 35) gave 4 mg of the title compound (at $R_t$=19.8-26.8 min).

Analytical chiral HPLC (method see example 35): $R_t$=6.58 min.

Optical rotation: $[\alpha]_D$=−21.4°+/−1.94° (c=1.3 mg/ml in methanol)

Example 37

3-(3-fluoro-2-methoxyanilino)-2-(3-{[(3R)-4-methylmorpholin-3-yl]methoxy}pyridin-4-yl)-1,5,6,7-tetrahydro-4H-pyrrolo[3,2-c]pyridin-4-one

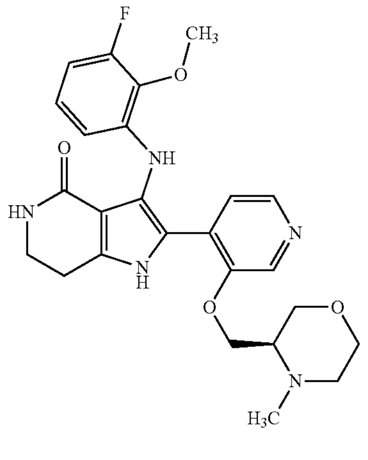 [SMILES: COc1c(F)cccc1Nc1c(-c2ccncc2OC[C@H]2COCCN2C)[nH]c2c1C(=O)NCC2]

Using an analogous method as described for example 1; N-(3-fluoro-2-methoxyphenyl)-4-{[(3-{[(3R)-4-methylmorpholin-3-yl]methoxy}pyridin-4-yl)methyl]amino}-2-oxo-1,2,5,6-tetrahydropyridine-3-carbothioamide (intermediate 6-37, 130 mg, 252 μmol) as the starting material, 35.00 mg (92% purity, 27% yield) of the title compound were prepared after preparative HPLC (method 7).

$^1$H-NMR (400 MHz, DMSO-$d_6$): δ [ppm]=2.277 (13.00), 2.292 (1.54), 2.307 (0.96), 2.324 (0.70), 2.329 (0.89), 2.334 (0.66), 2.407 (0.69), 2.428 (1.27), 2.435 (1.36), 2.520 (2.98), 2.525 (1.88), 2.667 (0.63), 2.671 (0.83), 2.676 (0.62), 2.777 (0.67), 2.801 (0.82), 2.818 (1.61), 2.825 (0.99), 2.835 (1.02), 2.844 (1.23), 2.860 (0.82), 2.911 (1.23), 2.940 (1.09), 3.388 (0.53), 3.408 (0.96), 3.425 (1.66), 3.431 (1.41), 3.441 (1.54), 3.455 (0.69), 3.548 (1.12), 3.576 (1.89), 3.592 (1.35), 3.597 (1.35), 3.602 (1.33), 3.621 (0.70), 3.626 (0.70), 3.783 (1.37), 3.785 (1.33), 3.818 (1.11), 3.843 (1.97), 3.849 (2.06), 3.870 (1.11), 3.878 (0.99), 3.941 (16.00), 3.954 (1.12), 4.078 (0.56), 4.349 (0.43), 4.358 (0.42), 4.376 (1.85), 4.388 (2.91), 4.416 (0.47), 6.013 (1.90), 6.034 (1.91), 6.516 (0.95), 6.520 (0.92), 6.537 (1.27), 6.541 (1.33), 6.547 (0.95), 6.564 (1.12), 6.568 (1.03), 6.657 (0.94), 6.672 (1.04), 6.678 (1.61), 6.693 (1.51), 6.698 (0.80), 6.714 (0.65), 7.180 (2.21), 7.313 (3.72), 7.325 (3.57), 7.605 (4.51), 7.980 (4.40), 7.993 (4.17), 8.360 (6.21), 8.414 (0.59), 12.014 (2.24).

LC-MS (method 6): $R_t$=0.51 min; MS (ESIpos): m/z=482 $[M+H]^+$

Example 38

2-[3-[(5,5-dimethyl-1,4-dioxan-2-yl)methoxy]-4-pyridyl]-3-(3-fluoro-2-methyl-anilino)-1,5,6,7-tetrahydropyrrolo[3,2-c]pyridin-4-one

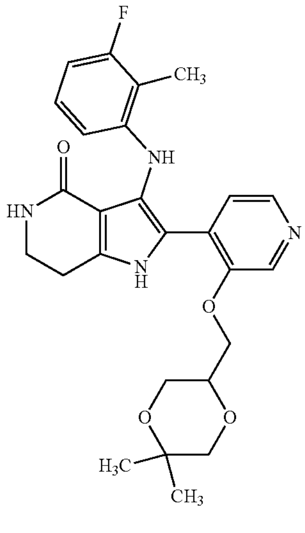 [SMILES: Cc1c(F)cccc1Nc1c(-c2ccncc2OCC2COC(C)(C)CO2)[nH]c2c1C(=O)NCC2]

Using an analogous method as described for example 1; 4-[[3-[(5,5-dimethyl-1,4-dioxan-2-yl)methoxy]-4-pyridyl]methylamino]-N-(3-fluoro-2-methyl-phenyl)-6-oxo-2,3-dihydro-1H-pyridine-5-carbothioamide (intermediate 6-38, 190 mg, 369 μmol) as the starting material, 30.2 mg (98% purity, 17% yield) of the title compound were prepared after preparative HPLC (method 10, gradient: 0.00-0.50 min 15% B, 0.50-5.59 min 15-51.7% B, 5.59-5.88 min 51.7% B, 5.88-5.93 min 51.7-52.1% B, 5.93-5.95 min 52.1% B, 5.95-6.32 min 52.1-55% B)

$^1$H-NMR (400 MHz, DMSO-$d_6$): δ [ppm]=1.073 (16.00), 1.243 (14.37), 2.177 (9.43), 2.180 (9.37), 2.520 (3.20), 2.525 (2.30), 2.542 (0.63), 2.826 (1.74), 2.843 (3.73), 2.861 (2.01), 3.406 (3.15), 3.417 (2.63), 3.424 (2.71), 3.434 (3.36), 3.569 (0.91), 3.577 (1.10), 3.598 (1.87), 3.607 (1.84), 3.643 (4.40), 3.671 (4.37), 3.699 (1.24), 3.881 (0.69), 3.890 (0.81), 3.898 (1.03), 3.907 (0.94), 3.915 (0.67), 3.923 (0.65), 4.121 (1.26), 4.137 (1.17), 4.147 (1.71), 4.163 (1.45), 4.265 (1.62), 4.274 (1.65), 4.291 (1.24), 4.300 (1.11), 6.059 (2.34), 6.080 (2.42), 6.427 (1.06), 6.449 (1.94), 6.470 (1.21), 6.721 (0.73), 6.742 (1.51), 6.759 (1.47), 6.779 (0.63), 7.168 (2.42), 7.232 (4.19), 7.244 (4.24), 7.308 (4.82), 7.997 (5.22), 8.009 (4.80), 8.373 (6.80), 11.029 (2.61).

LC-MS (method 6): $R_t$=0.74 min; MS (ESIpos): m/z=481 $[M+H]^+$

Example 39

2-[3-[(5,5-dimethyl-1,4-dioxan-2-yl)methoxy]-4-pyridyl]-3-(3-fluoro-2-methyl-anilino)-1,5,6,7-tetrahydropyrrolo[3,2-c]pyridin-4-one (stereoisomer 1)

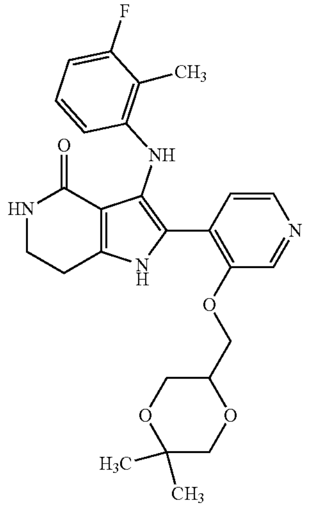 [SMILES: Cc1c(F)cccc1Nc1c(-c2ccncc2OCC2COC(C)(C)CO2)[nH]c2c1C(=O)NCC2]

The title compound from example 38 (30.2 mg) was separated into enantiomers by preparative chiral HPLC to give title compound (enantiomer 1, 10.00 mg, $R_t$=30.4-36.0 min, 5% yield) and enantiomer 2 (9 mg, $R_t$=45.9-51.7 min).

Preparative Chiral HPLC Method: NPB

Instrument: PrepCon Labomatic HPLC; Column: Chiralpak IF 5μ, 250×30; eluent A: hexane+0.1 vol % diethylamine; eluent B: ethanol+0.1 vol % diethylamine; isocratic: 90% A+10% B; flow: 50 ml/min; temperature: 25° C.; UV: 254 nm Analytical Chiral HPLC Method: NPB Instrument: Waters Alliance 2695; Column: Chiralpak IF 3μ, 100×4.6; eluent A: hexane+0.1 vol % diethylamine; eluent B: ethanol; isocratic: 90% A+10% B; flow: 1.4 ml/min; temperature: 25° C.; UV: 254 nm Analytical chiral HPLC: $R_t$=11.60 min.

Optical rotation: $[\alpha]_D$=−6.4°+/−0.47° (c=6.2 mg/ml in DMSO)

$^1$H-NMR (400 MHz, DMSO-$d_6$): δ [ppm]=0.700 (5.10), 0.744 (1.84), 0.764 (1.85), 0.836 (0.93), 0.854 (1.20), 1.073 (15.11), 1.152 (5.69), 1.235 (8.54), 1.243 (16.00), 1.296 (2.78), 1.350 (0.95), 1.378 (0.62), 1.672 (0.88), 2.179 (9.59), 2.525 (2.28), 2.827 (1.75), 2.844 (3.61), 2.861 (1.95), 3.407 (3.22), 3.418 (2.68), 3.424 (2.72), 3.434 (3.38), 3.570 (0.86), 3.578 (1.00), 3.599 (1.76), 3.607 (1.71), 3.644 (4.10), 3.671 (4.05), 3.700 (1.09), 3.882 (0.67), 3.890 (0.80), 3.899 (1.00), 3.907 (0.92), 3.915 (0.66), 3.924 (0.61), 4.121 (1.09), 4.138 (1.06), 4.147 (1.50), 4.164 (1.30), 4.267 (1.44), 4.275 (1.48), 4.292 (1.11), 4.301 (1.01), 6.060 (2.24), 6.080 (2.31), 6.428 (1.04), 6.450 (1.90), 6.472 (1.17), 6.722 (0.70), 6.742 (1.49), 6.759 (1.45), 6.780 (0.58), 6.959 (0.44), 7.170 (2.40), 7.201 (0.51), 7.222 (0.55), 7.234 (1.95), 7.246 (1.95), 7.309 (4.47), 7.999 (1.12), 8.010 (1.08), 8.375 (1.57), 11.031 (2.61).

Example 40

3-[2-(2,2-difluoroethyl)-3-fluoro-anilino]-2-[3-(1,4-dioxan-2-ylmethoxy)-4-pyridyl]-1,5,6,7-tetrahydropyrrolo[3,2-c]pyridin-4-one

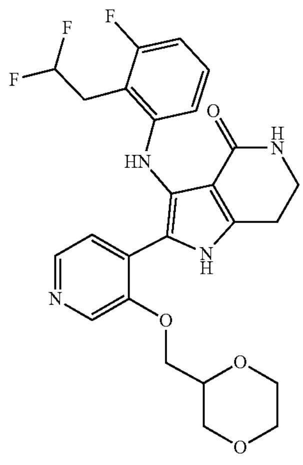 [SMILES: O=C1NCCc2[nH]c(-c3ccncc3OCC3COCCO3)c(Nc3cccc(F)c3CC(F)F)c21]

Using an analogous method as described for example 1 with N-[2-(2,2-difluoroethyl)-3-fluorophenyl]-4-{[(3-{[1,4-dioxan-2-yl]methoxy}pyridin-4-yl)methyl]amino}-2-oxo-1,2,5,6-tetrahydropyridine-3-carbothioamide (intermediate 6-40, 19.5 mg, 36.3 μmol) as the starting material; 3.80 mg (92% purity, 19% yield) of the title compound were prepared after purification by preparative HPLC (method 10, gradient: 0.00-0.50 min 30% B, 0.50-6.00 min 30-70% B).

$^1$H-NMR (400 MHz, DMSO-$d_6$): δ [ppm]=2.86 (t, 2H), 3.22-3.30 (m, 1H), 3.39-3.48 (m, 3H), 3.50-3.58 (td, 1H), 3.67-3.93 (m, 5H), 3.97-4.06 (m, 1H), 4.09-4.18 (m, 1H), 4.25-4.31 (dd, 1H), 6.07-6.17 (d, 1H), 6.29-6.63 (q, 2H), 6.83-6.94 (m, 1H), 7.10 (s, 1H), 7.34 (s, 1H), 7.37 (d, 2H), 8.00 (d, 1H), 8.38 (s, 1H), 11.07 (s, 1H).

LC-MS (method 2): $R_t$=0.99 min; MS (ESIpos): m/z=503 $[M+H]^+$

Example 41

3-[2-(2,2-difluoroethyl)-3-fluoroanilino]-2-(3-{[(2S)-4-methylmorpholin-2-yl]methoxy}pyridin-4-yl)-1,5,6,7-tetrahydro-4H-pyrrolo[3,2-c]pyridin-4-one

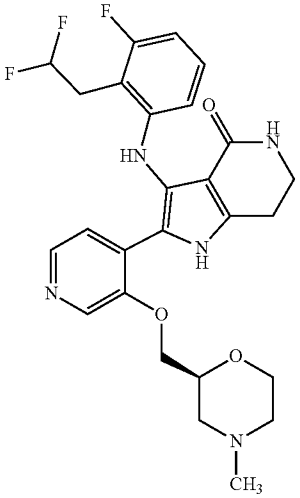 [SMILES: CN1CCO[C@H](COc2cnccc2-c2[nH]c3c(c2Nc2cccc(F)c2CC(F)F)C(=O)NCC3)C1]

3-[2-(2,2-difluoroethyl)-3-fluoroanilino]-2-(3-{[(2S)-morpholin-2-yl]methoxy}pyridin-4-yl)-1,5,6,7-tetrahydro-4H-pyrrolo[3,2-c]pyridin-4-one (intermediate 41, 22.0 mg, 43.9 μmol) was suspended in MeOH, formaldehyde (6.6 μl, 37% purity in water, 88 μmol) and acetic acid (2.5 μl, 44 μmol) were added. The reaction mixture was stirred for 15 min at room temperature. Sodium triacetoxyborohydride (13.9 mg, 65.8 μmol) was added the the mixture was stirred for 1 h at room temperature. The mixture was filtered through a SCX column and washed with MeOH and ammonia (7M in MeOH). The ammonia filtrate was evaporated and purified by preparative HPLC (method 10, gradient: 0.00-0.50 min 15% B, 0.50-6.00 min 15-55% B) to give 8.8 mg (90% purity, 35% yield) of the title compound.

$^1$H-NMR (400 MHz, DMSO-$d_6$): δ [ppm]=2.07 (m, 3H), 2.22 (s, 3H), 2.63-2.83 (m, 2H), 2.86 (t, 2H), 3.27-3.31 (m, 1H), 3.35-3.38 (m, 1H), 3.42 (td, 2H), 3.68 (td, 1H), 3.91-4.00 (m, 2H), 4.12-4.19 (dd, 1H), 4.33 (dd, 1H), 6.13 (d, 1H), 6.29-6.64 (m, 1H), 6.89 (q, 1H), 7.07-7.14 (m, 1H), 7.33-7.40 (t, 2H), 7.99 (d, 1H), 8.39 (s, 1H), 11.07 (s, 1H).

LC-MS (method 2): $R_t$=0.98 min; MS (ESIpos): m/z=516 [M+H]$^+$

Example 42

3-(3-chloro-2-methylanilino)-2-(3-{[(2S)-4-methylmorpholin-2-yl]methoxy}pyridin-4-yl)-1,5,6,7-tetrahydro-4H-pyrrolo[3,2-c]pyridin-4-one

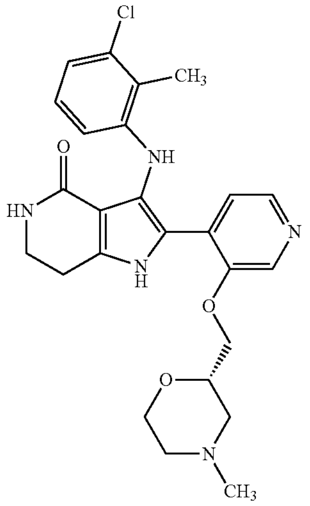 [SMILES: Cc1c(Cl)cccc1Nc1c(-c2ccncc2OC[C@@H]2CN(C)CCO2)[nH]c2c1C(=O)NCC2]

Using an analogous method as described for example 41 with 3-(3-chloro-2-methylanilino)-2-(3-{[(2S)-morpholin-2-yl]methoxy}pyridin-4-yl)-1,5,6,7-tetrahydro-4H-pyrrolo[3,2-c]pyridin-4-one (intermediate 42, 18.0 mg, 38.5 μmol) as the starting material; 10.9 mg (94% purity, 55% yield) of the title compound were prepared after purification by preparative HPLC (method 10, gradient: 0.00-0.50 min 15% B, 0.50-6.00 min 15-55% B).

$^1$H-NMR (400 MHz, DMSO-$d_6$): δ [ppm]=1.234 (0.45), 1.874 (1.12), 1.901 (1.88), 1.928 (1.19), 2.006 (0.51), 2.015 (0.63), 2.035 (1.18), 2.043 (1.18), 2.064 (0.68), 2.072 (0.56), 2.207 (15.79), 2.324 (0.67), 2.329 (0.91), 2.334 (0.71), 2.338 (0.45), 2.357 (16.00), 2.374 (1.16), 2.520 (2.98), 2.525 (1.85), 2.647 (1.22), 2.671 (1.61), 2.676 (1.69), 2.736 (1.32), 2.764 (1.23), 2.847 (1.67), 2.865 (3.57), 2.882 (1.86), 3.411 (1.24), 3.417 (1.33), 3.428 (2.40), 3.434 (2.36), 3.445 (1.17), 3.451 (1.06), 3.639 (0.62), 3.645 (0.95), 3.667 (1.35), 3.672 (1.38), 3.695 (0.78), 3.701 (0.66), 3.937 (1.97), 3.960 (1.51), 4.111 (1.22), 4.128 (1.10), 4.137 (1.63), 4.153 (1.36), 4.253 (1.46), 4.262 (1.52), 4.279 (1.14), 4.287 (1.03), 6.190 (1.81), 6.194 (1.78), 6.209 (1.99), 6.213 (1.81), 6.722 (0.90), 6.726 (1.25), 6.742 (3.67), 6.746 (2.96), 6.753 (2.81), 6.773 (2.59), 6.792 (0.84), 7.190 (2.30), 7.232 (3.39), 7.244 (3.38), 7.377 (4.48), 7.990 (3.43), 8.003 (3.19), 8.370 (5.23), 11.051 (2.53).

LC-MS (method 6): $R_t$=0.52 min; MS (ESIpos): m/z=482 [M+H]$^+$

Example 43

3-(3-chloro-2-methylanilino)-2-(3-{[(3R)-4-methylmorpholin-3-yl]methoxy}pyridin-4-yl)-1,5,6,7-tetrahydro-4H-pyrrolo[3,2-c]pyridin-4-one

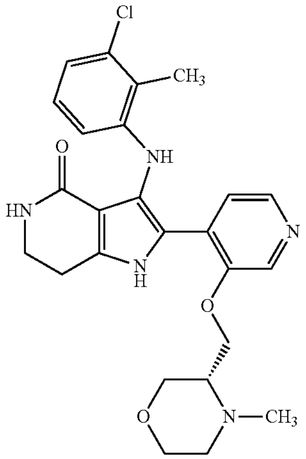 [SMILES: Cc1c(Cl)cccc1Nc1c(-c2ccncc2OC[C@H]2COCCN2C)[nH]c2c1C(=O)NCC2]

Using an analogous method as described for example 41 with 3-(3-chloro-2-methylanilino)-2-(3-{[(3R)-morpholin-3-yl]methoxy}pyridin-4-yl)-1,5,6,7-tetrahydro-4H-pyrrolo[3,2-c]pyridin-4-one (30.0 mg, 64.1 μmol) as the starting material; 7.0 mg (94% purity, 21% yield) of the title compound were prepared after purification by preparative HPLC (method 10, gradient: 0.00-0.50 min 15% B, 0.50-6.00 min 15-55% B).

$^1$H-NMR (400 MHz, DMSO-$d_6$): δ [ppm]=−0.002 (3.00), 0.879 (0.57), 2.085 (5.27), 2.272 (14.21), 2.318 (0.47), 2.382 (16.00), 2.397 (1.43), 2.423 (1.05), 2.431 (1.10), 2.460 (1.63), 2.518 (5.17), 2.523 (3.38), 2.660 (0.46), 2.810 (0.81), 2.828 (2.27), 2.845 (1.96), 2.864 (0.87), 2.909 (1.32), 2.938 (1.16), 3.411 (0.70), 3.428 (1.64), 3.435 (1.37), 3.444 (1.50), 3.464 (0.63), 3.540 (1.08), 3.568 (2.41), 3.595 (2.18), 3.620 (0.70), 3.818 (1.11), 3.844 (2.09), 3.864 (1.06), 3.872 (0.93), 4.357 (1.94), 4.368 (3.51), 4.395 (0.46), 6.209 (1.79), 6.212 (1.85), 6.228 (1.98), 6.232 (1.91), 6.756 (1.10), 6.760 (1.40), 6.776 (3.46), 6.779 (2.93), 6.793 (2.52), 6.813 (2.75), 6.833 (0.95), 7.200 (2.25), 7.250 (3.55), 7.263 (3.70), 7.431 (4.31), 7.946 (3.93), 7.958 (3.66), 8.338 (5.51), 12.003 (2.32).

LC-MS (method 6): $R_t$=0.57 min; MS (ESIpos): m/z=512 $[M+H]^+$

Example 44

3-(3-chloro-2-methyl-anilino)-2-[3-[(5,5-dimethyl-1,4-dioxan-2-yl)methoxy]-4-pyridyl]-1,5,6,7-tetrahydropyrrolo[3,2-c]pyridin-4-one

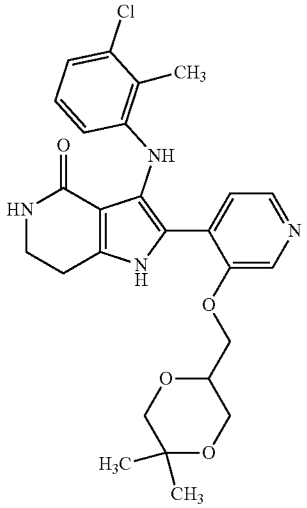 [SMILES: Cc1c(Cl)cccc1Nc1c(-c2ccncc2OCC2COC(C)(C)CO2)[nH]c2c1C(=O)NCC2]

In analogy to example 1 N-(3-chloro-2-methyl-phenyl)-4-[[3-[(5,5-dimethyl-1,4-dioxan-2-yl)methoxy]-4-pyridyl]methylamino]-6-oxo-2,3-dihydro-1H-pyridine-5-carbothioamide (intermediate 6-44, 320 mg, 603 μmol) was used to prepare 32 mg of the title compound (98% purity, 10% yield) after stirring for 2 h at room temperature and purification by preparative HPLC (method 10, gradient: 0.00-0.50 min 15% B, 0.50-5.92 min 15-54.2% B, 5.92-7.34 min 54.2% B, 7.34-7.42 min 54.2-55% B).

$^1$H-NMR (400 MHz, DMSO-$d_6$): δ [ppm]=1.072 (14.59), 1.241 (13.05), 2.325 (0.47), 2.329 (0.73), 2.344 (16.00), 2.520 (1.82), 2.525 (1.27), 2.671 (0.54), 2.828 (1.59), 2.845 (3.40), 2.862 (1.80), 3.402 (2.68), 3.417 (2.39), 3.423 (2.57), 3.431 (2.75), 3.565 (0.87), 3.574 (1.01), 3.595 (1.70), 3.603 (1.65), 3.640 (3.45), 3.668 (4.15), 3.697 (1.17), 3.872 (0.64), 3.880 (0.75), 3.888 (0.95), 3.897 (0.88), 3.905 (0.63), 3.914 (0.58), 4.122 (1.12), 4.139 (1.05), 4.149 (1.54), 4.165 (1.34), 4.254 (1.47), 4.263 (1.52), 4.281 (1.10), 4.289 (0.98), 6.196 (1.81), 6.199 (1.76), 6.215 (1.97), 6.218 (1.81), 6.705 (0.97), 6.709 (1.30), 6.725 (3.57), 6.729 (2.82), 6.738 (2.56), 6.757 (2.50), 6.778 (0.82), 7.165 (2.26), 7.230 (3.85), 7.243 (3.87), 7.323 (4.45), 8.004 (5.13), 8.016 (4.69), 8.374 (6.56), 11.049 (2.45).

LC-MS (method 6): $R_t$=0.79 min; MS (ESIpos): m/z=497 $[M+H]^+$

Example 45

3-(3-chloro-2-methyl-anilino)-2-[3-[(5,5-dimethyl-1,4-dioxan-2-yl)methoxy]-4-pyridyl]-1,5,6,7-tetrahydropyrrolo[3,2-c]pyridin-4-one (stereoisomer 1)

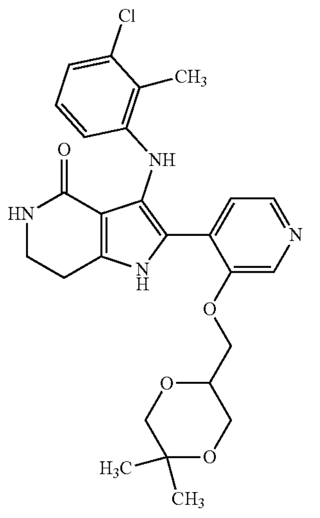 [SMILES: Cc1c(Cl)cccc1Nc1c(-c2ccncc2OCC2COC(C)(C)CO2)[nH]c2c1C(=O)NCC2]

The title compound from example 44 (32.0 mg) was separated into enantiomers by preparative chiral HPLC to give title compound (enantiomer 1, 15.50 mg, $R_t$=12.1-14.2 min) and enantiomer 2 (12.6 mg, $R_t$=14.5-19.0 min, see example 46).

Preparative Chiral HPLC Method: POB

Instrument: PrepCon Labomatic HPLC; Column: Chiralcel OD-H 5μ, 250×20; eluent A: ethanol+0.1 vol % diethylamine; eluent B: methanol; isocratic: 70% A+30% B; flow: 10 ml/min; temperature: 25° C.; UV: 280 nm Analytical Chiral HPLC Method: POB Instrument: Waters Alliance 2695; Column: Chiralcel OD-H 5μ, 100×4.6; eluent A: ethanol+0.1 vol % diethylamine; eluent B: methanol; isocratic: 70% A+30% B; flow: 1.4 ml/min; temperature: 25° C.; UV: 280 nm Analytical chiral HPLC: $R_t$=3.52 min.

Optical rotation: $[\alpha]_D$=30.31°+/−1.05° (c=2.7 mg/ml in Chloroform)

$^1$H-NMR (400 MHz, DMSO-$d_6$): δ [ppm]=1.050 (0.51), 1.070 (14.54), 1.119 (0.40), 1.137 (0.77), 1.155 (0.80), 1.190 (0.47), 1.239 (13.63), 2.085 (0.73), 2.318 (0.77), 2.323 (1.71), 2.327 (2.48), 2.332 (2.11), 2.342 (16.00), 2.518 (7.25), 2.523 (5.03), 2.660 (0.73), 2.665 (1.64), 2.669 (2.30), 2.673 (1.60), 2.679 (0.73), 2.825 (1.60), 2.842 (3.43), 2.859 (1.86), 3.306 (0.95), 3.399 (2.77), 3.415 (2.44), 3.421 (2.59), 3.429 (2.84), 3.563 (0.87), 3.572 (1.02), 3.592 (1.71), 3.601 (1.68), 3.638 (3.46), 3.665 (4.15), 3.695 (1.17), 3.869 (0.77), 3.878 (0.77), 3.886 (0.95), 3.894 (0.87), 3.903 (0.62), 3.911 (0.58), 4.120 (1.13), 4.137 (1.06), 4.147 (1.53), 4.163 (1.31), 4.252 (1.46), 4.261 (1.53), 4.278 (1.09), 4.287 (0.98), 6.193 (1.82), 6.197 (1.75), 6.212 (1.93), 6.216 (1.82), 6.703 (0.98), 6.707 (1.28), 6.723 (3.50), 6.727 (2.81), 6.736 (2.59), 6.756 (2.51), 6.775 (0.84), 7.162 (2.22), 7.228 (3.64), 7.241 (3.64), 7.321 (4.48), 8.002 (4.30), 8.014 (4.01), 8.372 (5.94), 11.046 (2.48).

LC-MS (method 6): $R_t$=0.80 min; MS (ESIpos): m/z=497 $[M+H]^+$

Example 46

3-(3-chloro-2-methyl-anilino)-2-[3-[(5,5-dimethyl-1,4-dioxan-2-yl)methoxy]-4-pyridyl]-1,5,6,7-tetrahydropyrrolo[3,2-c]pyridin-4-one (stereoisomer 2)

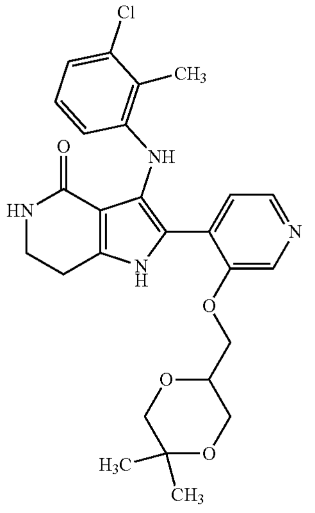 [SMILES: Cc1c(Cl)cccc1Nc1c(-c2ccncc2OCC2COC(C)(C)CO2)[nH]c2c1C(=O)NCC2]

For the preparation of the racemic title compound see example 44. Separation of enantiomers by preparative chiral HPLC (method see example 45) to give 12.6 mg of the title compound ($R_t$=14.5-19.0 min).

Analytical chiral HPLC (method see example 45): $R_t$=4.43 min.

Optical rotation: $[\alpha]_D$=−26.44°+/−1.41° (c=2.9 mg/ml in Chloroform)

$^1$H-NMR (400 MHz, DMSO-$d_6$): δ [ppm]=0.748 (0.44), 0.764 (0.44), 1.053 (0.52), 1.070 (14.81), 1.154 (1.45), 1.239 (13.86), 2.085 (1.85), 2.318 (0.46), 2.323 (0.99), 2.327 (1.45), 2.332 (1.39), 2.342 (16.00), 2.518 (4.03), 2.523 (2.82), 2.540 (0.54), 2.665 (0.89), 2.669 (1.25), 2.673 (0.85), 2.825 (1.61), 2.843 (3.39), 2.859 (1.81), 3.399 (2.78), 3.415 (2.48), 3.421 (2.64), 3.429 (2.88), 3.563 (0.83), 3.572 (0.99), 3.593 (1.69), 3.601 (1.67), 3.638 (3.49), 3.665 (4.15), 3.695 (1.15), 3.869 (0.83), 3.878 (0.77), 3.886 (0.95), 3.895 (0.89), 3.903 (0.64), 3.912 (0.58), 4.120 (1.09), 4.137 (1.03), 4.147 (1.53), 4.163 (1.33), 4.252 (1.45), 4.261 (1.51), 4.278 (1.09), 4.287 (0.97), 6.193 (1.77), 6.197 (1.75), 6.212 (1.97), 6.216 (1.85), 6.703 (0.95), 6.707 (1.27), 6.723 (3.51), 6.727 (2.82), 6.736 (2.58), 6.756 (2.54), 6.775 (0.85), 7.162 (2.26), 7.228 (3.10), 7.241 (3.12), 7.321 (4.45), 8.002 (2.54), 8.015 (2.36), 8.372 (3.89), 11.046 (2.46).

LC-MS (method 6): $R_t$=0.80 min; MS (ESIpos): m/z=497 $[M+H]^+$

Example 47

2-[3-(1,4-dioxan-2-ylmethoxy)-4-pyridyl]-3-(3-fluoro-2-methyl-anilino)-1,5,6,7-tetrahydropyrrolo[3,2-c]pyridin-4-one

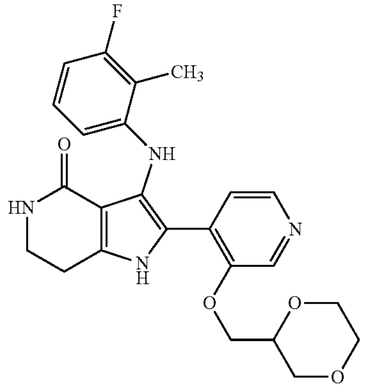 [SMILES: Cc1c(F)cccc1Nc1c(-c2ccncc2OCC2COCCO2)[nH]c2c1C(=O)NCC2]

In analogy to example 1 4-[[3-(1,4-dioxan-2-ylmethoxy)-4-pyridyl]methylamino]-N-(3-fluoro-2-methyl-phenyl)-6-oxo-2,3-dihydro-1H-pyridine-5-carbothioamide (intermediate 6-47, 399 mg, 820 μmol) was used to prepare 135 mg of the title compound (97% purity, 35% yield) after stirring for overnight at 60° C. and purification by preparative HPLC (method 9, gradient: 0.00-0.50 min 15% B, 0.50-6.00 min 15-55% B).

$^1$H-NMR (400 MHz, DMSO-$d_6$) δ [ppm]: 1.154 (4.20), 1.172 (8.22), 1.189 (3.94), 1.987 (16.00), 2.185 (2.36), 2.189 (2.36), 2.518 (0.75), 2.522 (0.47), 2.843 (0.44), 2.860 (0.94), 2.877 (0.50), 3.398 (0.42), 3.425 (1.01), 3.451 (0.56), 3.709 (0.44), 3.740 (0.57), 3.999 (1.26), 4.017 (3.61), 4.035 (3.57), 4.053 (1.15), 4.125 (0.48), 4.230 (0.43), 4.239 (0.42), 5.758 (0.88), 6.052 (0.58), 6.072 (0.60), 6.459 (0.48), 7.186 (0.59), 7.234 (1.00), 7.247 (1.01), 7.345 (1.17), 7.990 (1.32), 8.002 (1.20), 8.361 (1.76), 11.030 (0.60).

LC-MS (method 6): Rt=0.65 min; MS (ESipos): m/z=453 [M+H]$^+$

Example 48

2-[3-(1,4-dioxan-2-ylmethoxy)-4-pyridyl]-3-(3-fluoro-2-methyl-anilino)-1,5,6,7-tetrahydropyrrolo[3,2-c]pyridin-4-one (stereoisomer 1)

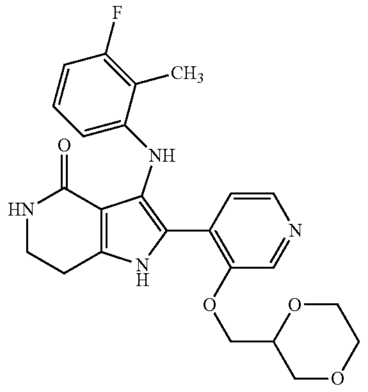 [SMILES: Cc1c(F)cccc1Nc1c(-c2ccncc2OCC2COCCO2)[nH]c2c1C(=O)NCC2]

The title compound from example 47 (15.0 mg) was separated into enantiomers by preparative chiral HPLC to give title compound (enantiomer 1, 3.0 mg, $R_t$=5.5-6.2 min) and enantiomer 2 (2.0 mg, $R_t$=9.0-9.9 min, see example 49).

Preparative Chiral HPLC Method: MTBE

Instrument: PrepCon Labomatic HPLC; Column: YMC Cellulose SB 5μ, 250×30; eluent A: methyl tert-butyl ether+0.1 vol % diethylamine; eluent B: acetonitrile; isocratic: 55% B+45% A; flow: 80 ml/min; temperature: 25° C.; UV: 280 nm;

Analytical Chiral HPLC Method: MTBE

Instrument: Waters Alliance 2695; Column: YMC Cellulose SB 3μ, 100×4.6; eluent A: methyl tert-butyl ether+0.2 vol % diethylamine; eluent B: acetonitrile; isocratic: 50% A+50% B; flow: 1.4 ml/min; temperature: 25° C.; UV: 280 nm;

Analytical chiral HPLC: $R_t$=2.90 min.

Optical rotation: $[\alpha]_D$=−19.1°+/−1.65° (c=2.19 mg/ml in Chloroform)

$^1$H-NMR (400 MHz, DMSO-$d_6$): δ [ppm]=−0.008 (0.55), 0.000 (16.00), 0.008 (0.53), 0.700 (0.57), 0.752 (0.76), 0.770 (0.76), 1.140 (1.18), 1.160 (2.36), 1.234 (1.64), 1.296 (0.42), 2.189 (11.55), 2.191 (11.53), 2.521 (2.85), 2.525 (1.90), 2.846 (2.15), 2.863 (4.59), 2.880 (2.42), 3.401 (1.96), 3.410 (1.71), 3.417 (1.88), 3.428 (4.95), 3.444 (1.64), 3.454 (2.68), 3.505 (0.67), 3.510 (0.82), 3.532 (1.56), 3.539 (1.58), 3.560 (1.14), 3.569 (1.03), 3.712 (2.13), 3.721 (1.35), 3.743 (2.76), 3.750 (1.24), 3.771 (1.14), 3.778 (0.84), 3.800 (1.69), 3.806 (1.85), 3.829 (1.52), 3.835 (1.54), 3.885 (1.66), 3.912 (1.22), 3.992 (0.42), 4.001 (0.68), 4.008 (1.01), 4.017 (1.14), 4.025 (1.10), 4.033 (0.93), 4.042 (0.78), 4.049 (0.53), 4.103 (1.71), 4.119 (1.24), 4.129 (2.26), 4.145 (1.73), 4.233 (2.09), 4.243 (2.05), 4.259 (1.54), 4.269 (1.33), 6.056 (2.82), 6.076 (2.91), 6.440 (1.29), 6.463 (2.36), 6.484 (1.46), 6.734 (0.89), 6.754 (1.85), 6.771 (1.77), 6.792 (0.72), 7.187 (2.91), 7.237 (3.80), 7.250 (3.82), 7.348 (5.65), 7.994 (2.64), 8.006 (2.47), 8.365 (4.17), 11.029 (3.12).

LC-MS (method 6): $R_t$=0.66 min; MS (ESipos): m/z=453 [M+H]$^+$

Example 49

2-[3-(1,4-dioxan-2-ylmethoxy)-4-pyridyl]-3-(3-fluoro-2-methyl-anilino)-1,5,6,7-tetrahydropyrrolo[3,2-c]pyridin-4-one (stereoisomer 2)

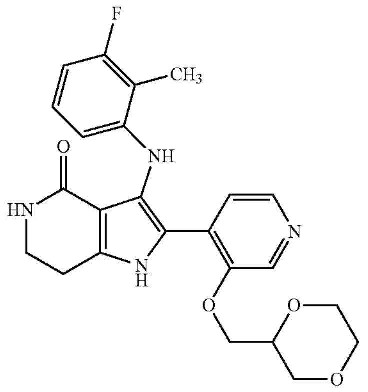 [SMILES: Cc1c(F)cccc1Nc1c(-c2ccncc2OCC2COCCO2)[nH]c2c1C(=O)NCC2]

For the preparation of the racemic title compound see example 47. Separation of enantiomers by preparative chiral HPLC (method see example 48) to give 2.0 mg of the title compound ($R_t$=9.0-9.9 min).

Analytical chiral HPLC (method see example 48): $R_t$=4.67 min.

Optical rotation: $[\alpha]_D$=24.3°+/−7.66° (c=1.29 mg/ml in Chloroform)

$^1$H-NMR (400 MHz, DMSO-$d_6$) δ [ppm]: −0.008 (0.54), 0.000 (16.00), 0.008 (0.54), 0.700 (0.74), 0.752 (0.54), 0.771 (0.57), 0.854 (0.52), 1.139 (0.91), 1.160 (1.70), 1.234 (2.19), 1.296 (0.52), 2.087 (0.66), 2.189 (11.26), 2.191 (11.28), 2.521 (4.55), 2.525 (3.00), 2.846 (2.09), 2.863 (4.47), 2.880 (2.36), 3.401 (1.99), 3.410 (1.67), 3.417 (1.87), 3.428 (4.87), 3.444 (1.65), 3.454 (2.65), 3.505 (0.69), 3.510 (0.84), 3.532 (1.52), 3.539 (1.55), 3.560 (1.13), 3.569 (1.03), 3.712 (2.09), 3.721 (1.35), 3.744 (2.70), 3.750 (1.23), 3.771 (1.16), 3.778 (0.81), 3.800 (1.67), 3.806 (1.77), 3.829 (1.50), 3.835 (1.52), 3.885 (1.62), 3.912 (1.20), 3.992 (0.42), 4.001 (0.66), 4.009 (0.98), 4.017 (1.11), 4.025 (1.08), 4.033 (0.91), 4.042 (0.76), 4.049 (0.54), 4.103 (1.70), 4.119 (1.20), 4.129 (2.19), 4.145 (1.72), 4.233 (2.04), 4.243 (2.04), 4.259 (1.52), 4.269 (1.33), 6.055 (2.75), 6.076 (2.85), 6.440 (1.25), 6.463 (2.31), 6.484 (1.45), 6.734 (0.86), 6.754 (1.79), 6.772 (1.72), 6.792 (0.74), 7.187 (2.83), 7.237 (3.37), 7.250 (3.42), 7.349 (5.43), 7.994 (2.24), 8.007 (2.14), 8.365 (3.56), 11.030 (3.02).

Example 50

3-(3-chloro-2-methylanilino)-2-(3-{[(2S)-1,4-dioxan-2-yl]methoxy}pyridin-4-yl)-1,5,6,7-tetrahydro-4H-pyrrolo[3,2-c]pyridin-4-one

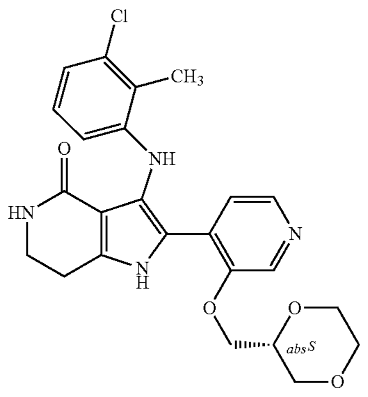

Using an analogous method as described for example 1 with N-(3-chloro-2-methyl-phenyl)-4-[[3-(1,4-dioxan-2-ylmethoxy)-4-pyridyl]methylamino]-6-oxo-2,3-dihydro-1H-pyridine-5-carbothioamide (intermediate 6-50, 150 mg, 298 μmol) as the starting material, 35.0 mg (25% yield) of the racemic title compound were prepared after preparative HPLC (method 10, gradient: 0.00-0.50 min 15% B, 0.50-6.00 min 15-55% B).

LC-MS (method 6): $R_t$=0.71 min; MS (ESIpos): m/z=469 $[M+H]^+$

Racemic 3-(3-chloro-2-methyl-anilino)-2-[3-(1,4-dioxan-2-ylmethoxy)-4-pyridyl]-1,5,6,7-tetrahydropyrrolo[3,2-c]pyridin-4-one (35.0 mg) was separated into enantiomers by preparative chiral HPLC to give title compound (enantiomer 1, 12.5 mg, $R_t$=14.3-16.6 min,) and enantiomer 2 (13.4 mg, $R_t$=21.1-25.3 min, see example 51).

Preparative Chiral HPLC Method: MTBE

Instrument: PrepCon Labomatic HPLC; Column: YMC Cellulose SB 5μ, 250×30; eluent A: methyl tert-butyl ether+0.1 vol % diethylamine; eluent B: ethanol; gradient; flow: 40 ml/min; temperature: 25° C.; UV: 254 nm Analytical Chiral HPLC Method: MTBE Instrument: Waters Alliance 2695; Column: YMC Cellulose SB 3μ, 100×4.6; eluent A: methyl tert-butyl ether+0.1 vol % diethylamine; eluent B: ethanol; gradient; flow: 1.4 ml/min; temperature: 25° C.; UV: 254 nm Analytical chiral HPLC: $R_t$=3.23 min.

Optical rotation: $[\alpha]_D$=−20.5°+/−1.23° (c=2.7 mg/ml in Chloroform)

$^1$H-NMR (400 MHz, DMSO-$d_6$): δ [ppm]=1.234 (0.41), 2.338 (0.44), 2.355 (16.00), 2.520 (2.76), 2.524 (1.87), 2.847 (1.60), 2.864 (3.40), 2.882 (1.80), 3.398 (1.50), 3.410 (1.20), 3.416 (1.35), 3.427 (3.93), 3.432 (2.41), 3.444 (1.16), 3.451 (2.30), 3.502 (0.46), 3.508 (0.60), 3.530 (1.13), 3.537 (1.16), 3.558 (0.85), 3.566 (0.78), 3.711 (1.87), 3.718 (1.04), 3.740 (2.36), 3.768 (0.89), 3.775 (0.60), 3.796 (1.27), 3.802 (1.36), 3.825 (1.15), 3.831 (1.16), 3.883 (1.23), 3.909 (0.88), 3.994 (0.48), 4.001 (0.77), 4.009 (0.80), 4.018 (0.79), 4.025 (0.69), 4.033 (0.55), 4.104 (1.32), 4.120 (0.96), 4.130 (1.76), 4.146 (1.34), 4.223 (1.59), 4.232 (1.56), 4.249 (1.15), 4.258 (1.00), 6.190 (1.73), 6.194 (1.69), 6.210 (2.01), 6.213 (1.79), 6.718 (0.97), 6.722 (1.27), 6.738 (3.59), 6.742 (2.81), 6.751 (2.54), 6.771 (2.47), 6.790 (0.80), 7.184 (2.17), 7.234 (3.49), 7.247 (3.51), 7.364 (4.36), 7.999 (3.35), 8.012 (3.08), 8.365 (4.78), 11.044 (2.32).

LC-MS (method 6): $R_t$=0.70 min; MS (ESIpos): m/z=469 $[M+H]^+$

Enantioselective synthesis starting from 1-(3-{[(2S)-1,4-dioxan-2-yl]methoxy}pyridin-4-yl)methanamine (intermediate 2-8) confirmed the title compound as 3-(3-chloro-2-methylanilino)-2-(3-{[(2S)-1,4-dioxan-2-yl]methoxy}pyridin-4-yl)-1,5,6,7-tetrahydro-4H-pyrrolo[3,2-c]pyridin-4-one.

Example 51

3-(3-chloro-2-methylanilino)-2-(3-{[(2R)-1,4-dioxan-2-yl]methoxy}pyridin-4-yl)-1,5,6,7-tetrahydro-4H-pyrrolo[3,2-c]pyridin-4-one

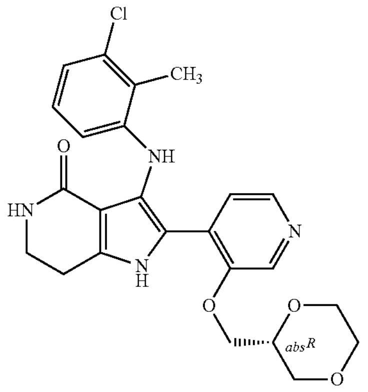

For the preparation of the racemic title compound see example 50. Separation of enantiomers by preparative chiral HPLC (method see example 50) gave 13.4 mg of the title compound ($R_t$=21.1-25.3 min).

Analytical chiral HPLC (method see example 50): $R_t$=5.22 min.

Optical rotation: $[\alpha]_D$=20.4°+/−1.23° (c=2.69 mg/ml in chloroform)

$^1$H-NMR (400 MHz, DMSO-$d_6$): δ [ppm]=1.173 (0.44), 1.234 (0.51), 2.355 (16.00), 2.521 (2.29), 2.525 (1.50), 2.848 (1.58), 2.865 (3.44), 2.882 (1.83), 3.346 (0.44), 3.399 (1.49), 3.410 (1.19), 3.416 (1.34), 3.428 (3.98), 3.432 (2.45), 3.444 (1.19), 3.452 (2.35), 3.503 (0.46), 3.508 (0.62), 3.531 (1.13), 3.538 (1.20), 3.558 (0.84), 3.567 (0.81), 3.711 (1.90), 3.718 (1.09), 3.740 (2.39), 3.768 (0.88), 3.775 (0.62), 3.797 (1.26), 3.803 (1.39), 3.825 (1.14), 3.832 (1.17), 3.883 (1.25), 3.910 (0.90), 3.995 (0.49), 4.001 (0.76), 4.010 (0.82), 4.018 (0.79), 4.026 (0.71), 4.035 (0.56), 4.042 (0.40), 4.104 (1.30), 4.121 (0.95), 4.130 (1.77), 4.147 (1.36), 4.224 (1.60), 4.233 (1.58), 4.250 (1.15), 4.259 (0.99), 6.191 (1.74), 6.195 (1.73), 6.210 (1.96), 6.214 (1.81), 6.719 (0.94), 6.723 (1.27), 6.738 (3.57), 6.743 (2.82), 6.752 (2.56), 6.771 (2.49), 6.791 (0.81), 7.185 (2.19), 7.235 (3.09), 7.248 (3.12), 7.365 (4.33), 8.000 (2.48), 8.013 (2.34), 8.366 (3.75), 11.045 (2.33).

LC-MS (method 6): $R_t$=0.70 min; MS (ESipos): m/z=469 $[M+H]^+$

Example 52

3-(3-chloro-2-ethyl-anilino)-2-[3-(1,4-dioxan-2-ylmethoxy)-4-pyridyl]-1,5,6,7-tetrahydropyrrolo[3,2-c]pyridin-4-one

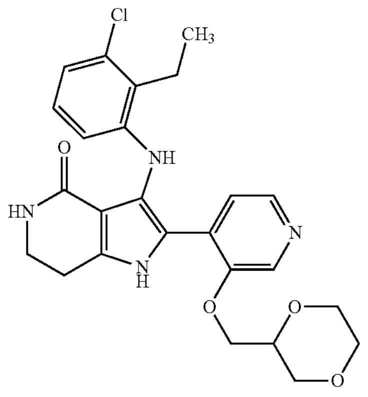 [SMILES: CCc1c(Cl)cccc1Nc1c(-c2ccncc2OCC2COCCO2)[nH]c2c1C(=O)NCC2]

In analogy to example 1 N-(3-chloro-2-ethyl-phenyl)-4-[[3-(1,4-dioxan-2-ylmethoxy)-4-pyridyl]methylamino]-6-oxo-2,3-dihydro-1H-pyridine-5-carbothioamide (intermediate 6-52, 150 mg, 290 μmol) was used to prepare 23.2 mg of the title compound (95% purity, 16% yield) after stirring for 4 h at 60° C. and purification by preparative HPLC (method 10, gradient: 0.00-0.50 min 10% B, 0.50-8.06 min 10-20% B, 8.06-9.02 min 20% B, 9.02-24.12 min 20-50% B, 24.12-27.44 min 50% B).

$^1$H-NMR (400 MHz, DMSO-$d_6$): δ ppm=1.23 (t, 3H), 2.86 (s, 4H), 3.38-3.46 (m, 4H), 3.49-3.58 (m, 1H), 3.68-3.78 (m, 2H), 3.78-3.85 (m, 1H), 3.86-3.92 (m, 1H), 3.98-4.06 (m, 1H), 4.09-4.17 (m, 1H), 4.21-4.28 (m, 1H), 6.22 (dd, 1H), 6.67-6.78 (m, 2H), 7.20 (d, 2H), 7.45 (s, 1H), 7.98 (d, 1H), 8.32-8.39 (m, 1H).

LC-MS (method 2): $R_t$=1.08 min; MS (ESIpos): m/z=483 $[M+H]^+$

Example 53

3-(3-chloro-2-ethylanilino)-2-(3-{[(2S)-1,4-dioxan-2-yl]methoxy}pyridin-4-yl)-1,5,6,7-tetrahydro-4H-pyrrolo[3,2-c]pyridin-4-one

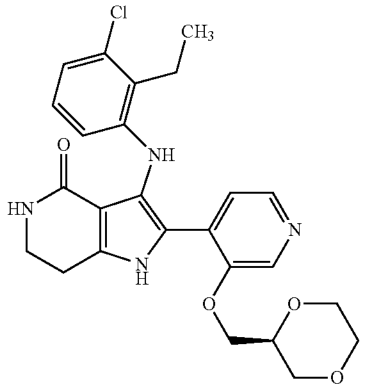 [SMILES: CCc1c(Cl)cccc1Nc1c(-c2ccncc2OC[C@@H]2COCCO2)[nH]c2c1C(=O)NCC2]

The title compound from example 52 (23.2 mg) was separated into enantiomers by preparative chiral HPLC to give title compound (enantiomer 1, 6.0 mg, $R_t$=6.6-7.-3 min) and enantiomer 2 (5.0 mg, $R_t$=10.7-11.6 min, see example 54).

Preparative Chiral HPLC Method: MTBE

Instrument: PrepCon Labomatic HPLC; Column: YMC Cellulose SB 5μ, 250×30; eluent A: methyl tert-butyl ether+0.1 vol % diethylamine; eluent B: acetonitrile; isocratic: 50% A+50% B; flow: 60 ml/min; temperature: 25° C.; UV: 254 nm Analytical Chiral HPLC Method: MTBE Instrument: Waters Alliance 2695; Column: YMC Cellulose SB 3μ, 100×4.6; eluent A: methyl tert-butyl ether+0.1 vol % diethylamine; eluent B: acetonitrile; isocratic: 50% A+50% B; flow: 1.4 ml/min; temperature: 25° C.; UV: 254 nm Analytical chiral HPLC: $R_t$=2.40 min.

$^1$H-NMR (400 MHz, DMSO-$d_6$): δ [ppm]=1.23 (t, 3H), 2.81-2.91 (m, 4H), 3.40-3.45 (m, 3H), 3.53 (dt, 1H), 3.69-3.79 (m, 2H), 3.79-3.85 (m, 1H), 3.86-3.93 (m, 1H), 3.99-4.06 (m, 1H), 4.12 (dd, 1H), 4.24 (dd, 1H), 6.23 (dd, 1H), 6.69-6.78 (m, 2H), 7.15-7.23 (m, 2H), 7.43-7.47 (m, 1H), 7.98 (d, 1H) 8.36 (s, 1H), 11.03 (br s, 1H).

Enantioselective synthesis confirmed the title compound as 3-(3-chloro-2-ethylanilino)-2-(3-{[(2S)-1,4-dioxan-2-yl]methoxy}pyridin-4-yl)-1,5,6,7-tetrahydro-4H-pyrrolo[3,2-c]pyridin-4-one. In analogy to example 1 the title compound (25 mg, 7.6% yield) was prepared by using N-(3-chloro-2-ethylphenyl)-4-{[(3-{[(2S)-1,4-dioxan-2-yl]methoxy} pyridin-4-yl)methyl]amino}-2-oxo-1,2,5,6-tetrahydropyridine-3-carbothioamide (intermediate 6-53, 320 mg, 0.62 mmol) as starting material, followed by purification with preparative HPLC (method 10, gradient: 0.00-0.50 min 5% B, 0.50-7.99 min 5-60% B, 7.99-11.20 min 60% B).

$^1$H-NMR (400 MHz, DMSO-$d_6$): δ [ppm]=11.03 (s, 1H), 8.36 (s, 1H), 7.98 (d, 1H), 7.43-7.49 (m, 1H), 7.15-7.24 (m, 2H), 6.68-6.80 (m, 2H), 6.14-6.28 (m, 1H), 4.21-4.33 (m, 1H), 4.10-4.17 (m, 1H), 4.00-4.05 (m, 1H), 3.70-3.92 (m, 4H), 3.51-3.59 (m, 1H), 3.39-3.47 (m, 3H), 2.81-2.90 (m, 4H), 1.23 (t, 3H).

Example 54

3-(3-chloro-2-ethylanilino)-2-(3-{[(2R)-1,4-dioxan-2-yl]methoxy}pyridin-4-yl)-1,5,6,7-tetrahydro-4H-pyrrolo[3,2-c]pyridin-4-one

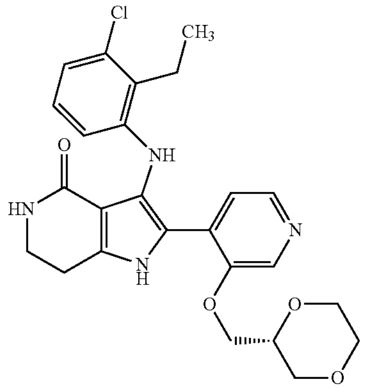 [SMILES: CCc1c(Cl)cccc1Nc1c(-c2ccncc2OC[C@H]2COCCO2)[nH]c2c1C(=O)NCC2]

For the preparation of the racemic title compound see example 52. Separation of enantiomers by preparative chiral HPLC (method see example 53) gave 5.0 mg of the title compound ($R_t$=10.7-11.6 min).

Analytical chiral HPLC (method see example 53): $R_t$=3.22 min.

$^1$H-NMR (400 MHz, DMSO-$d_6$): b [ppm]=1.14-1.34 (m, 6H), 2.81-2.91 (m, 4H), 3.38-3.48 (m, 3H), 3.55 (dd, 1H), 3.69-3.85 (m, 3H), 3.85-3.93 (m, 1H), 3.99-4.06 (m, 1H), 4.09-4.17 (m, 1H), 4.25 (dd, 1H), 6.23 (dd, 1H), 6.69-6.79 (m, 2H), 7.14-7.23 (m, 2H), 7.39-7.49 (m, 1H), 7.91-8.04 (m, 1H), 8.31-8.40 (m, 1H), 10.97-11.12 (m, 1H).

Example 55

3-(3-chloro-2-ethylanilino)-2-(3-{[(2R)-4-methylmorpholin-2-yl]methoxy}pyridin-4-yl)-1,5,6,7-tetrahydro-4H-pyrrolo[3,2-c]pyridin-4-one

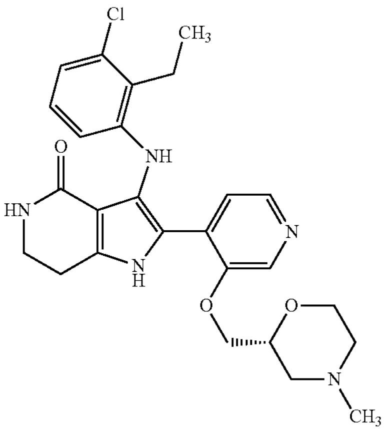 [SMILES: CCc1c(Cl)cccc1Nc1c(-c2ccncc2OC[C@H]2CN(C)CCO2)[nH]c2c1C(=O)NCC2]

Using an analogous method as described for example 41 with 3-(3-chloro-2-ethylanilino)-2-(3-{[(2R)-morpholin-2-yl]methoxy}pyridin-4-yl)-1,5,6,7-tetrahydro-4H-pyrrolo[3,2-c]pyridin-4-one (intermediate 55, 58.0 mg, 120 μmol) as the starting material; 27.5 mg (95% purity, 44% yield) of the title compound were prepared after purification by preparative HPLC (method 10, gradient: 0.00-0.50 min 30% B, 0.50-7.00 min 30-70% B).

$^1$H-NMR (400 MHz, DMSO-$d_6$): δ [ppm]=1.23 (t, 3H), 1.90 (t, 1H), 1.99-2.09 (td, 1H), 2.21 (s, 3H), 2.63-2.71 (d, 1H), 2.73-2.78 (d, 1H), 2.78-2.89 (m, 4H), 3.40-3.47 (td, 2H), 3.67 (td, 1H), 3.92-3.98 (m, 2H), 4.14 (dd, 1H), 4.27 (dd, 1H), 6.23 (dd, 1H), 6.71-6.78 (m, 2H), 7.16-7.21 (m, 2H), 7.46 (s, 1H), 7.97 (d, 1H), 8.36 (s, 1H), 11.04 (s, 1H).

LC-MS (method 2): $R_t$=1.10 min; MS (ESIpos): m/z=496 $[M+H]^+$

Example 56

3-(3-chloro-2-ethylanilino)-2-(3-{[(2S)-4-methylmorpholin-2-yl]methoxy}pyridin-4-yl)-1,5,6,7-tetrahydro-4H-pyrrolo[3,2-c]pyridin-4-one

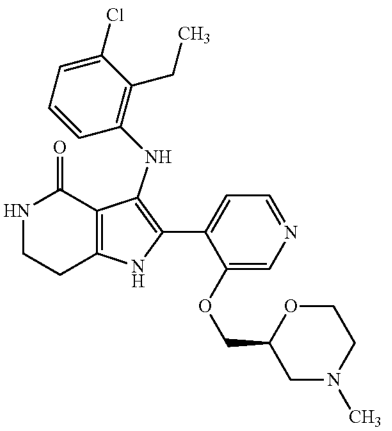 [SMILES: CCc1c(Cl)cccc1Nc1c(-c2ccncc2OC[C@@H]2CN(C)CCO2)[nH]c2c1C(=O)NCC2]

Using an analogous method as described for example 41 with 3-(3-chloro-2-ethylanilino)-2-(3-{[(2S)-morpholin-2-yl]methoxy}pyridin-4-yl)-1,5,6,7-tetrahydro-4H-pyrrolo[3,2-c]pyridin-4-one (intermediate 56, 68.0 mg, 141 μmol) as the starting material; 37.8 mg (95% purity, 51% yield) of the title compound were prepared after purification by preparative HPLC (method 10, gradient: 0.00-0.50 min 30% B, 0.50-7.00 min 30-70% B).

$^1$H-NMR (400 MHz, DMSO-$d_6$): δ [ppm]=1.23 (t, 3H), 1.90 (t, 1H), 2.00-2.08 (td, 1H), 2.21 (s, 3H), 2.63-2.72 (d, 1H), 2.72-2.81 (d, 1H), 2.81-2.90 (m, 4H), 3.44 (td, 2H), 3.67 (td, 1H), 3.91-3.99 (m, 2H), 4.13 (dd, 1H), 4.29 (dd, 1H), 6.23 (dd, 1H), 6.71-6.78 (m, 2H), 7.16-7.21 (m, 2H), 7.46 (s, 1H), 7.97 (d, 1H), 8.36 (s, 1H), 11.04 (s, 1H).

LC-MS (method 2): $R_t$=1.10 min; MS (ESIpos): m/z=496 $[M+H]^+$

Example 57

3-(3-chloro-2-methoxyanilino)-2-{3-[(1S)-1-(1,4-dioxan-2-yl)ethoxy]pyridin-4-yl}-1,5,6,7-tetrahydro-4H-pyrrolo[3,2-c]pyridin-4-one

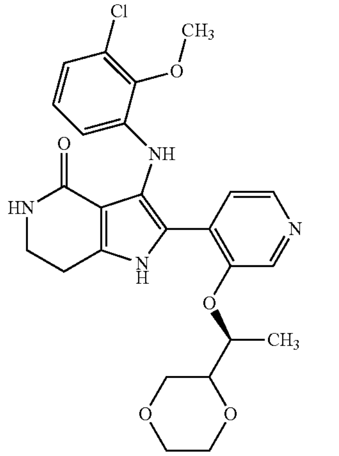 [SMILES: COc1c(Cl)cccc1Nc1c(-c2ccncc2O[C@@H](C)C2COCCO2)[nH]c2c1C(=O)NCC2]

In a microwave tube, a solution of N-(3-chloro-2-methoxyphenyl)-4-([{3-[(1 S)-1-(1,4-dioxan-2-yl)ethoxy] pyridin-4-yl}methyl)amino]-2-oxo-1,2,5,6-tetrahydropyridine-3-carbothioamide (intermediate 6-57, 380 mg, 713 μmol) in methanol (1.5 ml) was treated with TFA (55 μl, 710 μmol) followed by hydrogen peroxide (9.2 μl, 0.106 mmol), heated to 60° C. and stirred for 16 h. The reaction mixture was concentrated to dryness under reduced pressure, dissolved in DMSO and purified by preparative HPLC (method 10, gradient: 0.00-0.50 min 15% B, 0.50-5.00 min 15-50% B, 5.00-8.00 min 50% B) to give after freeze drying the desired product (174 mg, 44% yield) as mixture of two stereoisomers.

$^1$H-NMR (400 MHz, DMSO-$d_6$): δ [ppm]=1.176 (0.47), 1.192 (0.46), 1.245 (3.61), 1.261 (3.63), 1.326 (5.41), 1.342 (5.34), 2.074 (0.90), 2.518 (2.00), 2.523 (1.30), 2.832 (0.58), 2.853 (1.78), 2.871 (2.29), 2.889 (1.20), 3.374 (0.58), 3.402 (1.93), 3.412 (1.77), 3.419 (2.47), 3.427 (2.74), 3.435 (1.67), 3.442 (1.31), 3.455 (1.30), 3.464 (0.88), 3.485 (1.04), 3.493 (0.81), 3.500 (0.81), 3.522 (0.58), 3.614 (0.42), 3.643 (1.28), 3.650 (1.69), 3.669 (0.97), 3.699 (1.00), 3.725 (1.81), 3.734 (0.89), 3.748 (1.07), 3.754 (0.91), 3.768 (0.44), 3.777 (0.54), 3.783 (0.42), 3.806 (1.65), 3.813 (2.16), 3.823 (1.17), 3.836 (1.62), 3.843 (1.75), 3.850 (1.00), 3.863 (9.50), 3.890 (16.00), 3.919 (0.92), 3.948 (0.61), 4.068 (2.33), 4.626 (0.70), 4.630 (0.86), 4.643 (1.15), 4.653 (0.66), 4.658 (0.86), 6.133 (0.95), 6.143 (2.18), 6.148 (0.96), 6.151 (1.32), 6.158 (1.98), 6.167 (1.48), 6.638 (1.70), 6.643 (2.02), 6.653 (3.46), 6.678 (0.58), 6.690 (6.05), 6.699 (2.71), 6.706 (2.31), 7.122 (0.98), 7.161 (1.50), 7.264 (0.72), 7.285 (0.52), 7.294 (1.80), 7.299 (2.64), 7.307 (1.85), 7.312 (2.64), 7.440 (2.17), 7.519 (3.36), 7.631 (0.44), 7.998 (3.33), 8.011 (3.08), 8.031 (2.20), 8.044 (1.98), 8.396 (4.10), 8.411 (2.66), 11.072 (1.20), 11.085 (1.69).

LC-MS (method 6): $R_t$=0.72 min; MS (ESipos): m/z=499 $[M+H]^+$

Example 58

3-(3-chloro-2-methoxyanilino)-2-{3-[(1 S)-1-(1,4-dioxan-2-yl)ethoxy]pyridin-4-yl}-1,5,6,7-tetrahydro-4H-pyrrolo[3,2-c]pyridin-4-one (Stereoisomer 1)

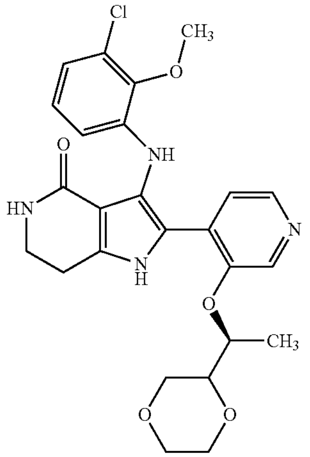 [SMILES: COc1c(Cl)cccc1Nc1c(-c2ccncc2O[C@@H](C)C2COCCO2)[nH]c2c1C(=O)NCC2]

The title compound from example 57 (170 mg) was separated into stereoisomers by preparative chiral HPLC to give title compound (stereoisomer 1, 58 mg, $R_t$=16.2-18.8 min) and stereoisomer 2 (35 mg, $R_t$=19.3-21.6 min, see example 60).

Preparative Chiral HPLC Method:

Instrument: PrepCon Labomatic HPLC; Column: YMC Cellulose SC 5μ, 250×30; eluent A: hexane+0.1 vol % diethylamine; eluent B: ethanol+0.1 vol % diethylamine; gradient: 0-15 min 20-30% B; flow: 40 ml/min; temperature: 25° C.; UV: 254 nm Analytical Chiral Analytical HPLC Method:

Instrument: Waters Alliance 2695; Column: YMC Cellulose SC 3μ, 100×4.6; eluent A: hexane+0.1 vol % diethylamine; eluent B: ethanol; isocratic: 70% A+30% B; flow: 1.4 ml/min; temperature: 25° C.; UV: 254 nm Analytical chiral HPLC: $R_t$=5.19 min.

1H-NMR (400 MHz, DMSO-$d_6$): δ [ppm]=1.157 (0.42), 1.326 (5.83), 1.342 (5.94), 2.518 (2.45), 2.523 (1.64), 2.854 (1.00), 2.872 (2.23), 2.889 (1.30), 3.159 (0.76), 3.172 (0.81), 3.403 (0.88), 3.409 (0.98), 3.420 (1.66), 3.427 (1.98), 3.435 (0.89), 3.456 (1.40), 3.469 (0.49), 3.485 (1.09), 3.493 (0.89), 3.500 (0.89), 3.522 (0.63), 3.530 (0.42), 3.699 (1.04), 3.725 (1.77), 3.748 (1.00), 3.755 (0.79), 3.777 (0.55), 3.783 (0.42), 3.806 (1.16), 3.812 (1.76), 3.824 (0.88), 3.836 (1.39), 3.843 (1.20), 3.850 (0.51), 3.890 (16.00), 3.919 (1.02), 3.948 (0.70), 4.631 (0.81), 4.646 (0.95), 4.659 (0.80), 6.143 (1.46), 6.151 (1.29), 6.159 (1.42), 6.167 (1.47), 6.679 (0.61), 6.691 (6.25), 6.699 (2.81), 6.706 (2.43), 6.727 (0.42), 7.159 (1.65), 7.298 (2.69), 7.311 (2.69), 7.518 (3.71), 7.998 (3.52), 8.010 (3.22), 8.395 (4.49), 11.084 (1.82).

Optical rotation: $[\alpha]_D$=30.21°+/−0.60° (c=1.0 g/100 ml chloroform)

LC-MS (method 6): $R_t$=0.72 min; MS (ESIpos): m/z=499 $[M+H]^+$

Example 59

3-(3-chloro-2-methoxyanilino)-2-{3-[(1 S)-1-(1,4-dioxan-2-yl)ethoxy]pyridin-4-yl}-1,5,6,7-tetrahydro-4H-pyrrolo[3,2-c]pyridin-4-one (Stereoisomer 2)

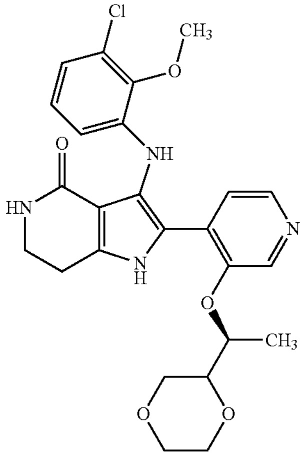 [SMILES: COc1c(Cl)cccc1Nc1c(-c2ccncc2O[C@@H](C)C2COCCO2)[nH]c2c1C(=O)NCC2]

The title compound from example 57 (170 mg) was separated into stereoisomers by preparative chiral HPLC to give title compound stereoisomer 2 (35 mg, $R_t$=19.3-21.6 min, see example 58 for method of separation).

Analytical chiral HPLC: $R_t$=5.91 min.

$^1$H-NMR (400 MHz, DMSO-$d_6$): δ [ppm]=0.798 (0.48), 0.815 (0.56), 0.822 (0.55), 0.905 (0.48), 1.084 (0.46), 1.137 (0.84), 1.156 (0.69), 1.233 (1.00), 1.246 (6.21), 1.261 (6.32), 2.084 (0.60), 2.332 (0.57), 2.518 (3.49), 2.522 (2.23), 2.673 (0.60), 2.833 (1.01), 2.850 (2.05), 2.867 (1.22), 3.308 (0.48), 3.373 (0.98), 3.402 (2.29), 3.412 (2.05), 3.418 (2.16), 3.427 (2.02), 3.435 (1.84), 3.442 (1.19), 3.465 (0.79), 3.607 (0.46), 3.614 (0.62), 3.643 (2.17), 3.670 (1.14), 3.726 (0.62), 3.732 (0.73), 3.738 (0.65), 3.744 (0.72), 3.751 (0.57), 3.757 (0.63), 3.762 (0.57), 3.768 (0.57), 3.805 (1.25), 3.815 (1.51), 3.821 (1.12), 3.834 (1.01), 3.844 (1.36), 3.850 (1.08), 3.863 (16.00), 3.889 (0.74), 4.625 (0.83), 4.637 (0.87), 4.641 (0.90), 4.653 (0.81), 6.133 (1.40), 6.143 (1.44), 6.147 (1.32), 6.157 (1.50), 6.639 (2.71), 6.643 (3.20), 6.653 (5.57), 6.663 (0.45), 7.120 (1.71), 7.294 (2.55), 7.307 (2.61), 7.438 (3.73), 8.031 (2.89), 8.043 (2.69), 8.411 (4.05), 11.071 (1.88).

Optical rotation: $[\alpha]_D$=19.87°+/−0.91° (c=1.0 g/100 ml chloroform)

LC-MS (method 6): $R_t$=0.72 min; MS (ESIpos): m/z=499 $[M+H]^+$

Example 60

3-(3-chloro-2-methoxyanilino)-2-{3-[(1R)-1-(1,4-dioxan-2-yl)ethoxy]pyridin-4-yl}-1,5,6,7-tetrahydro-4H-pyrrolo[3,2-c]pyridin-4-one (Stereoisomer 1)

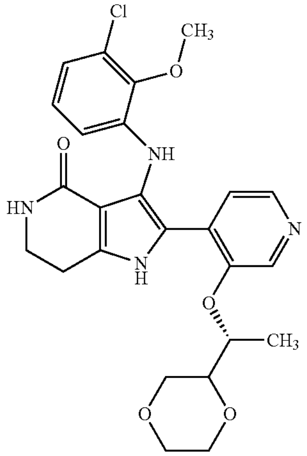 [SMILES: COc1c(Cl)cccc1Nc1c(-c2ccncc2O[C@H](C)C2COCCO2)[nH]c2c1C(=O)NCC2]

Using an analogous method as described for example 57 with N-(3-chloro-2-methoxyphenyl)-4-{[(3-{(1R)-1-[1,4-dioxan-2-yl]ethoxy}pyridin-4-yl)methyl]amino}-2-oxo-1,2,5,6-tetrahydropyridine-3-carbothioamide (intermediate 6-60, 340 mg, 638 μmol) as the starting material; 76.0 mg (99% purity, 24% yield) of the title compound (stereoisomer 1, $R_t$=18.7-22.0 min) were prepared after purification by preparative HPLC (method 10, gradient: 0.00-0.50 min 15% B, 0.50-5.00 min 15-50% B, 5.00-8.00 min 50% B) followed by chiral prep. HPLC. Additionally 7 mg of stereoisomer 2 (example 61) ($R_t$=16.5-17.9 min) was isolated.

Preparative Chiral HPLC Method:

Instrument: PrepCon Labomatic HPLC; Column: YMC Cellulose SB 5μ, 250×30; eluent A: hexane+0.1 vol % diethylamine; eluent B: ethanol+0.1 vol % diethylamine; isocratic: 80% A+20% B; flow: 60 ml/min; temperature: 25° C.; UV: 254 nm Analytical Chiral Analytical HPLC Method:

Instrument: Waters Alliance 2695; Column: YMC Cellulose SB 3μ, 100×4.6; eluent A: hexane+0.1 vol % diethylamine; eluent B: ethanol; isocratic: 80% A+20% B; flow: 1.4 ml/min; temperature: 25° C.; UV: 254 nm Analytical chiral HPLC: $R_t$=6.96 min.

$^1$H-NMR (400 MHz, DMSO-$d_6$): δ [ppm]=1.245 (5.93), 1.261 (5.97), 2.518 (0.96), 2.522 (0.61), 2.833 (0.89), 2.850 (1.81), 2.868 (1.07), 3.374 (0.88), 3.398 (1.92), 3.402 (2.05), 3.412 (1.84), 3.418 (1.88), 3.427 (1.81), 3.435 (1.62), 3.442 (1.07), 3.465 (0.71), 3.608 (0.45), 3.614 (0.62), 3.643 (2.07), 3.669 (1.04), 3.726 (0.57), 3.733 (0.70), 3.736 (0.65), 3.744 (0.69), 3.751 (0.53), 3.757 (0.58), 3.762 (0.53), 3.768 (0.55), 3.805 (1.12), 3.815 (1.32), 3.821 (0.99), 3.834 (0.89), 3.844 (1.24), 3.850 (0.97), 3.864 (16.00), 3.890 (0.81), 4.068 (0.46), 4.626 (0.76), 4.637 (0.80), 4.641 (0.83), 4.653 (0.76), 6.133 (1.41), 6.143 (1.51), 6.148 (1.26), 6.158 (1.48), 6.638 (2.78), 6.643 (3.34), 6.653 (5.70), 6.663 (0.46), 7.122 (1.57), 7.294 (2.67), 7.307 (2.70), 7.440 (3.53), 8.031 (3.75), 8.044 (3.34), 8.411 (4.42), 11.072 (1.72).

LC-MS (method 6): $R_t$=0.72 min; MS (ESipos): m/z=499 $[M+H]^+$

Example 61

3-(3-chloro-2-methoxyanilino)-2-(3-{(1R)-1-[(1,4-dioxan-2-yl]ethoxy}pyridin-4-yl)-1,5,6,7-tetrahydro-4H-pyrrolo[3,2-c]pyridin-4-one (Stereoisomer 2)

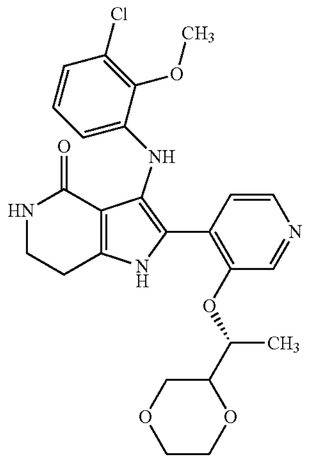 [SMILES: COc1c(Cl)cccc1Nc1c(-c2ccncc2O[C@H](C)C2COCCO2)[nH]c2c1C(=O)NCC2]

For the preparation of title compound as mixture of two diastereomeres see example 60. Separation of enantiomers by preparative chiral HPLC (method see example 60) gave 7.0 mg of the title compound ($R_t$=9.4-10.8 min).

Analytical chiral HPLC (method see example 60): $R_t$=6.10 min.

Optical rotation: $[\alpha]_D$=−3.38°+/−0.78° (c=3.7 mg/ml, chloroform).

Example 62

3-(3-fluoro-2-methylanilino)-2-(3-{[4-methylmorpholin-2-yl]methoxy}pyridin-4-yl)-1,5,6,7-tetrahydro-4H-pyrrolo[3,2-c]pyridin-4-one

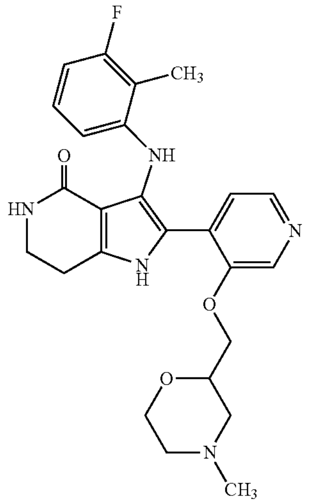 [SMILES: Cc1c(F)cccc1Nc1c(-c2ccncc2OCC2CN(C)CCO2)[nH]c2c1C(=O)NCC2]

To a solution of N-(3-fluoro-2-methylphenyl)-4-{[(3-{[4-methylmorpholin-2-yl]methoxy}pyridin-4-yl)methyl]amino}-2-oxo-1,2,5,6-tetrahydropyridine-3-carbothioamide (intermediate 6-62, 110 mg, 220 μmol) in acetic acid (1.1 ml) was added aqueous hydrogen peroxide (45 μl, 30% purity, 440 μM) and the mixture was heated at 80° C. for 2 h. The reaction mixture was quenched with saturated sodium thiosulfate solution and pH 7 was adjusted by addition of aqueous 4M sodium hydroxide solution. After addition of DCM the mixture was stirred for 15 min at RT. The phases were separated und the aqueous phase extracted with DCM. The combined organic layers were dried by hydrophobic filter paper and concentrated under reduced pressure. The mixture was purified by prep. HPLC (method 10) to give the title compound; 28 mg (97% purity, 26% yield).

$^1$H-NMR (400 MHz, DMSO-$d_6$): δ [ppm]=1.877 (1.11), 1.904 (1.76), 1.931 (1.15), 2.007 (0.48), 2.016 (0.62), 2.036 (1.18), 2.044 (1.14), 2.064 (0.65), 2.074 (0.91), 2.188 (9.04), 2.191 (9.20), 2.204 (16.00), 2.326 (0.50), 2.518 (1.93), 2.522 (1.23), 2.647 (1.09), 2.669 (1.06), 2.673 (1.34), 2.743 (1.21), 2.770 (1.13), 2.844 (1.64), 2.861 (3.54), 2.878 (1.85), 3.410 (1.18), 3.415 (1.29), 3.426 (2.35), 3.432 (2.33), 3.443 (1.13), 3.449 (1.04), 3.642 (0.55), 3.648 (0.70), 3.670 (1.28), 3.675 (1.30), 3.698 (0.76), 3.703 (0.63), 3.935 (1.65), 3.942 (1.53), 3.951 (0.92), 3.962 (1.44), 3.967 (1.29), 4.109 (1.20), 4.126 (1.08), 4.135 (1.56), 4.151 (1.27), 4.276 (1.43), 4.285 (1.48), 4.301 (1.18), 4.310 (1.07), 6.056 (2.20), 6.076 (2.25), 6.442 (1.00), 6.464 (1.83), 6.486 (1.13), 6.735 (0.68), 6.755 (1.42), 6.772 (1.36), 6.793 (0.57), 7.188 (2.26), 7.230 (3.88), 7.242 (3.85), 7.346 (4.43), 7.979 (5.07), 7.991 (4.58), 8.368 (6.78), 11.029 (2.41).

LC-MS (method 6): $R_t$=0.46 min; MS (ESIpos): m/z=466 $[M+H]^+$

Example 63

3-(3-fluoro-2-methylanilino)-2-(3-{[4-methylmorpholin-2-yl]methoxy}pyridin-4-yl)-1,5,6,7-tetrahydro-4H-pyrrolo[3,2-c]pyridin-4-one (stereoisomer 1)

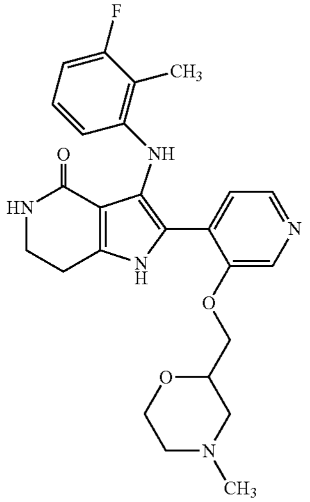 [SMILES: Cc1c(F)cccc1Nc1c(-c2ccncc2OCC2CN(C)CCO2)[nH]c2c1C(=O)NCC2]

The title compound from example 62 (21 mg) was separated into enantiomers by preparative chiral HPLC to give title compound (stereoisomer 1, 7.0 mg, $R_t$=7.1-8.1 min) and stereoisomer 2 (9.0 mg, $R_t$=9.4-10.8 min, see example 64).

Preparative Chiral HPLC Method:

Instrument: PrepCon Labomatic HPLC; Column: YMC Cellulose SB 5μ, 250×30; eluent A: methyl tert-butyl ether+0.1 vol % diethylamine; eluent B: acetonitrile; isocratic: 50% A+50% B; flow: 60 ml/min; temperature: 25° C.; UV: 254 nm Analytical Chiral HPLC Method:

Instrument: Waters Alliance 2695; Column: YMC Cellulose SB 3μ, 100×4.6; eluent A: methyl tert-butyl ether+0.1 vol % diethylamine; eluent B: acetonitrile; isocratic: 50% A+50% B; flow: 1.4 ml/min; temperature: 25° C.; UV: 254 nm Analytical chiral HPLC: $R_t$=2.60 min.

Optical rotation: $[\alpha]_D$=21.60°+/−1.04° (c=1.0 g/100 ml chloroform)

1H-NMR (400 MHz, DMSO-$d_6$): δ [ppm]=1.232 (0.89), 1.877 (1.15), 1.904 (1.74), 1.931 (1.14), 2.008 (0.48), 2.016 (0.62), 2.036 (1.17), 2.044 (1.15), 2.064 (0.65), 2.073 (0.56), 2.188 (9.17), 2.191 (9.34), 2.204 (16.00), 2.322 (0.45), 2.327 (0.62), 2.332 (0.45), 2.518 (2.49), 2.523 (1.54), 2.646 (1.12), 2.669 (1.21), 2.673 (1.46), 2.743 (1.23), 2.770 (1.15), 2.844 (1.60), 2.861 (3.42), 2.878 (1.82), 3.410 (1.23), 3.415 (1.32), 3.426 (2.40), 3.432 (2.38), 3.444 (1.15), 3.449 (1.07), 3.641 (0.56), 3.648 (0.70), 3.670 (1.28), 3.675 (1.31), 3.698 (0.76), 3.703 (0.61), 3.935 (1.67), 3.942 (1.57), 3.951 (0.95), 3.962 (1.45), 4.109 (1.14), 4.126 (1.03), 4.135 (1.51), 4.152 (1.21), 4.276 (1.39), 4.285 (1.43), 4.301 (1.14), 4.310 (1.03), 6.056 (2.16), 6.076 (2.23), 6.442 (1.01), 6.464 (1.85), 6.486 (1.14), 6.735 (0.67), 6.755 (1.42), 6.772 (1.37), 6.793 (0.56), 7.188 (2.29), 7.230 (3.04), 7.243 (3.00), 7.345 (4.40), 7.979 (3.05), 7.991 (2.83), 8.368 (4.67), 11.030 (2.40).

LC-MS (method 6): $R_t$=0.46 min; MS (ESipos): m/z=466 $[M+H]^+$

Example 64

3-(3-fluoro-2-methylanilino)-2-(3-{[4-methylmorpholin-2-yl]methoxy}pyridin-4-yl)-1,5,6,7-tetrahydro-4H-pyrrolo[3,2-c]pyridin-4-one (stereoisomer 2)

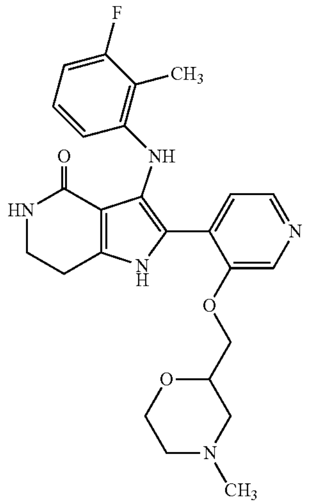 [SMILES: Cc1c(F)cccc1Nc1c(-c2ccncc2OCC2CN(C)CCO2)[nH]c2c1C(=O)NCC2]

For the preparation of the racemic title compound see example 63. Separation of enantiomers by preparative chiral HPLC (method see example 63) to give 9.0 mg of the title compound ($R_t$=9.4-10.8 min).

Analytical chiral HPLC (method see example 63): $R_t$=3.37 min.

Optical rotation: $[\alpha]_D$=−20.75°+/−1.29° (c=1.0 g/100 ml in Chloroform)

$^1$H-NMR (400 MHz, DMSO-$d_6$): δ [ppm]=1.232 (0.99), 1.877 (1.12), 1.904 (1.80), 1.931 (1.15), 2.008 (0.49), 2.016 (0.64), 2.036 (1.17), 2.044 (1.15), 2.065 (0.66), 2.073 (0.57), 2.188 (9.36), 2.191 (9.48), 2.204 (16.00), 2.323 (0.47), 2.327 (0.62), 2.332 (0.47), 2.518 (2.39), 2.522 (1.44), 2.647 (1.15), 2.669 (1.24), 2.673 (1.48), 2.743 (1.24), 2.770 (1.16), 2.844 (1.63), 2.861 (3.47), 2.878 (1.82), 3.410 (1.27), 3.415 (1.36), 3.426 (2.43), 3.432 (2.39), 3.443 (1.17), 3.449 (1.07), 3.642 (0.56), 3.648 (0.70), 3.670 (1.30), 3.675 (1.30), 3.698 (0.75), 3.703 (0.63), 3.935 (1.71), 3.942 (1.60), 3.962 (1.47), 4.109 (1.17), 4.126 (1.03), 4.135 (1.51), 4.152 (1.22), 4.276 (1.40), 4.285 (1.45), 4.301 (1.13), 4.310 (1.03), 6.056 (2.19), 6.076 (2.26), 6.442 (1.05), 6.464 (1.87), 6.486 (1.15), 6.735 (0.70), 6.755 (1.43), 6.772 (1.38), 6.793 (0.56), 7.188 (2.30), 7.230 (3.03), 7.243 (3.07), 7.346 (4.46), 7.979 (3.01), 7.992 (2.84), 8.368 (4.73), 11.030 (2.43).

LC-MS (method 6): $R_t$=0.46 min; MS (ESipos): m/z=466 $[M+H]^+$

Example 65

2-(3-{[1,4-dioxan-2-yl]methoxy}pyridin-4-yl)-3-(2-ethyl-3-fluoroanilino)-1,5,6,7-tetrahydro-4H-pyrrolo[3,2-c]pyridin-4-one

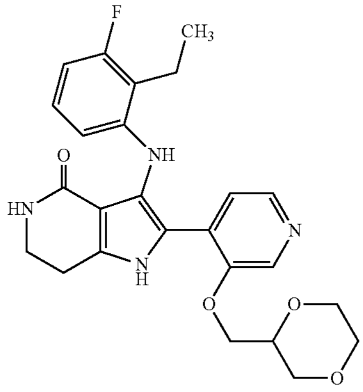 [SMILES: CCc1c(F)cccc1Nc1c(-c2ccncc2OCC2COCCO2)[nH]c2c1C(=O)NCC2]

Using an analogous method as described for example 62 with 4-{[(3-{[1,4-dioxan-2-yl]methoxy}pyridin-4-yl)methyl]amino}-N-(2-ethyl-3-fluorophenyl)-2-oxo-1,2,5,6-tetrahydropyridine-3-carbothioamide (intermediate 6-65, 215 mg, 429 μmol) as the starting material; 76.0 mg (95% purity, 36% yield) of the title compound were prepared after purification by preparative HPLC (basic conditions).

$^1$H-NMR (400 MHz, DMSO-$d_6$) delta [ppm]: 1.097 (0.45), 1.206 (6.70), 1.225 (16.00), 1.244 (6.93), 2.322 (0.88), 2.327 (1.21), 2.332 (0.88), 2.518 (4.46), 2.522 (2.73), 2.664 (1.18), 2.669 (1.70), 2.673 (2.02), 2.697 (3.88), 2.715 (3.73), 2.732 (1.31), 2.847 (3.66), 2.864 (7.84), 2.881 (4.11), 3.404 (3.38), 3.415 (2.84), 3.420 (3.17), 3.432 (8.74), 3.437 (5.90), 3.449 (2.86), 3.457 (4.93), 3.506 (1.16), 3.511 (1.46), 3.533 (2.58), 3.540 (2.78), 3.562 (2.02), 3.570 (1.77), 3.711 (3.25), 3.719 (1.53), 3.726 (2.41), 3.738 (2.86), 3.749 (3.64), 3.756 (2.33), 3.777 (2.11), 3.783 (1.59), 3.804 (2.97), 3.810 (3.25), 3.833 (2.65), 3.839 (2.67), 3.887 (2.80), 3.915 (2.07), 4.005 (0.73), 4.013 (1.16), 4.021 (1.72), 4.029 (1.94), 4.036 (1.90), 4.045 (1.57), 4.054 (1.36), 4.061 (0.97), 4.106 (3.19), 4.123 (2.20), 4.132 (4.05), 4.149 (3.10), 4.246 (3.66), 4.255 (3.60), 4.272 (2.73), 4.281 (2.45), 6.084 (4.91), 6.104 (5.10), 6.433 (2.28), 6.454 (4.07), 6.476 (2.61), 6.720 (1.92), 6.741 (3.81), 6.758 (3.70), 6.778 (1.62), 7.180 (5.15), 7.199 (8.92), 7.212 (8.89), 7.427 (9.02), 7.964 (12.58), 7.976 (11.33), 8.358 (15.85), 11.012 (5.43).

LC-MS (method 6): $R_t$=0.70 min; MS (ESipos): m/z=467 $[M+H]^+$

Example 66, Example 67

2-(3-{[(2R)-1,4-dioxan-2-yl]methoxy}pyridin-4-yl)-3-(2-ethyl-3-fluoroanilino)-1,5,6,7-tetrahydro-4H-pyrrolo[3,2-c]pyridin-4-one 2-(3-{[(2S)-1,4-dioxan-2-yl]methoxy}pyridin-4-yl)-3-(2-ethyl-3-fluoroanilino)-1,5,6,7-tetrahydro-4H-pyrrolo[3,2-c]pyridin-4-one Example 66

2-(3-{[1,4-dioxan-2-yl]methoxy}pyridin-4-yl)-3-(2-ethyl-3-fluoroanilino)-1,5,6,7-tetrahydro-4H-pyrrolo[3,2-c]pyridin-4-one (stereoisomer 1)

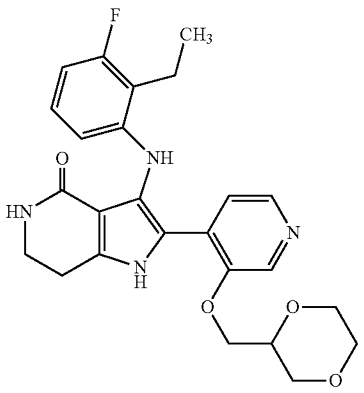 [SMILES: CCc1c(F)cccc1Nc1c(-c2ccncc2OCC2COCCO2)[nH]c2c1C(=O)NCC2]

The title compound from example 65 (74 mg) was separated into enantiomers by preparative chiral HPLC to give title compound (stereoisomer 1, 30 mg, $R_t$=4.5-5.3 min) and stereoisomer 2 (31 mg, $R_t$=5.3-6.2 min, see example 67).

Preparative Chiral HPLC Method:

Instrument: PrepCon Labomatic HPLC; Column: YMC Cellulose SB 10μ, 250×50; eluent A: methyl tert-butyl ether+0.1 vol % diethylamine; eluent B: methanol; isocratic: 90% A+10% B; flow: 150 ml/min; temperature: 25° C.; UV: 254 nm Analytical Chiral HPLC Method:

Instrument: Waters Alliance 2695; Column: YMC Cellulose SB 3μ, 100×4.6; eluent A: methyl tert-butyl ether+0.1 vol % diethylamine; eluent B: methanol; isocratic: 90% A+10% B; flow: 1.4 ml/min; temperature: 25° C.; UV: 254 nm Analytical chiral HPLC: $R_t$=4.41 min.

Optical rotation: $[\alpha]_D$=−21.9°+/−0.60° (c=1.0 g/100 ml chloroform)

$^1$H-NMR (400 MHz, DMSO-$d_6$) δ [ppm]: 1.097 (0.44), 1.104 (0.61), 1.206 (6.68), 1.225 (16.00), 1.243 (7.03), 2.074 (3.21), 2.322 (1.00), 2.326 (1.39), 2.332 (1.01), 2.518 (6.14), 2.522 (3.75), 2.664 (1.33), 2.669 (1.92), 2.673 (2.17), 2.696 (3.92), 2.715 (3.83), 2.732 (1.29), 2.846 (3.62), 2.864 (7.78), 2.881 (4.15), 3.404 (3.29), 3.414 (2.85), 3.420 (3.24), 3.431 (8.73), 3.437 (6.06), 3.448 (2.90), 3.457 (4.88), 3.505 (1.14), 3.511 (1.37), 3.533 (2.57), 3.540 (2.76), 3.562 (1.97), 3.570 (1.73), 3.711 (3.19), 3.719 (1.56), 3.726 (2.37), 3.738 (2.90), 3.749 (3.58), 3.755 (2.31), 3.777 (1.96), 3.783 (1.46), 3.804 (2.93), 3.810 (3.13), 3.833 (2.59), 3.839 (2.71), 3.887 (2.80), 3.914 (2.06), 4.013 (1.15), 4.020 (1.68), 4.029 (1.97), 4.036 (1.90), 4.045 (1.59), 4.053 (1.40), 4.060 (0.95), 4.106 (3.06), 4.122 (2.09), 4.132 (3.85), 4.148 (2.90), 4.245 (3.58), 4.255 (3.47), 4.271 (2.68), 4.280 (2.36), 6.083 (4.88), 6.104 (5.09), 6.433 (2.24), 6.454 (4.08), 6.476 (2.56), 6.720 (1.80), 6.741 (3.65), 6.758 (3.54), 6.778 (1.53), 7.179 (5.11), 7.199 (8.20), 7.211 (8.15), 7.426 (8.99), 7.963 (9.54), 7.976 (8.80), 8.357 (13.39), 11.012 (5.48).

LC-MS (method 6): $R_t$=0.70 min; MS (ESIpos): m/z=467 $[M+H]^+$

Example 67

2-(3-{[1,4-dioxan-2-yl]methoxy}pyridin-4-yl)-3-(2-ethyl-3-fluoroanilino)-1,5,6,7-tetrahydro-4H-pyrrolo[3,2-c]pyridin-4-one (stereoisomer 2)

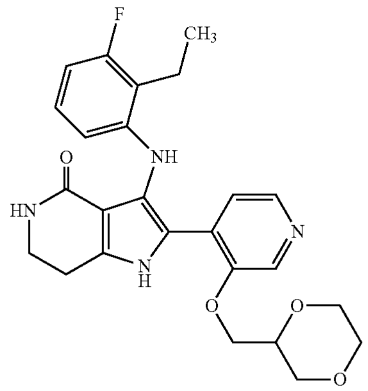 [SMILES: CCc1c(F)cccc1Nc1c(-c2ccncc2OCC2COCCO2)[nH]c2c1C(=O)NCC2]

For the preparation of the racemic title compound see example 65. Separation of enantiomers by preparative chiral HPLC (method see example 66) to give 31 mg of the title compound.

Analytical chiral HPLC (method see example 63): $R_t$=4.49 min.

Optical rotation: $[\alpha]_D$=22.51°+/−0.86° (c=1.0 g/100 ml in Chloroform)

$^1$H-NMR (400 MHz, DMSO-$d_6$) δ [ppm]: 1.104 (0.57), 1.164 (0.90), 1.206 (6.89), 1.225 (16.00), 1.244 (7.18), 2.322 (0.60), 2.326 (0.81), 2.332 (0.59), 2.518 (3.44), 2.522 (2.12), 2.665 (0.84), 2.669 (1.32), 2.677 (1.68), 2.696 (3.95), 2.715 (3.83), 2.732 (1.33), 2.847 (3.68), 2.864 (7.81), 2.881 (4.16), 3.404 (3.21), 3.415 (2.88), 3.421 (3.23), 3.432 (8.92), 3.437 (6.02), 3.449 (2.91), 3.457 (4.87), 3.506 (1.11), 3.511 (1.37), 3.533 (2.61), 3.540 (2.72), 3.562 (2.00), 3.570 (1.74), 3.712 (3.25), 3.719 (1.51), 3.726 (2.32), 3.738 (2.93), 3.749 (3.59), 3.756 (2.31), 3.777 (1.96), 3.784 (1.44), 3.804 (2.94), 3.810 (3.18), 3.833 (2.64), 3.839 (2.70), 3.887 (2.87), 3.915 (2.12), 4.005 (0.70), 4.014 (1.17), 4.020 (1.70), 4.029 (2.01), 4.037 (1.92), 4.045 (1.57), 4.053 (1.42), 4.060 (0.95), 4.106 (3.05), 4.123 (2.12), 4.132 (3.86), 4.148 (2.88), 4.246 (3.51), 4.255 (3.49), 4.271 (2.68), 4.281 (2.35), 6.084 (4.92), 6.105 (5.14), 6.433 (2.23), 6.454 (4.07), 6.476 (2.59), 6.720 (1.81), 6.741 (3.64), 6.758 (3.58), 6.778 (1.55), 7.180 (5.16), 7.199 (7.86), 7.212 (7.80), 7.426 (9.02), 7.963 (7.86), 7.976 (7.32), 8.358 (12.12), 11.012 (5.54).

LC-MS (method 6): $R_t$=0.70 min; MS (ESIpos): m/z=467 $[M+H]^+$

Example 68

2-(3-{[5,5-dimethyl-1,4-dioxan-2-yl]methoxy}pyridin-4-yl)-3-(2-ethyl-3-fluoroanilino)-1,5,6,7-tetrahydro-4H-pyrrolo[3,2-c]pyridin-4-one

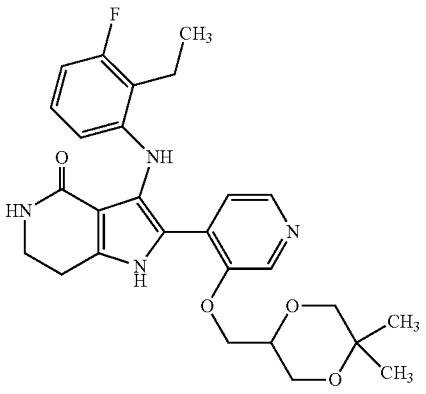 [SMILES: CCc1c(F)cccc1Nc1c(-c2ccncc2OCC2COC(C)(C)CO2)[nH]c2c1C(=O)NCC2]

Using an analogous method as described for example 62 with 4-{[(3-{[5,5-dimethyl-1,4-dioxan-2-yl]methoxy}pyridin-4-yl)methyl]amino}-N-(2-ethyl-3-fluorophenyl)-2-oxo-1,2,5,6-tetrahydropyridine-3-carbothioamide (intermediate 6-68, 350 mg, 662 μmol) as the starting material; 82 mg (85% purity, 21% yield) of the title compound were prepared after purification by preparative HPLC (basic conditions).

$^1$H-NMR (400 MHz, DMSO-$d_6$) δ [ppm]: 1.051 (1.89), 1.073 (11.18), 1.171 (0.57), 1.182 (0.76), 1.197 (3.04), 1.216 (5.73), 1.234 (3.31), 1.243 (10.52), 2.326 (0.46), 2.518 (1.69), 2.522 (1.07), 2.539 (16.00), 2.669 (0.94), 2.673 (0.76), 2.688 (1.36), 2.706 (1.38), 2.828 (1.23), 2.845 (2.62), 2.862 (1.40), 3.412 (2.22), 3.422 (1.93), 3.428 (1.91), 3.440 (2.37), 3.574 (0.81), 3.582 (0.90), 3.604 (1.34), 3.612 (1.29), 3.629 (0.40), 3.646 (2.91), 3.674 (3.37), 3.703 (0.90), 3.896 (0.52), 3.903 (0.59), 3.912 (0.74), 3.920 (0.70), 3.929 (0.49), 3.938 (0.47), 4.129 (0.89), 4.146 (0.81), 4.155 (1.16), 4.172 (1.00), 4.284 (1.20), 4.292 (1.15), 4.310 (0.88), 4.319 (0.81), 5.758 (2.21), 6.089 (1.68), 6.110 (1.75), 6.420 (0.77), 6.443 (1.38), 6.464 (0.88), 6.709 (0.64), 6.729 (1.28), 6.746 (1.24), 6.767 (0.55), 7.165 (1.72), 7.200 (2.88), 7.213 (2.92), 7.249 (0.48), 7.369 (0.47), 7.382 (0.67), 7.392 (2.91), 7.972 (3.81), 7.985 (3.48), 8.067 (0.61), 8.080 (0.54), 8.372 (5.10), 8.439 (0.78), 11.018 (1.92).

LC-MS (method 6): $R_t$=0.79 min; MS (ESIpos): m/z=495 $[M+H]^+$

Example 69, Example 70

2-(3-{[(2R)-5,5-dimethyl-1,4-dioxan-2-yl]methoxy}pyridin-4-yl)-3-(2-ethyl-3-fluoroanilino)-1,5,6,7-tetrahydro-4H-pyrrolo[3,2-c]pyridin-4-one 2-(3-{[(2S)-5,5-dimethyl-1,4-dioxan-2-yl]methoxy}pyridin-4-yl)-3-(2-ethyl-3-fluoroanilino)-1,5,6,7-tetrahydro-4H-pyrrolo[3,2-c]pyridin-4-one Example 69

2-(3-{[5,5-dimethyl-1,4-dioxan-2-yl]methoxy}pyridin-4-yl)-3-(2-ethyl-3-fluoroanilino)-1,5,6,7-tetrahydro-4H-pyrrolo[3,2-c]pyridin-4-one (stereoisomer 1)

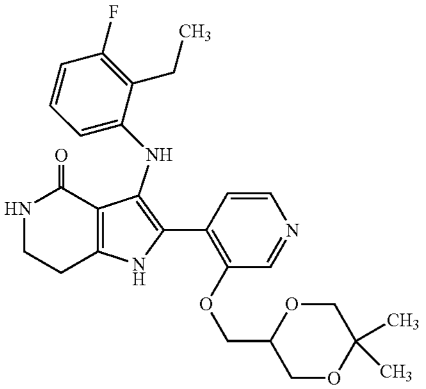 [SMILES: CCc1c(F)cccc1Nc1c(-c2ccncc2OCC2COC(C)(C)CO2)[nH]c2c1C(=O)NCC2]

The title compound from example 68 (32 mg) was separated into enantiomers by preparative chiral HPLC to give title compound (stereoisomer 1, 13 mg, $R_t$=36.8-46.0 min) and stereoisomer 2 (10 mg, $R_t$=21.9-26.4 min., see example 70)

Preparative Chiral HPLC Method:

Instrument: PrepCon Labomatic HPLC-4; Column: Chiralcel OD-H 5μ, 250×20; eluent A: hexane+0.1 vol % diethylamine; eluent B: 2-propanol; isocratic: 70% A+30% B; flow: 10 ml/min; temperature: 25° C.; UV: 254 nm Analytical Chiral HPLC Method:

Instrument: Thermo Fisher UltiMate 3000; Column: Chiralcel OD-H 5μ, 100×4.6; eluent A: hexane+0.1 vol % diethylamine; eluent B: 2-propanol; isocratic: 70% A+30% B; flow: 1.4 ml/min; temperature: 25° C.; UV: 254 nm Analytical chiral HPLC: $R_t$=7.38 min.

Optical rotation: $[\alpha]_D$=−24.42°+/−0.72° (c=1.0 g/100 ml chloroform)

$^1$H-NMR (400 MHz, DMSO-$d_6$) δ [ppm]: 0.698 (1.11), 0.742 (0.61), 0.834 (0.47), 0.851 (0.63), 1.072 (16.00), 1.147 (1.48), 1.195 (4.00), 1.214 (8.27), 1.233 (6.80), 1.242 (15.37), 1.294 (0.70), 2.322 (0.63), 2.326 (0.85), 2.331 (0.63), 2.517 (3.89), 2.522 (2.40), 2.664 (1.17), 2.668 (1.54), 2.673 (1.19), 2.687 (1.95), 2.705 (1.86), 2.722 (0.66), 2.826 (1.78), 2.843 (3.74), 2.860 (2.02), 3.411 (3.06), 3.420 (2.79), 3.427 (2.73), 3.440 (3.33), 3.573 (0.89), 3.581 (1.05), 3.603 (1.84), 3.611 (1.82), 3.646 (3.73), 3.674 (4.44), 3.703 (1.16), 3.893 (0.70), 3.901 (0.84), 3.910 (1.06), 3.918 (0.98), 3.926 (0.71), 3.935 (0.66), 4.126 (1.20), 4.143 (1.14), 4.152 (1.62), 4.169 (1.39), 4.281 (1.52), 4.290 (1.61), 4.307 (1.22), 4.316 (1.10), 6.088 (2.37), 6.108 (2.47), 6.417 (1.08), 6.440 (1.96), 6.461 (1.24), 6.707 (0.87), 6.728 (1.74), 6.745 (1.70), 6.765

(0.75), 7.159 (2.50), 7.197 (3.08), 7.209 (3.08), 7.378 (4.32), 7.967 (2.35), 7.980 (2.25), 8.368 (3.77), 11.014 (2.75).

LC-MS (method 6): $R_t$=0.78 min; MS (ESIpos): m/z=495 $[M+H]^+$

Example 70

2-(3-{[5,5-dimethyl-1,4-dioxan-2-yl]methoxy}pyridin-4-yl)-3-(2-ethyl-3-fluoroanilino)-1,5,6,7-tetrahydro-4H-pyrrolo[3,2-c]pyridin-4-one (stereoisomer 2)

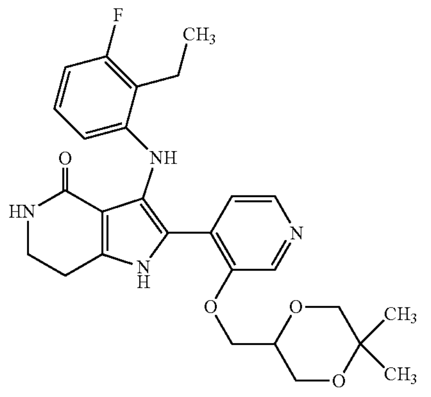 [SMILES: CCc1c(F)cccc1Nc1c(-c2ccncc2OCC2COC(C)(C)CO2)[nH]c2c1C(=O)NCC2]

For the preparation of the racemic title compound see example 68. Separation of enantiomers by preparative chiral HPLC (method see example 69) to give 10 mg of the title compound.

Analytical chiral HPLC (method see example 69): $R_t$=5.50 min.

Optical rotation: $[\alpha]_D$=33.52°+/−1.07° (c=1.0 g/100 ml in Chloroform)

$^1$H-NMR (400 MHz, DMSO-$d_6$) δ [ppm]: 0.852 (0.50), 1.072 (16.00), 1.147 (0.81), 1.195 (3.63), 1.214 (8.06), 1.233 (5.99), 1.242 (15.29), 2.322 (0.67), 2.326 (0.93), 2.331 (0.67), 2.518 (4.20), 2.522 (2.70), 2.664 (1.19), 2.668 (1.61), 2.673 (1.22), 2.687 (1.88), 2.705 (1.81), 2.722 (0.65), 2.826 (1.76), 2.843 (3.72), 2.860 (1.98), 3.411 (2.99), 3.420 (2.72), 3.427 (2.69), 3.440 (3.28), 3.573 (0.90), 3.582 (1.04), 3.603 (1.85), 3.611 (1.82), 3.646 (3.73), 3.674 (4.50), 3.703 (1.19), 3.893 (0.69), 3.901 (0.82), 3.910 (1.04), 3.918 (0.98), 3.927 (0.70), 3.935 (0.65), 4.126 (1.23), 4.143 (1.15), 4.152 (1.63), 4.169 (1.40), 4.281 (1.53), 4.290 (1.62), 4.307 (1.24), 4.316 (1.12), 6.088 (2.36), 6.108 (2.47), 6.419 (1.10), 6.440 (1.96), 6.461 (1.24), 6.707 (0.90), 6.728 (1.77), 6.744 (1.72), 6.765 (0.75), 7.159 (2.47), 7.196 (3.38), 7.209 (3.41), 7.378 (4.36), 7.967 (2.84), 7.980 (2.69), 8.368 (4.39), 11.014 (2.71).

LC-MS (method 6): $R_t$=0.78 min; MS (ESIpos): m/z=495 $[M+H]^+$

Example 71

3-(3-chloro-2-methoxyanilino)-2-[3-({1-[4-methylmorpholin-2-yl]ethyl}oxy)pyridin-4-yl]-1,5,6,7-tetrahydro-4H-pyrrolo[3,2-c]pyridin-4-one

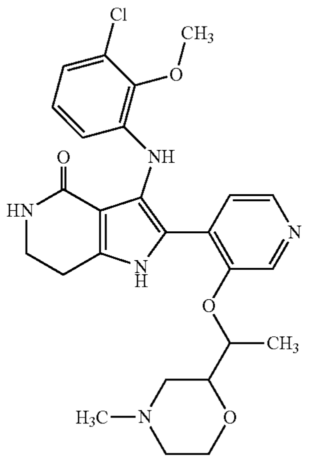 [SMILES: COc1c(Cl)cccc1Nc1c(-c2ccncc2OC(C)C2CN(C)CCO2)[nH]c2c1C(=O)NCC2]

Using an analogous method as described for example 62 with N-(3-chloro-2-methoxyphenyl)-4-({[3-({1-[4-methylmorpholin-2-yl]ethyl}oxy)pyridin-4-yl]methyl}amino)-2-oxo-1,2,5,6-tetrahydropyridine-3-carbothioamide (intermediate 6-71, 420 mg, 769 μmol) as the starting material; 139 mg (95% purity, 33% yield) of the title compound were prepared after purification by preparative HPLC (basic conditions).

$^1$H-NMR (400 MHz, DMSO-$d_6$) δ [ppm]: 1.277 (4.27), 1.293 (4.32), 1.333 (0.47), 1.350 (0.67), 1.358 (4.99), 1.374 (4.94), 1.824 (0.55), 1.851 (0.91), 1.878 (0.61), 1.893 (0.74), 1.906 (0.40), 1.920 (1.17), 1.934 (0.70), 1.947 (0.76), 1.956 (0.54), 1.965 (0.55), 1.987 (0.64), 1.995 (0.65), 2.128 (0.82), 2.159 (7.74), 2.180 (8.74), 2.322 (0.51), 2.326 (0.68), 2.332 (0.49), 2.518 (2.39), 2.522 (1.49), 2.577 (0.56), 2.606 (0.54), 2.642 (0.72), 2.665 (0.85), 2.669 (1.29), 2.673 (1.01), 2.748 (1.31), 2.775 (1.22), 2.835 (0.82), 2.852 (2.10), 2.867 (2.15), 2.882 (1.06), 3.403 (1.26), 3.414 (1.72), 3.420 (2.29), 3.437 (1.06), 3.546 (0.63), 3.551 (0.64), 3.640 (0.42), 3.663 (1.06), 3.668 (1.07), 3.680 (0.51), 3.691 (0.88), 3.696 (0.73), 3.712 (0.46), 3.717 (0.51), 3.724 (0.46), 3.729 (0.51), 3.738 (0.48), 3.743 (0.44), 3.750 (0.47), 3.754 (0.43), 3.867 (12.16), 3.891 (16.00), 3.969 (0.62), 3.993 (0.54), 4.637 (0.80), 4.650 (1.17), 4.659 (0.74), 4.665 (1.09), 4.675 (0.61), 6.146 (2.23), 6.155 (2.15), 6.162 (1.69), 6.170 (2.32), 6.642 (2.11), 6.647 (2.51), 6.657 (4.69), 6.667 (0.52), 6.672 (0.41), 6.680 (0.65), 6.692 (5.88), 6.701 (2.71), 6.709 (2.25), 7.122 (1.19), 7.160 (1.40), 7.290 (2.01), 7.300 (2.69), 7.303 (2.35), 7.313 (2.45), 7.426 (0.41), 7.435 (2.71), 7.520 (3.23), 7.989 (3.33), 8.002 (3.13), 8.019 (2.70), 8.031 (2.40), 8.402 (3.96), 8.421 (3.26), 11.070 (1.28), 11.110 (1.54).

LC-MS (method 6): $R_t$=0.54 min; MS (ESipos): m/z=512 $[M+H]^+$

Example 72, Example 73, Example 74, Example 75

3-(3-chloro-2-methoxyanilino)-2-[3-({(1R)-1-[(2R)-4-methylmorpholin-2-yl]ethyl}oxy)pyridin-4-yl]-1,5,6,7-tetrahydro-4H-pyrrolo[3,2-c]pyridin-4-one 3-(3-chloro-2-methoxyanilino)-2-[3-({(1S)-1-[(2S)-4-methylmorpholin-2-yl]ethyl}oxy)pyridin-4-yl]-1,5,6,7-tetrahydro-4H-pyrrolo[3,2-c]pyridin-4-one 3-(3-chloro-2-methoxyanilino)-2-[3-({(1R)-1-[(2S)-4-methylmorpholin-2-yl]ethyl}oxy)pyridin-4-yl]-1,5,6,7-tetrahydro-4H-pyrrolo[3,2-c]pyridin-4-one 3-(3-chloro-2-methoxyanilino)-2-[3-({(1S)-1-[(2R)-4-methylmorpholin-2-yl]ethyl}oxy)pyridin-4-yl]-1,5,6,7-tetrahydro-4H-pyrrolo[3,2-c]pyridin-4-one Example 72

3-(3-chloro-2-methoxyanilino)-2-[3-({1-[4-methylmorpholin-2-yl]ethyl}oxy)pyridin-4-yl]-1,5,6,7-tetrahydro-4H-pyrrolo[3,2-c]pyridin-4-one (stereoisomer 1)

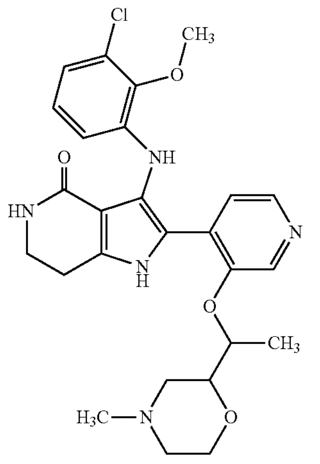 [SMILES: COc1c(Cl)cccc1Nc1c(-c2ccncc2OC(C)C2CN(C)CCO2)[nH]c2c1C(=O)NCC2]

The title compound from example 71 (135 mg) was separated into four stereoisomers by preparative chiral HPLC. The title compound stereoisomer 1, (20 mg, $R_t$=6.8-7.6 min) was obtained besides stereoisomer 2 (27 mg, $R_t$=9.6-10.9 min., see example 73), stereoisomer 3 (37 mg, see example 74) and stereoisomer 4 (37 mg, see example 75).

Preparative Chiral HPLC Method:

Instrument: PrepCon Labomatic HPLC 4; Column: YMC Cellulose SB 10μ, 250×50; eluent A: methyl tert-butyl ether+0.1 vol % diethylamine; eluent B: acetonitrile; isocratic: 80% A+20% B; flow: 140 mL/min; temperature: 25° C.; UV: 254 nm Analytical Chiral HPLC Method:

Instrument: Waters Alliance 2695; Column: YMC Cellulose SB 3μ, 100×4.6; eluent A: methyl tert-butyl ether+0.1 vol % diethylamine; eluent B: acetonitrile; isocratic: 80% A+20% B; flow: 1.4 ml/min; temperature: 25° C.; UV: 254 nm Analytical chiral HPLC: $R_t$=3.85 min.

Optical rotation: $[\alpha]_D$=16.84°+/−0.40° (c=1.0 g/100 ml chloroform)

1H-NMR (400 MHz, DMSO-$d_6$) delta [ppm]: 1.137 (0.95), 1.159 (0.63), 1.232 (0.54), 1.277 (5.83), 1.293 (5.97), 1.826 (0.63), 1.853 (1.16), 1.880 (0.71), 1.907 (0.46), 1.928 (0.77), 1.935 (0.78), 1.956 (0.45), 2.160 (9.53), 2.326 (0.58), 2.522 (2.28), 2.579 (0.94), 2.608 (0.86), 2.665 (0.41), 2.669 (0.54), 2.673 (0.40), 2.748 (0.95), 2.776 (0.90), 2.835 (1.17), 2.852 (2.46), 2.869 (1.37), 3.402 (1.17), 3.413 (1.92), 3.419 (1.92), 3.431 (0.97), 3.523 (0.52), 3.545 (0.95), 3.551 (0.92), 3.573 (0.56), 3.660 (0.71), 3.670 (0.67), 3.690 (0.73), 3.866 (16.00), 3.891 (0.61), 4.649 (0.83), 4.659 (0.85), 4.664 (0.85), 4.675 (0.80), 5.758 (1.51), 6.145 (1.46), 6.155 (1.45), 6.159 (1.36), 6.169 (1.48), 6.643 (2.83), 6.647 (3.21), 6.657 (5.61), 6.667 (0.55), 7.123 (1.81), 7.291 (2.03), 7.303 (2.10), 7.435 (3.81), 8.018 (1.65), 8.031 (1.59), 8.420 (2.63), 11.071 (2.01).

LC-MS (method 6): $R_t$=0.53 min; MS (ESIpos): m/z=512 $[M+H]^+$

Example 73

3-(3-chloro-2-methoxyanilino)-2-[3-({1-[4-methylmorpholin-2-yl]ethyl}oxy)pyridin-4-yl]-1,5,6,7-tetrahydro-4H-pyrrolo[3,2-c]pyridin-4-one (stereoisomer 2)

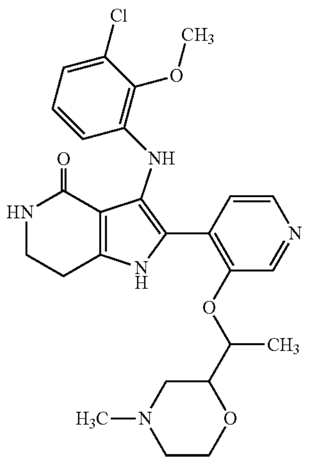 [SMILES: COc1c(Cl)cccc1Nc1c(-c2ccncc2OC(C)C2CN(C)CCO2)[nH]c2c1C(=O)NCC2]

For the preparation of the racemic title compound see example 71. Separation of stereoisomers by preparative chiral HPLC (method see example 72) to give 27 mg of the title compound stereoisomer 2.

Analytical chiral HPLC (method see example 72): $R_t$=5.24 min.

Optical rotation: $[\alpha]_D$=16.84°+/−0.40° (c=1.0 g/100 ml in Chloroform)

1H-NMR (400 MHz, DMSO-$d_6$) delta [ppm]: 1.137 (0.95), 1.159 (0.63), 1.232 (0.54), 1.277 (5.83), 1.293 (5.97), 1.826 (0.63), 1.853 (1.16), 1.880 (0.71), 1.907 (0.46), 1.928 (0.77), 1.935 (0.78), 1.956 (0.45), 2.160 (9.53), 2.326 (0.58), 2.522 (2.28), 2.579 (0.94), 2.608 (0.86), 2.665 (0.41), 2.669 (0.54), 2.673 (0.40), 2.748 (0.95), 2.776 (0.90), 2.835 (1.17), 2.852 (2.46), 2.869 (1.37), 3.402 (1.17), 3.413 (1.92), 3.419 (1.92), 3.431 (0.97), 3.523 (0.52), 3.545 (0.95), 3.551 (0.92), 3.573 (0.56), 3.660 (0.71), 3.670 (0.67), 3.690 (0.73), 3.866 (16.00), 3.891 (0.61), 4.649 (0.83), 4.659 (0.85), 4.664 (0.85), 4.675 (0.80), 5.758 (1.51), 6.145 (1.46), 6.155 (1.45), 6.159 (1.36), 6.169 (1.48), 6.643 (2.83), 6.647 (3.21), 6.657 (5.61), 6.667 (0.55), 7.123 (1.81), 7.291 (2.03), 7.303 (2.10), 7.435 (3.81), 8.018 (1.65), 8.031 (1.59), 8.420 (2.63), 11.071 (2.01).

LC-MS (method 6): $R_t$=0.53 min; MS (ESIpos): m/z=512 $[M+H]^+$

Example 74

3-(3-chloro-2-methoxyanilino)-2-[3-({1-[-4-methyl-morpholine-2-yl]ethyl}oxy)pyridin-4-yl]-1,5,6,7-tetrahydro-4H-pyrrolo[3,2-c]pyridin-4-one (stereoisomer 3)

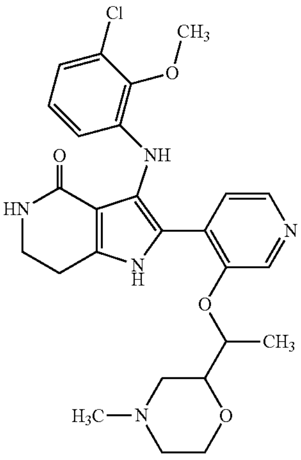 [SMILES: COc1c(Cl)cccc1Nc1c(-c2ccncc2OC(C)C2CN(C)CCO2)[nH]c2c1C(=O)NCC2]

For the preparation of the racemic title compound see example 71. For the separation of stereoisomers 3 and stereoisomer 4 (see example 75) first a preparative chiral HPLC was carried out using the method described in example 72. One fraction ($R_t$=5.5-6.5 min.) was further separated by another preparative chiral HPLC using the following method to give 37 mg of the title compound stereoisomer 3.

Preparative Chiral HPLC Method:

Instrument: Sepiatec: Prep SFC100; Column: Chiralpak IG 5μ 250×30 mm; eluent A: C02; eluent B: 2-propanol+0.4 vol % diethylamin; isocratic: 40% B; flow: 100 ml/min; temperature: 40° C.; BPR: 150 bar; UV: 254 nm Analytical chiral HPLC method: Instrument: Agilent: 1260, Aurora SFC-Modul; Column: Chiralpak IG 5μ 100×4.6 mm; eluent A: C02; eluent B: 2-propanol+0.4 vol % diethylamin; isocratic: 40% B; flow: 4 ml/min; temperature: 37.5° C.; BPR: 100 bar; UV: 254 nm Analytical chiral HPLC: $R_t$=3.98 min.

Optical rotation: $[\alpha]_D$=30.08°+/−0.91° (c=1.0 g/100 ml in Chloroform)

1H-NMR (400 MHz, DMSO-$d_6$) delta [ppm]: 0.697 (0.90), 1.026 (1.27), 1.042 (1.28), 1.088 (0.45), 1.137 (0.56), 1.232 (1.77), 1.293 (0.50), 1.358 (5.47), 1.374 (5.50), 1.893 (0.68), 1.920 (1.22), 1.947 (0.76), 1.959 (1.07), 1.966 (0.44), 1.987 (0.74), 1.995 (0.74), 2.016 (0.44), 2.180 (9.88), 2.327 (0.45), 2.523 (1.85), 2.643 (0.83), 2.669 (1.19), 2.749 (0.84), 2.776 (0.82), 2.847 (0.81), 2.865 (1.90), 2.882 (1.25), 3.409 (0.92), 3.419 (1.42), 3.425 (1.62), 3.439 (0.79), 3.640 (0.45), 3.663 (0.82), 3.668 (0.85), 3.691 (0.49), 3.712 (0.49), 3.718 (0.58), 3.724 (0.55), 3.730 (0.61), 3.738 (0.58), 3.744 (0.54), 3.750 (0.58), 3.755 (0.50), 3.891 (16.00), 3.970 (0.75), 3.993 (0.66), 4.638 (0.75), 4.653 (0.92), 4.666 (0.75), 6.146 (1.43), 6.154 (1.30), 6.162 (1.45), 6.170 (1.48), 6.681 (0.60), 6.693 (6.14), 6.701 (2.75), 6.709 (2.40), 6.729 (0.44), 7.162 (1.65), 7.301 (1.65), 7.313 (1.71), 7.521 (3.68), 7.990 (1.16), 8.002 (1.10), 8.403 (1.76), 11.111 (1.82).

LC-MS (method 6): $R_t$=0.53 min; MS (ESipos): m/z=512 $[M+H]^+$

Example 75

3-(3-chloro-2-methoxyanilino)-2-[3-({1-[-4-methyl-morpholin-2-yl]ethyl}oxy)pyridin-4-yl]-1,5,6,7-tetrahydro-4H-pyrrolo[3,2-c]pyridin-4-one_(stereoisomer 4)

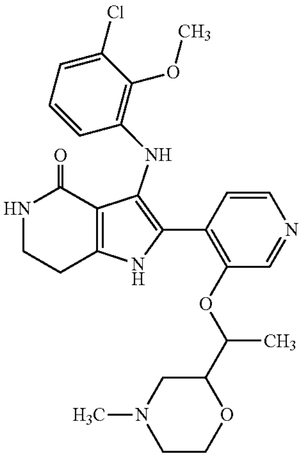 [SMILES: COc1c(Cl)cccc1Nc1c(-c2ccncc2OC(C)C2CN(C)CCO2)[nH]c2c1C(=O)NCC2]

For the preparation of the racemic title compound see example 71. For the separation of stereoisomers 3 (see example 74) and stereoisomer 4 (example 75) first a preparative chiral HPLC was carried out using the method described in example 72. One fraction ($R_t$=5.5-6.5 min.), was further separated by another preparative chiral HPLC (method see example 74) to give 37 mg of the title compound stereoisomer 4.

Analytical chiral HPLC: $R_t$=7.23 min.

Optical rotation: $[\alpha]_D$=−24.97°+/−0.50° (c=1.0 g/100 ml in Chloroform)

1H-NMR (400 MHz, DMSO-$d_6$) delta [ppm]: 0.697 (2.05), 0.742 (1.32), 0.760 (1.30), 0.832 (0.55), 0.851 (0.74), 0.973 (0.66), 0.984 (0.67), 0.991 (0.96), 0.999 (0.64), 1.009 (0.72), 1.026 (0.75), 1.042 (0.77), 1.070 (0.82), 1.088 (1.27), 1.106 (1.27), 1.151 (4.27), 1.232 (4.01), 1.293 (1.22), 1.358 (5.91), 1.373 (6.07), 1.894 (0.71), 1.921 (1.28), 1.948 (0.80), 1.959 (1.52), 1.988 (0.82), 1.995 (0.85), 2.017 (0.51), 2.181 (10.00), 2.322 (0.74), 2.326 (0.99), 2.331 (0.74), 2.522 (4.96), 2.643 (0.98), 2.669 (1.77), 2.749 (0.99), 2.777 (0.93), 2.849 (0.99), 2.865 (2.18), 2.882 (1.43), 3.408 (1.14), 3.424 (1.91), 3.640 (0.51), 3.663 (0.93), 3.668 (0.95), 3.692 (0.56), 3.718 (0.67), 3.730 (0.69), 3.743 (0.64), 3.750 (0.64), 3.891 (16.00), 3.969 (0.87), 3.993 (0.79), 4.638 (0.82), 4.653 (1.03), 4.667 (0.80), 6.145 (1.44), 6.154 (1.38), 6.161 (1.41), 6.169 (1.51), 6.681 (0.63), 6.693 (5.87), 6.701 (2.92), 6.709 (2.49), 6.729 (0.47), 7.162 (1.85), 7.300 (1.91), 7.313 (1.96), 7.520 (3.80), 7.990 (1.46), 8.002 (1.40), 8.402 (2.29), 11.110 (1.99).

LC-MS (method 6): $R_t$=0.53 min; MS (ESipos): m/z=512 $[M+H]^+$

Experimental Section—Biological Assays

The pharmacological activity of the compounds according to the invention can be assessed using in vitro- and/or in vivo-assays, as known to the person skilled in the art. The following examples describe the biological activity of the compounds according to the invention, without the invention being limited to said examples.

Example compounds according to the invention were tested in selected biological assays one or more times. When tested more than once, data are reported as either average values or as median values, wherein

- the average value, also referred to as the arithmetic mean value, represents the sum of the values obtained divided by the number of times tested, and
- the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from biological assays represent average values or median values calculated utilizing data sets obtained from testing of one or more synthetic batch.

The in vitro activity of the compounds of the present invention can be demonstrated in the following assays:

Expression and Purification of the EGFR Proteins Used in the Biochemical Kinase Assays The different EGFR proteins used in the biochemical kinase activity inhibition assays were generated in house by expression in insect cells using Baculo Virus system and subsequent purification as described in the following paragraphs.

Expression Constructs:

The cDNAs encoding the various protein sequences from human EGFR human (P00533) were optimized for expression in eukaryotic cells and synthesized by the GeneArt Technology at Life Technologies.

These DNA sequences encoded the following sequence:

Construct EGFR #1 amino acid R669 to A1210

Construct EGFR #2 amino acid R669 to A1210 and the insertion of the amino acids sequence ASV between V769 and D770

Construct EGFR #3 amino acid R669 to A1210 and the insertion of the amino acids sequence SVD between D770 and N771

Additionally all constructs EGFR #1 to #3 encoded: at the N-terminus a TEV (Tobacco etch virus) protease cleavage site (DYDIPTTENLYFQG), at the C-terminus two stop codons and additionally 5' and 3' att-DNA sequences for Gateway Cloning.

Each of the four EFGR constructs was subcloned using the Gateway Technology into the Destination vector pD-Ins1. The vector pD-Ins1 is a Baculovirus transfer vector (based on vector pVL1393, Pharmingen) which provides a N-terminal fusion of a GST-tag to the integrated gene construct. The respective transfer vectors were termed pD-Ins1_EGFR #1, pD-Ins1_EGFR #2, pD-Ins1_EGFR #3.

EGFR Amino Acid Sequences:

```
GST-EGFR #1 (Wild Type)
                                                    SEQ ID 3
MSPILGYWKIKGLVQPTRLLLEYLEEKYEEHLYERDEGDKWRNKKFELGLEFPNLPYYID

GDVKLTQSMAIIRYIADKHNMLGGCPKERAEISMLEGAVLDIRYGVSRIAYSKDFETLKVD

FLSKLPEMLKMFEDRLCHKTYLNGDHVTHPDFMLYDALDVVLYMDPMCLDAFPKLVCFK

KRIEAIPQIDKYLKSSKYIAWPLQGWQATFGGGDHPPKSDPITSLYKKAGSDYDIPTTTEN

LYFQGRRRHIVRKRTLRRLLQERELVEPLTPSGEAPNQALLRILKETEFKKIKVLGSGAFG

TVYKGLWIPEGEKVKIPVAIKELREATSPKANKEILDEAYVMASVDNPHVCRLLGICLTSTV

QLITQLMPFGCLLDYVREHKDNIGSQYLLNWCVQIAKGMNYLEDRRLVHRDLAARNVLV

KTPQHVKITDFGLAKLLGAEEKEYHAEGGKVPIKWMALESILHRIYTHQSDVWSYGVTVW

ELMTFGSKPYDGIPASEISSILEKGERLPQPPICTIDVYMIMVKCWMIDADSRPKFRELIIEF

SKMARDPQRYLVIQGDERMHLPSPTDSNFYRALMDEEDMDDVVDADEYLIPQQGFFSS

PSTSRTPLLSSLSATSNNSTVACIDRNGLQSCPIKEDSFLQRYSSDPTGALTEDSIDDTFL

PVPEYINQSVPKRPAGSVQNPVYHNQPLNPAPSRDPHYQDPHSTAVGNPEYLNTVQPT

CVNSTFDSPAHWAQKGSHQISLDNPDYQQDFFPKEAKPNGIFKGSTAENAEYLRVAPQS

SEFIGA

GST-EGFR #2 (ASV between V769 and D770)
                                                    SEQ ID 4
MSPILGYWKIKGLVQPTRLLLEYLEEKYEEHLYERDEGDKWRNKKFELGLEFPNLPYYID

GDVKLTQSMAIIRYIADKHNMLGGCPKERAEISMLEGAVLDIRYGVSRIAYSKDFETLKVD

FLSKLPEMLKMFEDRLCHKTYLNGDHVTHPDFMLYDALDVVLYMDPMCLDAFPKLVCFK

KRIEAIPQIDKYLKSSKYIAWPLQGWQATFGGGDHPPKSDPITSLYKKAGSDYDIPTTTEN

LYFQGRRRHIVRKRTLRRLLQERELVEPLTPSGEAPNQALLRILKETEFKKIKVLGSGAFG
```

-continued

```
TVYKGLWIPEGEKVKIPVAIKELREATSPKANKEILDEAYVMASVASVDNPHVCRLLGICLT

STVQLITQLMPFGCLLDYVREHKDNIGSQYLLNWCVQIAKGMNYLEDRRLVHRDLAARN

VLVKTPQHVKITDFGLAKLLGAEEKEYHAEGGKVPIKWMALESILHRIYTHQSDVWSYGV

TVWELMTFGSKPYDGIPASEISSILEKGERLPQPPICTIDVYMIMVKCWMIDADSRPKFRE

LIIEFSKMARDPQRYLVIQGDERMHLPSPTDSNFYRALMDEEDMDDVVDADEYLIPQQGF

FSSPSTSRTPLLSSLSATSNNSTVACIDRNGLQSCPIKEDSFLQRYSSDPTGALTEDSIDD

TFLPVPEYINQSVPKRPAGSVQNPVYHNQPLNPAPSRDPHYQDPHSTAVGNPEYLNTVQ

PTCVNSTFDSPAHWAQKGSHQISLDNPDYQQDFFPKEAKPNGIFKGSTAENAEYLRVAP

QSSEFIGA

GST-EGFR #3 (SVD between D770 and N771)
                                                  SEQ ID 5
MSPILGYWKIKGLVQPTRLLLEYLEEKYEEHLYERDEGDKWRNKKFELGLEFPNLPYYID

GDVKLTQSMAIIRYIADKHNMLGGCPKERAEISMLEGAVLDIRYGVSRIAYSKDFETLKVD

FLSKLPEMLKMFEDRLCHKTYLNGDHVTHPDFMLYDALDVVLYMDPMCLDAFPKLVCFK

KRIEAIPQIDKYLKSSKYIAWPLQGWQATFGGGDHPPKSDPITSLYKKAGSDYDIPTTTEN

LYFQGRRRHIVRKRTLRRLLQERELVEPLTPSGEAPNQALLRILKETEFKKIKVLGSGAFG

TVYKGLWIPEGEKVKIPVAIKELREATSPKANKEILDEAYVMASVDSVDNPHVCRLLGICLT

STVQLITQLMPFGCLLDYVREHKDNIGSQYLLNWCVQIAKGMNYLEDRRLVHRDLAARN

VLVKTPQHVKITDFGLAKLLGAEEKEYHAEGGKVPIKWMALESILHRIYTHQSDVWSYGV

TVWELMTFGSKPYDGIPASEISSILEKGERLPQPPICTIDVYMIMVKCWMIDADSRPKFRE

LIIEFSKMARDPQRYLVIQGDERMHLPSPTDSNFYRALMDEEDMDDVVDADEYLIPQQGF

FSSPSTSRTPLLSSLSATSNNSTVACIDRNGLQSCPIKEDSFLQRYSSDPTGALTEDSIDD

TFLPVPEYINQSVPKRPAGSVQNPVYHNQPLNPAPSRDPHYQDPHSTAVGNPEYLNTVQ

PTCVNSTFDSPAHWAQKGSHQISLDNPDYQQDFFPKEAKPNGIFKGSTAENAEYLRVAP

QSSEFIGA
```

Generation of Recombinant Baculovirus:

In separate approaches each of the three transfer vectors was co-transfected in Sf9 cells with Baculovirus DNA (Flashbac Gold DNA, Oxford Expression Technologies) using Fugene HD (Roche). After 5 days the supernatant of the transfected cells containing the recombinant Baculovirus encoding the various EGFR proteins was used for further infection of Sf9 cells for virus amplification whereby the virus titer was monitored using qPCR.

EGFR Expression in Sf9 Cells Using Bioreactor:

Sf9 cells cultured (Insect-xpress medium, Lonza, 27° C.) in a Wave-bioreactor with a disposable culture bag were infected at a cell density of 106 cells/ml with one of the recombinant baculovirus stocks at a multiplicity of infection of 1 and incubated for 48 h. Subsequently the cells were harvested by centrifugation and the cell pellet frozen at −80° C.

Purification of the GST-EGFR Fusion Proteins:

Purification of the GST-EGFR fusion proteins was achieved by affinity chromatography using Glutathion Sepharose 4B matrix (GE Healthcare Life Sciences).

The pelleted cells (from 4 I cell culture) were resuspended in Lysis-Buffer (50 mM HEPES pH 7.4, 150 mM NaCl, 5% Glycerol, 1 mM MgCl2, 1 mM MnCl2, 0.5 mM Na3VO4) and lysed by a freeze-thaw cycle followed by an incubation on ice for 60 min. The supernatant was centrifuged at 4000×g for 30 min. at 4° C. The supernatant was than incubated with Glutathion Sepharose 4B matrix (in a glass bottle rotating for 16 h, at 4° C.) for binding of the GST EGFR fusion protein, rinsed with Wash-Buffer and finally the bound protein was eluted using Elusion-Buffer (Lysis Buffer plus 25 mM Glutathione) and shock frozen with liquid nitrogen.

WT-EGFR Kinase Assay

Inhibitory activity of compounds of the present invention against wild-type Epidermal Growth Factor Receptor (EGFR) was quantified employing the TR-FRET based EGFR assay as described in the following paragraphs.

Recombinant fusion protein of N-terminal Glutathion-S-Transferase (GST) and a fragment of human EGFR (amino acids R669 to A1210), expressed in Sf9 insect cells and purified via affinity chromatography using Glutathion Sepharose as described above, was used as a kinase. As substrate for the kinase reaction the biotinylated peptide biotin-Ahx-AEEEEYFELVAKKK—SEQ ID 6 (C-terminus in amide form) was used, which can be purchased e.g. form the company Biosynthan GmbH (Berlin-Buch, Germany).

For the assay 50 nl of a 100 fold concentrated solution of the test compound in DMSO was pipetted into either a black low volume 384 well microtiter plate or a black 1536 well microtiter plate (both Greiner Bio-One, Frickenhausen, Germany), 2 μl of a solution of EGFR in aqueous assay buffer

[50 mM Hepes pH 7.0, 10 mM MgCl2, 1 mM dithiothreitol, 0.5 mM EGTA, 0.3 mM activated sodium ortho-vanadate, 0.005% (w/v) bovine serum albumin, 0.005% (v/v) Tween-20] were added and the mixture was incubated for 15 min at 22° C. to allow pre binding of the test compounds to the enzyme before the start of the kinase reaction. Then the kinase reaction was started by the addition of 3 μL of a solution of adenosine tri phosphate (ATP, 3.33 mM=>final conc. in the 5 μL assay volume is 2 mM) and substrate (1.67 μM=>final conc. in the 5 μL assay volume is 1 μM) in assay buffer and the resulting mixture was incubated for a reaction time of 30 min at 22° C. The concentration of EGFR was adjusted depending of the activity of the enzyme lot and was chosen appropriate to have the assay in the linear range, typical concentration was 7.6 pg/μl. The reaction was stopped by the addition of 3 μl of a solution of HTRF detection reagents (83.3 nM streptavidine-XL665 [Cisbio Bioassays, Codolet, France] and 1.67 nM PT66-Tb-Cryptate, an terbium-cryptate labelled anti-phospho-tyrosine antibody from Cisbio Bioassays [instead of the PT66 Tb cryptate PT66 Eu Chelate from Perkin Elmer can also be used]) in an aqueous EDTA-solution (133.3 mM EDTA, 0.2% (w/v) bovine serum albumin in 50 mM HEPES pH 7.5).

The resulting mixture was incubated 1 h at 22° C. to allow the binding of the biotinylated phosphorylated peptide to the streptavidine-XL665 and the PT66-Tb-Cryptate. Subsequently the amount of phosphorylated substrate was evaluated by measurement of the resonance energy transfer from the PT66-Tb-Cryptate to the streptavidine-XL665. Therefore, the fluorescence emissions at 620 nm and 665 nm after excitation at 337 nm were measured in a HTRF reader, e.g. a Pherastar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 μM to 0.07 nM (20 μM, 5.7 μM, 1.6 μM, 0.47 μM, 0.13 μM, 38 nM, 11 nM, 3.1 nM, 0.9 nM, 0.25 nM and 0.07 nM, the dilution series prepared separately before the assay on the level of the 100-fold concentrated solutions in DMSO by serial dilutions, exact concentrations may vary depending pipettors used) in duplicate values for each concentration and $IC_{50}$ values were calculated using Genedata Screener™ software.

Exon20-Mutant-EGFR(D770_N771insSVD) Kinase Assay

Inhibitory activity of compounds of the present invention against an Epidermal Growth Factor Receptor (EGFR) with an insertion of the amino acids sequence SVD between D770 and N771 was quantified employing the TR-FRET based kinase activity assay as described in the following paragraphs.

A recombinant fusion protein of N-terminal Glutathion-S-Transferase (GST) and a fragment of human EGFR variant (amino acids R669 to A1210 with insertion of the amino acids sequence SVD between D770 and N771 ("EGFR ins SVD"), expressed in Sf9 insect cells and purified via affinity chromatography using Glutathion Sepharose as described above, was used as a kinase. As substrate for the kinase reaction the biotinylated peptide biotin-Ahx-AEEEEYFEL-VAKKK—SEQ ID 6 (C-terminus in amide form) was used which can be purchased e.g. form the company Biosynthan GmbH (Berlin-Buch, Germany).

For the assay 50 nl of a 100-fold concentrated solution of the test compound in DMSO was pipetted into either a black low volume 384 well microtiter plate or a black 1536 well microtiter plate (both Greiner Bio-One, Frickenhausen, Germany), 2 μl of a solution of EGFR in aqueous assay buffer [50 mM Hepes pH 7.0, 10 mM MgCl2, 1 mM dithiothreitol, 0.5 mM EGTA, 0.3 mM activated sodium ortho-vanadate, 0.005% (w/v) bovine serum albumin, 0.005% (v/v) Tween-20] were added and the mixture was incubated for 15 min at 22° C. to allow pre binding of the test compounds to the enzyme before the start of the kinase reaction. Then the kinase reaction was started by the addition of 3 μL of a solution of adenosine tri phosphate (ATP, 3.33 mM=>final conc. in the 5 μL assay volume is 2 mM) and substrate (1.67 μM=>final conc. in the 5 μL assay volume is 1 μM) in assay buffer and the resulting mixture was incubated for a reaction time of 30 min at 22° C. The concentration of EGFR was adjusted depending of the activity of the enzyme lot and was chosen appropriate to have the assay in the linear range, typical concentration was 15 pg/μl. The reaction was stopped by the addition of 3 μl of a solution of HTRF detection reagents (83.3 nM streptavidine-XL665 [Cisbio Bioassays, Codolet, France] and 1.67 nM PT66-Tb-Cryptate, a terbium-cryptate labelled anti-phospho-tyrosine antibody from Cisbio Bioassays [instead of the PT66 Tb cryptate PT66 Eu Chelate from Perkin Elmer can also be used]) in an aqueous EDTA-solution (133.3 mM EDTA, 0.2% (w/v) bovine serum albumin in 50 mM HEPES pH 7.5).

The resulting mixture was incubated 1 h at 22° C. to allow the binding of the biotinylated phosphorylated peptide to the streptavidine-XL665 and the PT66-Tb-Cryptate. Subsequently the amount of phosphorylated substrate was evaluated by measurement of the resonance energy transfer from the PT66-Tb-Cryptate to the streptavidine-XL665. Therefore, the fluorescence emissions at 620 nm and 665 nm after excitation at 337 nm were measured in a HTRF reader, e.g. a Pherastar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 μM to 0.07 nM (20 μM, 5.7 μM, 1.6 μM, 0.47 μM, 0.13 μM, 38 nM, 11 nM, 3.1 nM, 0.9 nM, 0.25 nM and 0.07 nM, the dilution series prepared separately before the assay on the level of the 100 fold concentrated solutions in DMSO by serial dilutions, exact concentrations may vary depending pipettors used) in duplicate values for each concentration and $IC_{50}$ values were calculated using Genedata Screener™ software.

Exon20-Mutant-EGFR(V769_D770insASV) Kinase Assay

Inhibitory activity of compounds of the present invention against an Epidermal Growth Factor Receptor (EGFR) with an insertion of the amino acids sequence ASV between V769 and D770 was quantified employing the TR-FRET based kinase activity assay as described in the following paragraphs.

A recombinant fusion protein of N-terminal Glutathion-S-Transferase (GST) and a fragment of human EGFR variant (amino acids R669 to A1210 with insertion of the amino acids sequence ASV between V769 and D770; ("EGFR ins ASV"), expressed in Sf9 insect cells and purified via affinity chromatography using Glutathion Sepharose as described above, was used as kinase. As substrate for the kinase reaction the biotinylated peptide biotin-Ahx-AEEEEYFEL-VAKKK—SEQ ID 6 (C-terminus in amide form) was used which can be purchased e.g. form the company Biosynthan GmbH (Berlin-Buch, Germany).

For the assay 50 nl of a 100-fold concentrated solution of the test compound in DMSO was pipetted into either a black low volume 384 well microtiter plate or a black 1536 well microtiter plate (both Greiner Bio-One, Frickenhausen, Germany), 2 μl of a solution of EGFR in aqueous assay buffer [50 mM Hepes pH 7.0, 10 mM MgCl2, 1 mM dithiothreitol, 0.5 mM EGTA, 0.3 mM activated sodium ortho-vanadate, 0.005% (w/v) bovine serum albumin, 0.005% (v/v) Tween-20] were added and the mixture was incubated for 15 min at 22° C. to allow pre binding of the test compounds to the enzyme before the start of the kinase reaction. Then the kinase reaction was started by the addition of 3 μL of a solution of adenosine tri phosphate (ATP, 3.33 mM=>final conc. in the 5 μL assay volume is 2 mM) and substrate (1.67 μM=>final conc. in the 5 μL assay volume is 1 μM) in assay buffer and the resulting mixture was incubated for a reaction time of 30 min at 22° C. The concentration of EGFR was adjusted depending of the activity of the enzyme lot and was chosen appropriate to have the assay in the linear range, typical concentration was 2.5 pg/μl. The reaction was stopped by the addition of 3 μl of a solution of HTRF detection reagents (83.3 nM streptavidine-XL665 [Cisbio Bioassays, Codolet, France] and 1.67 nM PT66-Tb-Cryptate, an terbium-cryptate labelled anti-phospho-tyrosine antibody from Cisbio Bioassays [instead of the PT66 Tb cryptate PT66 Eu Chelate from Perkin Elmer can also be used]) in an aqueous EDTA-solution (133.3 mM EDTA, 0.2% (w/v) bovine serum albumin in 50 mM HEPES pH 7.5).

The resulting mixture was incubated 1 h at 22° C. to allow the binding of the biotinylated phosphorylated peptide to the streptavidine-XL665 and the PT66-Tb-Cryptate. Subsequently the amount of phosphorylated substrate was evaluated by measurement of the resonance energy transfer from the PT66-Tb-Cryptate to the streptavidine-XL665. Therefore, the fluorescence emissions at 620 nm and 665 nm after excitation at 337 nm were measured in a HTRF reader, e.g. a Pherastar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 μM to 0.07 nM (20 μM, 5.7 μM, 1.6 μM, 0.47 μM, 0.13 μM, 38 nM, 11 nM, 3.1 nM, 0.9 nM, 0.25 nM and 0.07 nM, the dilution series prepared separately before the assay on the level of the 100-fold concentrated solutions in DMSO by serial dilutions, exact concentrations may vary depending pipettors used) in duplicate values for each concentration and $IC_{50}$ values were calculated using Genedata Screener™ software. Table 2 shows the results of the inhibition in mutant EGFR biochemical assay.

TABLE 2

| Example No. | mutEGFR (D770_N771insSVD) kinase assay $IC_{50}$ [mol/l] |
|---|---|
| 1 | 1.59E−10 |
| 2 | <7.25E−11 |
| | 7.79E−11 |
| | 7.87E−11 |
| | 9.12E−11 |
| | 1.65E−10 |
| | 2.00E−10 |
| 3 | 1.37E−10 |
| 4 | 2.56E−10 |
| 5 | <7.25E−11 |
| | 8.51E−11 |
| | 1.12E−10 |
| | 1.14E−10 |
| | 1.20E−10 |
| | 1.24E−10 |
| | 1.36E−10 |
| 6 | 1.00E−10 |
| 7 | 1.37E−10 |
| 8 | 7.99E−11 |
| 9 | 8.91E−11 |
| 10 | 6.69E−10 |
| 11 | 2.86E−10 |
| 12 | 7.94E−11 |
| 13 | 1.39E−10 |
| 14 | 1.30E−10 |
| 15 | 1.51E−10 |
| 16 | 2.28E−10 |
| 17 | 1.56E−10 |
| 18 | 1.47E−10 |
| 19 | 1.13E−10 |
| 20 | 8.72E−11 |
| 21 | 1.26E−10 |
| 22 | 1.53E−10 |
| 23 | 1.69E−10 |
| 24 | 2.61E−10 |
| 25 | 2.82E−10 |
| 26 | 2.13E−10 |
| 27 | 1.18E−10 |
| 28 | 2.49E−10 |
| 29 | 5.47E−10 |
| 36 | 3.96E−10 |
| 31 | 1.33E−10 |
| 32 | 1.27E−10 |
| 33 | 2.13E−10 |
| 34 | 1.93E−10 |
| 35 | 8.73E−11 |
| 36 | 1.14E−10 |
| 37 | 4.00E−10 |
| 38 | 1.19E−10 |
| 39 | 3.04E−10 |
| 40 | 1.15E−10 |
| 41 | 2.91E−10 |
| 42 | 1.55E−10 |
| 43 | 2.25E−10 |
| 44 | 1.50E−10 |
| 45 | 4.92E−10 |
| 46 | 4.33E−10 |
| 47 | <7.25E−11 |
| | 1.69E−10 |
| | 2.27E−10 |
| | 2.30E−10 |
| 48 | 2.49E−10 |
| 49 | 1.70E−10 |
| 50 | 1.70E−10 |
| 51 | 1.36E−10 |
| 52 | 2.26E−10 |
| 53 | 4.26E−10 |
| 54 | 5.71E−10 |
| 55 | 2.57E−10 |
| 56 | 2.58E−10 |
| 57 | 2.69E−10 |
| 58 | 1.70E−10 |
| | 2.15E−10 |
| | <2.54E−10 |
| | 3.64E−10 |
| 59 | 2.35E−10 |
| 60 | 3.05E−10 |
| 61 | 9.35E−10 |
| 62 | 2.37E−10 |
| 63 | 2.65E−10 |
| 64 | 1.87E−10 |
| 65 | 1.36E−10 |
| 66 | 1.82E−10 |
| 67 | 2.17E−10 |

TABLE 2-continued

| Example No. | mutEGFR (D770_N771insSVD) kinase assay $IC_{50}$ [mol/l] |
|---|---|
| 68 | 2.67E−10 |
| 69 | 2.33E−10 |
| 70 | 1.68E−10 |
| 71 | 4.05E−10 |
| 72 | 1.41E−9 |
| 73 | 1.12E−9 |
| 74 | 6.61E−10 |
| 75 | 4.99E−9 |

Bub1 High ATP Kinase Assay

Bub1-inhibitory activity of compounds of the present invention at a high ATP concentration was quantified employing the Bub1 TR-FRET high ATP kinase assay as described in the following paragraphs.

N-terminally $His_6$-tagged recombinant catalytic domain of human Bub1 (amino acids 704-1085), expressed in insect cells (Hi5) and purified by Ni-NTA affinity chromatography and subsequent size exclusion chromatography, was used as enzyme. As substrate for the kinase reaction the biotinylated peptide biotin-Ahx-VLLPKKSFAEPG—SEQ ID 7 (C-terminus in amid form) was used which can be purchased e.g. form the company Biosyntan (Berlin, Germany).

For the assay 50 nl of a 100-fold concentrated solution of the test compound in DMSO was pipetted into either a black low volume 384 well microtiter plate or a black 1536 well microtiter plate (both Greiner Bio-One, Frickenhausen, Germany), 3 μl of a solution of adenosine-tri-phosphate (ATP, 3.33 mM=>final conc. in the 5 μl assay volume is 2 mM) and substrate (1.67 μM=>final conc. in the 5 μl assay volume is 1 μM) in aqueous assay buffer [50 mM Tris/HCl pH 7.5, 10 mM magnesium chloride ($MgCl_2$), 200 mM potassium chloride (KCl), 1.0 mM dithiothreitol (DTT), 0.1 mM sodium ortho-vanadate, 1% (v/v) glycerol, 0.01% (w/v) bovine serum albumine (BSA), 0.005% (v/v) Trition X-100 (Sigma), 1× Complete EDTA-free protease inhibitor mixture (Roche)] were added. Then the kinase reaction was started by the addition of 2 μl of a solution of Bub1 in assay buffer and the resulting mixture was incubated for a reaction time of 60 min at 22° C. The concentration of Bub1 was adjusted depending of the activity of the enzyme lot and was chosen appropriate to have the assay in the linear range, a typical concentration is about 200 ng/ml. The reaction was stopped by the addition of 3 μl of a solution of TR-FRET detection reagents (0.167 μM streptavidine-XL665 [Cisbio Bioassays, Codolet, France] and 1.67 nM anti-phosho-Serine antibody [Merck Millipore, cat. #35-002] and 0.67 nM LANCE EU-W1024 labeled anti-mouse IgG antibody [Perkin-Elmer, product no. AD0077, as an alternative a Terbium-cryptate-labeled anti-mouse IgG antibody from Cisbio Bioassays can be used]) in an aqueous EDTA-solution (83.3 mM EDTA, 0.2% (w/v) bovine serum albumin in 100 mM HEPES pH 7.5).

The resulting mixture was incubated 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL. Therefore, the fluorescence emissions at 620 nm and 665 nm after excitation at 350 nm was measured in a TR-FRET reader, e.g. a Pherastar or Pherastar FS (both from BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 μM to 0.7 nM (20 μM, 5.7 μM, 1.6 μM, 0.47 μM, 0.13 μM, 38 nM, 11 nM, 3.1 nM, 0.9 nM, 0.25 nM and 0.07 nM, the dilution series prepared separately before the assay on the level of the 100 fold concentrated solutions in DMSO by serial dilutions, exact concentrations may vary depending pipettors used) in duplicate values for each concentration and $IC_{50}$ values were calculated by a 4 parameter fit. Table 3 shows the results of the inhibition in Bub1 high ATP kinase assay.

TABLE 3

| Example No. | Bub1 high ATP (2 mM) $IC_{50}$ [mol/l] |
|---|---|
| 1 | 3.36E−6 |
| 2 | 6.04E−6 |
| 3 | 3.33E−6 |
| 4 | 1.13E−5 |
| 5 | 1.29E−5 |
| 6 | 6.31E−6 |
| 7 | 1.06E−5 |
| 8 | 7.88E−6 |
| 9 | 4.23E−6 |
| 10 | 1.78E−6 |
| 11 | 4.33E−6 |
| 12 | >2.00E−5 |
| 13 | >2.00E−5 |
| 14 | >2.00E−5 |
| 15 | >2.00E−5 |
| 16 | >2.00E−5 |
| 17 | >2.00E−5 |
| 18 | >2.00E−5 |
| 19 | 1.14E−5 |
| 20 | 9.53E−6 |
| 21 | 3.79E−6 |
| 22 | >2.00E−5 |
| 23 | >2.00E−5 |
| 24 | 1.94E−6 |
| 25 | >2.00E−5 |
| 26 | 1.08E−6 |
| 27 | >2.00E−5 |
| 28 | >2.00E−5 |
| 29 | 1.72E−5 |
| 30 | >2.00E−5 |
| 33 | >2.00E−5 |
| 34 | >2.00E−5 |
| 35 | >2.00E−5 |
| 36 | 2.82E−6 |
| 37 | 1.90E−5 |
| 38 | >5.71E−6 |
| 39 | >2.00E−5 |
| 40 | 8.62E−6 |
| 41 | >2.00E−5 |
| 42 | >2.00E−5 |
| 43 | 2.41E−6 |
| 45 | >5.71E−6 |
| 46 | 1.30E−5 |
| 47 | 5.01E−6 |
| 48 | 1.22E−5 |
| 49 | 3.93E−6 |
| 50 | 3.54E−6 |
| 51 | 1.52E−6 |
| 52 | 7.29E−7 |
| 53 | 1.36E−6 |
| 54 | 9.94E−7 |
| 55 | 7.59E−6 |
| 56 | 1.65E−5 |
| 57 | 1.40E−5 |
| 58 | 1.39E−5 |
| 59 | 1.22E−5 |
| 60 | 1.64E−5 |
| 62 | >2.00E−5 |

TABLE 3-continued

| Example No. | Bub1 high ATP (2 mM) $IC_{50}$ [mol/l] |
|---|---|
| 63 | >2.00E−5 |
| 64 | >2.00E−5 |
| 63 | 3.58E−6 |
| 66 | 5.04E−6 |
| 67 | 2.08E−6 |
| 68 | >2.00E−5 |
| 69 | >2.00E−5 |
| 70 | >2.00E−5 |
| 71 | >2.00E−5 |
| 72 | >2.00E−5 |
| 73 | >2.00E−5 |
| 74 | >2.00E−5 |
| 75 | >2.00E−5 |

Compounds of the present invention may show additional advantageous properties, such as, more potent inhibition of mutant EGFR with exon20 insertions than inhibition of wild-type EGFR, which may be useful to reduce potential toxicity arising from excessive inhibition of wild-type EGFR.

Cellular Data Description (WT, insSVD)

293T cells from ATCC were transfected with pBABEpuro expression constructs for WT EGFR or EGFR-insSVD and pCL-Eco packaging vector using Fugene-6 transfection reagent from Promega. Plates were incubated at at 37° C. for 48 h. Retrovirus was harvested by filtering the media supernatant through a 0.45 μm filter.

Ba/F3 cells purchased from DSMZ were grown in RPMI+10% FBS+10 ng/mL IL-3 and infected with filtered retroviral supernatant at a 1:2 dilution. Polybrene was added to a concentration of 8 μg/mL, plates were spun for 90 min, and incubated overnight at 37° C. 2 μg/mL puromycin was added to the infected cells 24 h after infection and cells were continually grown in the presence of puromycin and 10 ng/mL IL-3. Following stably expressing Ba/F3 cell lines were generated: Ba/F3-EGFR-WT, Ba/F3-EGFR-insSVD, (Ba/F3-vector-control).

For cell survival assays, Ba/F3 cells were grown to a density of 1-2 million cells per mL, spun down and resuspended in media without IL-3, and replated at a concentration 200,000-500,000 cells per mL. The cells ectopically expressing WT EGFR or EGFR-insSVD were plated with 10 ng/mL Millipore Culture grade EGF. The cells ectopically expressing pBABEpuro empty vector were plated with 10 ng/mL IL-3. 2 days later, cells were plated in 50 μL in a 384 well plate at a concentration of 4000 cells per well for cells assayed in the absence of IL-3 and 2000 cells per well for cells assayed in the presence of IL-3. 100 nL of compound was added to each well using a 100 nL pin head, and plates were incubated at 37° C. for 48 h.

Cell viability was measured by adding 20 μL of Cell Titer-Glo Luminescent Cell Viability Reagent diluted 1:3 in PBS. Plates were sealed with Perkin Elmer Top-Seal, inverted several times to mix, and immediately centrifuged at 1000 rpm for 2 min. Plates were incubated in low light conditions for 8-10 min and luminescence was measured. The $IC_{50}$ values for the examples are shown in Table 4.

TABLE 4

| Example No. | BA/F3 (insSVD) $IC_{50}$ [mol/l] | BA/F3 (wild type) $IC_{50}$ [mol/l] |
|---|---|---|
| 1 | 9.80E−9 | 3.66E−7 |
| 2 | 7.12E−9 | 2.92E−7 |
| 3 | 2.28E−8 | 7.55E−7 |
| 4 | 1.95E−8 | 4.52E−7 |
| 5 | 9.73E−9 | 2.62E−7 |
| 6 | 5.03E−8 | 7.85E−7 |
| 7 | 1.80E−8 | 2.92E−7 |
| 8 | 8.18E−9 | 1.21E−7 |
| 9 | 3.27E−8 | 3.03E−7 |
| 10 | 1.11E−8 | 4.96E−7 |
| 11 | 1.87E−8 | 7.01E−7 |
| 12 | 2.28E−8 | 5.74E−7 |
| 13 | 1.57E−7 | 1.52E−6 |
| 14 | 1.05E−8 | 3.87E−7 |
| 15 | 1.53E−8 | 4.26E−7 |
| 16 | 1.26E−7 | 1.05E−6 |
| 17 | 9.53E−9 | 2.31E−7 |
| 18 | 2.79E−8 | 5.79E−7 |
| 19 | 2.91E−8 | 5.32E−7 |
| 20 | 8.25E−9 | 3.13E−7 |
| 21 | 3.49E−9 | 3.41E−7 |
| 22 | 4.19E−8 | 5.44E−7 |
| 23 | 7.10E−8 | 6.48E−7 |
| 24 | 3.46E−8 | 4.44E−7 |
| 25 | 1.83E−8 | 3.49E−7 |
| 26 | 8.99E−8 | 8.39E−7 |
| 27 | 1.69E−8 | 5.02E−7 |
| 28 | 1.26E−7 | 1.24E−6 |
| 29 | 3.36E−8 | 6.21E−7 |
| 30 | 1.93E−8 | 4.07E−7 |
| 33 | 1.02E−7 | 5.57E−7 |
| 34 | 1.20E−8 | 2.04E−7 |
| 35 | 2.15E−8 | 2.61E−7 |
| 36 | 6.81E−8 | 8.45E−7 |
| 37 | 3.57E−8 | 3.48E−7 |
| 38 | 2.93E−8 | 4.19E−7 |
| 39 | 4.40E−8 | 6.30E−7 |
| 40 | 1.19E−7 | 8.67E−7 |
| 41 | 7.75E−8 | 6.95E−7 |
| 42 | 1.98E−8 | 5.96E−7 |
| 43 | 6.05E−8 | 1.25E−6 |
| 44 | 2.57E−8 | |
| 45 | 1.11E−7 | 1.64E−6 |
| 46 | 1.01E−8 | 3.76E−7 |
| 47 | 4.16E−8 | 7.15E−7 |
| 48 | 1.88E−8 | 3.79E−7 |
| 49 | 5.36E−8 | 7.85E−7 |
| 50 | 8.82E−9 | 3.61E−7 |
| 51 | 4.67E−8 | 7.42E−7 |
| 52 | 1.34E−8 | 5.47E−7 |
| 53 | 2.13E−8 | 4.08E−7 |
| 54 | 8.09E−8 | 9.17E−7 |
| 55 | 1.24E−7 | 1.31E−6 |
| 56 | 1.19E−8 | 4.35E−7 |
| 57 | 2.80E−8 | 5.39E−7 |
| 58 | 2.98E−8 | 5.19E−7 |
| 59 | 1.86E−8 | 3.36E−7 |
| 60 | 5.27E−8 | 9.46E−7 |
| 61 | 3.00E−7 | 3.77E−6 |
| 62 | 2.67E−8 | 6.97E−7 |
| 63 | 1.47E−7 | 1.37E−6 |
| 64 | 7.58E−9 | 2.71E−7 |
| 65 | 1.34E−8 | 2.87E−7 |
| 66 | 7.52E−9 | 2.52E−7 |
| 67 | 2.90E−8 | 1.98E−7 |
| 68 | 3.73E−8 | 6.44E−7 |
| 69 | 7.17E−9 | 3.12E−7 |
| 70 | 6.79E−8 | 7.14E−7 |
| 71 | 1.32E−7 | 1.42E−6 |
| 72 | 6.73E−8 | 9.57E−7 |
| 73 | 7.80E−8 | 1.28E−6 |
| 74 | 5.11E−8 | 8.28E−7 |
| 75 | 5.71E−7 | 3.90E−6 |

In contrast to the claimed compounds of this invention the compounds claimed in the closest prior art WO 2016/120196 do not show the advantageous combined properties described above. This can be seen in Table 5.

TABLE 5

| WO 2016/120196 Example No. | mutEGFR (D770_N771insSVD) kinase assay $IC_{50}$ [mol/l] | BA/F3 (insSVD) $IC_{50}$ [mol/l] | BA/F3 (wild type) $IC_{50}$ [mol/l] |
|---|---|---|---|
| 38 | 2.24E−7 | >2.00E−6 | 5.91E−6 |
| 41 | 3.43E−8 | >2.00E−6 | 5.02E−6 |
| 45 | 1.28E−8 | >2.00E−6 | 4.04E−6 |

Cellular Data Description (Ba/F3 Cells Overexpressing Mutant EGFR Different from Inssvd)

293T cells from ATCC were transfected with pBABEpuro expression constructs for mutant EGFR (V769_D770insASV, D770_N771insNPG, N771_P772insH, H773_V774insNPH, E746_A750del, L858R, D770_N771insSVD C797S, E746_A750del C797S, L858R C797S, L861Q) or mutant ERBB2 (A775_G776insYVMA) and pCL-Eco packaging vector using Fugene-6 transfection reagent from Promega. Plates were incubated at at 37° C. for 48 h. Retrovirus was harvested by filtering the media supernatant through a 0.45 μm filter.

Ba/F3 cells purchased from DSMZ were grown in RPMI+10% FBS+10 ng/mL IL-3 and infected with filtered retroviral supernatant at a 1:2 dilution. Polybrene was added to a concentration of 8 μg/mL, plates were spun for 90 min, and incubated overnight at 37° C. 2 μg/mL puromycin was added to the infected cells 24 h after infection and cells were continually grown in the presence of puromycin and 10 ng/mL IL-3. Following stably expressing Ba/F3 cell lines were generated: Ba/F3-EGFR-V769_D770insASV, Ba/F3-EGFR-D770_N771insNPG, Ba/F3-EGFR-N771_P772insH, Ba/F3-EGFR-H773_V774insNPH, Ba/F3-EGFR-E746_A750del, Ba/F3-EGFR-L858R, Ba/F3-EGFR-D770_N771 insSVD C797S, Ba/F3-EGFR-E746_A750del C797S, Ba/F3-EGFR-L858R C797S, Ba/F3-EGFR L861Q and Ba/F3-ERBB2-A775_G776insYVMA (Ba/F3-vector-control).

For cell survival assays, Ba/F3 cells were grown to a density of 1-2 million cells per mL, spun down and resuspended in media without IL-3, and replated at a concentration 200,000-500,000 cells per mL. The cells ectopically expressing WT EGFR plated with 10 ng/mL Millipore Culture grade EGF and Ba/F3 cells containing mutant EGFR or Mutant ERBB2 were cultivated without EGF. The cells ectopically expressing pBABEpuro empty vector were plated with 10 ng/mL IL-3.

2 days later, cells were plated in 50 μL in a 384 well plate at a concentration of 4000 cells per well for cells assayed in the absence of IL-3 and 2000 cells per well for cells assayed in the presence of IL-3. 100 nL of compound was added to each well using a 100 nL pin head, and plates were incubated at 37° C. for 48 h.

Cell viability was measured by adding 20 μL of Cell Titer-Glo Luminescent Cell Viability Reagent diluted 1:3 in PBS. Plates were sealed with Perkin Elmer Top-Seal, inverted several times to mix, and immediately centrifuged at 1000 rpm for 2 min. Plates were incubated in low light conditions for 8-10 min and luminescence was measured. The $IC_{50}$ values for the examples are shown in Tables 6, 7, 8 and 9.

Cellular Data Description (PC9 Cells, EGFRex19del)

PC9 cells were purchased from ATCC. 400 PC9 cells per well were seeded in growth medium (DMEM, 10% FCS) in a 384-well plate (CORNING #3571). Seed reference plate for time zero determination on the same day. All plates were incubated overnight at 37° C. After 24 hours, test compound were added in 7-step dilution using HP Compound printer and incubated at 37° C. for 72 h. After 3 days, 30 μL/well CTG solution (Promega Cell Titer Glo solution; catalog # G755B and G756B) were added to each well, incubated for 30 minutes and the plate were read on PheraStar. Proliferation is calculated after subtracting time zero luminescence values from day 4 values and comparing to untreated wells. The $IC_{50}$ values were determined using the four parameter fit. The $IC_{50}$ values for the examples are shown in Table 9.

Cellular Data Description (HCC-827 Cells, EGFRex19del)

HCC-827 cells were purchased from ATCC. 400 HCC-829 cells per well were seeded in growth medium (RPM11640, 10% FCS) in a 384-well plate (CORNING #3571). Seed reference plate for time zero determination on the same day. All plates were incubated overnight at 37° C. After 24 hours, test compound were added in 7-step dilution using HP Compound printer and incubated at 37° C. for 72 h. After 3 days, 30 μL/well CTG solution (Promega Cell Titer Glo solution; catalog # G755B and G756B) were added to each well, incubated for 30 minutes and the plate were read on PheraStar. Proliferation is calculated after subtracting time zero luminescence values from day 4 values and comparing to untreated wells.

The $IC_{50}$ values were determined using the four parameter fit. The $IC_{50}$ values for the examples are shown in Table 9.

TABLE 6

| (EGFR Exon20 insertion mutations) | | | | |
|---|---|---|---|---|
| Example No. | BA/F3 (insNPG) $IC_{50}$ [mol/l] | BA/F3 (ASV) $IC_{50}$ [mol/l] | BA/F3 (EGFR N771_772 insH) $IC_{50}$ [mol/l] | BA/F3 (EGFR 773_774insNPH) $IC_{50}$ [mol/l] |
| 2 | 4.44E−9 | 4.66E−9 | 7.48E−9 | 2.82E−8 |
| 5 | 2.63E−8 | 2.87E−8 | 1.15E−8 | 7.93E−8 |
| 8 | 1.16E−8 | 9.62E−9 | 4.91E−9 | 2.31E−8 |
| 14 | 1.25E−8 | 1.64E−8 | 7.60E−9 | 6.58E−8 |
| 20 | 1.47E−8 | 1.17E−8 | 6.59E−9 | 5.67E−8 |
| 21 | 5.65E−9 | 7.78E−9 | 4.22E−9 | 2.76E−8 |
| 32 | 9.38E−9 | 1.32E−8 | 1.10E−8 | 4.73E−8 |
| 42 | 1.20E−8 | 1.41E−8 | 6.01E−9 | 4.85E−8 |
| 46 | 1.43E−8 | 1.17E−8 | 5.77E−9 | 3.89E−8 |
| 48 | 4.24E−8 | 4.18E−8 | 1.76E−8 | 1.42E−7 |
| 50 | 1.13E−8 | 1.04E−8 | 7.42E−9 | 4.03E−8 |
| 56 | 6.96E−9 | 1.41E−8 | 7.36E−9 | 4.89E−8 |

TABLE 7

| (classical activating and rare EGFR mutations) | | | |
|---|---|---|---|
| Example No. | BA/F3 (EGFR E746_A750del) $IC_{50}$ [mol/l] | BA/F3 (EGFR L858R) $IC_{50}$ [mol/l] | BA/F3 (EGFR L861Q) $IC_{50}$ [mol/l] |
| 2 | <1.58E−10 | 5.25E−10 | 1.48E−8 |
| 5 | 7.39E−10 | 2.03E−9 | 3.09E−8 |
| 8 | <1.58E−10 | 7.01E−10 | 1.37E−8 |
| 14 | 1.72E−9 | 1.22E−9 | 2.01E−8 |
| 29 | 3.32E−10 | 9.64E−10 | 1.62E−8 |
| 21 | 2.03E−10 | 6.44E−10 | 7.34E−9 |
| 32 | 2.89E−9 | 1.06E−9 | 1.74E−8 |
| 42 | 4.86E−10 | 1.51E−9 | 1.88E−8 |
| 46 | 1.05E−9 | 9.57E−10 | 1.58E−8 |
| 48 | 1.43E−9 | 2.36E−9 | 3.97E−8 |
| 50 | 1.10E−9 | 1.07E−9 | 2.40E−8 |
| 56 | 8.92E−10 | 1.34E−9 | 2.95E−8 |

TABLE 8

| (aquired resistance space) | | | |
|---|---|---|---|
| Example No. | BA/F3 (EGFR 0770_N771 insSVD C797S) $IC_{50}$ [mol/l] | BA/F3 (EGFR E746_A750del C797S) $IC_{50}$ [mol/l] | BA/F3 (EGFR L858R C797S) $IC_{50}$ [mol/l] |
| 2 | 8.22E−9 | 2.20E−10 | 6.03E−10 |
| 5 | 3.70E−8 | 6.68E−10 | 2.67E−9 |
| 8 | 1.46E−8 | 2.47E−10 | 1.20E−9 |
| 14 | 2.49E−8 | 3.79E−10 | 1.91E−9 |
| 20 | 1.22E−8 | 3.49E−10 | 7.91E−10 |
| 21 | 7.84E−9 | 2.59E−10 | 4.44E−10 |
| 32 | 1.58E−8 | 5.11E−10 | 1.12E−9 |
| 42 | 1.93E−8 | 4.94E−10 | 1.63E−9 |
| 48 | 1.85E−8 | 4.00E−10 | 1.13E−9 |
| 48 | 5.66E−8 | 7.76E−10 | 2.56E−9 |
| 50 | 2.67E−8 | 3.48E−10 | 1.60E−9 |
| 56 | 1.40E−8 | 4.23E−10 | 1.31E−9 |

TABLE 9

| (ERBB2 mutants, PC9, HCC-827) | | | |
|---|---|---|---|
| Example No. | BA/F3 (ERBB2 A775_G776 insYVMA) $IC_{50}$ [mol/l] | PC9 $IC_{50}$ [mol/l] | HCC-827 $IC_{50}$ [mol/l] |
| 2 | 8.31E−9 | 6.73E−10 | <3.00E−9 |
| 6 | 3.18E−8 | 1.94E−9 | <3.00E−9 |
| 8 | 1.31E−8 | 7.38E−10 | <3.00E−9 |
| 14 | 1.36E−8 | 2.12E−9 | <3.00E−9 |
| 20 | 2.35E−8 | 2.68E−9 | <3.00E−9 |
| 21 | 1.34E−8 | 1.16E−9 | <3.00E−9 |
| 32 | 1.67E−8 | 1.70E−9 | <3.00E−9 |
| 42 | 1.32E−8 | 4.03E−9 | <3.00E−9 |
| 46 | 1.10E−8 | 2.89E−9 | <3.00E−9 |
| 48 | 3.98E−8 | 3.40E−9 | <3.00E−9 |
| 50 | 1.03E−8 | 6.82E−9 | <3.00E−9 |
| 56 | 1.35E−8 | 1.74E−9 | <3.00E−9 |

REFERENCES

Arcila et al., 2012: Arcila et al., Clin Cancer Res. 2012 Sep. 15; 18(18):4910-8.

Chen et al., 2016: Chen et al., Onco Targets Ther. 2016 Jul. 8; 9:4181-6

Chiu et al., 2015: Chiu et al., J Thorac Oncol. 2015; 10: 793-799

Doebele et al., 2018: Doebele et al., Poster 338, presented at the 54th Annual Meeting of the American Society of Clinical Oncology, Jun. 1-5, 2018, Chicago, Illinois Floc'h et al., 2018: Floc'h et al., Mol Cancer Ther. 2018 May 17(5): 885-896

Hasako et al., 2018: Hasako et al., Mol Cancer Ther. 2018 August; 17(8):1648-1658

Jang et al., 2018: Jang et al., Angew Chem Int Ed Engl. 2018 Sep. 3; 57(36): 11629-11633

Mok et al., 2009: Mok et al., N Engl J Med. 2009 Sep. 3; 361(10):947-57

Mok et al., 2017: Mok et al., N Engl J Med. 2017 Feb. 16; 376(7):629-640

Oxnard et al., 2013: Oxnard et al., J Thorac Oncol. 2013 February; 8(2): 179-184

Oxnard et al., 2018: Oxnard et al., JAMA Oncol. 2018; 4(11):1527-1534

Paez et al., 2004: Paez et al., Science. 2004 Jun. 4; 304 (5676):1497-500

Pao et al., 2005: Pao et al., PLoS Med. 2005 March; 2(3):e73

Pao et al., 2010: Pao and Chmielecki, Nat Rev Cancer. 2010 November; 10(11):760-74

Ramalingam et al., 2018a: Ramalingam et al., J Clin Oncol. 2018 Mar. 20; 36(9):841-849.

Ramalingam et al., 2018b: Ramalingam et al., ESMO 2018; Annals Oncol. 2018 October: 29 (Suppl 8)

Robichaux et al., 2018: Robichaux et al., Nat Med. 2018 May; 24(5):638-646

Sequist et al., 2013: Sequist et al., J Clin Oncol. 2013 Sep. 20; 31(27):3327-34

Soria et al., 2018: Soria et al., N Engl J Med. 2018 Jan. 11; 378(2):113-125.

Thress et al., 2015: Thress et al., Nat Med. 2015 June; 21(6): 560-562.

Yang et al., 2015: Yang et al., Lancet Oncol. 2015 July; 16(7):830-8

Yasuda, 2013: Yasuda, Sci Transl Med. 2013 Dec. 18; 5(216):216ra177.

The invention claimed is:

1. A compound of formula (I)

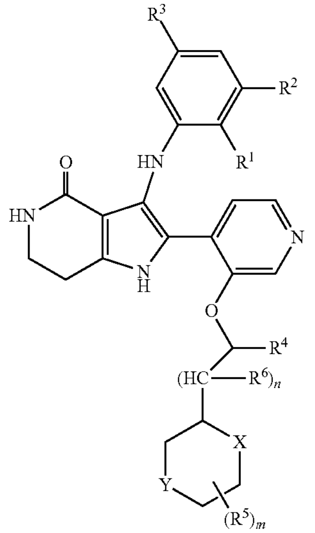

(I)

in which:

$R^1$ represents methyl, ethyl, trifluoromethyl, 2,2-difluoroethyl, cyano, chloro, bromo, methoxy or difluoromethoxy;

$R^2$ represents hydrogen, methyl, ethyl, fluoro, chloro or bromo;

$R^3$ represents hydrogen or fluoro;

$R^4$ represents hydrogen or methyl;

$R^5$ independently at each occurrence represents hydrogen, trifluoromethyl or $C_1$-$C_3$ alkyl, $R^5$ being bound to any carbon atom of the ring;

$R^6$ independently at each occurrence represents hydrogen, $C_1$-$C_3$-alkyl or $C_1$-$C_3$-haloalkyl;

$R^7$ represents $C_1$-$C_3$-alkyl or $C_2$-$C_3$-haloalkyl;

$R^8$ represents $C_1$-$C_3$-alkyl or $C_2$-$C_3$-haloalkyl;

X represents $NR^7$ or O;

Y represents $NR^8$ or O;

m represents 0, 1, 2 or 3;

n represents 0 or 1;

or an N-oxide, a salt or a tautomer of said compound, or a salt of said N-oxide or tautomer.

2. The compound of formula (I) according to claim 1, wherein:

$R^1$ represents methyl, ethyl, chloro, methoxy or difluoromethoxy;

$R^2$ represents methyl, ethyl, fluoro or chloro;

$R^3$ represents hydrogen or fluoro;

$R^4$ represents hydrogen or methyl;

$R^5$ represents hydrogen, methyl or trifluoromethyl, $R^5$ being bound to any carbon atom of the ring;

$R^6$ represents hydrogen, methyl or trifluoromethyl;

$R^7$ represents $C_1$-$C_2$-alkyl or $C_2$-$C_3$-fluoroalkyl;

$R^8$ represents $C_1$-$C_2$-alkyl or $C_2$-$C_3$-fluoroalkyl;

X represents $NR^7$ or O;

Y represents $NR^8$ or O;

m represents 0, 1 or 2;

n represents 0 or 1;

or an N-oxide, a salt or a tautomer of said compound, or a salt of said N-oxide or tautomer.

3. The compound of formula (I) according to claim 1, wherein:

$R^1$ represents methyl, ethyl, chloro or methoxy;

$R^2$ represents, fluoro or chloro;

$R^3$ represents hydrogen or fluoro;

$R^4$ represents hydrogen;

$R^5$ represents hydrogen or methyl, $R^5$ being bound to any carbon atom of the ring;

$R^6$ represents hydrogen;

$R^7$ represents methyl;

$R^8$ represents methyl, 2,2,2-trifluoroethyl or 2,2-difluoroethyl;

X represents $NR^7$ or O;

Y represents $NR^8$ or O;

m represents 0, 1, or 2;

n represents 0 or 1;

or an N-oxide, a salt or a tautomer of said compound, or a salt of said N-oxide or tautomer.

4. The compound of formula (I) according to claim 1, which is selected from the group consisting of:

3-(3-chloro-2-methoxyanilino)-2-{3-[(1,4-dioxan-2-yl)methoxy]pyridin-4-yl}-1,5,6,7-tetrahydro-4H-pyrrolo[3,2-c]pyridin-4-one 3-(3-chloro-2-methoxyanilino)-2-(3-{[(2S)-1,4-dioxan-2-yl]methoxy}pyridin-4-yl)-1,5,6,7-tetrahydro-4H-pyrrolo[3,2-c]pyridin-4-one 3-(3-chloro-2-methoxyanilino)-2-(3-{[(2R)-1,4-dioxan-2-yl]methoxy}pyridin-4-yl)-1,5,6,7-tetrahydro-4H-pyrrolo[3,2-c]pyridin-4-one 2-{3-[(1,4-dioxan-2-yl)methoxy]pyridin-4-yl}-3-(3-fluoro-2-methoxyanilino)-1,5,6,7-tetrahydro-4H-pyrrolo[3,2-c]pyridin-4-one 2-(3-{[(2S)-1,4-dioxan-2-yl]methoxy}pyridin-4-yl)-3-(3-fluoro-2-methoxyanilino)-1,5,6,7-tetrahydro-4H-pyrrolo[3,2-c]pyridin-4-one 2-(3-{[(2R)-1,4-dioxan-2-yl]methoxy}pyridin-4-yl)-3-(3-fluoro-2-methoxyanilino)-1,5,6,7-tetrahydro-4H-pyrrolo[3,2-c]pyridin-4-one 3-(2,3-dichloroanilino)-2-{3-[(1,4-dioxan-2-yl)methoxy]pyridin-4-yl}-1,5,6,7-tetrahydro-4H-pyrrolo[3,2-c]pyridin-4-one 3-(2,3-dichloroanilino)-2-(3-{[(2S)-1,4-dioxan-2-yl]methoxy}pyridin-4-yl)-1,5,6,7-tetrahydro-4H-pyrrolo[3,2-c]pyridin-4-one 3-(2,3-dichloroanilino)-2-(3-{[(2R)-1,4-dioxan-2-yl]methoxy}pyridin-4-yl)-1,5,6,7-tetrahydro-4H-pyrrolo[3,2-c]pyridin-4-one 3-(3-chloro-2-methylanilino)-2-{3-[(1,4-dioxan-2-yl)methoxy]pyridin-4-yl}-1,5,6,7-tetrahydro-4H-pyrrolo[3,2-c]pyridin-4-one 3-(3-chloro-2-methoxy anilino)-2-(3-{[(3R)-4-methylmorpholin-3-yl]methoxy}pyridin-4-yl)-1,5,6,7-tetrahydro-4H-pyrrolo[3,2-c]pyridin-4-one 3-(3-fluoro-2-methoxyanilino)-2-{3-[(4-methylmorpholin-2-yl)methoxy]pyridin-4-yl}-1,5,6,7-tetrahydro-4H-pyrrolo[3,2-c]pyridin-4-one 3-(3-fluoro-2-methoxyanilino)-2-(3-{[(2R)-4-methylmorpholin-2-yl]methoxy}pyridin-4-yl)-1,5,6,7-tetrahydro-4H-pyrrolo[3,2-c]pyridin-4-one 3-(3-fluoro-2-methoxyanilino)-2-(3-{[(2S)-4-methylmorpholin-2-yl]methoxy}pyridin-4-yl)-1,5,6,7-tetrahydro-4H-pyrrolo[3,2-c]pyridin-4-one 3-(3-chloro-2-methoxyanilino)-2-{3-[(4-methylmorpholin-2-yl)methoxy]pyridin-4-yl}-1,5,6,7-tetrahydro-4H-pyrrolo[3,2-c]pyridin-4-one 3-(3-chloro-2-methoxy anilino)-2-(3-{[(2R)-4-methylmorpholin-2-yl]methoxy}pyridin-4-yl)-1,5,6,7-tetrahydro-4H-pyrrolo[3,2-c]pyridin-4-one 3-(3-chloro-2-methoxyanilino)-2-(3-{[(2S)-4-methylmorpholin-2-yl]methoxy}pyridin-4-yl)-1,5,6,7-tetrahydro-4H-pyrrolo[3,2-c]pyridin-4-one 3-(3-chloro-5-fluoro-2-methoxyanilino)-2-(3-{[4-methylmorpholin-2-yl]methoxy}pyridin-4-yl)-1,5,6,7-tetrahydro-4H-pyrrolo[3,2-c]pyridin-4-one 3-(3-chloro-5-fluoro-2-methoxyanilino)-2-(3-{[1,4-dioxan-2-yl]methoxy}pyridin-4-yl)-1,5,6,7-tetrahydro-4H-pyrrolo[3,2-c]pyridin-4-one 3-(3-fluoro-2-methoxyanilino)-2-(3-{[(3S)-4-methylmorpholin-3-yl]methoxy}pyridin-4-yl)-1,5,6,7-tetrahydro-4H-pyrrolo[3,2-c]pyridin-4-one 3-(3-chloro-2-methoxyanilino)-2-(3-{[(3S)-4-methylmorpholin-3-yl]methoxy}pyridin-4-yl)-1,5,6,7-tetrahydro-4H-pyrrolo[3,2-c]pyridin-4-one 2-(3-{[(2S)-4-(2,2-difluoroethyl)morpholin-2-yl]methoxy}pyridin-4-yl)-3-(3-fluoro-2-methoxyanilino)-1,5,6,7-tetrahydro-4H-pyrrolo[3,2-c]pyridin-4-one 3-(3-fluoro-2-methoxyanilino)-2-(3-{[(2S)-4-(2,2,2-trifluoroethyl)morpholin-2-yl]methoxy}pyridin-4-yl)-1,5,6,7-tetrahydro-4H-pyrrolo[3,2-c]pyridin-4-one 3-(3-chloro-2-methoxyanilino)-2-{3-[2-(4-dioxan-2-yl)ethoxy]pyridin-4-yl}-1,5,6,7-tetrahydro-4H-pyrrolo[3,2-c]pyridin-4-one 3-(3-chloro-2-methoxyanilino)-2-(3-{2-[(2R)-1,4-dioxan-2-yl]ethoxy}pyridin-4-yl)-1,5,6,7-tetrahydro-4H-pyrrolo[3,2-c]pyridin-4-one 3-(3-chloro-2-methoxyanilino)-2-(3-{2-[(2S)-1,4-dioxan-2-yl]ethoxy}pyridin-4-yl)-1,5,6,7-tetrahydro-4H-pyrrolo[3,2-c]pyridin-4-one 3-(3-chloro-5-fluoro-2-methoxyanilino)-2-(3-{[(2S)-4-methylmorpholin-2-yl]methoxy}pyridin-4-yl)-1,5,6,7-tetrahydro-4H-pyrrolo[3,2-c]pyridin-4-one 3-(3-chloro-5-fluoro-2-methoxyanilino)-2-(3-{[(2S)-4-(2,2,2-trifluoroethyl)morpholin-2-yl]methoxy}pyridin-4-yl)-1,5,6,7-tetrahydro-4H-pyrrolo[3,2-c]pyridin-4-one 3-(3-chloro-2-ethylanilino)-2-{3-[(4-methylmorpholin-2-yl)methoxy]pyridin-4-yl}-1,5,6,7-tetrahydro-4H-pyrrolo[3,2-c]pyridin-4-one 3-(3-chloro-2-methoxyanilino)-2-{3-[(5,5-dimethyl-1,4-dioxan-2-yl)methoxy]pyridin-4-yl}-1,5,6,7-tetrahydro-4H-pyrrolo[3,2-c]pyridin-4-one 3-(3-chloro-2-methoxyanilino)-2-(3-{[(2R)-5,5-dimethyl-1,4-dioxan-2-yl]methoxy}pyridin-4-yl)-1,5,6,7-tetrahydro-4H-pyrrolo[3,2-c]pyridin-4-one 3-(3-chloro-2-methoxyanilino)-2-(3-{[(2S)-5,5-dimethyl-1,4-dioxan-2-yl]methoxy}pyridin-4-yl)-1,5,6,7-tetrahydro-4H-pyrrolo[3,2-c]pyridin-4-one 2-(3-{[(2R)-5,5-dimethyl-1,4-dioxan-2-yl]methoxy}pyridin-4-yl)-3-(3-fluoro-2-methoxyanilino)-1,5,6,7-tetrahydro-4H-pyrrolo[3,2-c]pyridin-4-one 2-(3-{[(2S)-5,5-dimethyl-1,4-dioxan-2-yl]methoxy}pyridin-4-yl)-3-(3-fluoro-2-methoxyanilino)-1,5,6,7-tetrahydro-4H-pyrrolo[3,2-c]pyridin-4-one 2-(3-{2-[(2R)-1,4-dioxan-2-yl]ethoxy}pyridin-4-yl)-3-(3-fluoro-2-methoxyanilino)-1,5,6,7-tetrahydro-4H-pyrrolo[3,2-c]pyridin-4-one 2-(3-{2-[(2S)-1,4-dioxan-2-yl]ethoxy}pyridin-4-yl)-3-(3-fluoro-2-methoxyanilino)-1,5,6,7-tetrahydro-4H-pyrrolo[3,2-c]pyridin-4-one, 3-(3-fluoro-2-methoxyanilino)-2-(3-{[(3R)-4-methylmorpholin-3-yl]methoxy}pyridin-4-yl)-1,5,6,7-tetrahydro-4H-pyrrolo[3,2-c]pyridin-4-one 2-{3-[(5,5-dimethyl-1,4-dioxan-2-yl)methoxy]pyridin-4-yl}-3-(3-fluoro-2-methylanilino)-1,5,6,7-tetrahydro-4H-pyrrolo[3,2-c]pyridin-4-one 2-(3-{[(2S)-5,5-dimethyl-1,4-dioxan-2-yl]methoxy}pyridin-4-yl)-3-(3-fluoro-2-methylanilino)-1,5,6,7-tetrahydro-4H-pyrrolo[3,2-c]pyridin-4-one 3-[2-(2,2-difluoroethyl)-3-fluoroanilino]-2-{3-[(1,4-dioxan-2-yl)methoxy]pyridin-4-yl}-1,5,6,7-tetrahydro-4H-pyrrolo[3,2-c]pyridin-4-one 3-[2-(2,2-difluoroethyl)-3-fluoroanilino]-2-(3-{[(2S)-4-methylmorpholin-2-yl]methoxy}pyridin-4-yl)-1,5,6,7-tetrahydro-4H-pyrrolo[3,2-c]pyridin-4-one 3-(3-chloro-2-methylanilino)-2-(3-{[(2S)-4-methylmorpholin-2-yl]methoxy}pyridin-4-yl)-1,5,6,7-tetrahydro-4H-pyrrolo[3,2-c]pyridin-4-one 3-(3-chloro-2-methylanilino)-2-(3-{[(3R)-4-methylmorpholin-3-yl]methoxy}pyridin-4-yl)-1,5,6,7-tetrahydro-4H-pyrrolo[3,2-c]pyridin-4-one 3-(3-chloro-2-methylanilino)-2-{3-[(5,5-dimethyl-1,4-dioxan-2-yl)methoxy]pyridin-4-yl}-1,5,6,7-tetrahydro-4H-pyrrolo[3,2-c]pyridin-4-one 3-(3-chloro-2-methylanilino)-2-(3-{[(2S)-5,5-dimethyl-1,4-dioxan-2-yl]methoxy}pyridin-4-yl)-1,5,6,7-tetrahydro-4H-pyrrolo[3,2-c]pyridin-4-one 3-(3-chloro-2-methylanilino)-2-(3-{[(2R)-5,5-dimethyl-1,4-dioxan-2-yl]methoxy}pyridin-4-yl)-1,5,6,7-tetrahydro-4H-pyrrolo[3,2-c]pyridin-4-one 2-{3-[(1,4-dioxan-2-yl)methoxy]pyridin-4-yl}-3-(3-fluoro-2-methylanilino)-1,5,6,7-tetrahydro-4H-pyrrolo[3,2-c]pyridin-4-one 2-(3-{[(2S)-1,4-dioxan-2-yl]methoxy}pyridin-4-yl)-3-(3-fluoro-2-methylanilino)-1,5,6,7-tetrahydro-4H-pyrrolo[3,2-c]pyridin-4-one 2-(3-{[(2R)-1,4-dioxan-2-yl]methoxy}pyridin-4-yl)-3-(3-fluoro-2-methylanilino)-1,5,6,7-tetrahydro-4H-pyrrolo[3,2-c]pyridin-4-one 3-(3-chloro-2-methylanilino)-2-(3-{[(2S)-1,4-dioxan-2-yl]methoxy}pyridin-4-yl)-1,5,6,7-tetrahydro-4H-pyrrolo[3,2-c]pyridin-4-one 3-(3-chloro-2-methylanilino)-2-(3-{[(2R)-1,4-dioxan-2-yl]methoxy}pyridin-4-yl)-1,5,6,7-tetrahydro-4H-pyrrolo[3,2-c]pyridin-4-one 3-(3-chloro-2-ethylanilino)-2-{3-[(1,4-dioxan-2-yl)methoxy]pyridin-4-yl}-1,5,6,7-tetrahydro-4H-pyrrolo[3,2-c]pyridin-4-one 3-(3-chloro-2-ethylanilino)-2-(3-{[(2S)-1,4-dioxan-2-yl]methoxy}pyridin-4-yl)-1,5,6,7-tetrahydro-4H-pyrrolo[3,2-c]pyridin-4-one 3-(3-chloro-2-ethylanilino)-2-(3-{[(2R)-1,4-dioxan-2-yl]methoxy}pyridin-4-yl)-1,5,6,7-tetrahydro-4H-pyrrolo[3,2-c]pyridin-4-one 3-(3-chloro-2-ethylanilino)-2-(3-{[(2R)-4-methylmorpholin-2-yl]methoxy}pyridin-4-yl)-1,5,6,7-tetrahydro-4H-pyrrolo[3,2-c]pyridin-4-one 3-(3-chloro-2-ethylanilino)-2-(3-{[(2S)-4-methylmorpholin-2-yl]methoxy}pyridin-4-yl)-1,5,6,7-tetrahydro-4H-pyrrolo[3,2-c]pyridin-4-one 3-(3-chloro-2-methoxyanilino)-2-(3-{1-[1,4-dioxan-2-yl]ethoxy}pyridin-4-yl)-1,5,6,7-tetrahydro-4H-pyrrolo[3,2-c]pyridin-4-one 3-(3-chloro-2-methoxyanilino)-2-(3-{(1S)-1-[(2S)-1,4-dioxan-2-yl]ethoxy}pyridin-4-yl)-1,5,6,7-tetrahydro-4H-pyrrolo[3,2-c]pyridin-4-one 3-(3-chloro-2-methoxyanilino)-2-(3-{(1S)-1-[(2R)-1,4-dioxan-2-yl]ethoxy}pyridin-4-yl)-1,5,6,7-tetrahydro-4H-pyrrolo[3,2-c]pyridin-4-one
3-(3-chloro-2-methoxyanilino)-2-(3-{(1R)-1-[(2S)-1,4-dioxan-2-yl]ethoxy}pyridin-4-yl)-1,5,6,7-tetrahydro-4H-pyrrolo[3,2-c]pyridin-4-one
3-(3-chloro-2-methoxyanilino)-2-(3-{(1R)-1-[(2R)-1,4-dioxan-2-yl]ethoxy}pyridin-4-yl)-1,5,6,7-tetrahydro-4H-pyrrolo[3,2-c]pyridin-4-one
3-(3-fluoro-2-methylanilino)-2-{3-[(4-methylmorpholin-2-yl)methoxy]pyridin-4-yl}-1,5,6,7-tetrahydro-4H-pyrrolo[3,2-c]pyridin-4-one
3-(3-fluoro-2-methylanilino)-2-(3-{[(2R)-4-methylmorpholin-2-yl]methoxy}pyridin-4-yl)-1,5,6,7-tetrahydro-4H-pyrrolo[3,2-c]pyridin-4-one
3-(3-fluoro-2-methylanilino)-2-(3-{[(2S)-4-methylmorpholin-2-yl]methoxy}pyridin-4-yl)-1,5,6,7-tetrahydro-4H-pyrrolo[3,2-c]pyridin-4-one
2-(3-{[1,4-dioxan-2-yl]methoxy}pyridin-4-yl)-3-(2-ethyl-3-fluoroanilino)-1,5,6,7-tetrahydro-4H-pyrrolo[3,2-c]pyridin-4-one
2-(3-{[(2R)-1,4-dioxan-2-yl]methoxy}pyridin-4-yl)-3-(2-ethyl-3-fluoroanilino)-1,5,6,7-tetrahydro-4H-pyrrolo[3,2-c]pyridin-4-one
2-(3-{[(2S)-1,4-dioxan-2-yl]methoxy}pyridin-4-yl)-3-(2-ethyl-3-fluoroanilino)-1,5,6,7-tetrahydro-4H-pyrrolo[3,2-c]pyridin-4-one
2-(3-{[5,5-dimethyl-1,4-dioxan-2-yl]methoxy}pyridin-4-yl)-3-(2-ethyl-3-fluoroanilino)-1,5,6,7-tetrahydro-4H-pyrrolo[3,2-c]pyridin-4-one
2-(3-{[(2R)-5,5-dimethyl-1,4-dioxan-2-yl]methoxy}pyridin-4-yl)-3-(2-ethyl-3-fluoroanilino)-1,5,6,7-tetrahydro-4H-pyrrolo[3,2-c]pyridin-4-one
2-(3-{[(2S)-5,5-dimethyl-1,4-dioxan-2-yl]methoxy}pyridin-4-yl)-3-(2-ethyl-3-fluoroanilino)-1,5,6,7-tetrahydro-4H-pyrrolo[3,2-c]pyridin-4-one
3-(3-chloro-2-methoxyanilino)-2-[3-({1-[4-methylmorpholin-2-yl]ethyl}oxy)pyridin-4-yl]-1,5,6,7-tetrahydro-4H-pyrrolo[3,2-c]pyridin-4-one
3-(3-chloro-2-methoxyanilino)-2-[3-({(1R)-1-[(2R)-4-methylmorpholin-2-yl]ethyl}oxy)pyridin-4-yl]-1,5,6,7-tetrahydro-4H-pyrrolo[3,2-c]pyridin-4-one
3-(3-chloro-2-methoxyanilino)-2-[3-({(1S)-1-[(2S)-4-methylmorpholin-2-yl]ethyl}oxy)pyridin-4-yl]-1,5,6,7-tetrahydro-4H-pyrrolo[3,2-c]pyridin-4-one
3-(3-chloro-2-methoxyanilino)-2-[3-({(1R)-1-[(2S)-4-methylmorpholin-2-yl]ethyl}oxy)pyridin-4-yl]-1,5,6,7-tetrahydro-4H-pyrrolo[3,2-c]pyridin-4-one
3-(3-chloro-2-methoxyanilino)-2-[3-({(1S)-1-[(2R)-4-methylmorpholin-2-yl]ethyl}oxy)pyridin-4-yl]-1,5,6,7-tetrahydro-4H-pyrrolo[3,2-c]pyridin-4-one.

5. A method of treating disease associated with mutant EGFR in a subject in need thereof comprising administration of a compound of general formula (I) according to claim 1 to the subject in need thereof, wherein the mutant EGFR comprises one or more exon 20 insertion mutations, an L858R mutation, or a small in-frame deletion of exon 19, in the presence or absence of a C787S mutation.

6. The method according to claim 5, wherein the disease is a hyperproliferative disease and/or a disorder responsive to induction of cell death.

7. The method according to claim 6, wherein the hyperproliferative disease and/or disorder is a haematological tumour, a solid tumour, or a metastases thereof.

8. The method according to claim 7, wherein the haematological tumour and/or solid tumour is lung cancer.

9. The method according to claim 6, wherein the tumour is lung cancer.

10. A pharmaceutical composition comprising at least one compound of general formula (I) according claim 1, together with at least one pharmaceutically acceptable auxiliary.

11. A combination comprising one or more first active ingredients selected from a compound of general formula (I) according to claim 1, and one or more second active ingredients selected from chemotherapeutic anti-cancer agents and target-specific anti-cancer agents.

12. A method of inhibiting EGF-receptor kinase activity in a cancer cell, the method comprising contacting the cancer cell with a compound of general formula (I) according to claim 1.

13. A method of reducing the survival of a cancer cell or inducing death in a cancer cell comprising a mutation in an EGF-receptor, the method comprising contacting a cancer cell comprising a mutation in an EGF-receptor with a compound of general formula (I) according to claim 1.

14. A method of treating cancer associated with mutant EGFR in a subject, the method comprising administering to the subject an effective amount of a compound of general formula (I) according to claim 1, wherein the mutant EGFR comprises one or more exon 20 insertion mutations, an L858R mutation, or a small in-frame deletion of exon 19, in the presence or absence of a C787S mutation.

15. A method of treating cancer in a subject, wherein the cancer is or has acquired resistance to an anti-EGF receptor therapy, the method comprising administering to the subject an effective amount of a compound of general formula (I) according to claim 1.

16. A method of enhancing the efficacy of an anti-EGF-receptor therapy in a subject, the method comprising administering to the subject an anti-EGF receptor therapy in combination with a compound of general formula (I) according to claim 1.

17. The method of claim 14, wherein the cancer is selected from the group consisting of leukemia, myelodysplastic syndrome, malignant lymphoma, head and neck tumours, tumours of the thorax, gastrointestinal tumours, endocrine tumours, mammary and other gynaecological tumours, urological tumours, skin tumours, and sarcomas.

18. The method of claim 15, wherein the EGF-receptor comprises an insertion between amino acids V769-D770 and/or between D770-N771.

19. A method of treating cancer in a subject, the method comprising detecting the presence of a mutation in exon 20 of the EGF-receptor in a biological sample of the subject, thereby determining that the subject should be treated with a compound according to claim 1, and administering the compound to the subject that should be treated with the compound.

20. A method of treating a subject with cancer, the method comprising administering to the subject an anti-EGF receptor therapy in combination with a compound of general formula (I) according to claim 1, wherein the subject is selected for therapy by detecting the presence of a mutation in exon 20 of the EGF-receptor in a biological sample of the subject.

21. The compound according to claim 1, wherein the compound is 3-(3-chloro-2-methoxyanilino)-2-(3-{[(2S)-1,4-dioxan-2-yl]methoxy}pyridin-4-yl)-1,5,6,7-tetrahydro-4H-pyrrolo[3,2-c]pyridin-4-one having the structure:

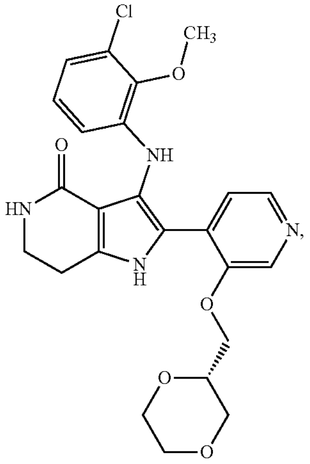

or a pharmaceutically acceptable salt of said compound.

22. The pharmaceutical composition according to claim 10, wherein the compound is 3-(3-chloro-2-methoxyanilino)-2-(3-{[(2S)-1,4-dioxan-2-yl]methoxy}pyridin-4-yl)-1,5,6,7-tetrahydro-4H-pyrrolo[3,2-c]pyridin-4-one having the structure:

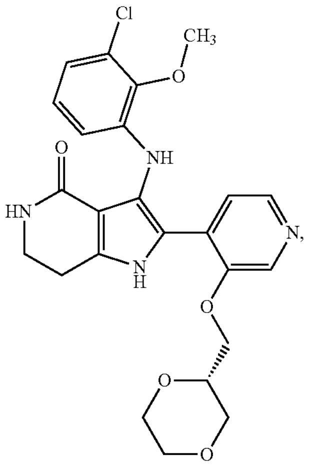

or a pharmaceutically acceptable salt of said compound.

23. The combination according to claim 11, wherein the compound is 3-(3-chloro-2-methoxyanilino)-2-(3-{[(2S)-1,4-dioxan-2-yl]methoxy}pyridin-4-yl)-1,5,6,7-tetrahydro-4H-pyrrolo[3,2-c]pyridin-4-one having the structure:

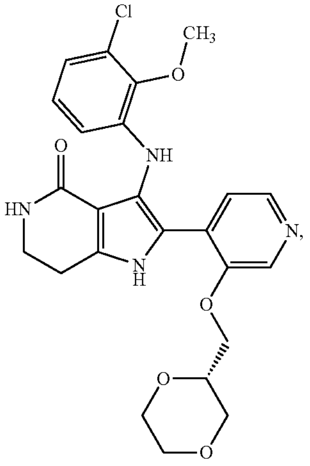 [SMILES: COc1c(Cl)cccc1Nc1c(-c2ccncc2OC[C@@H]2COCCO2)[nH]c2c1C(=O)NCC2]

or a pharmaceutically acceptable salt of said compound.

24. The method according to claim 12, wherein the compound is 3-(3-chloro-2-methoxyanilino)-2-(3-{[(2S)-1,4-dioxan-2-yl]methoxy}pyridin-4-yl)-1,5,6,7-tetrahydro-4H-pyrrolo[3,2-c]pyridin-4-one having the structure:

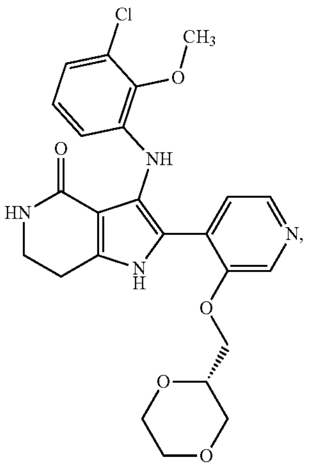 [SMILES: COc1c(Cl)cccc1Nc1c(-c2ccncc2OC[C@@H]2COCCO2)[nH]c2c1C(=O)NCC2]

or a pharmaceutically acceptable salt of said compound.

25. The method according to claim 13, wherein the compound is 3-(3-chloro-2-methoxyanilino)-2-(3-{[(2S)-1,4-dioxan-2-yl]methoxy}pyridin-4-yl)-1,5,6,7-tetrahydro-4H-pyrrolo[3,2-c]pyridin-4-one having the structure:

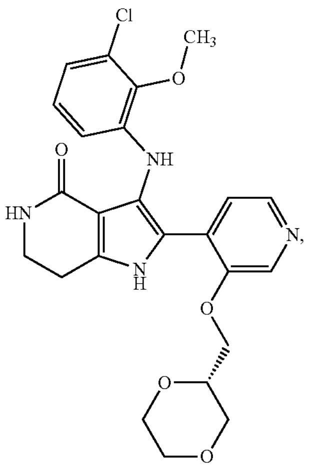

or a pharmaceutically acceptable salt of said compound.

26. The method according to claim 14, wherein the compound is 3-(3-chloro-2-methoxyanilino)-2-(3-{[(2S)-1,4-dioxan-2-yl]methoxy}pyridin-4-yl)-1,5,6,7-tetrahydro-4H-pyrrolo[3,2-c]pyridin-4-one having the structure:

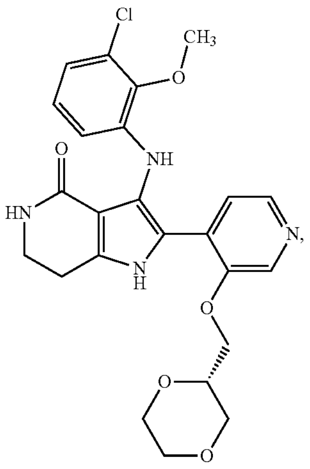

or a pharmaceutically acceptable salt of said compound.

27. The method according to claim 15, wherein the compound is 3-(3-chloro-2-methoxyanilino)-2-(3-{[(2S)-1,4-dioxan-2-yl]methoxy}pyridin-4-yl)-1,5,6,7-tetrahydro-4H-pyrrolo[3,2-c]pyridin-4-one having the structure:

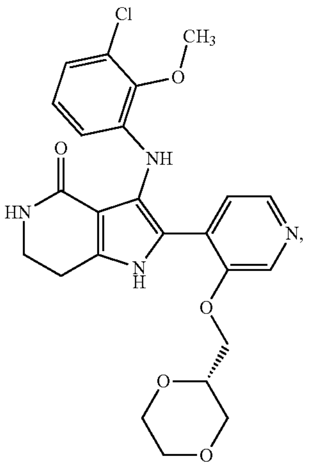 [SMILES: COc1c(Cl)cccc1Nc1c(-c2ccncc2OC[C@@H]2COCCO2)[nH]c2c1C(=O)NCC2]

or a pharmaceutically acceptable salt of said compound.

28. The method according to claim 16, wherein the compound is 3-(3-chloro-2-methoxyanilino)-2-(3-{[(2S)-1,4-dioxan-2-yl]methoxy}pyridin-4-yl)-1,5,6,7-tetrahydro-4H-pyrrolo[3,2-c]pyridin-4-one having the structure:

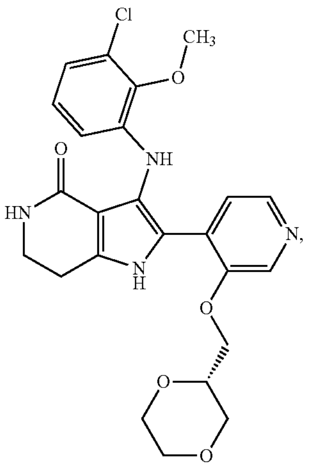 [SMILES: COc1c(Cl)cccc1Nc1c(-c2ccncc2OC[C@@H]2COCCO2)[nH]c2c1C(=O)NCC2]

or a pharmaceutically acceptable salt of said compound.

29. The method according to claim 17, wherein the compound is 3-(3-chloro-2-methoxyanilino)-2-(3-{[(2S)-1,4-dioxan-2-yl]methoxy}pyridin-4-yl)-1,5,6,7-tetrahydro-4H-pyrrolo[3,2-c]pyridin-4-one having the structure:

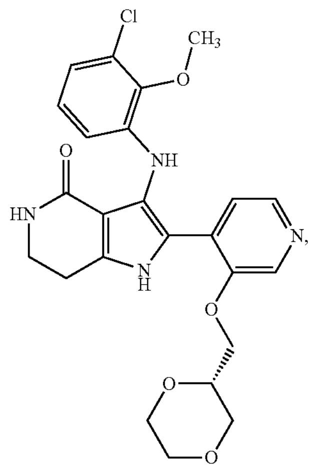

or a pharmaceutically acceptable salt of said compound.

30. The method according to claim 18, wherein the compound is 3-(3-chloro-2-methoxyanilino)-2-(3-{[(2S)-1,4-dioxan-2-yl]methoxy}pyridin-4-yl)-1,5,6,7-tetrahydro-4H-pyrrolo[3,2-c]pyridin-4-one having the structure:

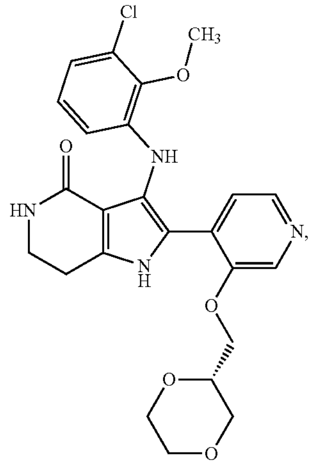

or a pharmaceutically acceptable salt of said compound.

31. The method according to claim 19, wherein the compound is 3-(3-chloro-2-methoxyanilino)-2-(3-{[(2S)-1,4-dioxan-2-yl]methoxy}pyridin-4-yl)-1,5,6,7-tetrahydro-4H-pyrrolo[3,2-c]pyridin-4-one having the structure:

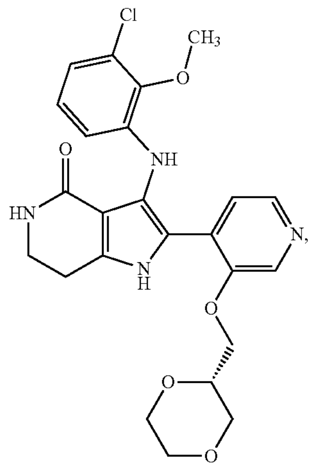 [SMILES: COc1c(Cl)cccc1Nc1c(-c2ccncc2OC[C@@H]2COCCO2)[nH]c2c1C(=O)NCC2]

or a pharmaceutically acceptable salt of said compound.

32. The method according to claim 20, wherein the compound is 3-(3-chloro-2-methoxyanilino)-2-(3-{[(2S)-1,4-dioxan-2-yl]methoxy}pyridin-4-yl)-1,5,6,7-tetrahydro-4H-pyrrolo[3,2-c]pyridin-4-one having the structure:

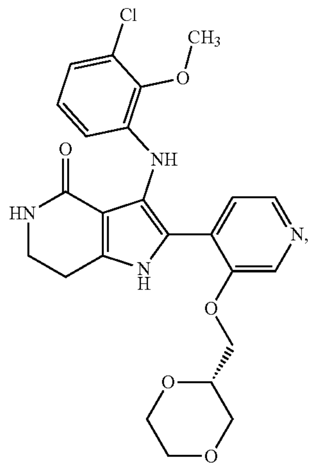 [SMILES: COc1c(Cl)cccc1Nc1c(-c2ccncc2OC[C@@H]2COCCO2)[nH]c2c1C(=O)NCC2]

or a pharmaceutically acceptable salt of said compound.

33. A compound having the structure:

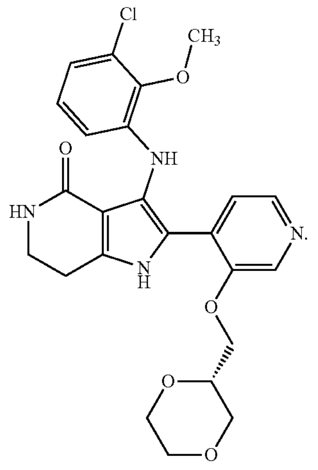 [SMILES: COc1c(Cl)cccc1Nc1c(-c2ccncc2OC[C@@H]2COCCO2)[nH]c2c1C(=O)NCC2]

34. A pharmaceutical composition comprising a compound together with at least one pharmaceutically acceptable auxiliary, wherein the compound is 3-(3-chloro-2-methoxyanilino)-2-(3-{[(2S)-1,4-dioxan-2-yl]methoxy}pyridin-4-yl)-1,5,6,7-tetrahydro-4H-pyrrolo[3,2-c]pyridin-4-one having the structure:

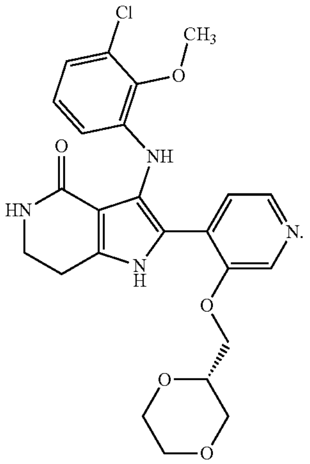 [SMILES: COc1c(Cl)cccc1Nc1c(-c2ccncc2OC[C@@H]2COCCO2)[nH]c2c1C(=O)NCC2]

35. A combination comprising a first active agent and one or more second active ingredients selected from chemotherapeutic anti-cancer agents and target-specific anti-cancer agents, wherein the first active agent is is 3-(3-chloro-2-methoxyanilino)-2-(3-{[(2S)-1,4-dioxan-2-yl]methoxy}pyridin-4-yl)-1,5,6,7-tetrahydro-4H-pyrrolo[3,2-c]pyridin-4-one having the structure:

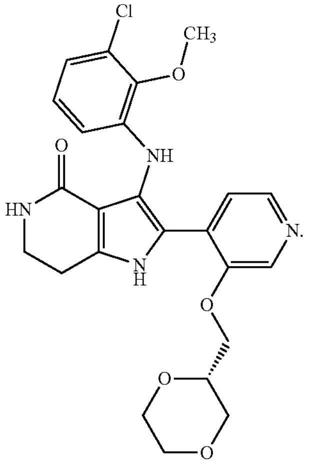 [SMILES: COc1c(Cl)cccc1Nc1c(-c2ccncc2OC[C@@H]2COCCO2)[nH]c2c1C(=O)NCC2]

36. A method of inhibiting EGF-receptor kinase activity in a cancer cell, the method comprising contacting the cancer cell with 3-(3-chloro-2-methoxyanilino)-2-(3-{[(2S)-1,4-dioxan-2-yl]methoxy}pyridin-4-yl)-1,5,6,7-tetrahydro-4H-pyrrolo[3,2-c]pyridin-4-one having the structure:

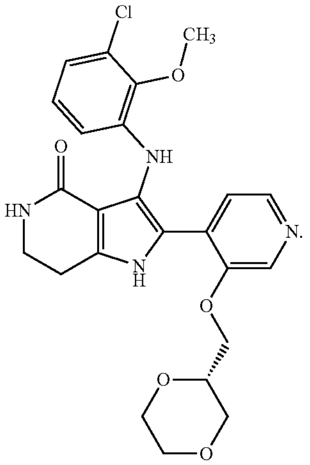 [SMILES: COc1c(Cl)cccc1Nc1c(-c2ccncc2OC[C@@H]2COCCO2)[nH]c2c1C(=O)NCC2]

37. A method of reducing the survival of a cancer cell or inducing death in a cancer cell comprising a mutation in an EGF-receptor, the method comprising contacting a cancer cell comprising a mutation in an EGF-receptor with 3-(3-chloro-2-methoxyanilino)-2-(3-{[(2S)-1,4-dioxan-2-yl]methoxy}pyridin-4-yl)-1,5,6,7-tetrahydro-4H-pyrrolo[3,2-c]pyridin-4-one having the structure:

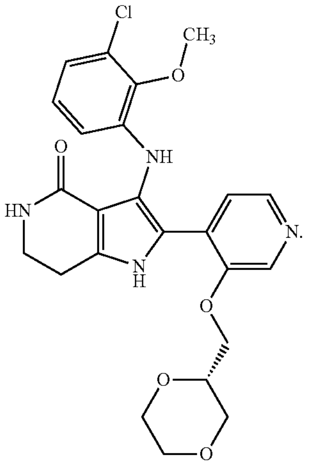 [SMILES: COc1c(Cl)cccc1Nc1c(-c2ccncc2OC[C@@H]2COCCO2)[nH]c2c1C(=O)NCC2]

38. A method of treating cancer associated with mutant EGFR in a subject, the method comprising administering to the subject an effective amount of 3-(3-chloro-2-methoxyanilino)-2-(3-{[(2S)-1,4-dioxan-2-yl]methoxy}pyridin-4-yl)-

1,5,6,7-tetrahydro-4H-pyrrolo[3,2-c]pyridin-4-one having the structure:

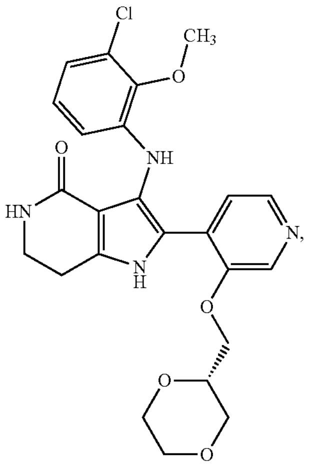

wherein the mutant EGFR comprises one or more exon 20 insertion mutations, an L858R mutation, or a small in-frame deletion of exon 19, in the presence or absence of a C787S mutation.

39. A method of treating cancer in a subject, wherein the cancer is or has acquired resistance to an anti-EGF receptor therapy, the method comprising administering to the subject an effective amount of 3-(3-chloro-2-methoxyanilino)-2-(3-{[(2S)-1,4-dioxan-2-yl]methoxy}pyridin-4-yl)-1,5,6,7-tetrahydro-4H-pyrrolo[3,2-c]pyridin-4-one having the structure:

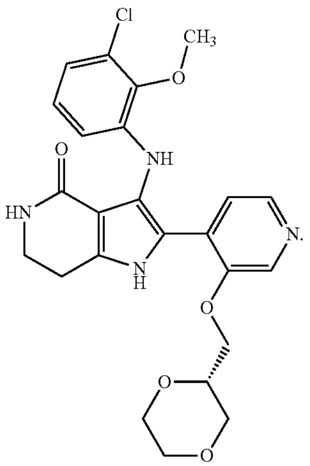 [SMILES: COc1c(Cl)cccc1Nc1c(-c2ccncc2OC[C@@H]2COCCO2)[nH]c2c1C(=O)NCC2]

40. A method of enhancing the efficacy of an anti-EGF-receptor therapy in a subject, the method comprising administering to the subject an anti-EGF receptor therapy in combination with 3-(3-chloro-2-methoxyanilino)-2-(3-{[(2S)-1,4-dioxan-2-yl]methoxy}pyridin-4-yl)-1,5,6,7-tetrahydro-4H-pyrrolo[3,2-c]pyridin-4-one having the structure:

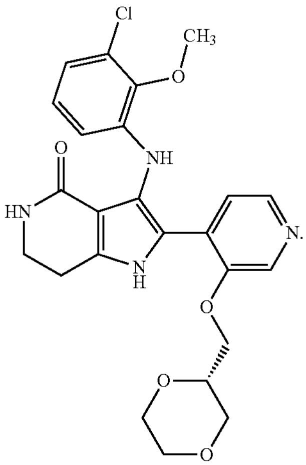 [SMILES: COc1c(Cl)cccc1Nc1c(-c2ccncc2OC[C@@H]2COCCO2)[nH]c2c1C(=O)NCC2]

41. A method of treating cancer associated with mutant EGFR in a subject, the method comprising administering to the subject an effective amount of 3-(3-chloro-2-methoxyanilino)-2-(3-{[(2S)-1,4-dioxan-2-yl]methoxy}pyridin-4-yl)-1,5,6,7-tetrahydro-4H-pyrrolo[3,2-c]pyridin-4-one having the structure:

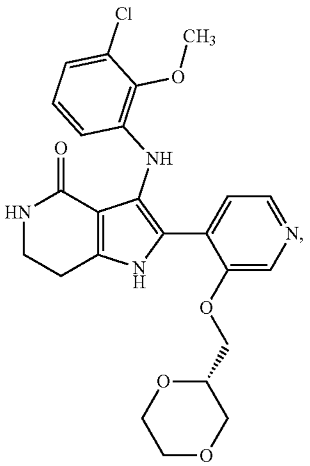 [SMILES: COc1c(Cl)cccc1Nc1c(-c2ccncc2OC[C@@H]2COCCO2)[nH]c2c1C(=O)NCC2]

wherein the cancer is selected from the group consisting of leukemia, myelodysplastic syndrome, malignant lymphoma, head and neck tumours, tumours of the thorax, gastrointestinal tumours, endocrine tumours, mammary and other gynaecological tumours, urological tumours, skin tumours, and sarcomas.

42. A method of treating cancer in a subject, wherein the cancer is or has acquired resistance to an anti-EGF receptor therapy, the method comprising administering to the subject an effective amount of 3-(3-chloro-2-methoxyanilino)-2-(3-{[(2S)-1,4-dioxan-2-yl]methoxy}pyridin-4-yl)-1,5,6,7-tetrahydro-4H-pyrrolo[3,2-c]pyridin-4-one having the structure:

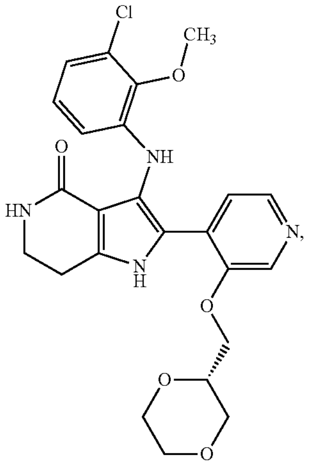

wherein the EGF-receptor comprises an insertion between amino acids V769-D770 and/or between D770-N771.

43. A method of treating cancer in a subject, the method comprising detecting the presence of a mutation in exon 20 of the EGF-receptor in a biological sample of the subject, thereby determining that the subject should be treated with a compound having the structure:

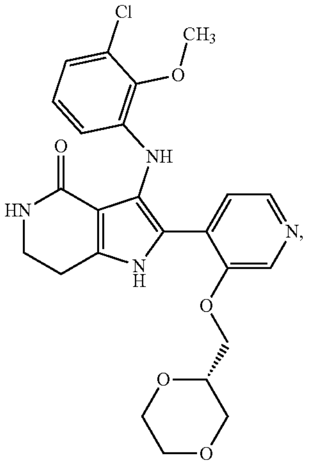 [SMILES: COc1c(Cl)cccc1Nc1c(-c2ccncc2OC[C@@H]2COCCO2)[nH]c2c1C(=O)NCC2]

and administering the compound to the subject that should be treated with the compound.

44. A method of treating a subject with cancer, the method comprising administering to the subject an anti-EGF receptor therapy in combination with 3-(3-chloro-2-methoxyanilino)-2-(3-{[(2S)-1,4-dioxan-2-yl]methoxy}pyridin-4-yl)-1,5,6,7-tetrahydro-4H-pyrrolo[3,2-c]pyridin-4-one having the structure:

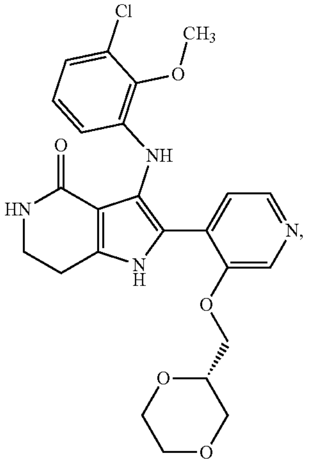 [SMILES: COc1c(Cl)cccc1Nc1c(-c2ccncc2OC[C@@H]2COCCO2)[nH]c2c1C(=O)NCC2]

wherein the subject is selected for therapy by detecting the presence of a mutation in exon 20 of the EGF-receptor in a biological sample of the subject.

* * * * *

SEQUENCE LISTING

```
<160> NUMBER OF SEQ ID NOS: 7

<210> SEQ ID NO 1
<211> LENGTH: 1210
<212> TYPE: PRT
<213> ORGANISM: Homo sapien
<220> FEATURE:
<223> OTHER INFORMATION: human EGFR, UniProt Accession No. P00533-1

<400> SEQUENCE: 1

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60
```

-continued

```
Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
```

-continued

```
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Asn Leu Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
    610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
            660                 665                 670

Ile Val Arg Lys Arg Thr Leu Arg Arg Leu Leu Gln Glu Arg Glu Leu
        675                 680                 685

Val Glu Pro Leu Thr Pro Ser Gly Glu Ala Pro Asn Gln Ala Leu Leu
    690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
        755                 760                 765

Val Asp Asn Pro His Val Cys Arg Leu Leu Gly Ile Cys Leu Thr Ser
    770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
            820                 825                 830

Leu Val His Arg Asp Leu Ala Ala Arg Asn Val Leu Val Lys Thr Pro
        835                 840                 845

Gln His Val Lys Ile Thr Asp Phe Gly Leu Ala Lys Leu Leu Gly Ala
    850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
            900                 905                 910
```

```
Lys Pro Tyr Asp Gly Ile Pro Ala Ser Glu Ile Ser Ser Ile Leu Glu
        915                 920                 925

Lys Gly Glu Arg Leu Pro Gln Pro Pro Ile Cys Thr Ile Asp Val Tyr
    930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
            980                 985                 990

Thr Asp Ser Asn Phe Tyr Arg Ala Leu Met Asp Glu Glu Asp Met Asp
        995                 1000                1005

Asp Val Val Asp Ala Asp Glu Tyr Leu Ile Pro Gln Gln Gly Phe Phe
    1010                1015                1020

Ser Ser Pro Ser Thr Ser Arg Thr Pro Leu Leu Ser Ser Leu Ser Ala
1025                1030                1035                1040

Thr Ser Asn Asn Ser Thr Val Ala Cys Ile Asp Arg Asn Gly Leu Gln
                1045                1050                1055

Ser Cys Pro Ile Lys Glu Asp Ser Phe Leu Gln Arg Tyr Ser Ser Asp
            1060                1065                1070

Pro Thr Gly Ala Leu Thr Glu Asp Ser Ile Asp Asp Thr Phe Leu Pro
        1075                1080                1085

Val Pro Glu Tyr Ile Asn Gln Ser Val Pro Lys Arg Pro Ala Gly Ser
    1090                1095                1100

Val Gln Asn Pro Val Tyr His Asn Gln Pro Leu Asn Pro Ala Pro Ser
1105                1110                1115                1120

Arg Asp Pro His Tyr Gln Asp Pro His Ser Thr Ala Val Gly Asn Pro
                1125                1130                1135

Glu Tyr Leu Asn Thr Val Gln Pro Thr Cys Val Asn Ser Thr Phe Asp
            1140                1145                1150

Ser Pro Ala His Trp Ala Gln Lys Gly Ser His Gln Ile Ser Leu Asp
        1155                1160                1165

Asn Pro Asp Tyr Gln Gln Asp Phe Phe Pro Lys Glu Ala Lys Pro Asn
    1170                1175                1180

Gly Ile Phe Lys Gly Ser Thr Ala Glu Asn Ala Glu Tyr Leu Arg Val
1185                1190                1195                1200

Ala Pro Gln Ser Ser Glu Phe Ile Gly Ala
                1205                1210


<210> SEQ ID NO 2
<211> LENGTH: 3859
<212> TYPE: DNA
<213> ORGANISM: Homo sapien
<220> FEATURE:
<223> OTHER INFORMATION: human EGFR, NCBI Reference Sequence:
      NM_001346897.1

<400> SEQUENCE: 2

gtccgggcag cccccggcgc agcgcggccg cagcagcctc cgcccccgc acggtgtgag      60

cgcccgacgc ggccgaggcg gccggagtcc cgagctagcc ccggcggccg ccgccgccca     120

gaccggacga caggccacct cgtcggcgtc cgcccgagtc cccgcctcgc cgccaacgcc     180

acaaccaccg cgcacggccc cctgactccg tccagtattg atcgggagag ccggagcgag     240

ctcttcgggg agcagcgatg cgaccctccg ggacggccgg ggcagcgctc ctggcgctgc     300
```

-continued

```
tggctgcgct ctgcccggcg agtcgggctc tggaggaaaa gaaagtttgc caaggcacga    360
gtaacaagct cacgcagttg ggcacttttg aagatcattt tctcagcctc cagaggatgt    420
tcaataactg tgaggtggtc cttgggaatt tggaaattac ctatgtgcag aggaattatg    480
atctttcctt cttaaagacc atccaggagg tggctggtta tgtcctcatt gccctcaaca    540
cagtggagcg aattcctttg gaaaacctgc agatcatcag aggaaatatg tactacgaaa    600
attcctatgc cttagcagtc ttatctaact atgatgcaaa taaaaccgga ctgaaggagc    660
tgcccatgag aaatttacag ggccaaaagt gtgatccaag ctgtcccaat gggagctgct    720
ggggtgcagg agaggagaac tgccagaaac tgaccaaaat catctgtgcc cagcagtgct    780
ccgggcgctg ccgtggcaag tcccccagtg actgctgcca caaccagtgt gctgcaggct    840
gcacaggccc ccgggagagc gactgcctgg tctgccgcaa attccgagac gaagccacgt    900
gcaaggacac ctgcccccca ctcatgctct acaaccccac cacgtaccag atggatgtga    960
accccgaggg caaatacagc tttggtgcca cctgcgtgaa gaagtgtccc cgtaattatg   1020
tggtgacaga tcacggctcg tgcgtccgag cctgtggggc cgacagctat gagatggagg   1080
aagacggcgt ccgcaagtgt aagaagtgcg aagggccttg ccgcaaagtg tgtaacggaa   1140
taggtattgg tgaatttaaa gactcactct ccataaatgc tacgaatatt aaacacttca   1200
aaaactgcac ctccatcagt ggcgatctcc acatcctgcc ggtggcattt aggggtgact   1260
ccttcacaca tactcctcct ctggatccac aggaactgga tattctgaaa accgtaaagg   1320
aaatcacagg gtttttgctg attcaggctt ggcctgaaaa caggacggac ctccatgcct   1380
ttgagaacct agaaatcata cgcggcagga ccaagcaaca tggtcagttt tctcttgcag   1440
tcgtcagcct gaacataaca tccttgggat tacgctccct caaggagata agtgatggag   1500
atgtgataat ttcaggaaac aaaaatttgt gctatgcaaa tacaataaac tggaaaaaac   1560
tgtttgggac ctccggtcag aaaaccaaaa ttataagcaa cagaggtgaa aacagctgca   1620
aggccacagg ccaggtctgc catgccttgt gctcccccga gggctgctgg ggcccggagc   1680
ccagggactg cgtctcttgc cggaatgtca gccgaggcag ggaatgcgtg gacaagtgca   1740
accttctgga gggtgagcca agggagtttg tggagaactc tgagtgcata cagtgccacc   1800
cagagtgcct gcctcaggcc atgaacatca cctgcacagg acggggacca gacaactgta   1860
tccagtgtgc ccactacatt gacggccccc actgcgtcaa gacctgcccg gcaggagtca   1920
tgggagaaaa caacaccctg gtctggaagt acgcagacgc cggccatgtg tgccacctgt   1980
gccatccaaa ctgcacctac ggatgcactg ggccaggtct tgaaggctgt ccaacgaatg   2040
ggcctaagat cccgtccatc gccactggga tggtgggggc cctcctcttg ctgctggtgg   2100
tggccctggg gatcggcctc ttcatgcgaa ggcgccacat cgttcggaag cgcacgctgc   2160
ggaggctgct gcaggagagg gagcttgtgg agcctcttac acccagtgga gaagctccca   2220
accaagctct cttgaggatc ttgaaggaaa ctgaattcaa aaagatcaaa gtgctgggct   2280
ccggtgcgtt cggcacggtg tataagggac tctggatccc agaaggtgag aaagttaaaa   2340
ttcccgtcgc tatcaaggaa ttaagagaag caacatctcc gaaagccaac aaggaaatcc   2400
tcgatgaagc ctacgtgatg gccagcgtgg acaaccccca cgtgtgccgc ctgctgggca   2460
tctgcctcac ctccaccgtg cagctcatca cgcagctcat gcccttcggc tgcctcctgg   2520
actatgtccg ggaacacaaa gacaatattg gctcccagta cctgctcaac tggtgtgtgc   2580
agatcgcaaa gggcatgaac tacttggagg accgtcgctt ggtgcaccgc gacctggcag   2640
ccaggaacgt actggtgaaa acaccgcagc atgtcaagat cacagatttt gggctggcca   2700
```

```
aactgctggg tgcggaagag aaagaatacc atgcagaagg aggcaaagtg cctatcaagt   2760

ggatggcatt ggaatcaatt ttacacagaa tctataccca ccagagtgat gtctggagct   2820

acggggtgac tgtttgggag ttgatgacct ttggatccaa gccatatgac ggaatccctg   2880

ccagcgagat ctcctccatc ctggagaaag gagaacgcct ccctcagcca cccatatgta   2940

ccatcgatgt ctacatgatc atggtcaagt gctggatgat agacgcagat agtcgcccaa   3000

agttccgtga gttgatcatc gaattctcca aaatggcccg agacccccag cgctaccttg   3060

tcattcaggg ggatgaaaga atgcatttgc caagtcctac agactccaac ttctaccgtg   3120

ccctgatgga tgaagaagac atggacgacg tggtggatgc cgacgagtac ctcatcccac   3180

agcagggctt cttcagcagc ccctccacgt cacggactcc cctcctgagc tctctgagtg   3240

caaccagcaa caattccacc gtggcttgca ttgatagaaa tgggctgcaa agctgtccca   3300

tcaaggaaga cagcttcttg cagcgataca gctcagaccc cacaggcgcc ttgactgagg   3360

acagcataga cgacaccttc ctcccagtgc ctggtgagtg gcttgtctgg aaacagtcct   3420

gctcctcaac ctcctcgacc cactcagcag cagccagtct ccagtgtcca agccaggtgc   3480

tccctccagc atctccagag ggggaaacag tggcagattt gcagacacag tgaagggcgt   3540

aaggagcaga taaacacatg accgagcctg cacaagctct ttgttgtgtc tggttgtttg   3600

ctgtacctct gttgtaagaa tgaatctgca aaatttctag cttatgaagc aaatcacgga   3660

catacacatc tgtgtgtgtg agtgttcatg atgtgtgtac atctgtgtat gtgtgtgtgt   3720

gtatgtgtgt gtttgtgaca gatttgatcc ctgttctctc tgctggctct atcttgacct   3780

gtgaaacgta tatttaacta attaaatatt agttaatatt aataaatttt aagctttatc   3840

cagaaaaaaa aaaaaaaaa                                                 3859
```

```
<210> SEQ ID NO 3
<211> LENGTH: 788
<212> TYPE: PRT
<213> ORGANISM: Homo sapien
<220> FEATURE:
<223> OTHER INFORMATION: GST-EGFR (Wild Type)

<400> SEQUENCE: 3

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
```

-continued

```
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Pro Ile Thr Ser
    210                 215                 220

Leu Tyr Lys Lys Ala Gly Ser Asp Tyr Asp Ile Pro Thr Thr Thr Glu
225                 230                 235                 240

Asn Leu Tyr Phe Gln Gly Arg Arg Arg His Ile Val Arg Lys Arg Thr
                245                 250                 255

Leu Arg Arg Leu Leu Gln Glu Arg Glu Leu Val Glu Pro Leu Thr Pro
            260                 265                 270

Ser Gly Glu Ala Pro Asn Gln Ala Leu Leu Arg Ile Leu Lys Glu Thr
        275                 280                 285

Glu Phe Lys Lys Ile Lys Val Leu Gly Ser Gly Ala Phe Gly Thr Val
    290                 295                 300

Tyr Lys Gly Leu Trp Ile Pro Glu Gly Glu Lys Val Lys Ile Pro Val
305                 310                 315                 320

Ala Ile Lys Glu Leu Arg Glu Ala Thr Ser Pro Lys Ala Asn Lys Glu
                325                 330                 335

Ile Leu Asp Glu Ala Tyr Val Met Ala Ser Val Asp Asn Pro His Val
            340                 345                 350

Cys Arg Leu Leu Gly Ile Cys Leu Thr Ser Thr Val Gln Leu Ile Thr
        355                 360                 365

Gln Leu Met Pro Phe Gly Cys Leu Leu Asp Tyr Val Arg Glu His Lys
    370                 375                 380

Asp Asn Ile Gly Ser Gln Tyr Leu Leu Asn Trp Cys Val Gln Ile Ala
385                 390                 395                 400

Lys Gly Met Asn Tyr Leu Glu Asp Arg Arg Leu Val His Arg Asp Leu
                405                 410                 415

Ala Ala Arg Asn Val Leu Val Lys Thr Pro Gln His Val Lys Ile Thr
            420                 425                 430

Asp Phe Gly Leu Ala Lys Leu Leu Gly Ala Glu Glu Lys Glu Tyr His
        435                 440                 445

Ala Glu Gly Gly Lys Val Pro Ile Lys Trp Met Ala Leu Glu Ser Ile
    450                 455                 460

Leu His Arg Ile Tyr Thr His Gln Ser Asp Val Trp Ser Tyr Gly Val
465                 470                 475                 480

Thr Val Trp Glu Leu Met Thr Phe Gly Ser Lys Pro Tyr Asp Gly Ile
                485                 490                 495

Pro Ala Ser Glu Ile Ser Ser Ile Leu Glu Lys Gly Glu Arg Leu Pro
            500                 505                 510

Gln Pro Pro Ile Cys Thr Ile Asp Val Tyr Met Ile Met Val Lys Cys
        515                 520                 525

Trp Met Ile Asp Ala Asp Ser Arg Pro Lys Phe Arg Glu Leu Ile Ile
    530                 535                 540

Glu Phe Ser Lys Met Ala Arg Asp Pro Gln Arg Tyr Leu Val Ile Gln
545                 550                 555                 560

Gly Asp Glu Arg Met His Leu Pro Ser Pro Thr Asp Ser Asn Phe Tyr
                565                 570                 575
```

```
Arg Ala Leu Met Asp Glu Glu Asp Met Asp Asp Val Val Asp Ala Asp
            580                 585                 590

Glu Tyr Leu Ile Pro Gln Gln Gly Phe Phe Ser Ser Pro Ser Thr Ser
        595                 600                 605

Arg Thr Pro Leu Leu Ser Ser Leu Ser Ala Thr Ser Asn Asn Ser Thr
    610                 615                 620

Val Ala Cys Ile Asp Arg Asn Gly Leu Gln Ser Cys Pro Ile Lys Glu
625                 630                 635                 640

Asp Ser Phe Leu Gln Arg Tyr Ser Ser Asp Pro Thr Gly Ala Leu Thr
                645                 650                 655

Glu Asp Ser Ile Asp Asp Thr Phe Leu Pro Val Pro Glu Tyr Ile Asn
            660                 665                 670

Gln Ser Val Pro Lys Arg Pro Ala Gly Ser Val Gln Asn Pro Val Tyr
        675                 680                 685

His Asn Gln Pro Leu Asn Pro Ala Pro Ser Arg Asp Pro His Tyr Gln
    690                 695                 700

Asp Pro His Ser Thr Ala Val Gly Asn Pro Glu Tyr Leu Asn Thr Val
705                 710                 715                 720

Gln Pro Thr Cys Val Asn Ser Thr Phe Asp Ser Pro Ala His Trp Ala
                725                 730                 735

Gln Lys Gly Ser His Gln Ile Ser Leu Asp Asn Pro Asp Tyr Gln Gln
            740                 745                 750

Asp Phe Phe Pro Lys Glu Ala Lys Pro Asn Gly Ile Phe Lys Gly Ser
        755                 760                 765

Thr Ala Glu Asn Ala Glu Tyr Leu Arg Val Ala Pro Gln Ser Ser Glu
    770                 775                 780

Phe Ile Gly Ala
785


<210> SEQ ID NO 4
<211> LENGTH: 791
<212> TYPE: PRT
<213> ORGANISM: Homo sapien
<220> FEATURE:
<223> OTHER INFORMATION: GST-EGFR (ASV between V769 and D770)

<400> SEQUENCE: 4

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140
```

```
Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Pro Ile Thr Ser
    210                 215                 220

Leu Tyr Lys Lys Ala Gly Ser Asp Tyr Asp Ile Pro Thr Thr Thr Glu
225                 230                 235                 240

Asn Leu Tyr Phe Gln Gly Arg Arg Arg His Ile Val Arg Lys Arg Thr
                245                 250                 255

Leu Arg Arg Leu Leu Gln Glu Arg Glu Leu Val Glu Pro Leu Thr Pro
            260                 265                 270

Ser Gly Glu Ala Pro Asn Gln Ala Leu Leu Arg Ile Leu Lys Glu Thr
        275                 280                 285

Glu Phe Lys Lys Ile Lys Val Leu Gly Ser Gly Ala Phe Gly Thr Val
    290                 295                 300

Tyr Lys Gly Leu Trp Ile Pro Glu Gly Glu Lys Val Lys Ile Pro Val
305                 310                 315                 320

Ala Ile Lys Glu Leu Arg Glu Ala Thr Ser Pro Lys Ala Asn Lys Glu
                325                 330                 335

Ile Leu Asp Glu Ala Tyr Val Met Ala Ser Val Ala Ser Val Asp Asn
            340                 345                 350

Pro His Val Cys Arg Leu Leu Gly Ile Cys Leu Thr Ser Thr Val Gln
        355                 360                 365

Leu Ile Thr Gln Leu Met Pro Phe Gly Cys Leu Leu Asp Tyr Val Arg
    370                 375                 380

Glu His Lys Asp Asn Ile Gly Ser Gln Tyr Leu Leu Asn Trp Cys Val
385                 390                 395                 400

Gln Ile Ala Lys Gly Met Asn Tyr Leu Glu Asp Arg Arg Leu Val His
                405                 410                 415

Arg Asp Leu Ala Ala Arg Asn Val Leu Val Lys Thr Pro Gln His Val
            420                 425                 430

Lys Ile Thr Asp Phe Gly Leu Ala Lys Leu Leu Gly Ala Glu Glu Lys
        435                 440                 445

Glu Tyr His Ala Glu Gly Gly Lys Val Pro Ile Lys Trp Met Ala Leu
    450                 455                 460

Glu Ser Ile Leu His Arg Ile Tyr Thr His Gln Ser Asp Val Trp Ser
465                 470                 475                 480

Tyr Gly Val Thr Val Trp Glu Leu Met Thr Phe Gly Ser Lys Pro Tyr
                485                 490                 495

Asp Gly Ile Pro Ala Ser Glu Ile Ser Ser Ile Leu Glu Lys Gly Glu
            500                 505                 510

Arg Leu Pro Gln Pro Pro Ile Cys Thr Ile Asp Val Tyr Met Ile Met
        515                 520                 525

Val Lys Cys Trp Met Ile Asp Ala Asp Ser Arg Pro Lys Phe Arg Glu
    530                 535                 540

Leu Ile Ile Glu Phe Ser Lys Met Ala Arg Asp Pro Gln Arg Tyr Leu
545                 550                 555                 560
```

-continued

```
Val Ile Gln Gly Asp Glu Arg Met His Leu Pro Ser Pro Thr Asp Ser
                565                 570                 575

Asn Phe Tyr Arg Ala Leu Met Asp Glu Glu Asp Met Asp Asp Val Val
            580                 585                 590

Asp Ala Asp Glu Tyr Leu Ile Pro Gln Gln Gly Phe Phe Ser Ser Pro
        595                 600                 605

Ser Thr Ser Arg Thr Pro Leu Leu Ser Ser Leu Ser Ala Thr Ser Asn
    610                 615                 620

Asn Ser Thr Val Ala Cys Ile Asp Arg Asn Gly Leu Gln Ser Cys Pro
625                 630                 635                 640

Ile Lys Glu Asp Ser Phe Leu Gln Arg Tyr Ser Ser Asp Pro Thr Gly
                645                 650                 655

Ala Leu Thr Glu Asp Ser Ile Asp Asp Thr Phe Leu Pro Val Pro Glu
            660                 665                 670

Tyr Ile Asn Gln Ser Val Pro Lys Arg Pro Ala Gly Ser Val Gln Asn
        675                 680                 685

Pro Val Tyr His Asn Gln Pro Leu Asn Pro Ala Pro Ser Arg Asp Pro
    690                 695                 700

His Tyr Gln Asp Pro His Ser Thr Ala Val Gly Asn Pro Glu Tyr Leu
705                 710                 715                 720

Asn Thr Val Gln Pro Thr Cys Val Asn Ser Thr Phe Asp Ser Pro Ala
                725                 730                 735

His Trp Ala Gln Lys Gly Ser His Gln Ile Ser Leu Asp Asn Pro Asp
            740                 745                 750

Tyr Gln Gln Asp Phe Phe Pro Lys Glu Ala Lys Pro Asn Gly Ile Phe
        755                 760                 765

Lys Gly Ser Thr Ala Glu Asn Ala Glu Tyr Leu Arg Val Ala Pro Gln
    770                 775                 780

Ser Ser Glu Phe Ile Gly Ala
785                 790
```

<210> SEQ ID NO 5
<211> LENGTH: 791
<212> TYPE: PRT
<213> ORGANISM: Homo sapien
<220> FEATURE:
<223> OTHER INFORMATION: GST-EGFR (SVD between D770 and N771)

<400> SEQUENCE: 5

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125
```

-continued

```
Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Pro Ile Thr Ser
    210                 215                 220

Leu Tyr Lys Lys Ala Gly Ser Asp Tyr Asp Ile Pro Thr Thr Thr Glu
225                 230                 235                 240

Asn Leu Tyr Phe Gln Gly Arg Arg Arg His Ile Val Arg Lys Arg Thr
                245                 250                 255

Leu Arg Arg Leu Leu Gln Glu Arg Glu Leu Val Glu Pro Leu Thr Pro
            260                 265                 270

Ser Gly Glu Ala Pro Asn Gln Ala Leu Leu Arg Ile Leu Lys Glu Thr
        275                 280                 285

Glu Phe Lys Lys Ile Lys Val Leu Gly Ser Gly Ala Phe Gly Thr Val
    290                 295                 300

Tyr Lys Gly Leu Trp Ile Pro Glu Gly Glu Lys Val Lys Ile Pro Val
305                 310                 315                 320

Ala Ile Lys Glu Leu Arg Glu Ala Thr Ser Pro Lys Ala Asn Lys Glu
                325                 330                 335

Ile Leu Asp Glu Ala Tyr Val Met Ala Ser Val Asp Ser Val Asp Asn
            340                 345                 350

Pro His Val Cys Arg Leu Leu Gly Ile Cys Leu Thr Ser Thr Val Gln
        355                 360                 365

Leu Ile Thr Gln Leu Met Pro Phe Gly Cys Leu Leu Asp Tyr Val Arg
    370                 375                 380

Glu His Lys Asp Asn Ile Gly Ser Gln Tyr Leu Leu Asn Trp Cys Val
385                 390                 395                 400

Gln Ile Ala Lys Gly Met Asn Tyr Leu Glu Asp Arg Arg Leu Val His
                405                 410                 415

Arg Asp Leu Ala Ala Arg Asn Val Leu Val Lys Thr Pro Gln His Val
            420                 425                 430

Lys Ile Thr Asp Phe Gly Leu Ala Lys Leu Leu Gly Ala Glu Glu Lys
        435                 440                 445

Glu Tyr His Ala Glu Gly Gly Lys Val Pro Ile Lys Trp Met Ala Leu
    450                 455                 460

Glu Ser Ile Leu His Arg Ile Tyr Thr His Gln Ser Asp Val Trp Ser
465                 470                 475                 480

Tyr Gly Val Thr Val Trp Glu Leu Met Thr Phe Gly Ser Lys Pro Tyr
                485                 490                 495

Asp Gly Ile Pro Ala Ser Glu Ile Ser Ser Ile Leu Glu Lys Gly Glu
            500                 505                 510

Arg Leu Pro Gln Pro Pro Ile Cys Thr Ile Asp Val Tyr Met Ile Met
        515                 520                 525

Val Lys Cys Trp Met Ile Asp Ala Asp Ser Arg Pro Lys Phe Arg Glu
    530                 535                 540

Leu Ile Ile Glu Phe Ser Lys Met Ala Arg Asp Pro Gln Arg Tyr Leu
```

-continued 545 550 555 560

Val Ile Gln Gly Asp Glu Arg Met His Leu Pro Ser Pro Thr Asp Ser
565 570 575

Asn Phe Tyr Arg Ala Leu Met Asp Glu Glu Asp Met Asp Asp Val Val
580 585 590

Asp Ala Asp Glu Tyr Leu Ile Pro Gln Gln Gly Phe Phe Ser Ser Pro
595 600 605

Ser Thr Ser Arg Thr Pro Leu Leu Ser Ser Leu Ser Ala Thr Ser Asn
610 615 620

Asn Ser Thr Val Ala Cys Ile Asp Arg Asn Gly Leu Gln Ser Cys Pro
625 630 635 640

Ile Lys Glu Asp Ser Phe Leu Gln Arg Tyr Ser Ser Asp Pro Thr Gly
645 650 655

Ala Leu Thr Glu Asp Ser Ile Asp Asp Thr Phe Leu Pro Val Pro Glu
660 665 670

Tyr Ile Asn Gln Ser Val Pro Lys Arg Pro Ala Gly Ser Val Gln Asn
675 680 685

Pro Val Tyr His Asn Gln Pro Leu Asn Pro Ala Pro Ser Arg Asp Pro
690 695 700

His Tyr Gln Asp Pro His Ser Thr Ala Val Gly Asn Pro Glu Tyr Leu
705 710 715 720

Asn Thr Val Gln Pro Thr Cys Val Asn Ser Thr Phe Asp Ser Pro Ala
725 730 735

His Trp Ala Gln Lys Gly Ser His Gln Ile Ser Leu Asp Asn Pro Asp
740 745 750

Tyr Gln Gln Asp Phe Phe Pro Lys Glu Ala Lys Pro Asn Gly Ile Phe
755 760 765

Lys Gly Ser Thr Ala Glu Asn Ala Glu Tyr Leu Arg Val Ala Pro Gln
770 775 780

Ser Ser Glu Phe Ile Gly Ala
785 790

<210> SEQ ID NO 6
<211> LENGTH: 14
<212> TYPE: PRT
<213> ORGANISM: Artificial Sequence
<220> FEATURE:
<223> OTHER INFORMATION: biotinylated peptide biotin-Ahx, (C-terminus in amide form)

<400> SEQUENCE: 6

Ala Glu Glu Glu Glu Tyr Phe Glu Leu Val Ala Lys Lys Lys
1 5 10

<210> SEQ ID NO 7
<211> LENGTH: 12
<212> TYPE: PRT
<213> ORGANISM: Artificial Sequence
<220> FEATURE:
<223> OTHER INFORMATION: biotinylated peptide biotin-Ahx, C-terminus in amide form

<400> SEQUENCE: 7

Val Leu Leu Pro Lys Lys Ser Phe Ala Glu Pro Gly
1 5 10